US010651389B2

(12) United States Patent
Jatsch et al.

(10) Patent No.: US 10,651,389 B2
(45) Date of Patent: May 12, 2020

(54) MATERIALS FOR ELECTRONIC DEVICES

(71) Applicant: Merck Patent GmbH, Darmstadt (DE)

(72) Inventors: Anja Jatsch, Frankfurt am Main (DE); Christof Pflumm, Darmstadt (DE); Thomas Eberle, Landau (DE); Amir Hossain Parham, Frankfurt am Main (DE); Jonas Valentin Kroeber, Frankfurt am Main (DE); Philipp Stoessel, Frankfurt am Main (DE); Joachim Kaiser, Darmstadt (DE)

(73) Assignee: Merck Patent GmbH (DE)

( * ) Notice: Subject to any disclaimer, the term of this patent is extended or adjusted under 35 U.S.C. 154(b) by 424 days.

(21) Appl. No.: 14/901,140

(22) PCT Filed: Jun. 11, 2014

(86) PCT No.: PCT/EP2014/001587
§ 371 (c)(1),
(2) Date: Dec. 28, 2015

(87) PCT Pub. No.: WO2015/000549
PCT Pub. Date: Jan. 8, 2015

(65) Prior Publication Data
US 2016/0141508 A1 May 19, 2016

(30) Foreign Application Priority Data
Jul. 2, 2013 (EP) .................................... 13003344

(51) Int. Cl.
H01L 51/00 (2006.01)
C07D 401/14 (2006.01)
C07D 403/10 (2006.01)
C07D 405/04 (2006.01)
C07D 405/10 (2006.01)
(Continued)

(52) U.S. Cl.
CPC ........ H01L 51/0061 (2013.01); C07D 251/14 (2013.01); C07D 251/24 (2013.01); C07D 401/04 (2013.01); C07D 401/12 (2013.01); C07D 401/14 (2013.01); C07D 403/04 (2013.01); C07D 403/10 (2013.01); C07D 403/12 (2013.01); C07D 405/04 (2013.01); C07D 405/10 (2013.01); C07D 405/12 (2013.01); C07D 405/14 (2013.01); C07D 409/04 (2013.01); C07D 409/10 (2013.01); C07D 409/14 (2013.01); C07D 413/04 (2013.01); C09K 11/025 (2013.01); C09K 11/06 (2013.01); H01L 51/006 (2013.01); H01L 51/0085 (2013.01); H01L 51/0087 (2013.01); H05B 33/10 (2013.01); C09K 2211/1007 (2013.01); C09K 2211/1011 (2013.01); C09K 2211/1014 (2013.01); C09K 2211/1029 (2013.01); C09K 2211/1074 (2013.01); C09K 2211/185 (2013.01); H01L 51/0035 (2013.01); H01L 51/0043 (2013.01); H01L 51/0052 (2013.01); H01L 51/0056 (2013.01); H01L 51/0058 (2013.01); H01L 51/0067 (2013.01); H01L 51/0071 (2013.01); H01L 51/0072 (2013.01); H01L 51/0073 (2013.01); H01L 51/0074 (2013.01); H01L 51/5012 (2013.01);
(Continued)

(58) Field of Classification Search
CPC ............. H01L 51/0061; H01L 51/0085; H01L 51/0087; H01L 51/006; H01L 51/5012; H01L 51/0052; H01L 51/0058; H01L 51/0067; H01L 51/0071; H01L 51/0056; H01L 51/0074; H01L 51/0073; H01L 51/0072; H01L 51/0035; H01L 51/0043; H01L 51/5016; H01L 51/5056; C07D 401/12; C07D 251/24; C07D 403/12; C07D 405/14; C07D 409/14; C07D 413/04; C07D 403/10; C07D 401/04; C07D 405/04; C07D 405/10; C07D 405/12; C07D 409/04; C07D 409/10; C07D 401/14; C07D 251/14; C07D 403/04; H05B 33/10; C09K 11/025; C09K 11/06; C09K 2211/1011; C09K 2211/1074; C09K 2211/185; C09K 2211/1029; C09K 2211/1014; C09K 2211/1007
See application file for complete search history.

(56) References Cited
U.S. PATENT DOCUMENTS 8,785,636 B2 7/2014 Parham et al.
2013/0256645 A1* 10/2013 Min ...................... C09K 11/06
257/40
(Continued)

FOREIGN PATENT DOCUMENTS

CN 102197027 A 9/2011
CN 104718208 A 6/2015
(Continued)

OTHER PUBLICATIONS

Hua Ye, "Conjugated polymers containing trifluoren-2-ylamine, trifluoren-2-ylbenzene and trifluoren-2-yltriazine for electroluminescence" Polymer 54 (2013) 162e173.*
(Continued)

Primary Examiner — Michael Y Sun
(74) Attorney, Agent, or Firm — Faegre Drinker Biddle & Reath LLP

(57) ABSTRACT

The present invention relates to a compound of a formula (I), in which an electron-deficient group and an arylamino group are connected to one another via an intermediate group. The compound of the formula (I) is suitable as functional material in electronic devices.

27 Claims, No Drawings

(51) Int. Cl.

| | | |
|---|---|---|
| *C07D 405/12* | (2006.01) | |
| *C07D 409/04* | (2006.01) | |
| *C09K 11/06* | (2006.01) | |
| *C07D 401/04* | (2006.01) | |
| *C07D 251/14* | (2006.01) | |
| *H05B 33/10* | (2006.01) | |
| *C07D 403/04* | (2006.01) | |
| *C07D 409/10* | (2006.01) | |
| *C07D 251/24* | (2006.01) | |
| *C07D 401/12* | (2006.01) | |
| *C07D 403/12* | (2006.01) | |
| *C07D 405/14* | (2006.01) | |
| *C07D 409/14* | (2006.01) | |
| *C07D 413/04* | (2006.01) | |
| *C09K 11/02* | (2006.01) | |
| *H01L 51/50* | (2006.01) | |

(52) U.S. Cl.
CPC ...... *H01L 51/5016* (2013.01); *H01L 51/5056* (2013.01)

(56) References Cited

U.S. PATENT DOCUMENTS

| | | |
|---|---|---|
| 2014/0151667 A1 | 6/2014 | Miyata |
| 2014/0155600 A1 | 6/2014 | Jin |
| 2014/0155601 A1 | 6/2014 | Jin |
| 2014/0296519 A1 | 10/2014 | Matsumoto et al. |
| 2014/0350247 A1 | 11/2014 | Imada |
| 2014/0371825 A1 | 12/2014 | Anemian et al. |
| 2015/0318483 A1 | 11/2015 | Kim et al. |
| 2015/0325794 A1 | 11/2015 | Nishimura et al. |
| 2015/0333276 A1 | 11/2015 | Bae et al. |

FOREIGN PATENT DOCUMENTS

| | | | |
|---|---|---|---|
| DE | 102009048791 A1 | | 4/2011 |
| EP | 1956022 A1 | | 8/2008 |
| JP | 2009246097 A | | 10/2009 |
| JP | 2010134121 A | * | 6/2010 |
| JP | 2012526804 A | | 11/2012 |
| JP | 2014101275 A | | 6/2014 |
| JP | 2014110313 A | | 6/2014 |
| JP | 2014110315 A | | 6/2014 |
| JP | 2014111556 A | | 6/2014 |
| JP | 2014227399 A | | 12/2014 |
| KR | 20110105258 A | * | 9/2011 |
| KR | 20110105285 A | * | 9/2011 |
| KR | 20110111692 A | | 10/2011 |
| KR | 20120072784 A | | 7/2012 |
| TW | 201105770 A | | 2/2011 |
| TW | 201129567 A | | 9/2011 |
| WO | WO-2010110553 A2 | | 9/2010 |
| WO | WO-2012074210 A2 | * | 6/2012 ............. C09K 11/06 |
| WO | WO-2013062043 A1 | | 5/2013 |
| WO | WO-2013107487 A1 | | 7/2013 |
| WO | WO-2014087657 A1 | | 6/2014 |

OTHER PUBLICATIONS

Qiang Wang, "Evaluation of propylene-, meta-, and para-linked triazine and tert-butyltriphenylamine as bipolar hosts for phosphorescent organic light-emitting diodes" J. Mater. Chem. C, 2013, 1, 2224 (Year: 2013).*

International Search Report for PCT/EP2014/001587 dated Jul. 30, 2014.

Jiang, Y., et al., "Multibranched triarylamine end-capped triazines with aggregation-induced emission and large two-photon absorption cross-sections", Chemical Communications, vol. 46, No. 26, (2010), pp. 4689-4691.

Omer, et al., "Electrochemical Behavior and Electrogenerated Chemiluminescence of Star-Shaped D-A Compounds with a 1,3,5-Triazine Core and Substituted Fluorene Arms", *J. Am. Chem. Soc.*, vol. 132, pp. 10944-10952 (2010).

Japanese Office Action dated Apr. 10, 2018 for Japanese Patent Application No. 2016-522304.

* cited by examiner

MATERIALS FOR ELECTRONIC DEVICES

CROSS-REFERENCE TO RELATED APPLICATIONS

This application is a national stage application (under 35 U.S.C. § 371) of PCT/EP2014/001587, filed Jun. 11, 2014, which claims benefit of European Application No. 13003344.2, filed Jul. 2, 2013, both of which are incorporated herein by reference in their entirety.

The present invention relates to a compound of a formula (I), in which an electron-deficient group and an arylamino group are connected to one another via an intermediate group. The compound of the formula (I) is suitable as functional material in electronic devices.

Electronic devices in the sense of this application are taken to mean, in particular, so-called organic electronic devices, which comprise organic semiconductor materials as functional materials. Again in particular, they are taken to mean organic electroluminescent devices (OLEDs) and other electronic devices which are mentioned below in the detailed description of the invention.

In general, the term OLED is taken to mean an electronic device which comprises at least one organic material and emits light on application of an electrical voltage. The precise structure of OLEDs is described, inter alia, in U.S. Pat. Nos. 4,539,507, 5,151,629, EP 0676461 and WO 98/27136.

In the case of electronic devices, in particular OLEDs, there is considerable interest in improving the performance data, in particular lifetime and efficiency and operating voltage. An important role is played here by organic emitter layers, in particular the matrix materials present therein, and organic layers having an electron-transporting function.

In order to achieve this technical object, there is a continuous search for novel materials which are suitable for use as matrix materials in emitting layers, in particular phosphorescent emitting layers. Furthermore, there is a search for materials having electron-transporting properties for use in corresponding functional layers.

Phosphorescent emitting layers in the sense of the present application are organic layers which comprise at least one phosphorescent emitter compound.

The term phosphorescent emitters in accordance with the present application encompasses compounds in which the light emission takes place through a spin-forbidden transition, for example a transition from an excited triplet state or a state having a relatively high spin quantum number, such as a quintet state.

A matrix material for the case of the emitting layer is taken to mean a material which is not an emitter compound.

Emitter compounds of an emitting layer are compounds which emit light on operation of the device.

In general, in particular in the case of functional layers other than emitting layers, a matrix material in a system comprising two materials is taken to mean the material whose proportion in the mixture is the larger. Correspondingly, a dopant in a system comprising two materials is taken to mean the material whose proportion in the mixture is the smaller.

The prior art discloses the use of compounds containing a triazine group and an arylamino group in OLEDs, where certain connecting groups, for example biphenylene groups, are present between the two groups (cf. JP 2002-193952, JP 2010-134121 and Q. Wang et al., J. Mat. Chem. C, 2013, 1, 2224-2232). The compounds are characterised in that only small aromatic ring systems, such as, for example, phenyl, are bonded to the nitrogen atom.

In spite of these inventions, there continues to be a demand for alternative compounds which are suitable as functional materials in electronic devices. In particular, there is a demand for compounds which, as functional materials in electronic devices, effect a long lifetime and high power efficiency of the devices, in particular on use as matrix materials in phosphorescent emitting layers. Furthermore, there is a demand for materials which effect a low operating voltage on use in electronic devices. Again furthermore, there is a demand for materials which effect a low roll-off, i.e. a small drop in the power efficiency of the device at high luminous densities.

It has now been found, unexpectedly, that compounds which contain a triazine group and an arylamino group and a group connecting these groups, where the amino group is substituted by at least one large aromatic or heteroaromatic ring system, achieve one or more of the above-mentioned technical objects, preferably all of the above-mentioned technical objects.

The present invention therefore relates to a compound of the formula (I)

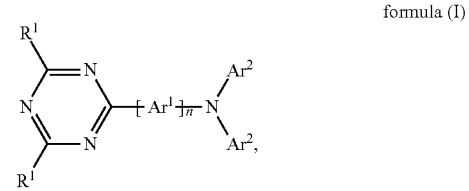

formula (I)

where:
Ar$^1$ is on each occurrence, identically or differently, an aromatic or heteroaromatic ring system having 5 to 24 aromatic ring atoms, which may be substituted by one or more radicals R$^2$;
Ar$^2$ is on each occurrence, identically or differently, an aromatic or heteroaromatic ring system having 5 to 24 aromatic ring atoms, which may be substituted by one or more radicals R$^2$,
where at least one group Ar$^2$ in the compound of the formula (I) represents a group Ar$^{2*}$;
Ar$^{2*}$ is on each occurrence, identically or differently, an aromatic or heteroaromatic ring system having 12 to 24 aromatic ring atoms, which may be substituted by one or more radicals R$^2$, where the aromatic ring system contains no condensed aryl or heteroaryl group having more than 10 aromatic ring atoms;
R$^1$, R$^2$ are on each occurrence, identically or differently, H, D, F, Cl, Br, I, C(=O)R$^3$, CN, Si(R$^3$)$_3$, N(R$^3$)$_2$, P(=O)(R$^3$)$_2$, OR$^3$, S(=O)R$^3$, S(=O)$_2$R$^3$, a straight-chain alkyl or alkoxy group having 1 to 20 C atoms or a branched or cyclic alkyl or alkoxy group having 3 to 20 C atoms or an alkenyl or alkynyl group having 2 to 20 C atoms, where the above-mentioned groups may each be substituted by one or more radicals R$^3$ and where one or more CH$_2$ groups in the above-mentioned groups may be replaced by —R$^3$C=CR$^3$—, —C≡C—, Si(R$^3$)$_2$, C=O, C=NR$^3$, —C(=O)O—, —C(=O)NR$^3$—, NR$^3$, P(=O)(R$^3$), —O—, —S—, SO or SO$_2$, or an aromatic or heteroaromatic ring system having 5 to 30 aromatic ring atoms, which may in each case be substituted by one or more radicals R$^3$, where two or more radicals R$^2$ may be linked to one another and may form a ring;

$R^3$ is on each occurrence, identically or differently, H, D, F, Cl, Br, I, C(=O)R$^4$, CN, Si(R$^4$)$_3$, N(R$^3$)$_2$, P(=O)(R$^4$)$_2$, OR$^4$, S(=O)R$^4$, S(=O)$_2$R$^4$, a straight-chain alkyl or alkoxy group having 1 to 20 C atoms or a branched or cyclic alkyl or alkoxy group having 3 to 20 C atoms or an alkenyl or alkynyl group having 2 to 20 C atoms, where the above-mentioned groups may each be substituted by one or more radicals R$^4$ and where one or more CH$_2$ groups in the above-mentioned groups may be replaced by —R$^4$C=CR$^4$—, —C≡C—, Si(R$^4$)$_2$, C=O, C=NR$^4$, —C(=O)O—, —C(=O)NR$^4$—, NR$^4$, P(=O)(R$^4$), —O—, —S—, SO or SO$_2$, or an aromatic or heteroaromatic ring system having 5 to 30 aromatic ring atoms, which may in each case be substituted by one or more radicals R$^4$, where two or more radicals R$^3$ may be linked to one another and may form a ring;

$R^4$ is on each occurrence, identically or differently, H, D, F or an aliphatic, heteroaliphatic, aromatic or heteroaromatic organic radical having 1 to 20 C atoms, in which, in addition, one or more H atoms may be replaced by D or F; two or more substituents R$^4$ here may be linked to one another and may form a ring;

n is equal to 1, 2, 3 or 4;

where, for n=1, the group Ar$^1$ is not optionally R$^2$-substituted phenylene or optionally R$^2$-substituted carbazole; and where Ar$^1$ is not optionally R$^2$-substituted fluorene bonded via positions 9 and 9'.

Positions 9 and 9' of the fluorene are taken to mean the bonding positions marked below:

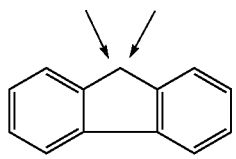

An aryl group in the sense of this invention contains 6 to 60 aromatic ring atoms; a heteroaryl group in the sense of this invention contains 5 to 60 aromatic ring atoms, at least one of which is a heteroatom. The heteroatoms are preferably selected from N, O and S. This represents the basic definition. If other preferences are indicated in the description of the present invention, for example with respect to the number of aromatic ring atoms or the heteroatoms present, these apply.

An aryl group or heteroaryl group here is taken to mean either a simple aromatic ring, i.e. benzene, or a simple heteroaromatic ring, for example pyridine, pyrimidine or thiophene, or a condensed (annellated) aromatic or heteroaromatic polycycle, for example naphthalene, phenanthrene, quinoline or carbazole. A condensed (annellated) aromatic or heteroaromatic polycycle in the sense of the present application consists of two or more simple aromatic or heteroaromatic rings condensed with one another, and is correspondingly also called a condensed aryl group or condensed heteroaryl group.

An aryl or heteroaryl group, which may in each case be substituted by the above-mentioned radicals and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, triphenylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aromatic ring system in the sense of this invention contains 6 to 60 C atoms in the ring system. A heteroaromatic ring system in the sense of this invention contains 5 to 60 aromatic ring atoms, at least one of which is a heteroatom. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a single bond or by a non-aromatic unit, such as, for example, one or more optionally substituted C, Si, N, O or S atoms. The non-aromatic unit here preferably contains less than 10% of the atoms other than H, based on the total number of atoms other than H in the system. Thus, for example, systems such as 9,9'-spiro-bifluorene, 9,9'-diarylfluorene, triarylamine, diaryl ether and stilbene, are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via single bonds are also taken to be aromatic or heteroaromatic ring systems in the sense of this invention, such as, for example, systems such as biphenyl, terphenyl or diphenyltriazine.

An aromatic or heteroaromatic ring system having 5-60 aromatic ring atoms, which may in each case also be substituted by radicals as defined above and which may be linked to the aromatic or heteroaromatic group via any desired positions, is taken to mean, in particular, groups which are derived from the groups mentioned above under aryl and heteroaryl groups, as well as from biphenyl, terphenyl, quaterphenyl, fluorene, spiro-bifluorene, dihydrophenanthrene, dihydropyrene, tetrahydropyrene, indenofluorene, truxene, isotruxene, spirotruxene, spiroisotruxene, indenocarbazole or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or CH$_2$ groups may be substituted by the groups mentioned above under the definition of the radicals, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, hept enyl, cycloheptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyl oxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoro ethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The formulation that two or more radicals may form a ring with one another is, for the purposes of the present application, to be taken to mean, inter alia, that the two radicals are linked to one another by a chemical bond. Furthermore, however, the above-mentioned formulation is also to be taken to mean that, in the case where one of the two radicals represents hydrogen, the second radical is bonded to the position to which the hydrogen atom was bonded, with formation of a ring.

The compound of the formula (I) preferably contains precisely one amino group.

The compound of the formula (I) preferably contains precisely one triazine group.

The compound of the formula (I) preferably contains no condensed aryl group having more than 14 aromatic ring atoms, particularly preferably no condensed aryl group having more than 10 aromatic ring atoms.

The compound of the formula (I) preferably contains no condensed heteroaryl group having more than 14 aromatic ring atoms, particularly preferably no condensed heteroaryl group having more than 10 aromatic ring atoms.

It is preferred for the index n to be equal to 1, 2 or 3, particularly preferably to be equal to 1 or 2, very particularly preferably to be equal to 1.

It is furthermore preferred for $Ar^1$ to be on each occurrence, identically or differently, an aromatic or heteroaromatic ring system having 5 to 20 aromatic ring atoms, which may be substituted by one or more radicals $R^2$. $Ar^1$ is particularly preferably selected on each occurrence, identically or differently, from phenyl, biphenyl, terphenyl, fluorenyl, spirobifluorenyl, indeno fluorenyl, naphthyl, anthracenyl, phenanthrenyl, chrysenyl, benzanthracenyl, pyrenyl, fluoranthenyl, triphenylenyl, furanyl, benzofuranyl, dibenzofuranyl, thiophenyl, benzothiophenyl, dibenzothiophenyl, indolyl, carbazolyl, indolocarbazolyl, indenocarbazolyl, pyridyl, quinolinyl, acridyl, dihydroacridyl, pyrazolyl, imidazolyl, benzimidazolyl, pyridazyl, pyrimidyl, pyrazinyl, phenanthrolyl, diphenyl ether, diphenyl thioether, diphenylsilylene and diphenylmethylene, each of which is optionally substituted by one or more radicals $R^2$.

The unit —$(Ar^1)_n$— is very particularly preferably selected from fluorenyl, spirobifluorenyl, indenofluorenyl, naphthyl, anthracenyl, phenanthrenyl, chrysenyl, benzanthracenyl, pyrenyl, fluoranthenyl, furanyl, benzofuranyl, dibenzofuranyl, thiophenyl, benzothiophenyl, dibenzothiophenyl, indolyl, indolocarbazolyl, indenocarbazolyl, pyridyl, quinolinyl, acridyl, dihydroacridyl, pyrazolyl, imidazolyl, benzimidazolyl, pyridazyl, pyrimidyl, pyrazinyl and phenanthrolyl, diphenyl ether, diphenyl thioether, diphenylsilylene, diphenylmethylene, each of which is optionally substituted by one or more radicals $R^2$, and from combinations containing one or more of the above-mentioned groups and one or more further groups selected from phenyl and carbazolyl, each of which is optionally substituted by one or more radicals $R^2$.

The unit —$(Ar^1)_n$— preferably represents a fully conjugated unsaturated divalent group. This means that it preferably contains no conjugation-interrupting groups, such as, for example, alkylene groups, which interrupt the conjugated system which extends from one side of the divalent unit —$(Ar^1)_n$— to the other. The unit —$(Ar^1)_n$— preferably contains a continuously conjugated pi-electron system from one side to the other side of the unit, so that triazine group and amino group are connected to one another in a conjugated manner.

Particularly preferred units —$(Ar^1)_n$— conform to the following formulae (L-1) to (L-368), where the groups $Ar^1$ are correspondingly bonded one behind the other and conform to the formulae ($Ar^1$-1) to ($Ar^1$-17), as indicated below:

|  | n | $Ar^1$ | $Ar^1$ | $Ar^1$ |
|---|---|---|---|---|
| (L-1) | 1 | ($Ar^1$-2) | — | — |
| (L-2) | " | ($Ar^1$-3) | — | — |
| (L-3) | " | ($Ar^1$-4) | — | — |
| (L-4) | " | ($Ar^1$-5) | — | — |
| (L-5) | " | ($Ar^1$-6) | — | — |
| (L-6) | " | ($Ar^1$-7) | — | — |
| (L-7) | " | ($Ar^1$-8) | — | — |
| (L-8) | " | ($Ar^1$-9) | — | — |
| (L-9) | " | ($Ar^1$-10) | — | — |
| (L-10) | " | ($Ar^1$-11) | — | — |
| (L-11) | " | ($Ar^1$-12) | — | — |
| (L-12) | " | ($Ar^1$-13) | — | — |
| (L-13) | " | ($Ar^1$-15) | — | — |
| (L-14) | " | ($Ar^1$-16) | — | — |
| (L-15) | " | ($Ar^1$-17) | — | — |
| (L-16) | 2 | ($Ar^1$-1) | ($Ar^1$-1) | — |
| (L-17) | " | " | ($Ar^1$-2) | — |
| (L-18) | " | " | ($Ar^1$-3) | — |
| (L-19) | " | " | ($Ar^1$-4) | — |
| (L-20) | " | " | ($Ar^1$-5) | — |
| (L-21) | " | " | ($Ar^1$-6) | — |
| (L-22) | " | " | ($Ar^1$-7) | — |
| (L-23) | " | " | ($Ar^1$-8) | — |
| (L-24) | " | " | ($Ar^1$-9) | — |
| (L-25) | " | " | ($Ar^1$-10) | — |
| (L-26) | " | " | ($Ar^1$-11) | — |
| (L-27) | " | " | ($Ar^1$-12) | — |
| (L-28) | " | " | ($Ar^1$-13) | — |
| (L-29) | " | " | ($Ar^1$-14) | — |
| (L-30) | " | " | ($Ar^1$-15) | — |
| (L-31) | " | " | ($Ar^1$-16) | — |
| (L-32) | " | " | ($Ar^1$-17) | — |
| (L-33) | " | ($Ar^1$-2) | ($Ar^1$-1) | — |
| (L-34) | " | " | ($Ar^1$-2) | — |
| (L-35) | " | " | ($Ar^1$-3) | — |
| (L-36) | " | " | ($Ar^1$-4) | — |
| (L-37) | " | " | ($Ar^1$-5) | — |
| (L-38) | " | " | ($Ar^1$-6) | — |
| (L-39) | " | " | ($Ar^1$-7) | — |
| (L-40) | " | " | ($Ar^1$-8) | — |
| (L-41) | " | " | ($Ar^1$-9) | — |
| (L-42) | " | " | ($Ar^1$-10) | — |
| (L-43) | " | " | ($Ar^1$-11) | — |
| (L-44) | " | " | ($Ar^1$-12) | — |
| (L-45) | " | " | ($Ar^1$-13) | — |
| (L-46) | " | " | ($Ar^1$-14) | — |
| (L-47) | " | " | ($Ar^1$-15) | — |
| (L-48) | " | " | ($Ar^1$-16) | — |
| (L-49) | " | " | ($Ar^1$-17) | — |
| (L-50) | " | ($Ar^1$-3) | ($Ar^1$-1) | — |

| | n | Ar¹ | Ar¹ | Ar¹ |
|---|---|---|---|---|
| (L-51) | " | " | (Ar¹-2) | — |
| (L-52) | " | " | (Ar¹-3) | — |
| (L-53) | " | " | (Ar¹-4) | — |
| (L-54) | " | " | (Ar¹-5) | — |
| (L-55) | " | " | (Ar¹-6) | — |
| (L-56) | " | " | (Ar¹-7) | — |
| (L-57) | " | " | (Ar¹-8) | — |
| (L-58) | " | " | (Ar¹-9) | — |
| (L-59) | " | " | (Ar¹-10) | — |
| (L-60) | " | " | (Ar¹-11) | — |
| (L-61) | " | " | (Ar¹-12) | — |
| (L-62) | " | " | (Ar¹-13) | — |
| (L-63) | " | " | (Ar¹-14) | — |
| (L-64) | " | " | (Ar¹-15) | — |
| (L-65) | " | " | (Ar¹-16) | — |
| (L-66) | " | " | (Ar¹-17) | — |
| (L-67) | " | (Ar¹-4) | (Ar¹-1) | — |
| (L-68) | " | " | (Ar¹-2) | — |
| (L-69) | " | " | (Ar¹-3) | — |
| (L-70) | " | " | (Ar¹-4) | — |
| (L-71) | " | " | (Ar¹-5) | — |
| (L-72) | " | " | (Ar¹-6) | — |
| (L-73) | " | " | (Ar¹-7) | — |
| (L-74) | " | " | (Ar¹-8) | — |
| (L-75) | " | " | (Ar¹-9) | — |
| (L-76) | " | " | (Ar¹-10) | — |
| (L-77) | " | " | (Ar¹-11) | — |
| (L-78) | " | " | (Ar¹-12) | — |
| (L-79) | " | " | (Ar¹-13) | — |
| (L-80) | " | " | (Ar¹-14) | — |
| (L-81) | " | " | (Ar¹-15) | — |
| (L-82) | " | " | (Ar¹-16) | — |
| (L-83) | " | " | (Ar¹-17) | — |
| (L-84) | " | (Ar¹-5) | (Ar¹-1) | — |
| (L-85) | " | " | (Ar¹-2) | — |
| (L-86) | " | " | (Ar¹-3) | — |
| (L-87) | " | " | (Ar¹-4) | — |
| (L-88) | " | " | (Ar¹-5) | — |
| (L-89) | " | " | (Ar¹-6) | — |
| (L-90) | " | " | (Ar¹-7) | — |
| (L-91) | " | " | (Ar¹-8) | — |
| (L-92) | " | " | (Ar¹-9) | — |
| (L-93) | " | " | (Ar¹-10) | — |
| (L-94) | " | " | (Ar¹-11) | — |
| (L-95) | " | " | (Ar¹-12) | — |
| (L-96) | " | " | (Ar¹-13) | — |
| (L-97) | " | " | (Ar¹-14) | — |
| (L-98) | " | " | (Ar¹-15) | — |
| (L-99) | " | " | (Ar¹-16) | — |
| (L-100) | " | " | (Ar¹-17) | — |
| (L-101) | " | (Ar¹-6) | (Ar¹-1) | — |
| (L-102) | " | " | (Ar¹-2) | — |
| (L-103) | " | " | (Ar¹-3) | — |
| (L-104) | " | " | (Ar¹-4) | — |
| (L-105) | " | " | (Ar¹-5) | — |
| (L-106) | " | " | (Ar¹-6) | — |
| (L-107) | " | " | (Ar¹-7) | — |
| (L-108) | " | " | (Ar¹-8) | — |
| (L-109) | " | " | (Ar¹-9) | — |
| (L-110) | " | " | (Ar¹-10) | — |
| (L-111) | " | " | (Ar¹-11) | — |
| (L-112) | " | " | (Ar¹-12) | — |
| (L-113) | " | " | (Ar¹-13) | — |
| (L-114) | " | " | (Ar¹-14) | — |
| (L-115) | " | " | (Ar¹-15) | — |
| (L-116) | " | " | (Ar¹-16) | — |
| (L-117) | " | " | (Ar¹-17) | — |
| (L-118) | " | (Ar¹-7) | (Ar¹-1) | — |
| (L-119) | " | " | (Ar¹-2) | — |
| (L-120) | " | " | (Ar¹-3) | — |
| (L-121) | " | " | (Ar¹-4) | — |
| (L-122) | " | " | (Ar¹-5) | — |
| (L-123) | " | " | (Ar¹-6) | — |
| (L-124) | " | " | (Ar¹-7) | — |
| (L-125) | " | " | (Ar¹-8) | — |
| (L-126) | " | " | (Ar¹-9) | — |
| (L-127) | " | " | (Ar¹-10) | — |
| (L-128) | " | " | (Ar¹-11) | — |
| (L-129) | " | " | (Ar¹-12) | — |
| (L-130) | " | " | (Ar¹-13) | — |
| (L-131) | " | " | (Ar¹-14) | — |
| (L-132) | " | " | (Ar¹-15) | — |
| (L-133) | " | " | (Ar¹-16) | — |
| (L-134) | " | " | (Ar¹-17) | — |
| (L-135) | " | (Ar¹-8) | (Ar¹-1) | — |
| (L-136) | " | " | (Ar¹-2) | — |
| (L-137) | " | " | (Ar¹-3) | — |
| (L-138) | " | " | (Ar¹-4) | — |
| (L-139) | " | " | (Ar¹-5) | — |
| (L-140) | " | " | (Ar¹-6) | — |
| (L-141) | " | " | (Ar¹-7) | — |
| (L-142) | " | " | (Ar¹-8) | — |
| (L-143) | " | " | (Ar¹-9) | — |
| (L-144) | " | " | (Ar¹-10) | — |
| (L-145) | " | " | (Ar¹-11) | — |
| (L-146) | " | " | (Ar¹-12) | — |
| (L-147) | " | " | (Ar¹-13) | — |
| (L-148) | " | " | (Ar¹-14) | — |
| (L-149) | " | " | (Ar¹-15) | — |
| (L-150) | " | " | (Ar¹-16) | — |
| (L-151) | " | " | (Ar¹-17) | — |
| (L-152) | " | (Ar¹-9) | (Ar¹-1) | — |
| (L-153) | " | " | (Ar¹-2) | — |
| (L-154) | " | " | (Ar¹-3) | — |
| (L-155) | " | " | (Ar¹-4) | — |
| (L-156) | " | " | (Ar¹-5) | — |
| (L-157) | " | " | (Ar¹-6) | — |
| (L-158) | " | " | (Ar¹-7) | — |
| (L-159) | " | " | (Ar¹-8) | — |
| (L-160) | " | " | (Ar¹-9) | — |
| (L-161) | " | " | (Ar¹-10) | — |
| (L-162) | " | " | (Ar¹-11) | — |
| (L-163) | " | " | (Ar¹-12) | — |
| (L-164) | " | " | (Ar¹-13) | — |
| (L-165) | " | " | (Ar¹-14) | — |
| (L-166) | " | " | (Ar¹-15) | — |
| (L-167) | " | " | (Ar¹-16) | — |
| (L-168) | " | " | (Ar¹-17) | — |
| (L-169) | " | (Ar¹-10) | (Ar¹-1) | — |
| (L-170) | " | " | (Ar¹-2) | — |
| (L-171) | " | " | (Ar¹-3) | — |
| (L-172) | " | " | (Ar¹-4) | — |
| (L-173) | " | " | (Ar¹-5) | — |
| (L-174) | " | " | (Ar¹-6) | — |
| (L-175) | " | " | (Ar¹-7) | — |
| (L-176) | " | " | (Ar¹-8) | — |
| (L-177) | " | " | (Ar¹-9) | — |
| (L-178) | " | " | (Ar¹-10) | — |
| (L-179) | " | " | (Ar¹-11) | — |
| (L-180) | " | " | (Ar¹-12) | — |
| (L-181) | " | " | (Ar¹-13) | — |
| (L-182) | " | " | (Ar¹-14) | — |
| (L-183) | " | " | (Ar¹-15) | — |
| (L-184) | " | " | (Ar¹-16) | — |
| (L-185) | " | " | (Ar¹-17) | — |
| (L-186) | " | (Ar¹-11) | (Ar¹-1) | — |
| (L-187) | " | " | (Ar¹-2) | — |
| (L-188) | " | " | (Ar¹-3) | — |
| (L-189) | " | " | (Ar¹-4) | — |
| (L-190) | " | " | (Ar¹-5) | — |
| (L-191) | " | " | (Ar¹-6) | — |
| (L-192) | " | " | (Ar¹-7) | — |
| (L-193) | " | " | (Ar¹-8) | — |
| (L-194) | " | " | (Ar¹-9) | — |
| (L-195) | " | " | (Ar¹-10) | — |
| (L-196) | " | " | (Ar¹-11) | — |
| (L-197) | " | " | (Ar¹-12) | — |
| (L-198) | " | " | (Ar¹-13) | — |
| (L-199) | " | " | (Ar¹-14) | — |
| (L-200) | " | " | (Ar¹-15) | — |
| (L-201) | " | " | (Ar¹-16) | — |
| (L-202) | " | " | (Ar¹-17) | — |
| (L-203) | " | (Ar¹-12) | (Ar¹-1) | — |
| (L-204) | " | " | (Ar¹-2) | — |

-continued

| | n | Ar¹ | Ar¹ | Ar¹ |
|---|---|---|---|---|
| (L-205) | " | " | (Ar¹-3) | — |
| (L-206) | " | " | (Ar¹-4) | — |
| (L-207) | " | " | (Ar¹-5) | — |
| (L-208) | " | " | (Ar¹-6) | — |
| (L-209) | " | " | (Ar¹-7) | — |
| (L-210) | " | " | (Ar¹-8) | — |
| (L-211) | " | " | (Ar¹-9) | — |
| (L-212) | " | " | (Ar¹-10) | — |
| (L-213) | " | " | (Ar¹-11) | — |
| (L-214) | " | " | (Ar¹-12) | — |
| (L-215) | " | " | (Ar¹-13) | — |
| (L-216) | " | " | (Ar¹-14) | — |
| (L-217) | " | " | (Ar¹-15) | — |
| (L-218) | " | " | (Ar¹-16) | — |
| (L-219) | " | " | (Ar¹-17) | — |
| (L-220) | " | (Ar¹-13) | (Ar¹-1) | — |
| (L-221) | " | " | (Ar¹-2) | — |
| (L-222) | " | " | (Ar¹-3) | — |
| (L-223) | " | " | (Ar¹-4) | — |
| (L-224) | " | " | (Ar¹-5) | — |
| (L-225) | " | " | (Ar¹-6) | — |
| (L-226) | " | " | (Ar¹-7) | — |
| (L-227) | " | " | (Ar¹-8) | — |
| (L-228) | " | " | (Ar¹-9) | — |
| (L-229) | " | " | (Ar¹-10) | — |
| (L-230) | " | " | (Ar¹-11) | — |
| (L-231) | " | " | (Ar¹-12) | — |
| (L-232) | " | " | (Ar¹-13) | — |
| (L-233) | " | " | (Ar¹-14) | — |
| (L-234) | " | " | (Ar¹-15) | — |
| (L-235) | " | " | (Ar¹-16) | — |
| (L-236) | " | " | (Ar¹-17) | — |
| (L-237) | " | (Ar¹-14) | (Ar¹-1) | — |
| (L-238) | " | " | (Ar¹-2) | — |
| (L-239) | " | " | (Ar¹-3) | — |
| (L-240) | " | " | (Ar¹-4) | — |
| (L-241) | " | " | (Ar¹-5) | — |
| (L-242) | " | " | (Ar¹-6) | — |
| (L-243) | " | " | (Ar¹-7) | — |
| (L-244) | " | " | (Ar¹-8) | — |
| (L-245) | " | " | (Ar¹-9) | — |
| (L-246) | " | " | (Ar¹-10) | — |
| (L-247) | " | " | (Ar¹-11) | — |
| (L-248) | " | " | (Ar¹-12) | — |
| (L-249) | " | " | (Ar¹-13) | — |
| (L-250) | " | " | (Ar¹-14) | — |
| (L-251) | " | " | (Ar¹-15) | — |
| (L-252) | " | " | (Ar¹-16) | — |
| (L-253) | " | " | (Ar¹-17) | — |
| (L-254) | " | (Ar¹-15) | (Ar¹-1) | — |
| (L-255) | " | " | (Ar¹-2) | — |
| (L-256) | " | " | (Ar¹-3) | — |
| (L-257) | " | " | (Ar¹-4) | — |
| (L-258) | " | " | (Ar¹-5) | — |
| (L-259) | " | " | (Ar¹-6) | — |
| (L-260) | " | " | (Ar¹-7) | — |
| (L-261) | " | " | (Ar¹-8) | — |
| (L-262) | " | " | (Ar¹-9) | — |
| (L-263) | " | " | (Ar¹-10) | — |
| (L-264) | " | " | (Ar¹-11) | — |
| (L-265) | " | " | (Ar¹-12) | — |
| (L-266) | " | " | (Ar¹-13) | — |
| (L-267) | " | " | (Ar¹-14) | — |
| (L-268) | " | " | (Ar¹-15) | — |
| (L-269) | " | " | (Ar¹-16) | — |
| (L-270) | " | " | (Ar¹-17) | — |
| (L-271) | " | (Ar¹-16) | (Ar¹-1) | — |
| (L-272) | " | " | (Ar¹-2) | — |
| (L-273) | " | " | (Ar¹-3) | — |
| (L-274) | " | " | (Ar¹-4) | — |
| (L-275) | " | " | (Ar¹-5) | — |
| (L-276) | " | " | (Ar¹-6) | — |
| (L-277) | " | " | (Ar¹-7) | — |
| (L-278) | " | " | (Ar¹-8) | — |
| (L-279) | " | " | (Ar¹-9) | — |
| (L-280) | " | " | (Ar¹-10) | — |
| (L-281) | " | " | (Ar¹-11) | — |
| (L-282) | " | " | (Ar¹-12) | — |
| (L-283) | " | " | (Ar¹-13) | — |
| (L-284) | " | " | (Ar¹-14) | — |
| (L-285) | " | " | (Ar¹-15) | — |
| (L-286) | " | " | (Ar¹-16) | — |
| (L-287) | " | " | (Ar¹-17) | — |
| (L-288) | " | (Ar¹-17) | (Ar¹-1) | — |
| (L-289) | " | " | (Ar¹-2) | — |
| (L-290) | " | " | (Ar¹-3) | — |
| (L-291) | " | " | (Ar¹-4) | — |
| (L-292) | " | " | (Ar¹-5) | — |
| (L-293) | " | " | (Ar¹-6) | — |
| (L-294) | " | " | (Ar¹-7) | — |
| (L-295) | " | " | (Ar¹-8) | — |
| (L-296) | " | " | (Ar¹-9) | — |
| (L-297) | " | " | (Ar¹-10) | — |
| (L-298) | " | " | (Ar¹-11) | — |
| (L-299) | " | " | (Ar¹-12) | — |
| (L-300) | " | " | (Ar¹-13) | — |
| (L-301) | " | " | (Ar¹-14) | — |
| (L-302) | " | " | (Ar¹-15) | — |
| (L-303) | " | " | (Ar¹-16) | — |
| (L-304) | " | " | (Ar¹-17) | — |
| (L-305) | 3 | (Ar¹-1) | (Ar¹-1) | (Ar¹-1) |
| (L-306) | " | " | " | (Ar¹-2) |
| (L-307) | " | " | " | (Ar¹-3) |
| (L-308) | " | " | " | (Ar¹-4) |
| (L-309) | " | " | (Ar¹-2) | (Ar¹-1) |
| (L-310) | " | " | " | (Ar¹-2) |
| (L-311) | " | " | " | (Ar¹-3) |
| (L-312) | " | " | " | (Ar¹-4) |
| (L-313) | " | " | (Ar¹-3) | (Ar¹-1) |
| (L-314) | " | " | " | (Ar¹-2) |
| (L-315) | " | " | " | (Ar¹-3) |
| (L-316) | " | " | " | (Ar¹-4) |
| (L-317) | " | " | (Ar¹-4) | (Ar¹-1) |
| (L-318) | " | " | " | (Ar¹-2) |
| (L-319) | " | " | " | (Ar¹-3) |
| (L-320) | " | " | " | (Ar¹-4) |
| (L-321) | " | (Ar¹-2) | (Ar¹-1) | (Ar¹-1) |
| (L-322) | " | " | " | (Ar¹-2) |
| (L-323) | " | " | " | (Ar¹-3) |
| (L-324) | " | " | " | (Ar¹-4) |
| (L-325) | " | " | (Ar¹-2) | (Ar¹-1) |
| (L-326) | " | " | " | (Ar¹-2) |
| (L-327) | " | " | " | (Ar¹-3) |
| (L-328) | " | " | " | (Ar¹-4) |
| (L-329) | " | " | (Ar¹-3) | (Ar¹-1) |
| (L-330) | " | " | " | (Ar¹-2) |
| (L-331) | " | " | " | (Ar¹-3) |
| (L-332) | " | " | " | (Ar¹-4) |
| (L-333) | " | " | (Ar¹-4) | (Ar¹-1) |
| (L-334) | " | " | " | (Ar¹-2) |
| (L-335) | " | " | " | (Ar¹-3) |
| (L-336) | " | " | " | (Ar¹-4) |
| (L-337) | " | (Ar¹-3) | (Ar¹-1) | (Ar¹-1) |
| (L-338) | " | " | " | (Ar¹-2) |
| (L-339) | " | " | " | (Ar¹-3) |
| (L-340) | " | " | " | (Ar¹-4) |
| (L-341) | " | " | (Ar¹-2) | (Ar¹-1) |
| (L-342) | " | " | " | (Ar¹-2) |
| (L-343) | " | " | " | (Ar¹-3) |
| (L-344) | " | " | " | (Ar¹-4) |
| (L-345) | " | " | (Ar¹-3) | (Ar¹-1) |
| (L-346) | " | " | " | (Ar¹-2) |
| (L-347) | " | " | " | (Ar¹-3) |
| (L-348) | " | " | " | (Ar¹-4) |
| (L-349) | " | " | (Ar¹-4) | (Ar¹-1) |
| (L-350) | " | " | " | (Ar¹-2) |
| (L-351) | " | " | " | (Ar¹-3) |
| (L-352) | " | " | " | (Ar¹-4) |
| (L-353) | " | (Ar¹-4) | (Ar¹-1) | (Ar¹-1) |
| (L-354) | " | " | " | (Ar¹-2) |
| (L-355) | " | " | " | (Ar¹-3) |
| (L-356) | " | " | " | (Ar¹-4) |
| (L-357) | " | " | (Ar¹-2) | (Ar¹-1) |
| (L-358) | " | " | " | (Ar¹-2) |

-continued

| | n | Ar¹ | Ar¹ | Ar¹ |
|---|---|---|---|---|
| (L-359) | " | | " | (Ar¹-3) |
| (L-360) | " | | " | (Ar¹-4) |
| (L-361) | " | | (Ar¹-3) | (Ar¹-1) |
| (L-362) | " | | " | (Ar¹-2) |
| (L-363) | " | | " | (Ar¹-3) |
| (L-364) | " | | " | (Ar¹-4) |
| (L-365) | " | | (Ar¹-4) | (Ar¹-1) |
| (L-366) | " | | " | (Ar¹-2) |
| (L-367) | " | | " | (Ar¹-3) |
| (L-368) | " | | " | (Ar¹-4) |

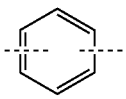

formula (Ar¹-1)

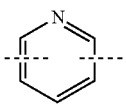

formula (Ar¹-2)

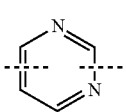

formula (Ar¹-3)

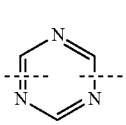

formula (Ar¹-4)

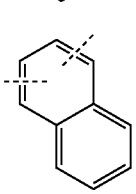

formula (Ar¹-5)

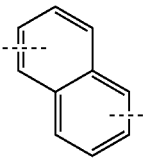

formula (Ar¹-6)

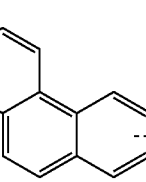

formula (Ar¹-7)

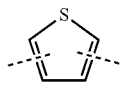

formula (Ar¹-8)

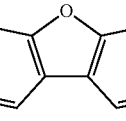

formula (Ar¹-9)

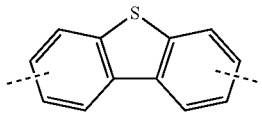

formula (Ar¹-10)

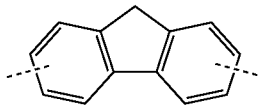

formula (Ar¹-11)

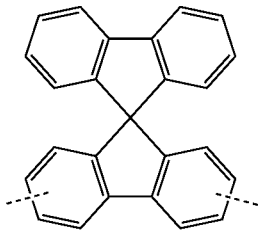

formula (Ar¹-12)

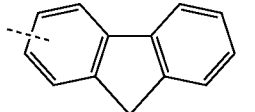

formula (Ar¹-13)

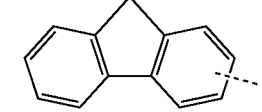

formula (Ar¹-14)

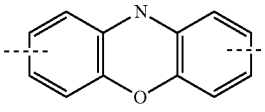

formula (Ar¹-15)

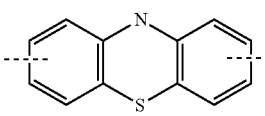

formula (Ar¹-16)

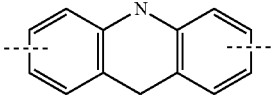

formula (Ar¹-17)

where the groups of the formulae (Ar¹-1) to (Ar¹-14) may optionally be substituted by one or more radicals R².

Preferably, both groups Ar² are selected from identical or different groups Ar²*.

Ar² is preferably selected on each occurrence, identically or differently, from an aromatic or heteroaromatic ring system having 5 to 20 aromatic ring atoms, which may be substituted by one or more radicals R². Ar² is particularly preferably selected on each occurrence, identically or differently, from phenyl, biphenyl, terphenyl, quaterphenyl, fluorenyl, spirobifluorenyl, indenofluorenyl, naphthyl, anthracenyl, phenanthrenyl, chrysenyl, benzanthracenyl, pyrenyl, triphenylenyl, fluoranthenyl, furanyl, benzofuranyl, dibenzofuranyl, thiophenyl, benzothiophenyl, dibenzothiophenyl, indolyl, carbazolyl, indolocarbazolyl, indenocarbazolyl, pyridyl, quinolinyl, acridyl, dihydroacridyl, pyrazolyl, imidazolyl, benzimidazolyl, pyridazyl, pyrimidyl, pyrazinyl and phenanthrolyl, each of which is optionally substituted by one or more radicals $R^2$.

$Ar^2$ is preferably selected on each occurrence, identically or differently, from groups of the following formulae $(Ar^2\text{-}1)$ to $(Ar^2\text{-}42)$

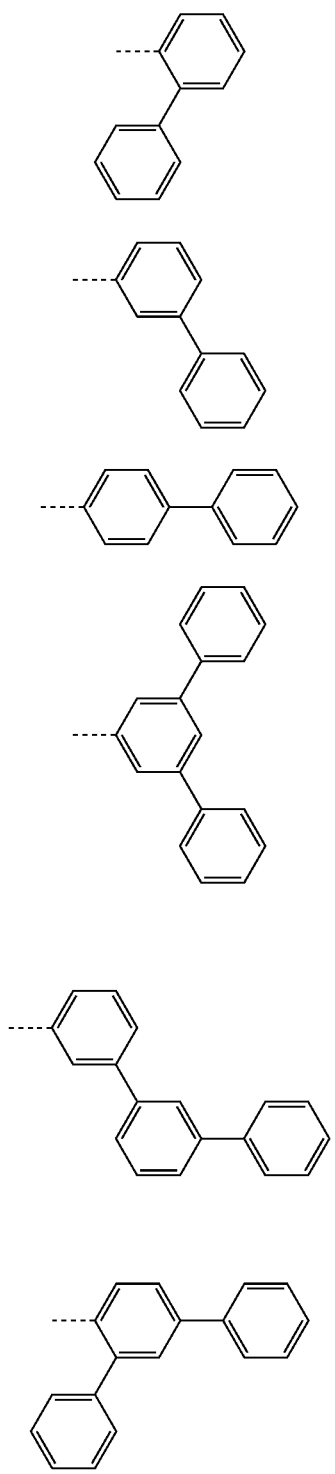

formula $(Ar^2\text{-}1)$ formula $(Ar^2\text{-}2)$ formula $(Ar^2\text{-}3)$ formula $(Ar^2\text{-}4)$ formula $(Ar^2\text{-}5)$ formula $(Ar^2\text{-}6)$

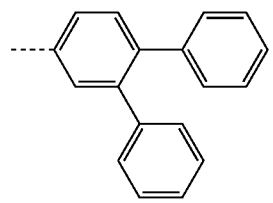

formula $(Ar^2\text{-}7)$

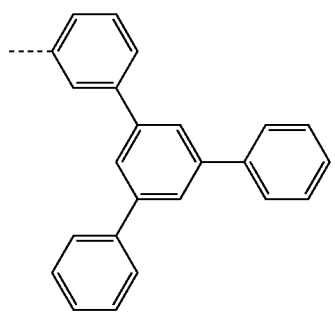

formula $(Ar^2\text{-}8)$

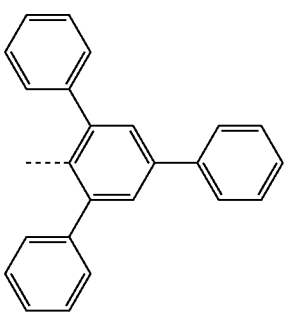

formula $(Ar^2\text{-}9)$

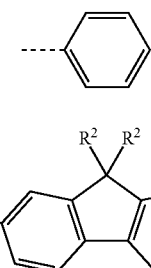

formula $(Ar^2\text{-}10)$

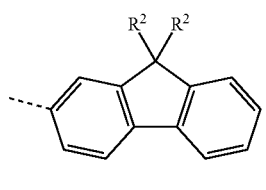

formula $(Ar^2\text{-}11)$

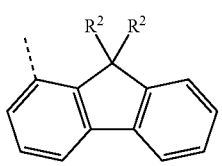

formula $(Ar^2\text{-}12)$

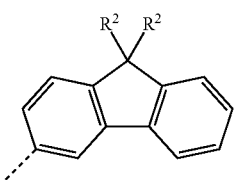

formula $(Ar^2\text{-}13)$

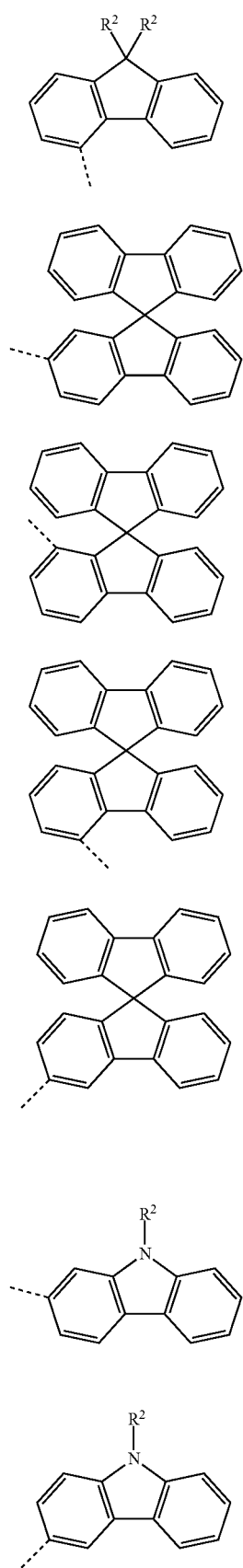
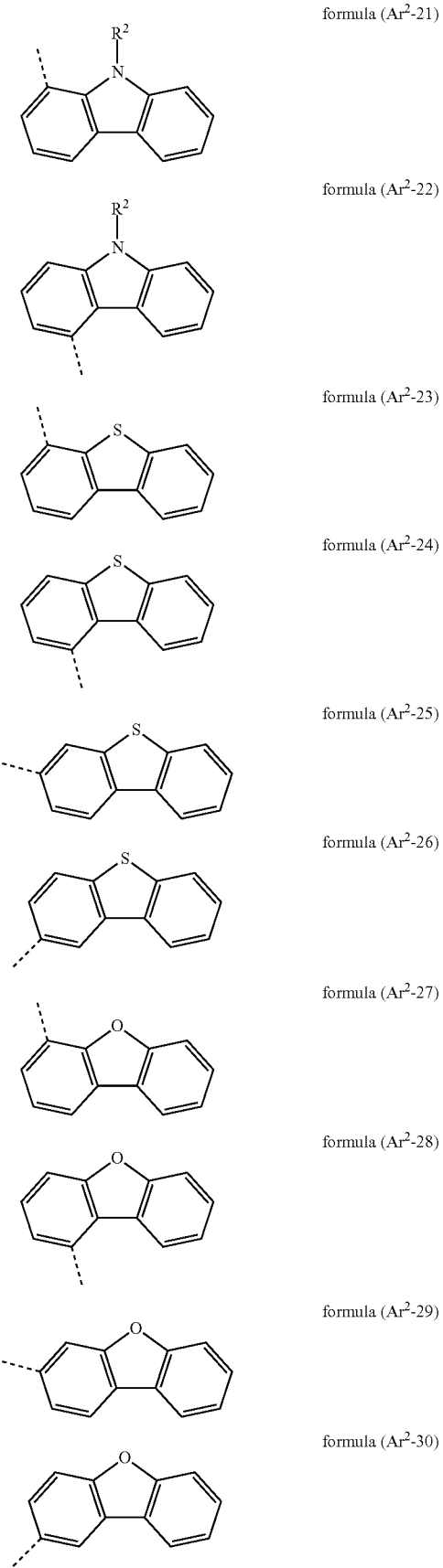

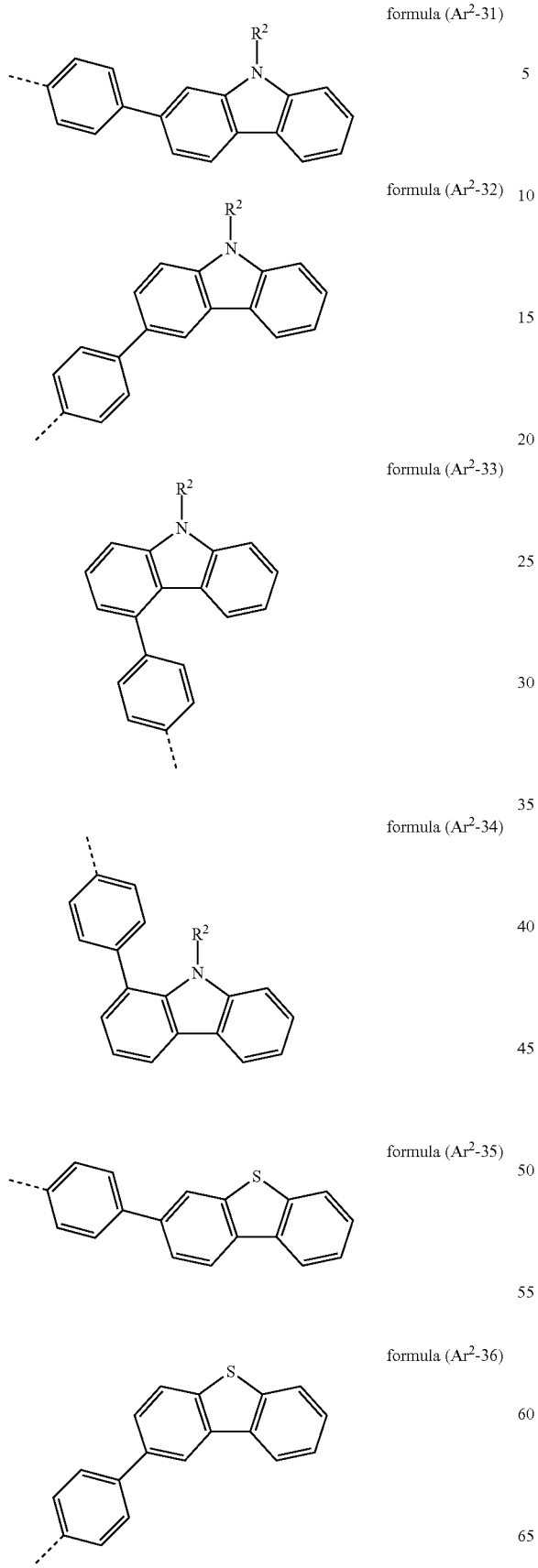
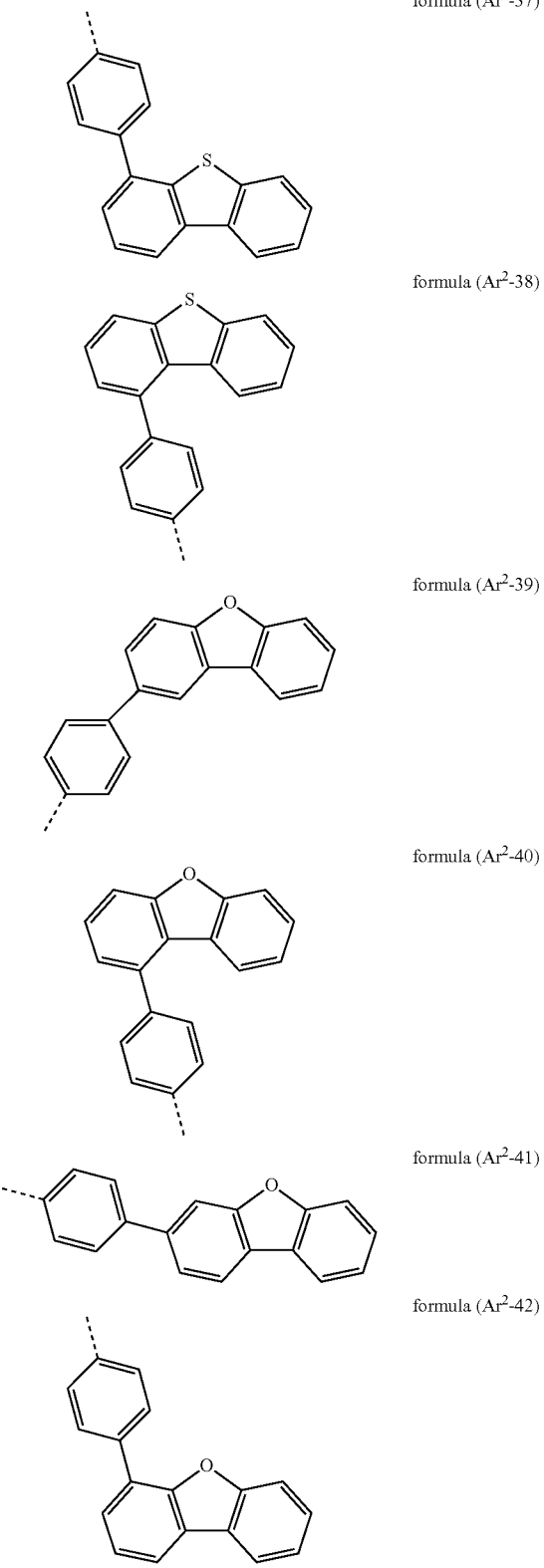
which may be substituted by one or more radicals R², and where one or more C atoms in the aromatic rings may be replaced by N. Preferably, no C atoms in the aromatic rings of the above-mentioned groups have been replaced by N.

Ar²* is preferably selected from groups of the formulae (Ar²-1) to (Ar²-9), (Ar²-11) to (Ar²-18) and (Ar²-31) to (Ar²-42).

R¹ is preferably selected on each occurrence, identically or differently, from CN, an alkyl group having 1 to 10 C atoms or an alkenyl group having 2 to 10 C atoms, where the above-mentioned groups may be substituted by one or more radicals R³, or an aromatic or heteroaromatic ring system having 5 to 30 aromatic ring atoms, which may be substituted by one or more radicals R³.

R² is preferably selected on each occurrence, identically or differently, from H, D, F, CN, Si(R³)₃, a straight-chain alkyl or alkoxy group having 1 to 10 C atoms or a branched or cyclic alkyl or alkoxy group having 3 to 10 C atoms, where the above-mentioned groups may each be substituted by one or more radicals R³ and where one or more CH₂ groups in the above-mentioned groups may be replaced by —C≡C—, —R³C=CR³—, Si(R³)₂, C=O, C=NR³, —NR³—, —O—, —S—, —C(=O)O— or —C(=O)NR³—, or an aromatic or heteroaromatic ring system having 5 to 20 aromatic ring atoms, which may in each case be substituted by one or more radicals R³, where two or more radicals R² may be linked to one another and may form a ring.

R² is particularly preferably selected on each occurrence, identically or differently, from H, D, F, CN, Si(R³)₃, a straight-chain alkyl group having 1 to 10 C atoms or a branched or cyclic alkyl group having 3 to 10 C atoms, each of which may be substituted by one or more radicals R³, or an aromatic or heteroaromatic ring system having 5 to 20 aromatic ring atoms, which may in each case be substituted by one or more radicals R³.

R³ is preferably selected on each occurrence, identically or differently, from H, D, F, CN, Si(R⁴)₃, a straight-chain alkyl or alkoxy group having 1 to 10 C atoms or a branched or cyclic alkyl or alkoxy group having 3 to 10 C atoms, where the above-mentioned groups may each be substituted by one or more radicals R⁴ and where one or more CH₂ groups in the above-mentioned groups may be replaced by —C≡C—, —R⁴C=CR⁴—, Si(R⁴)₂, C=O, C=NR⁴, —NR⁴—, —O—, —S—, —C(=O)O— or —C(=O)NR⁴—, or an aromatic or heteroaromatic ring system having 5 to 20 aromatic ring atoms, which may in each case be substituted by one or more radicals R⁴, where two or more radicals R³ may be linked to one another and may form a ring.

R³ is particularly preferably selected on each occurrence, identically or differently, from H, D, F, CN, Si(R⁴)₃, a straight-chain alkyl group having 1 to 10 C atoms or a branched or cyclic alkyl group having 3 to 10 C atoms, each of which may be substituted by one or more radicals R⁴, or an aromatic or heteroaromatic ring system having 5 to 20 aromatic ring atoms, which may in each case be substituted by one or more radicals R⁴.

For compounds of the formula (I), it is preferred for the preferred embodiments of the groups to occur in combination with one another. It is especially preferred for the preferred embodiments of the groups Ar¹ and the groups Ar² in formula (I) to occur in combination with one another.

The following compounds are examples of compounds of the formula (I).

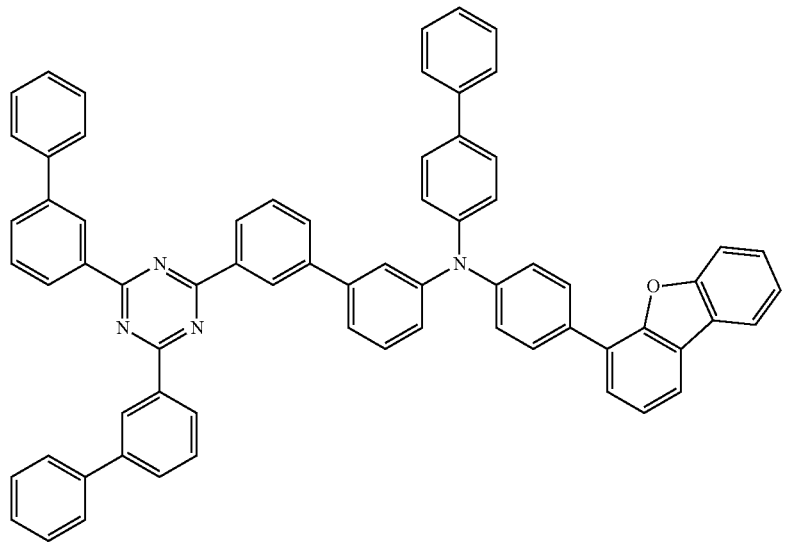

1

-continued
2
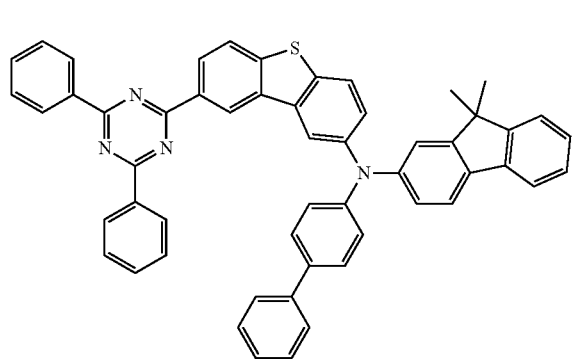
3
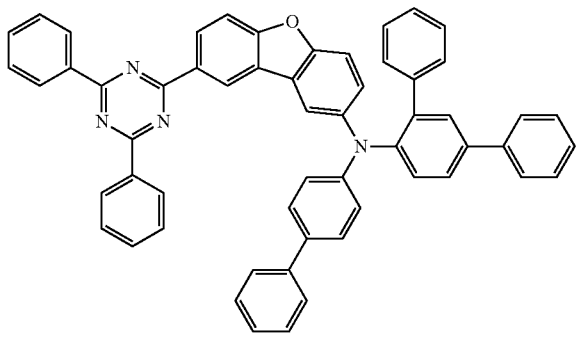
4
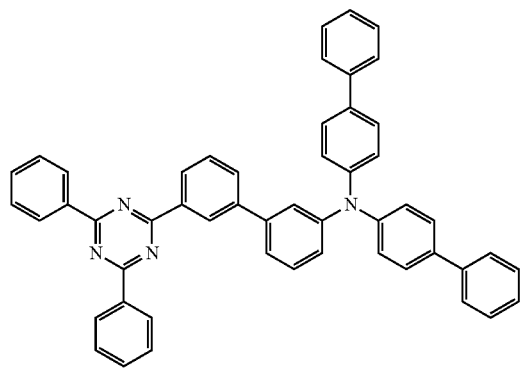
5
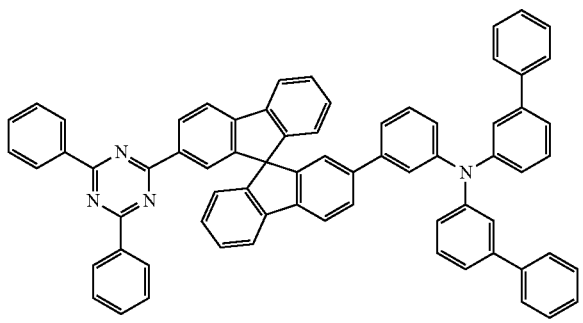
6
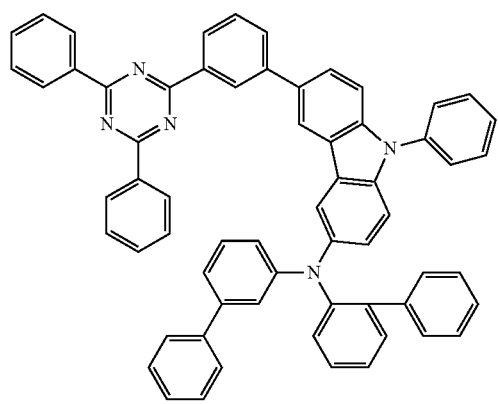
7
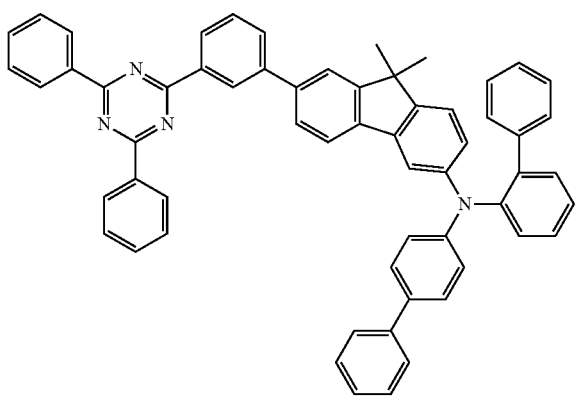

8
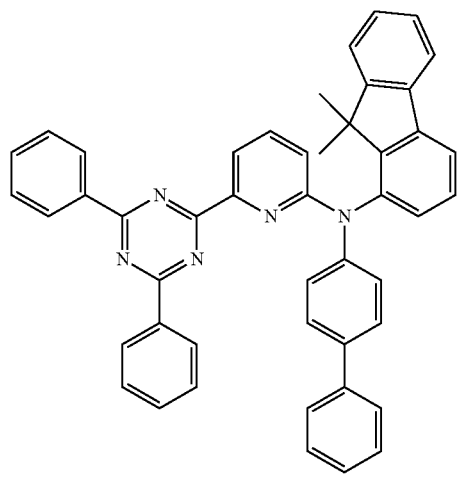
9
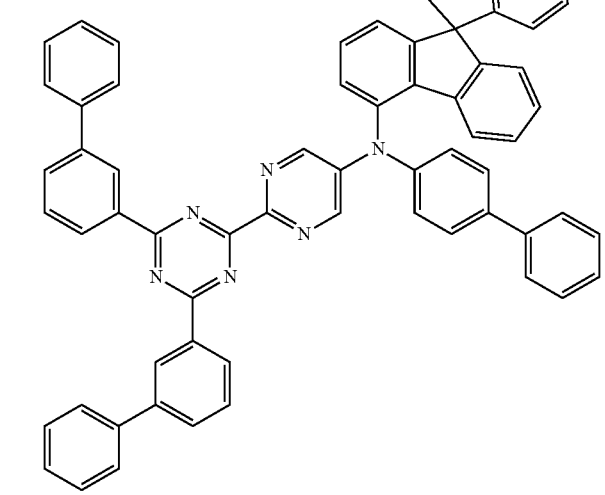
10
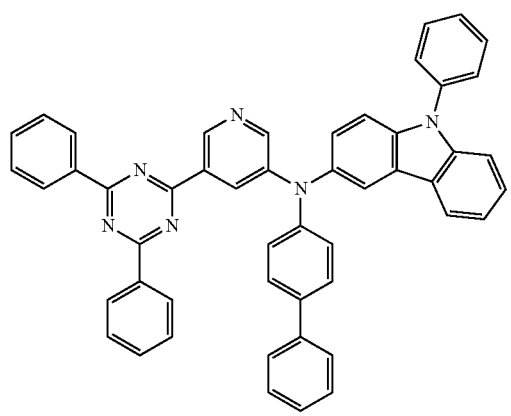
11
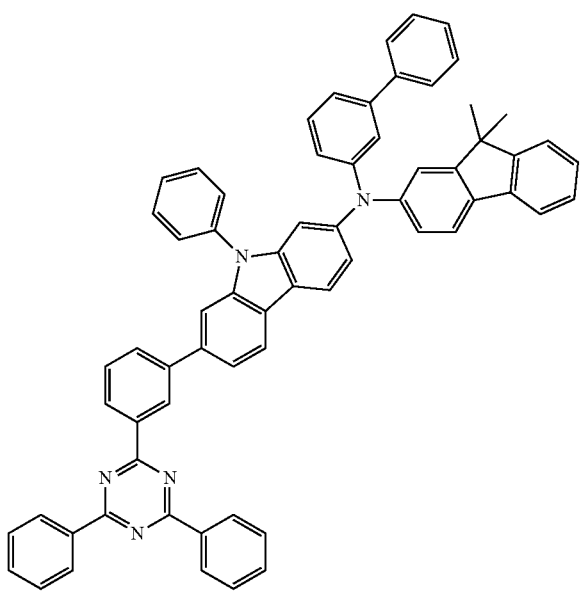
12
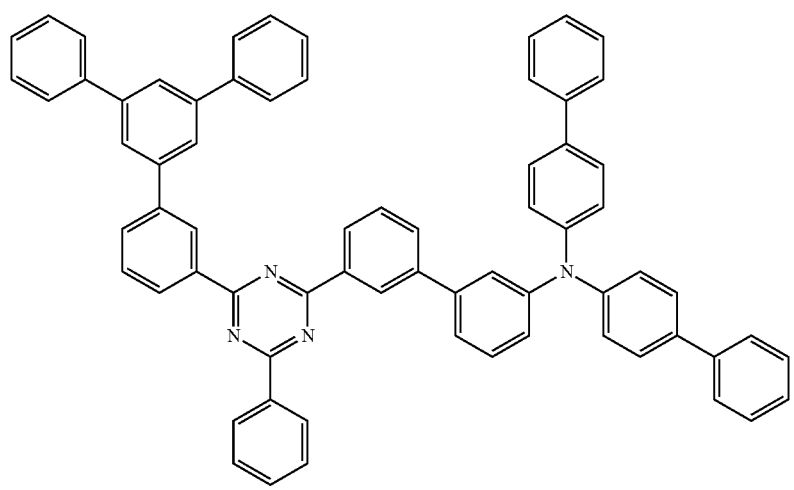

-continued
13
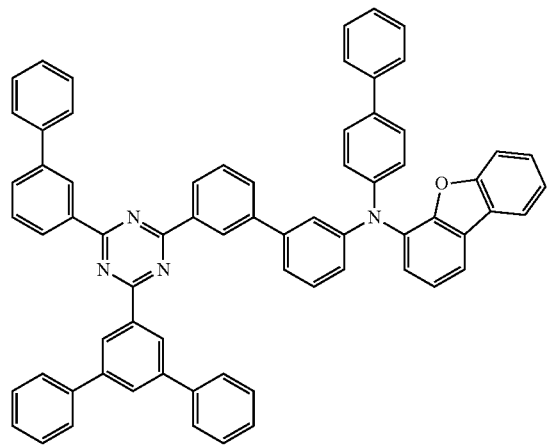
14
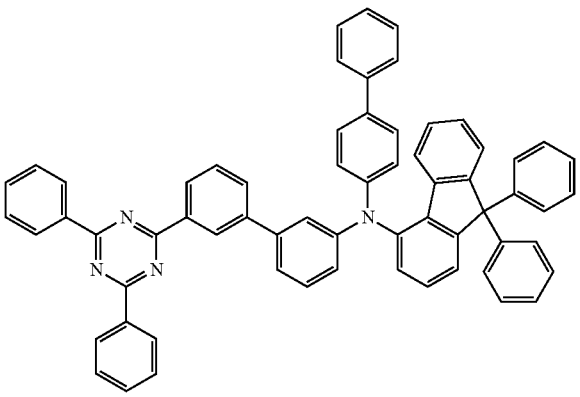
15
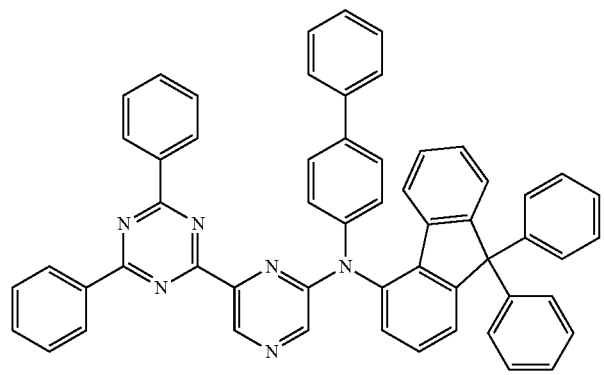
16
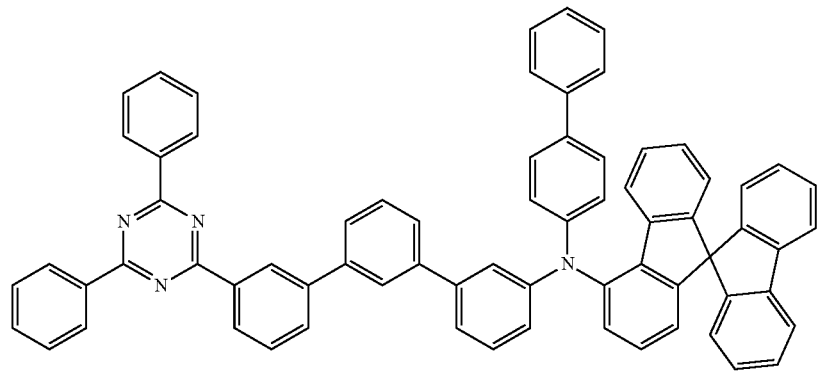
17
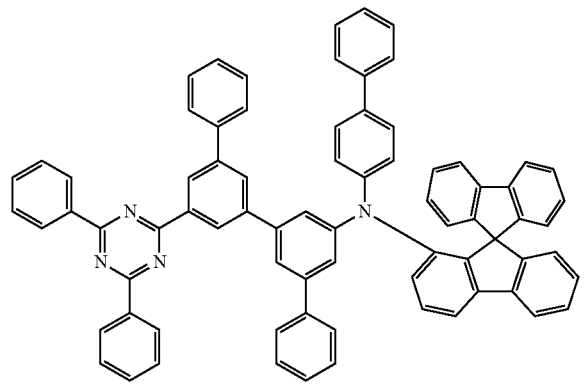
18
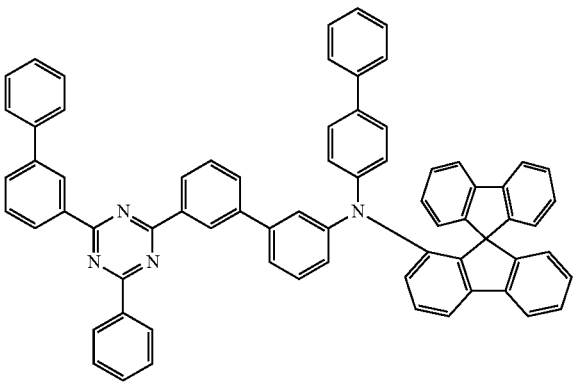

19
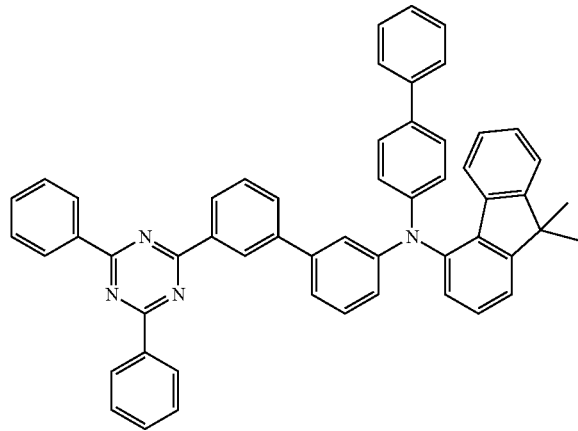
20
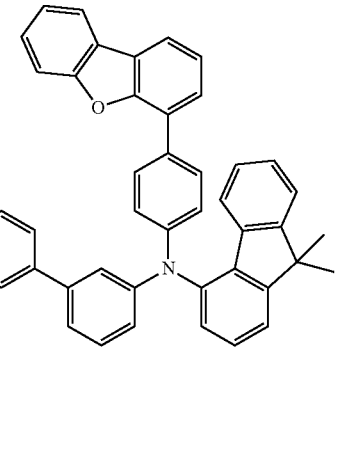
21
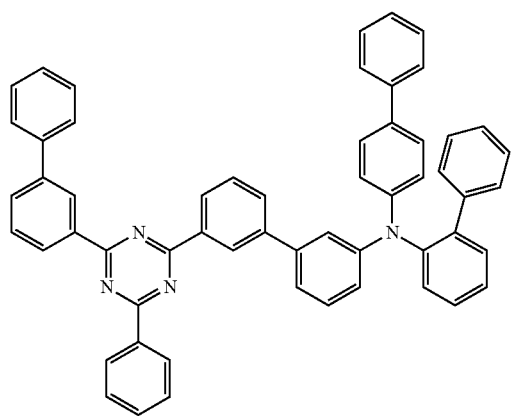
22
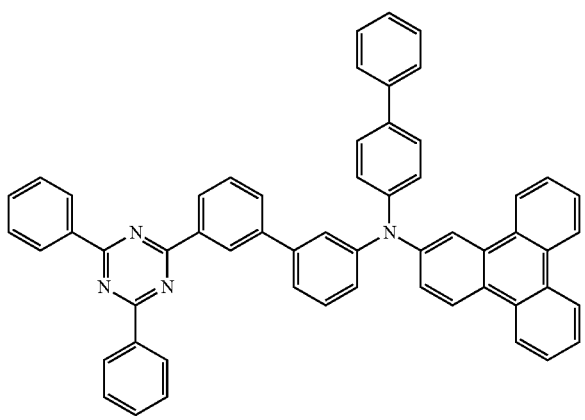
23
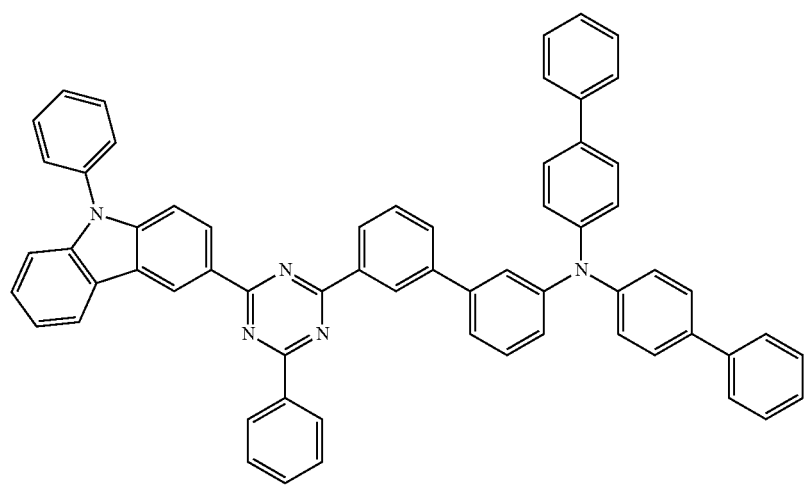

24
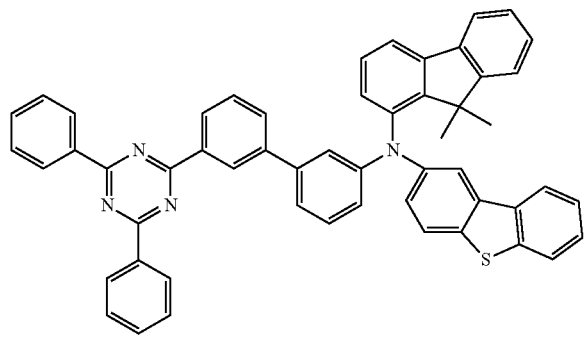
25
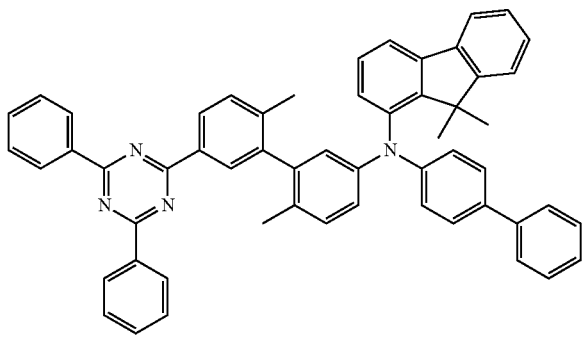
26
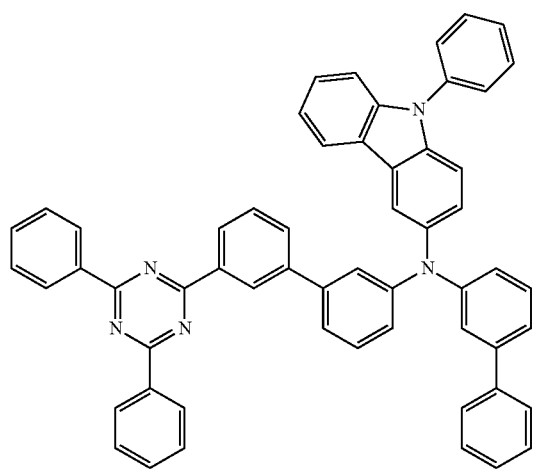
27
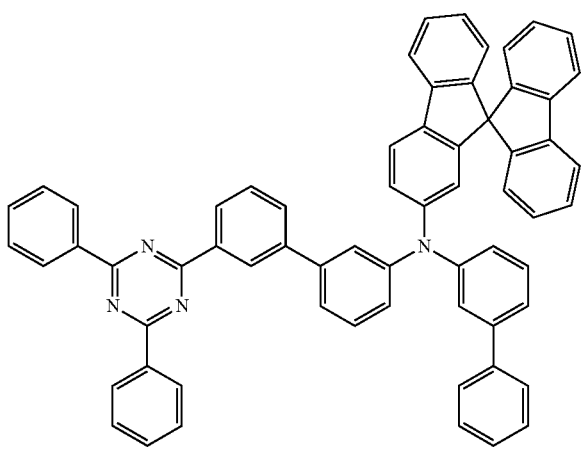
28
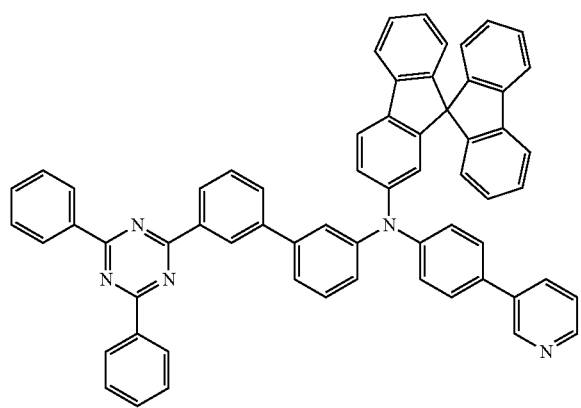
29
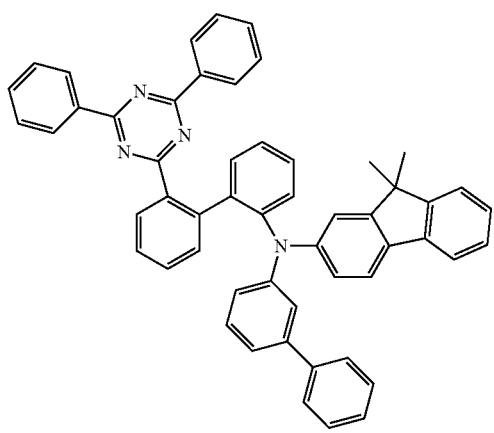

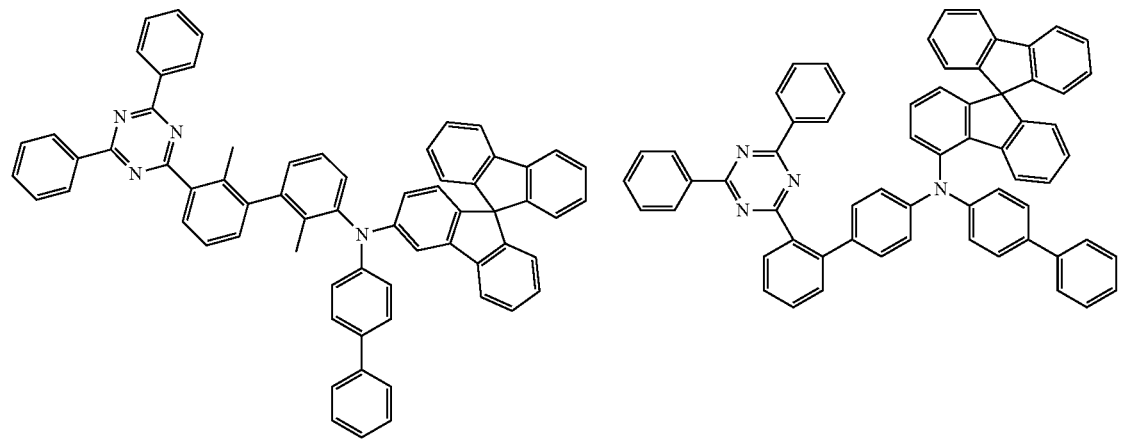
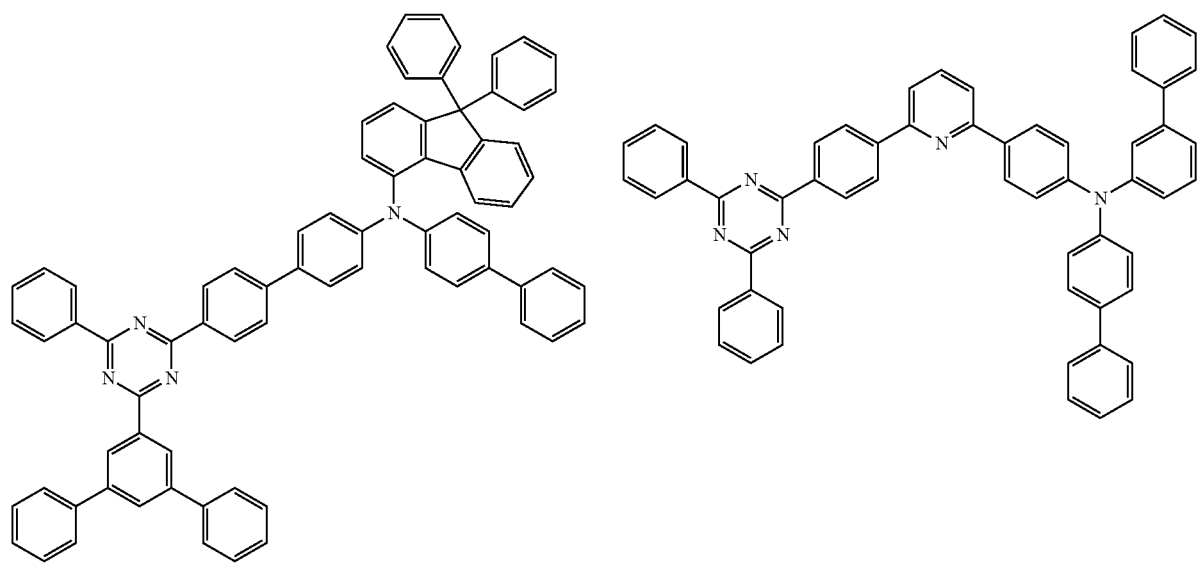
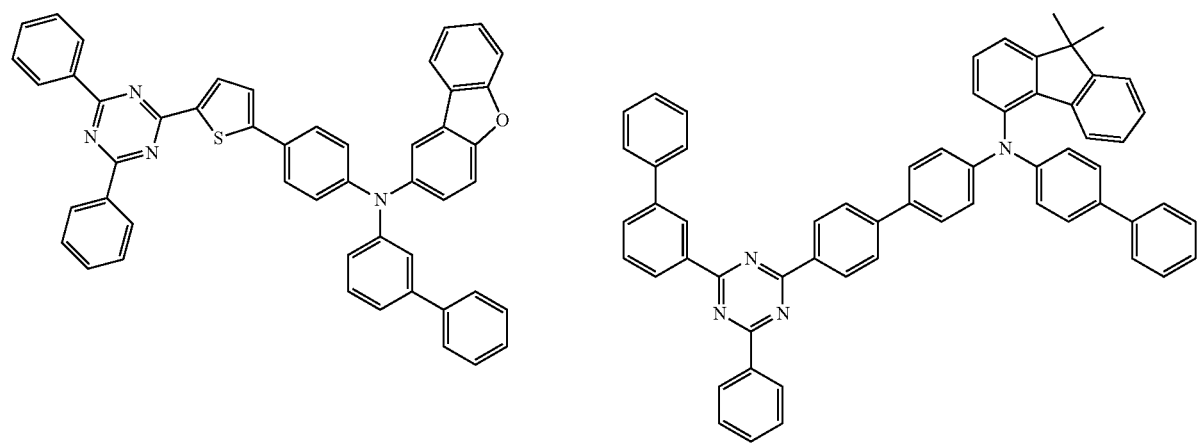

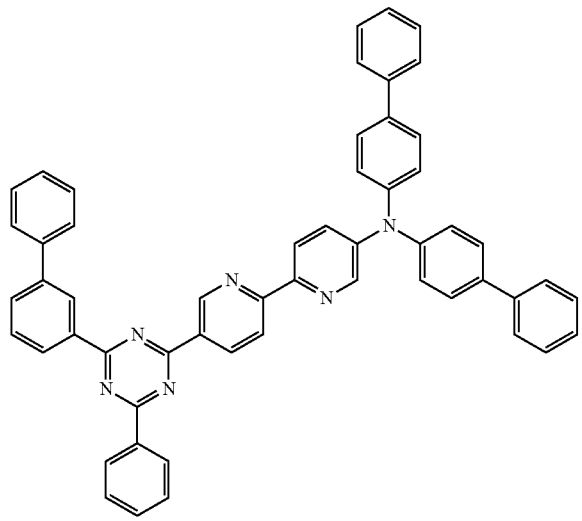
36
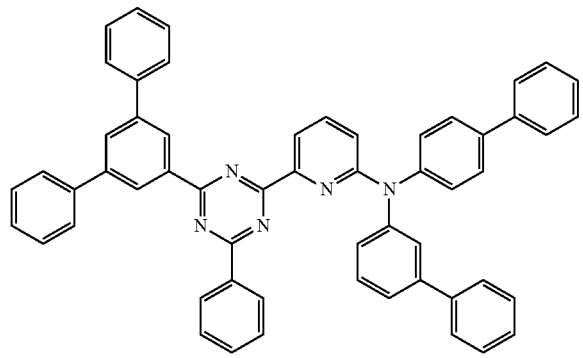
37
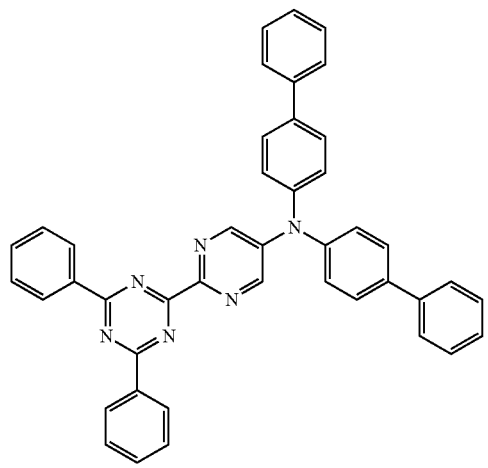
38
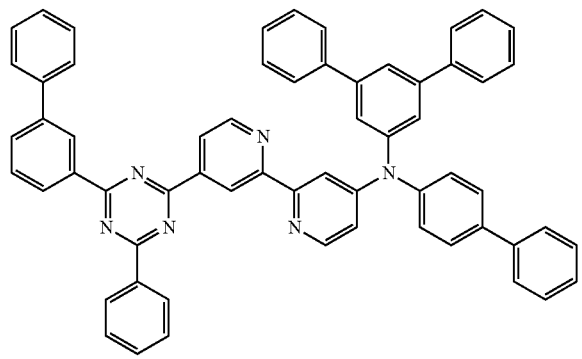
39
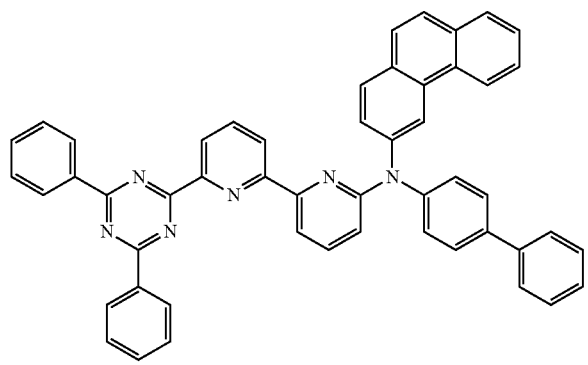
40
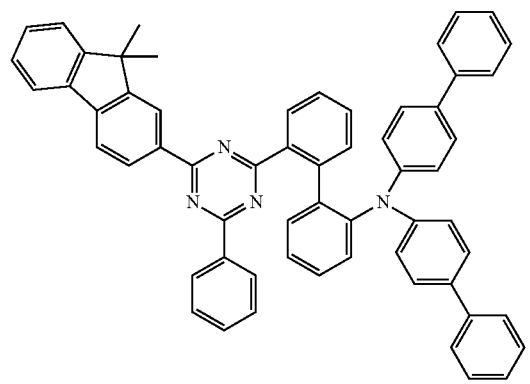
41

42
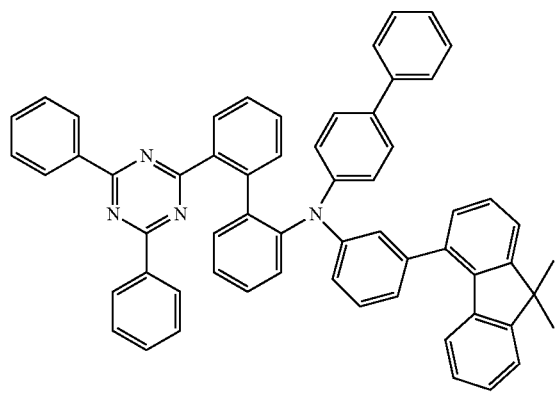
43
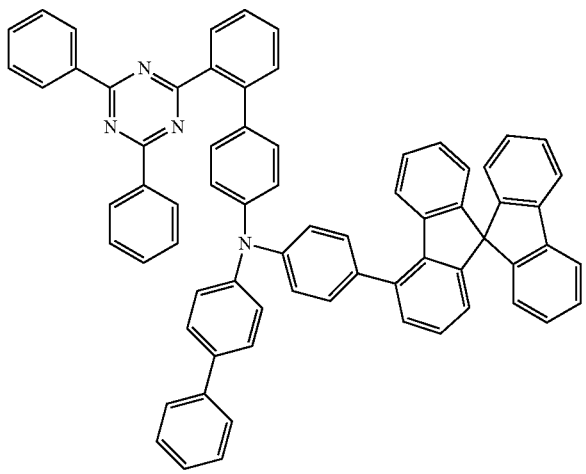
44
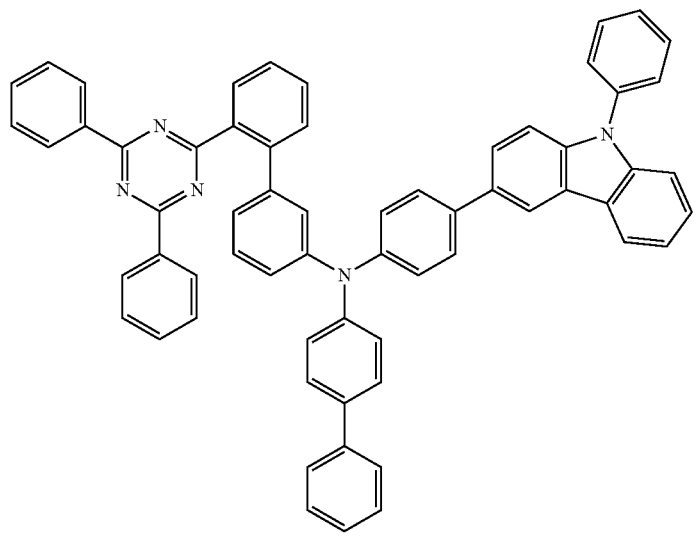
45
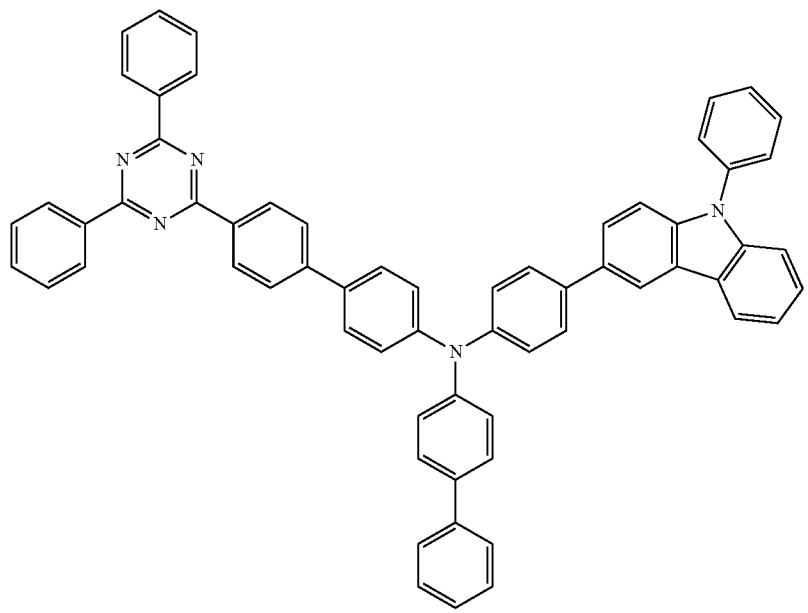

46
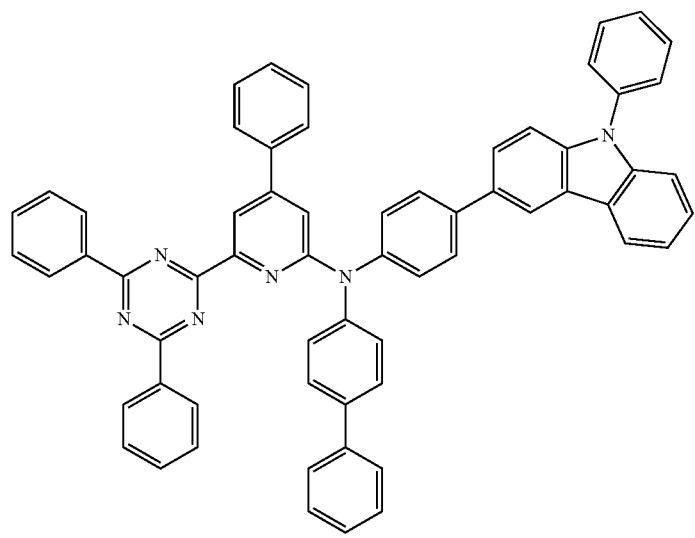
47
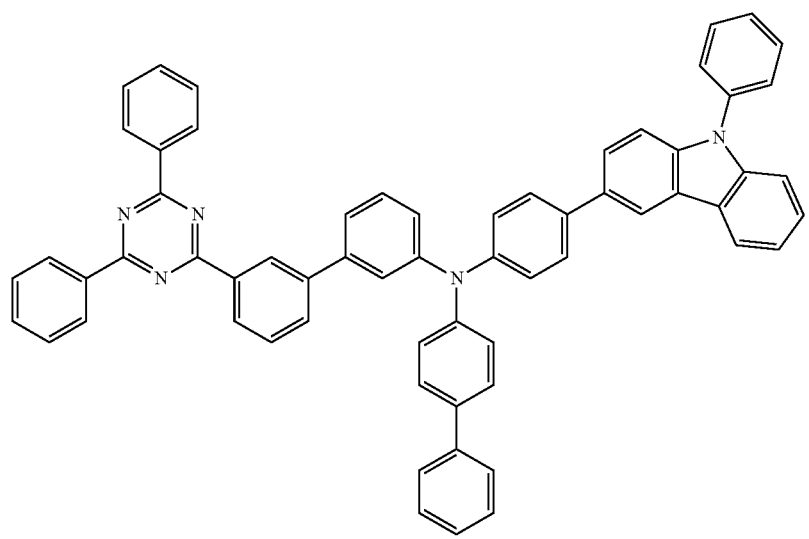
48
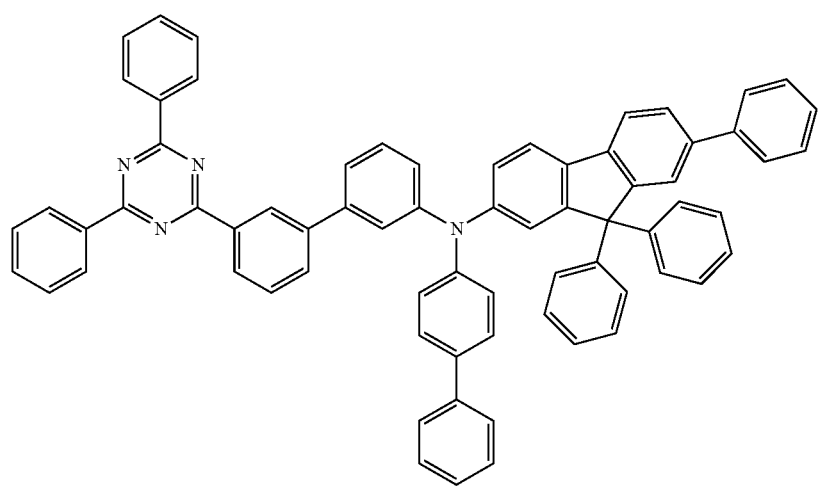

-continued
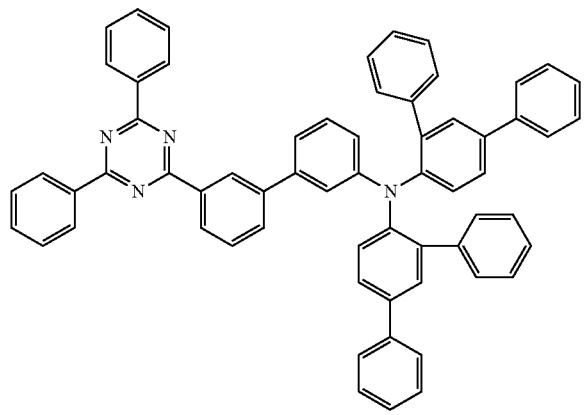
49
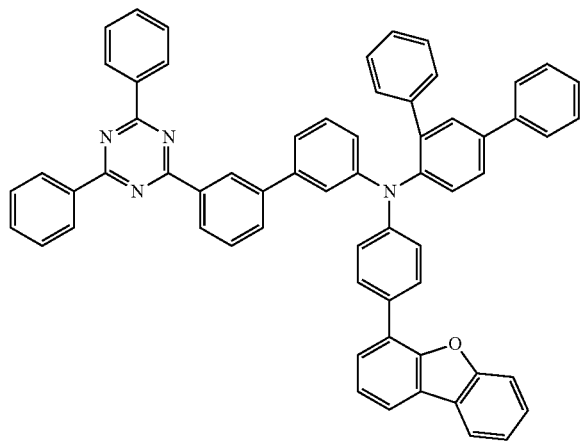
50
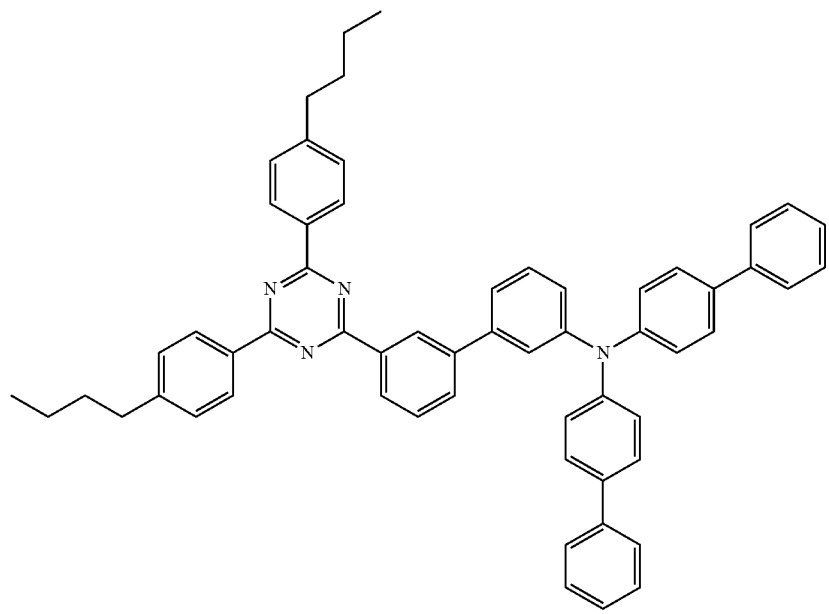
51
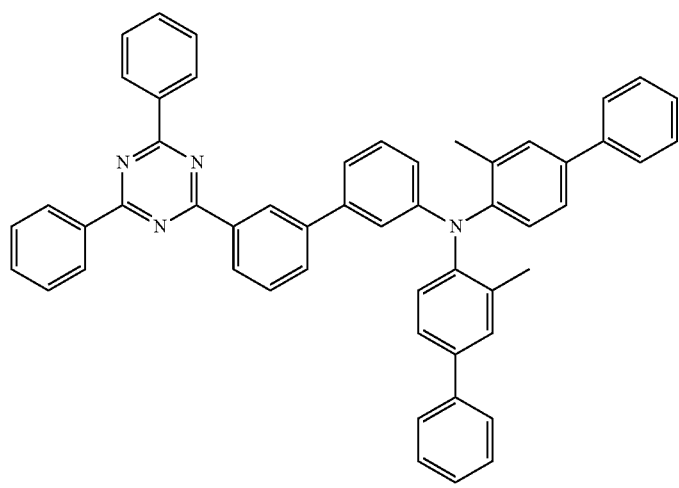
52

-continued
53
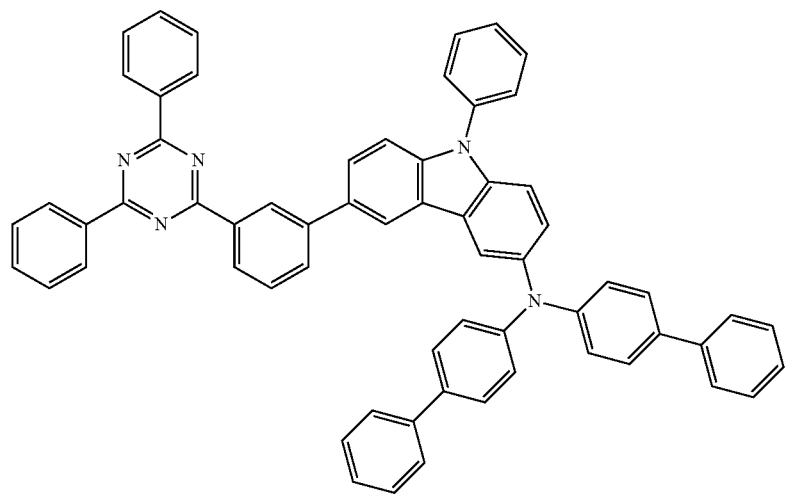
54
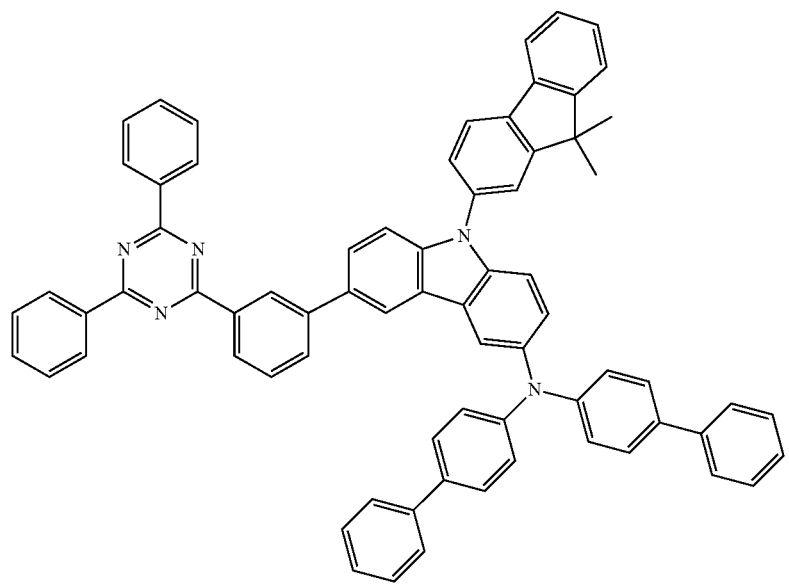
55
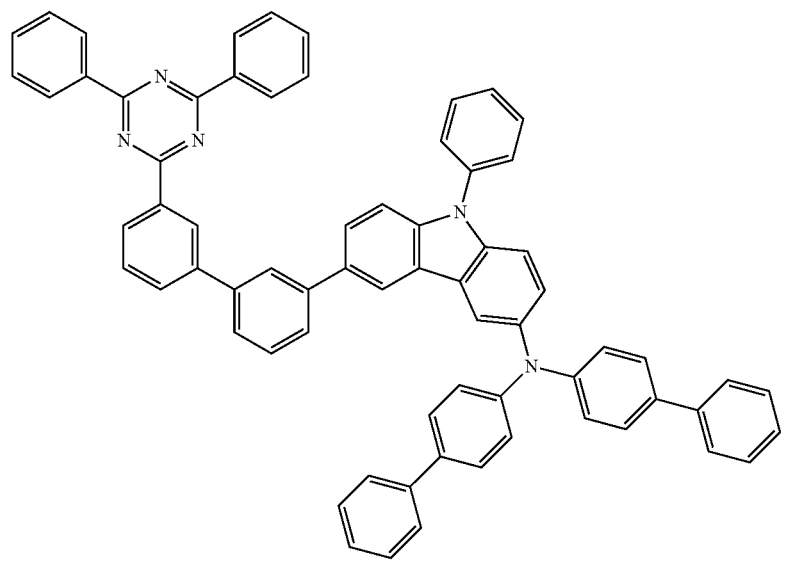

-continued
56
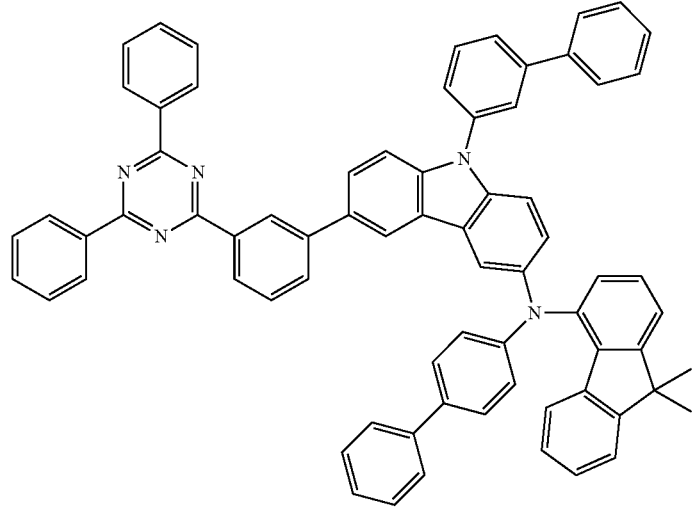
57
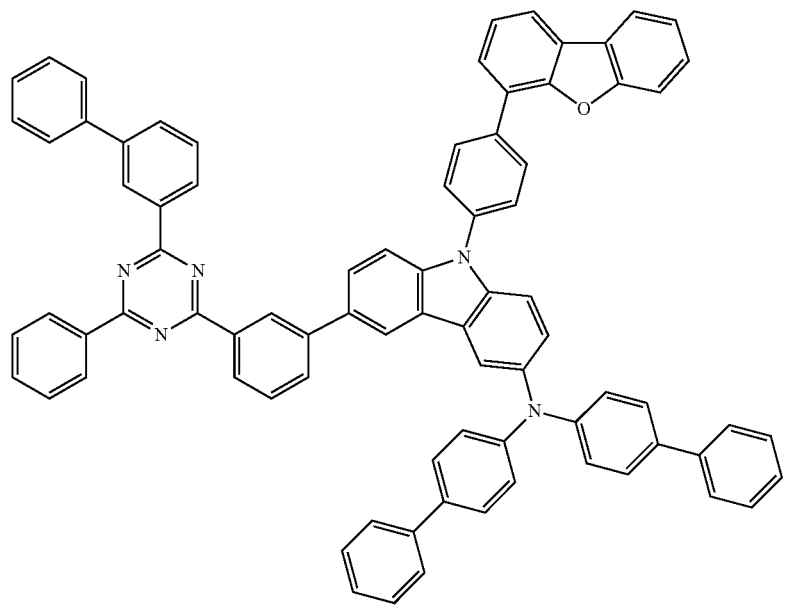
58
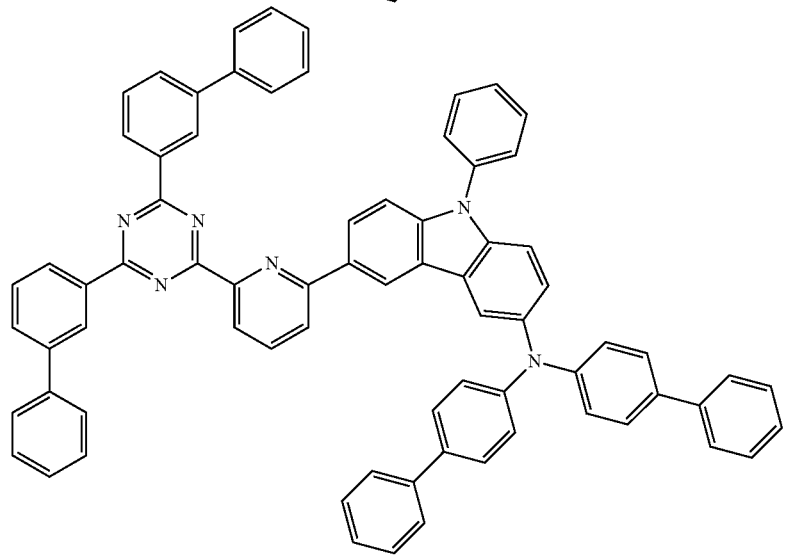

-continued
59
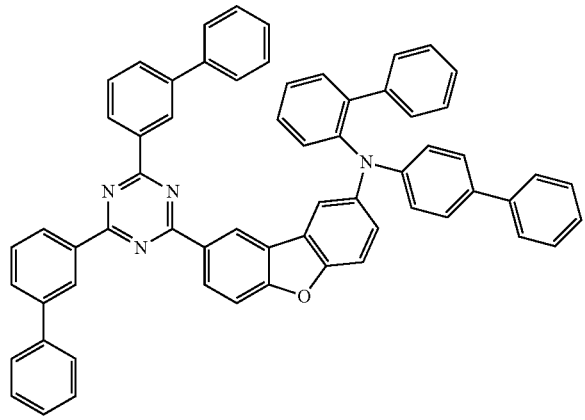
60
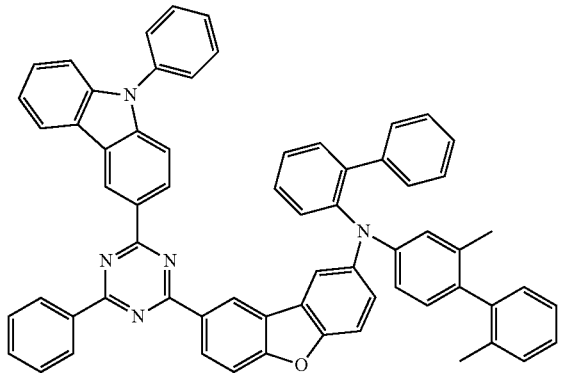
61
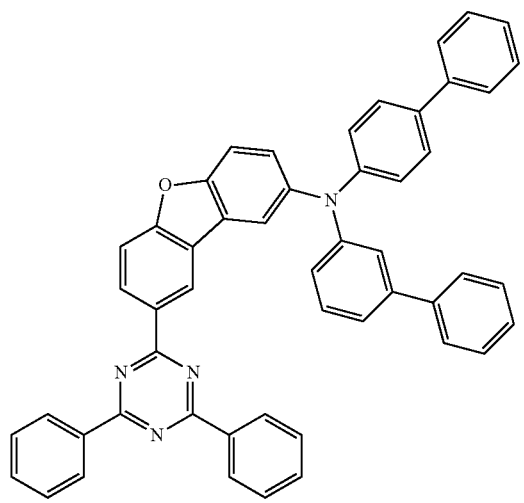
62
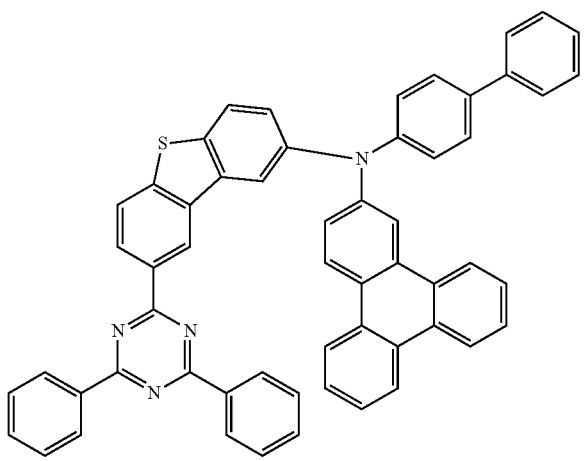
63
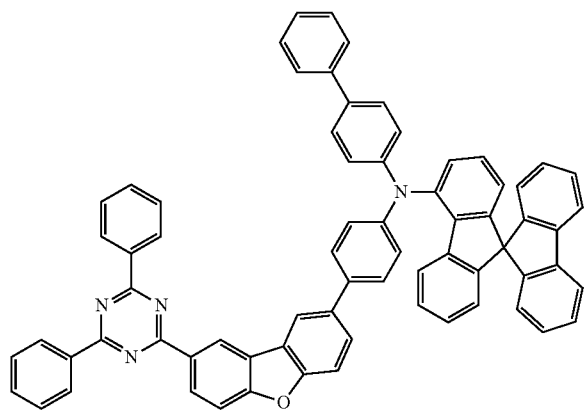
64
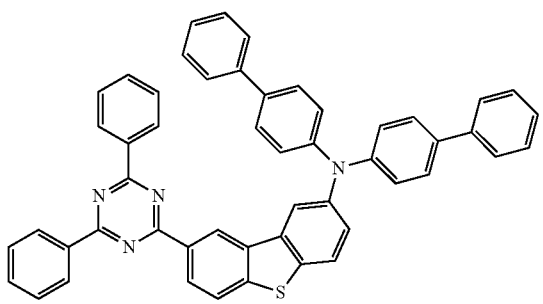

-continued
65
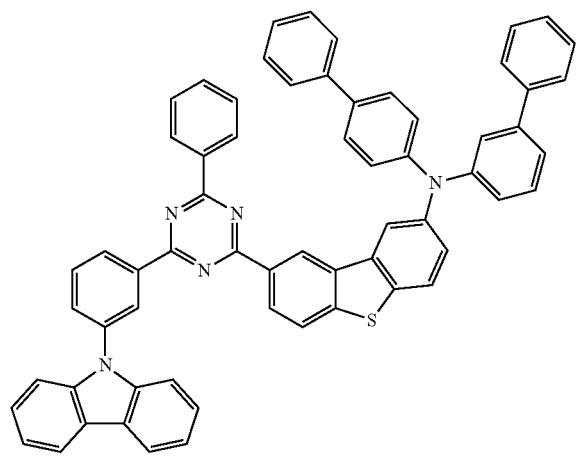
66
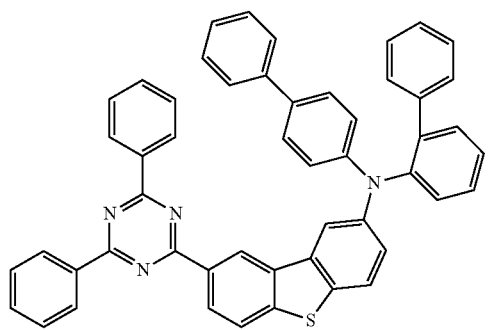
67
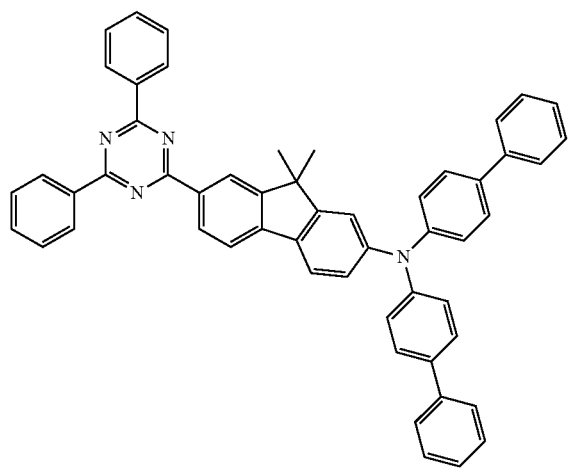
68
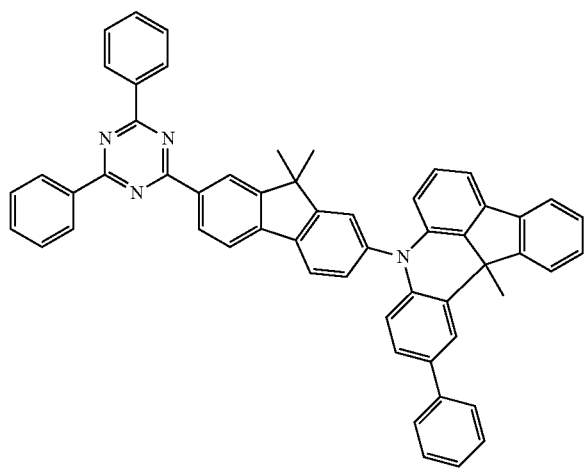
69
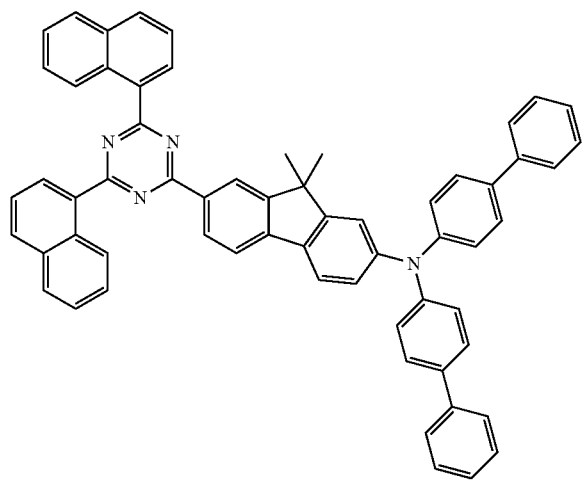
70
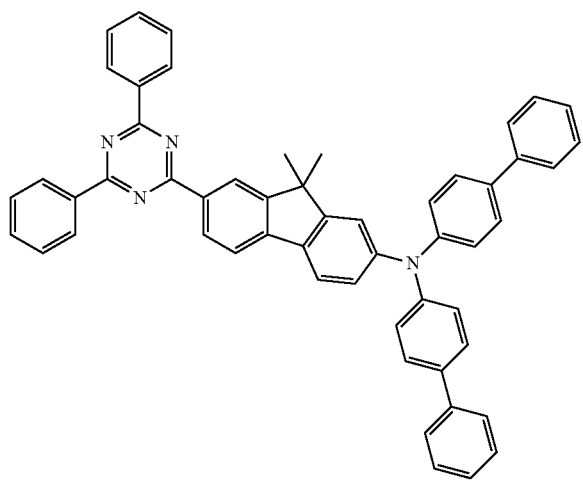

-continued
71
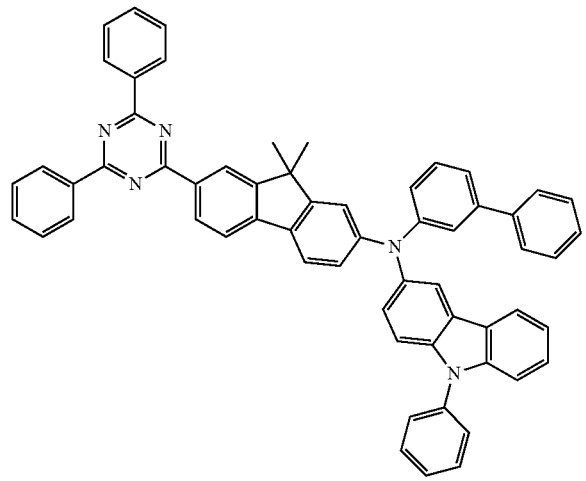
72
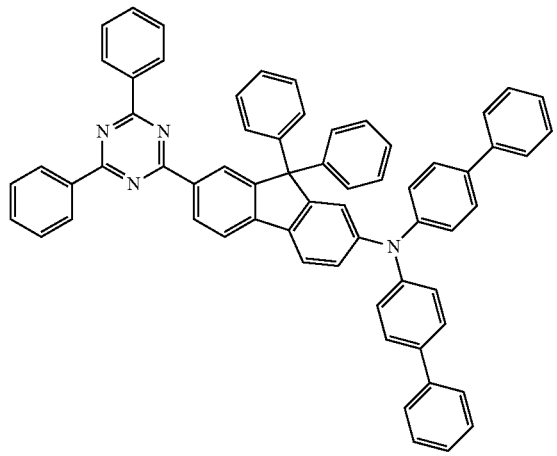
73
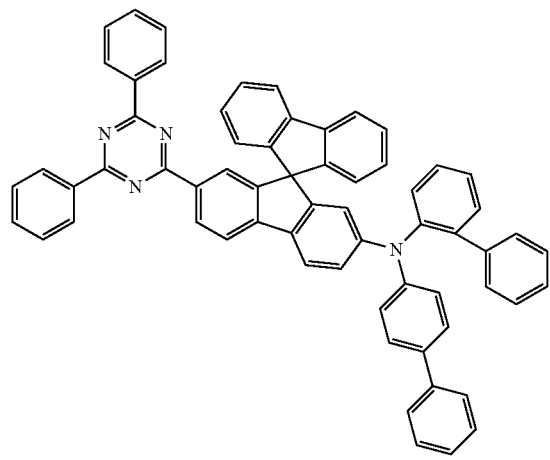
74
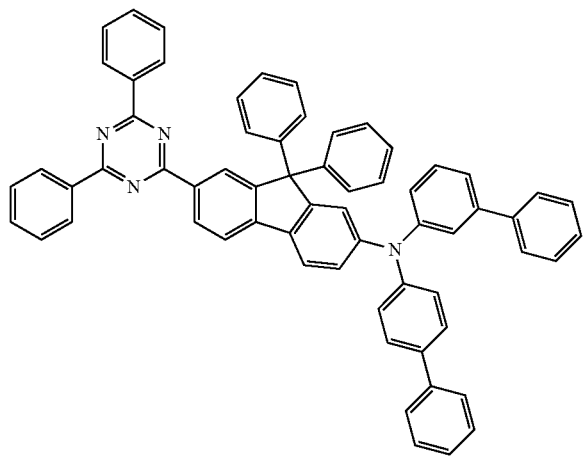
75
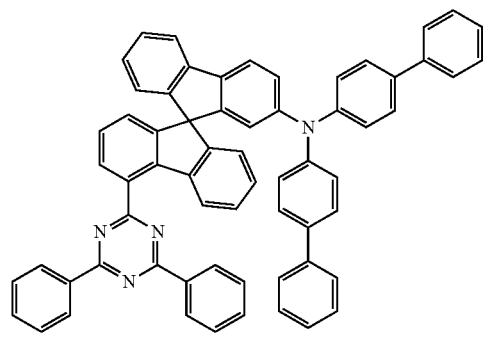
76
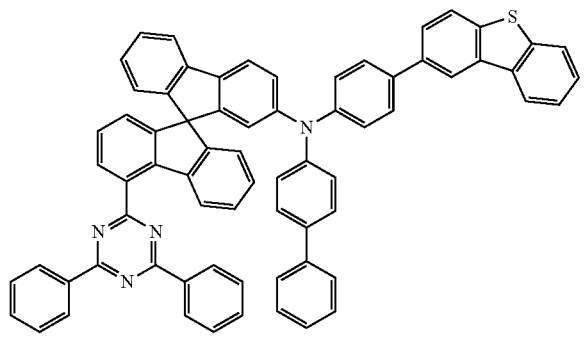

-continued
77
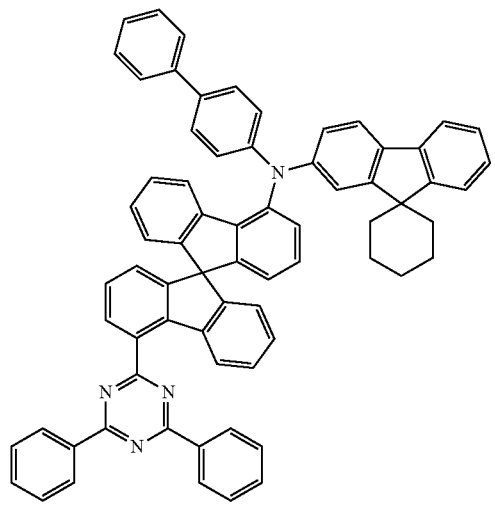
78
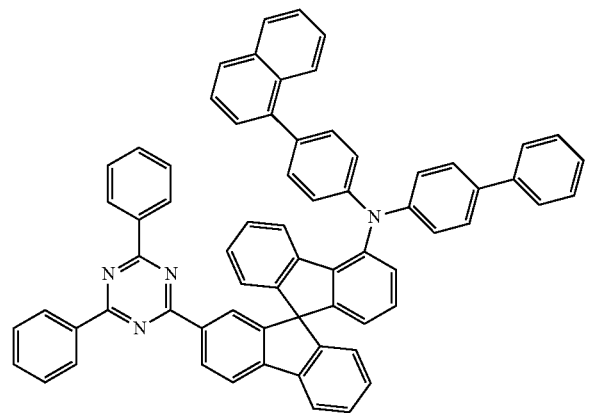
79
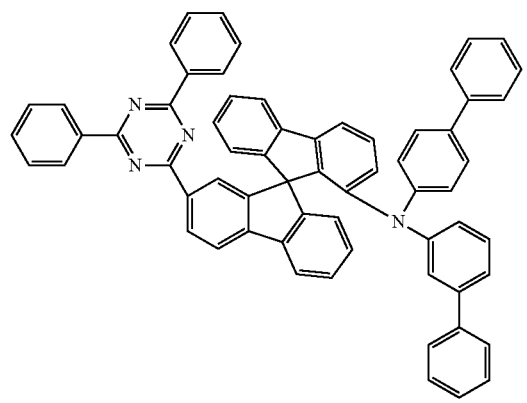
80
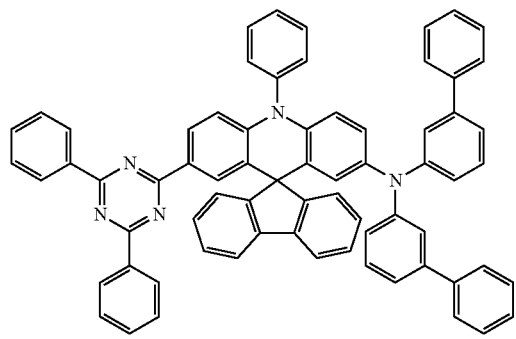
81
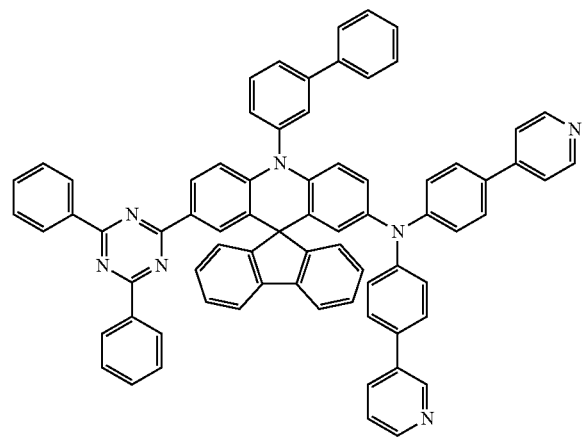
82

83
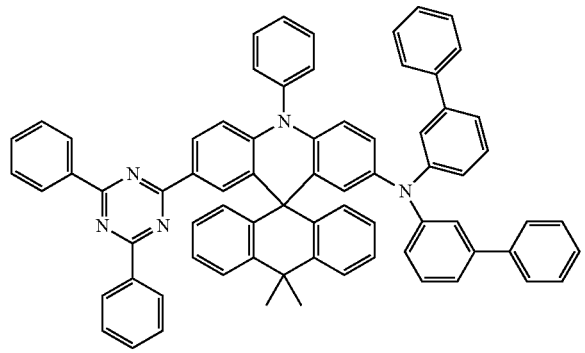
84
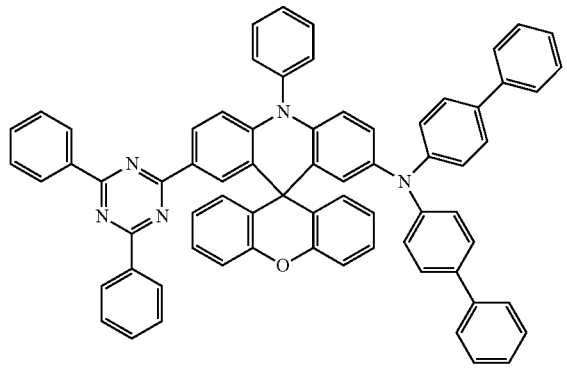
85
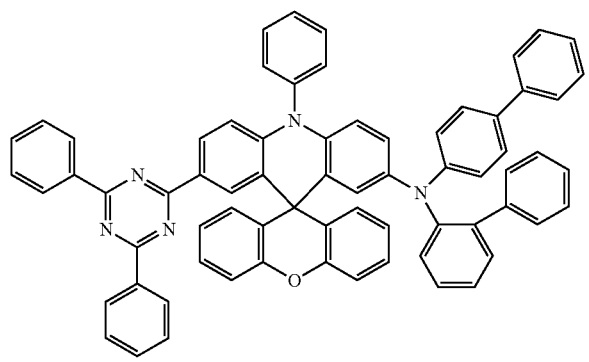
86
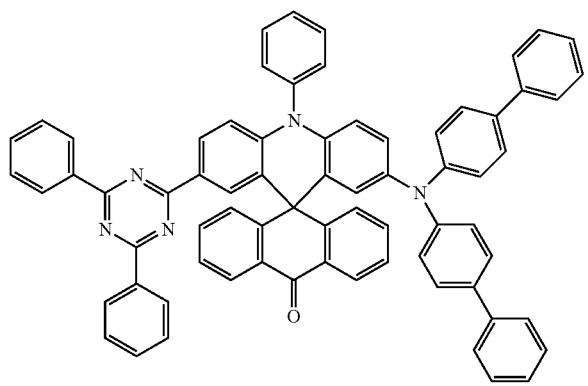
87
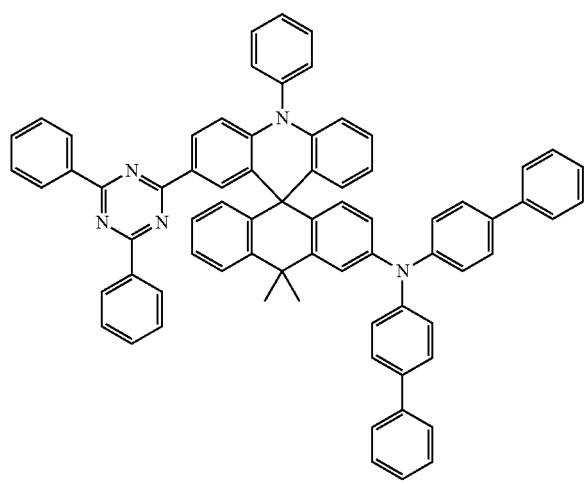
88
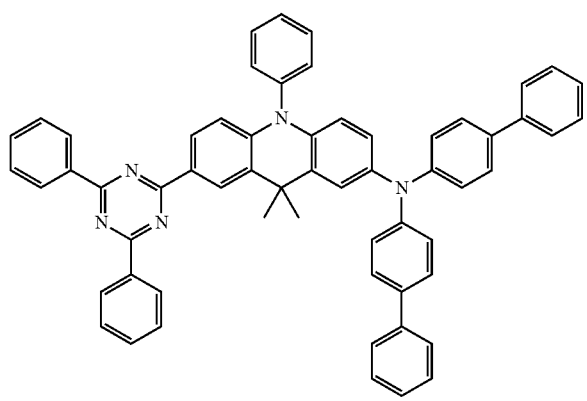

89
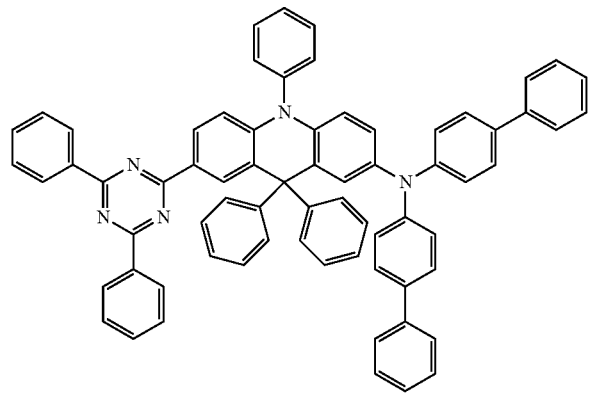
90
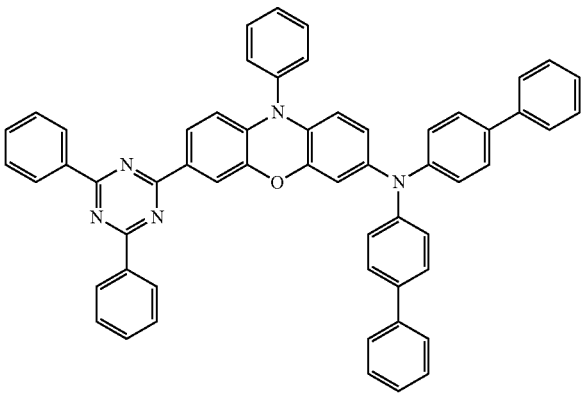
91
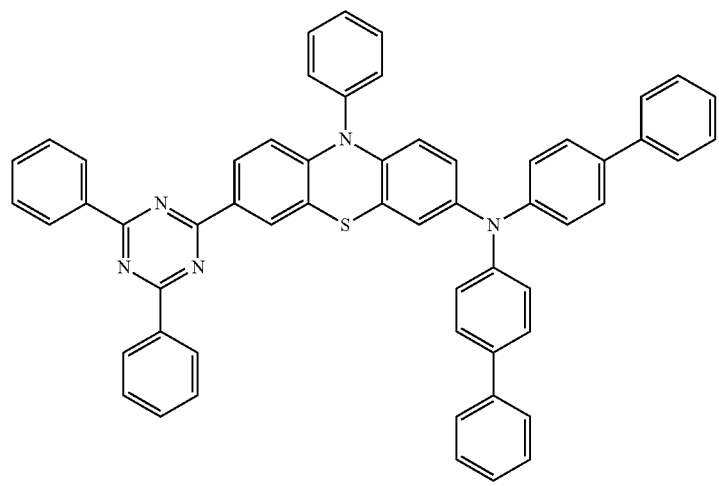
92
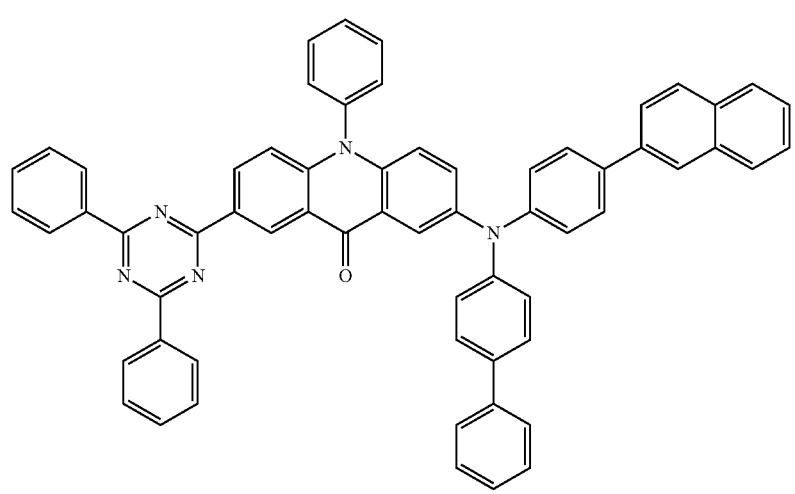

93
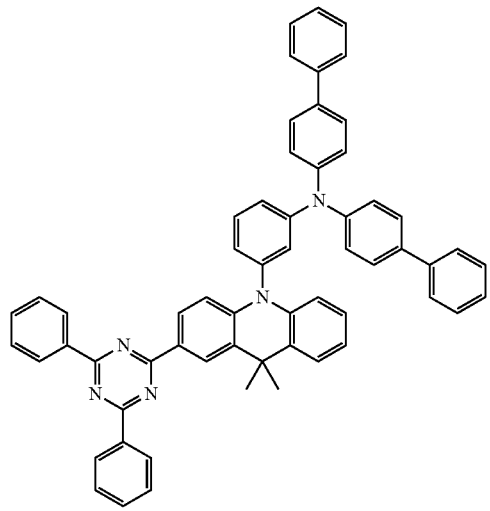
94
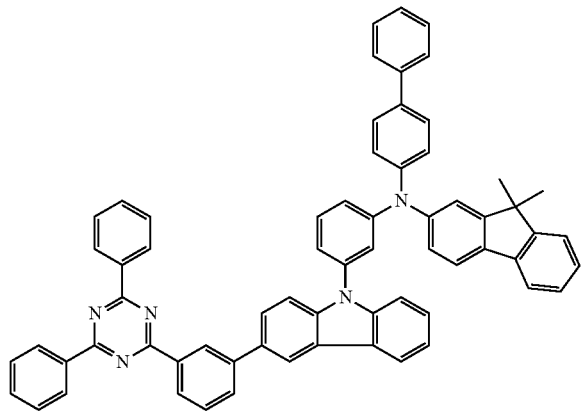
95
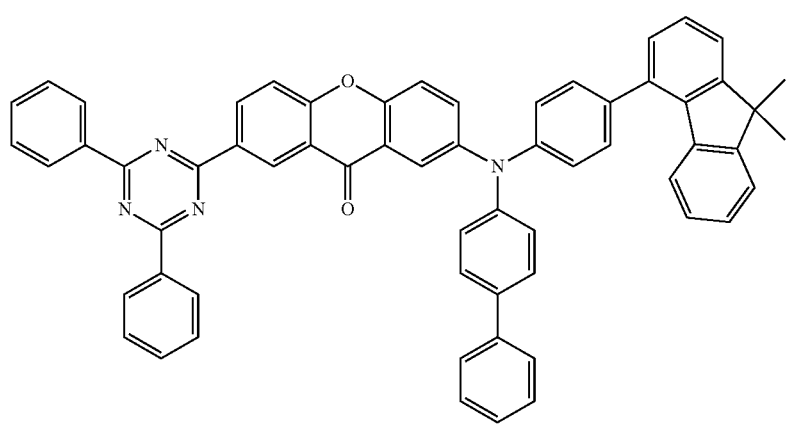
96
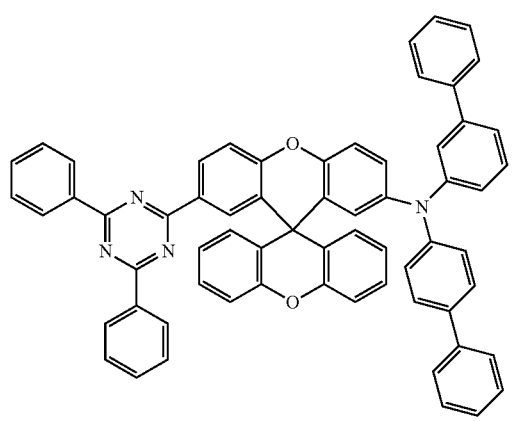
97
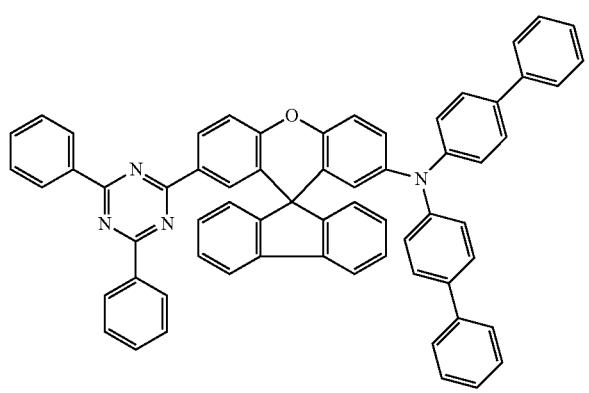

98
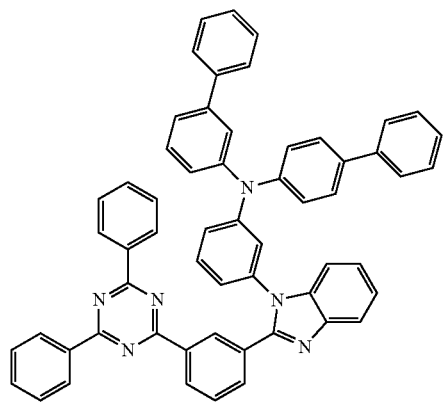
99
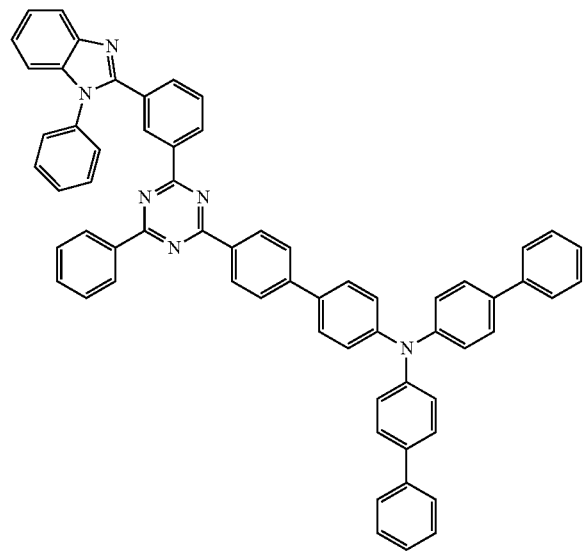
100
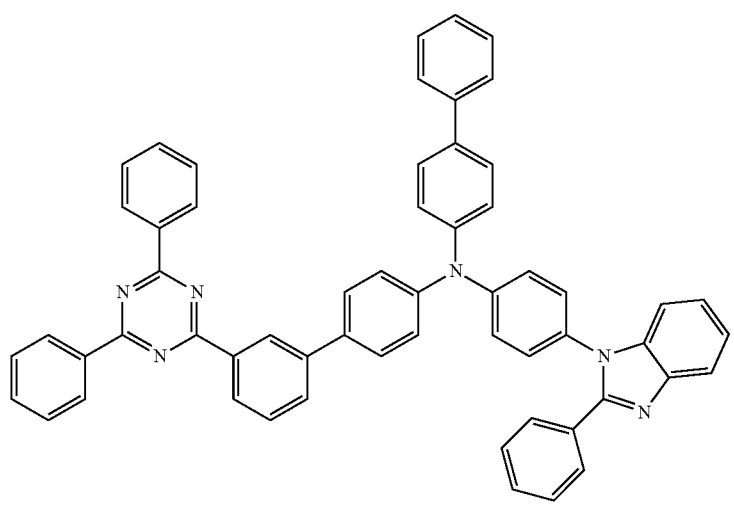
101
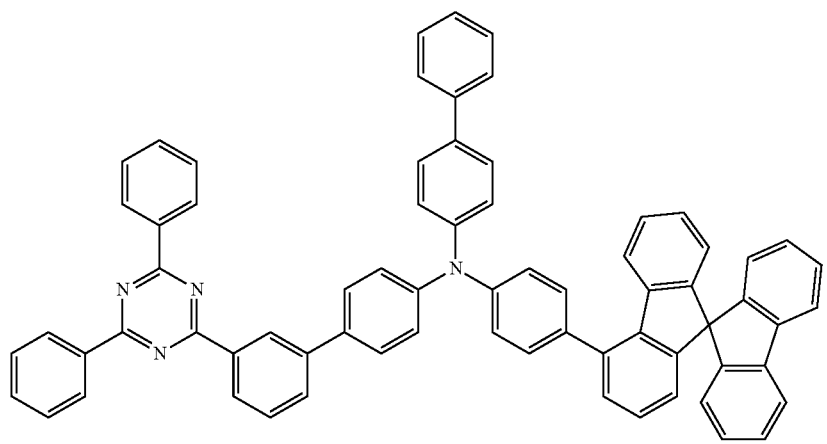

102
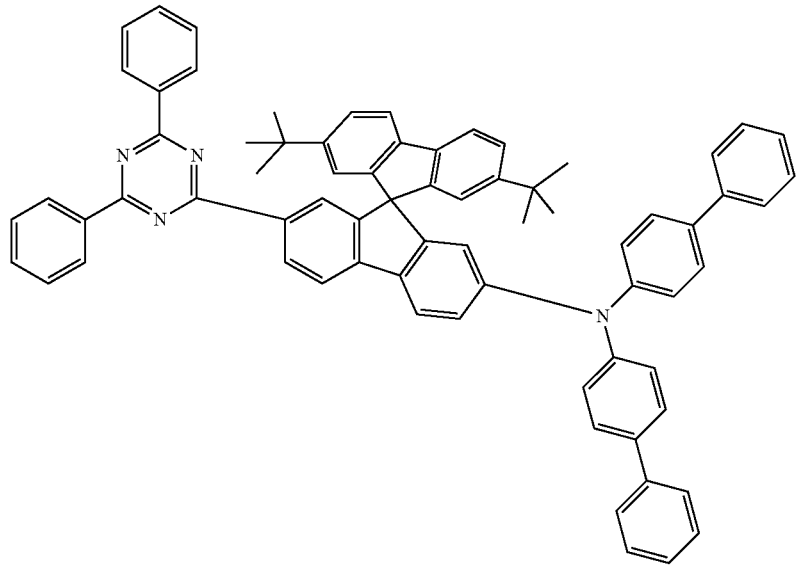
103
104
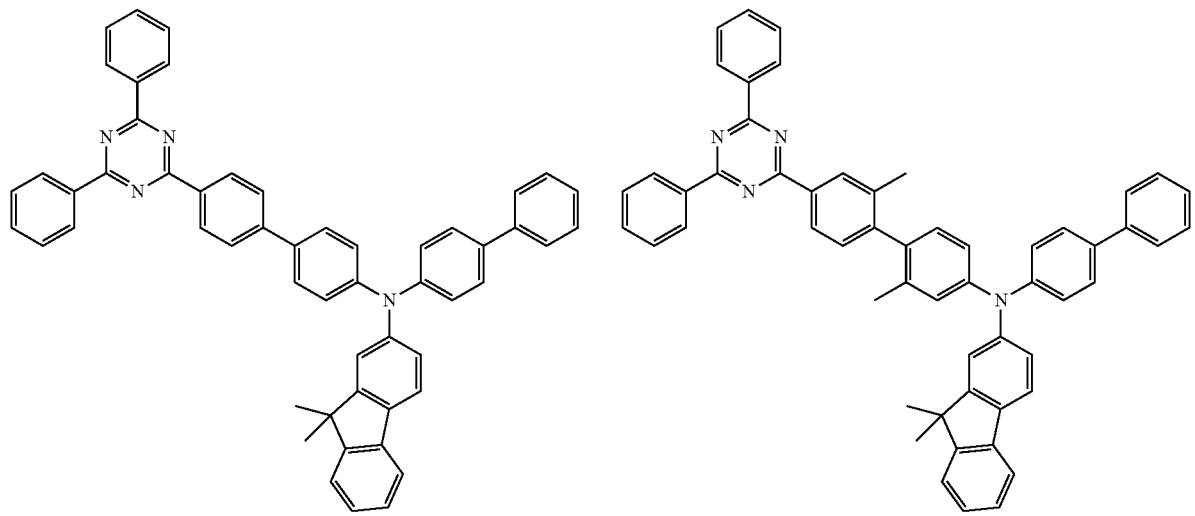
105
106
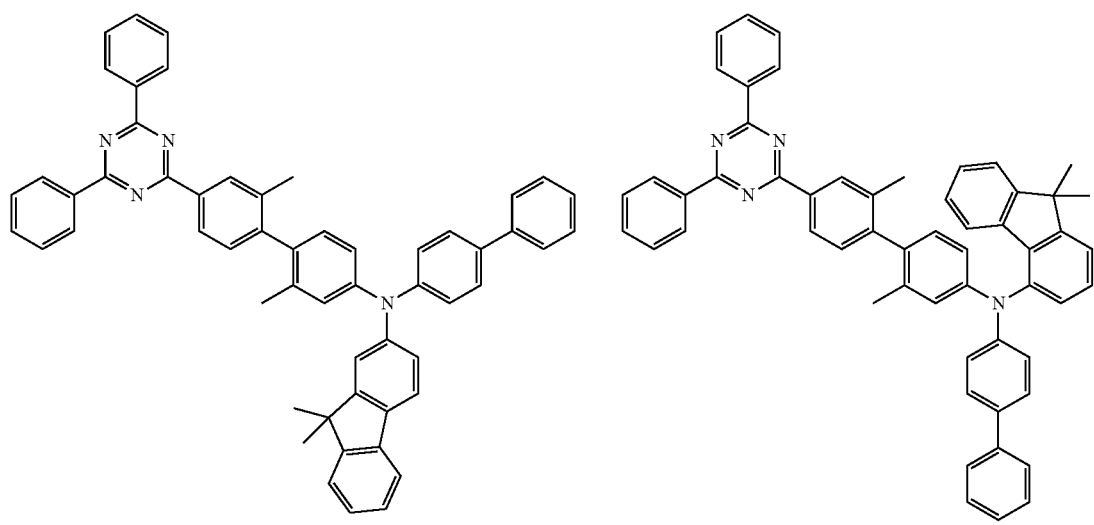

107
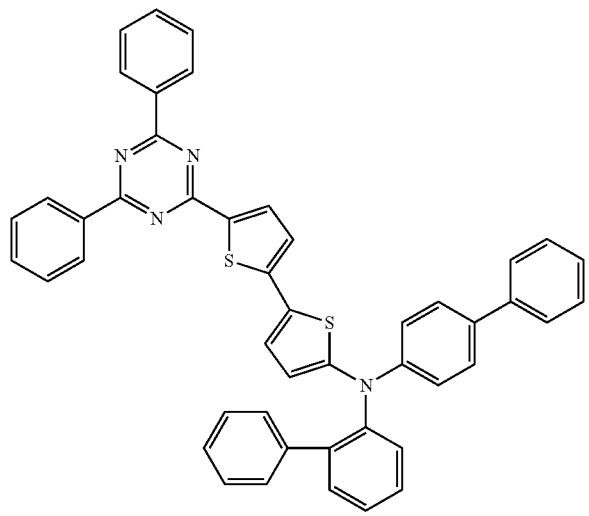
108
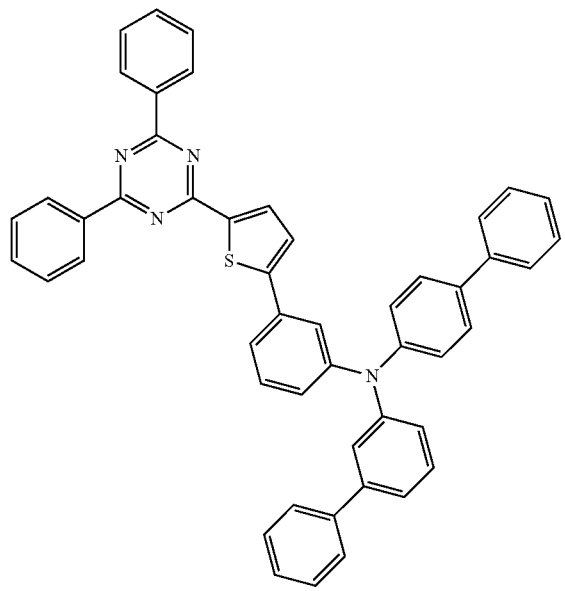
109
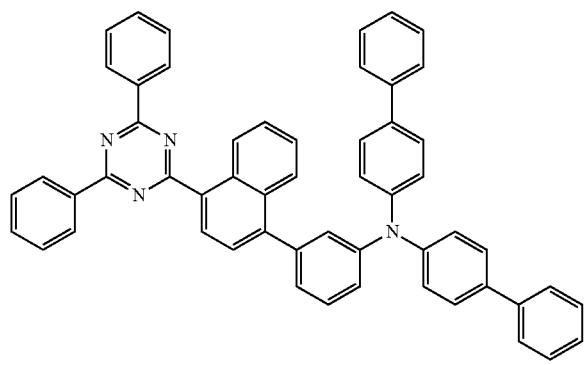
110
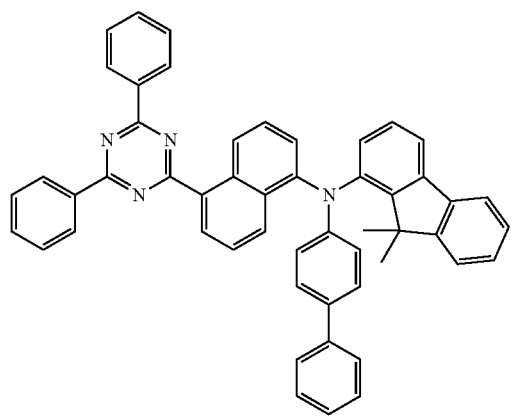
111
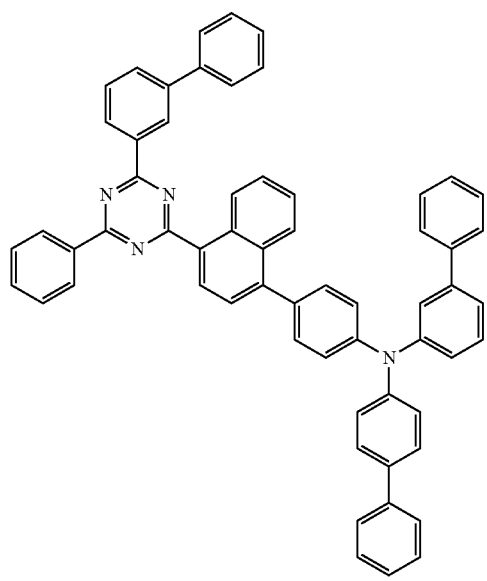
112
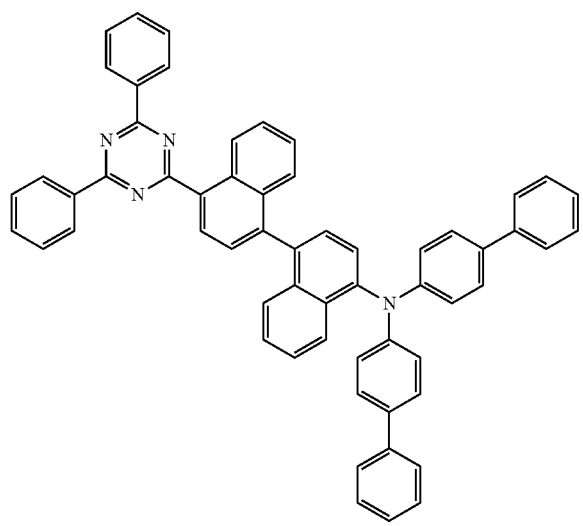

113
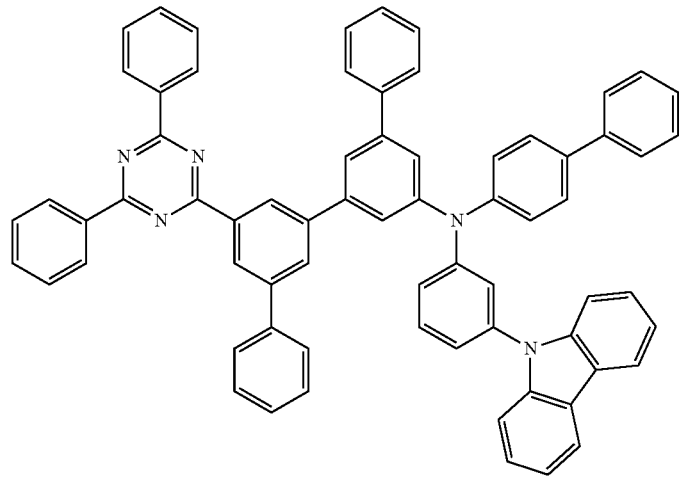
114
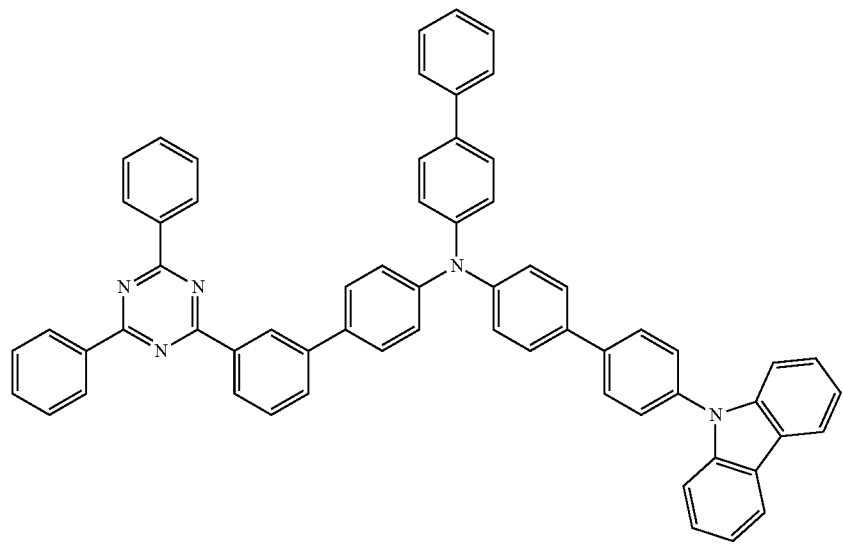
115
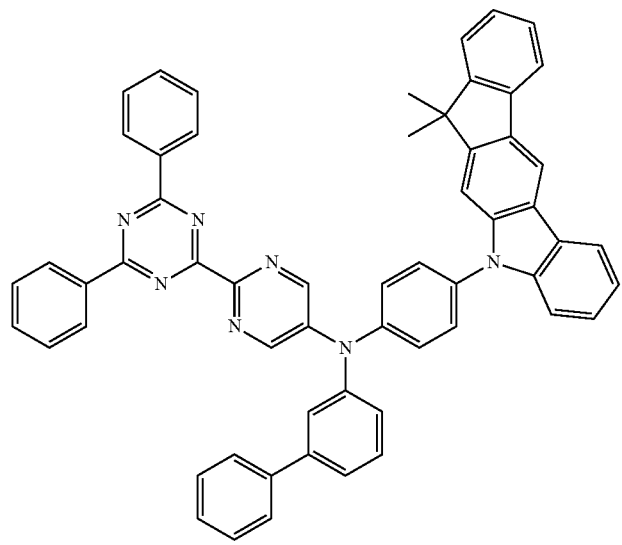

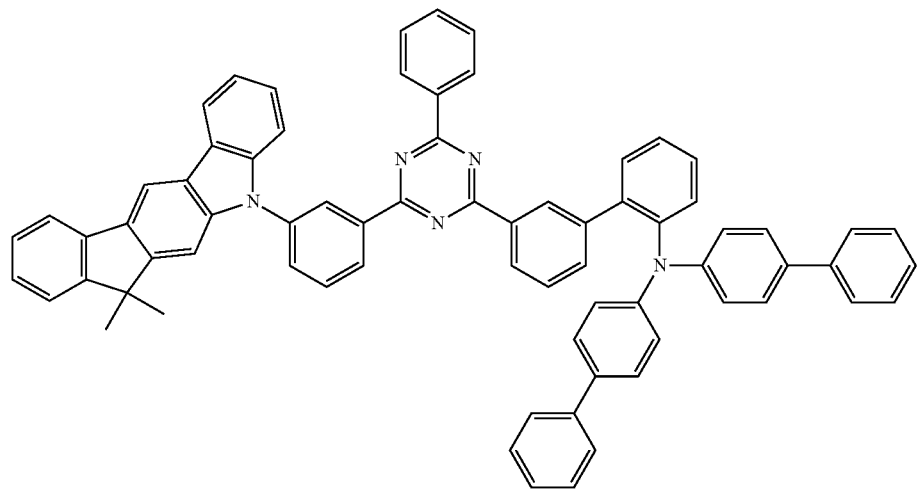
116
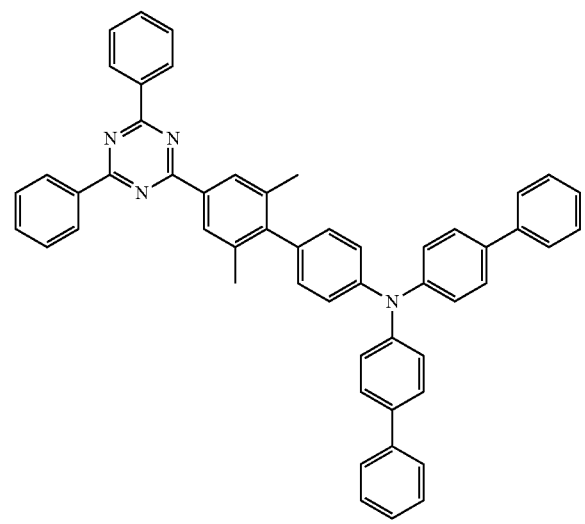
118
117
119
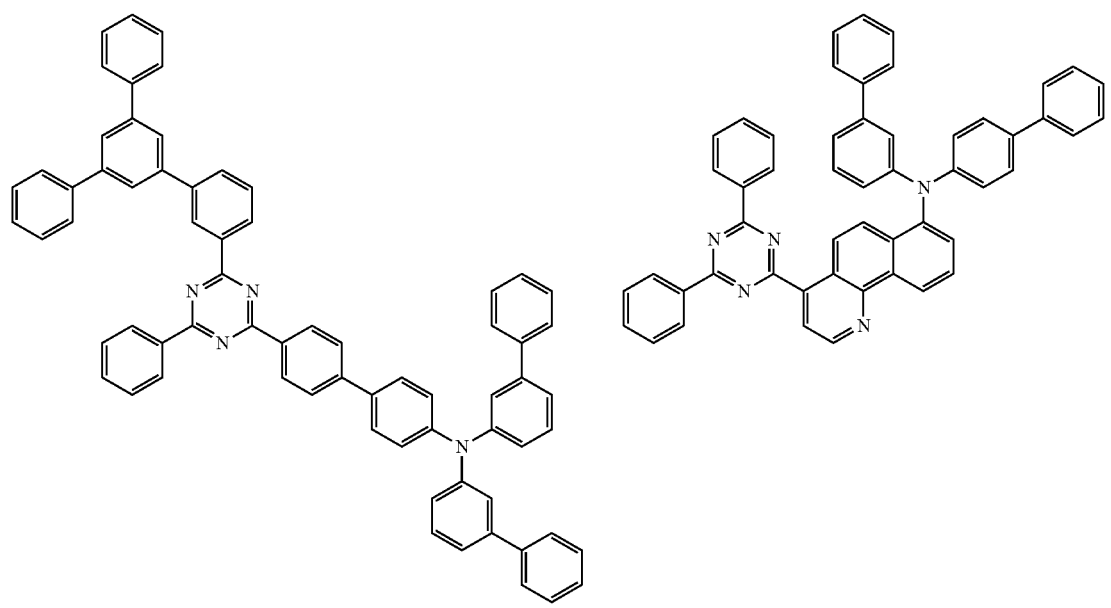
120

-continued
121
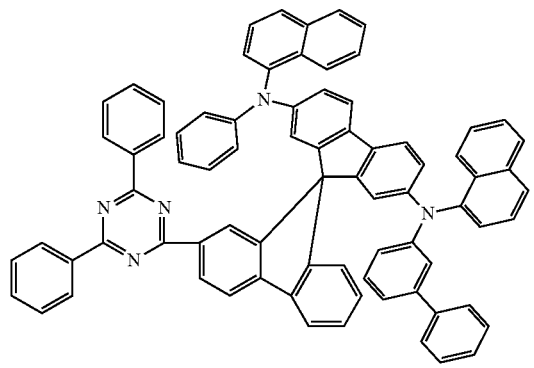
122
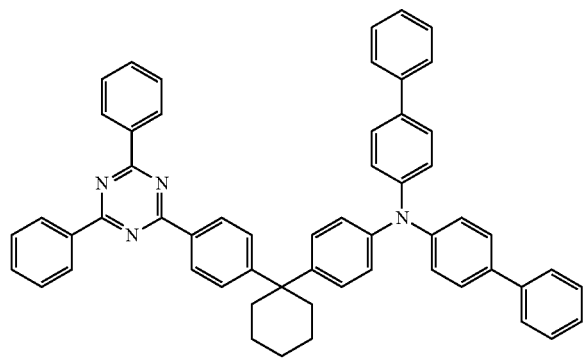
123
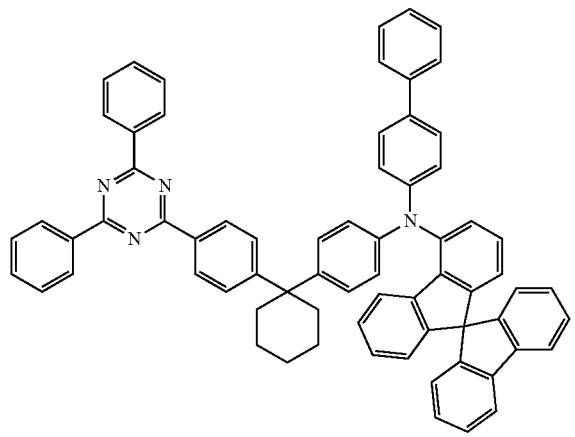
124
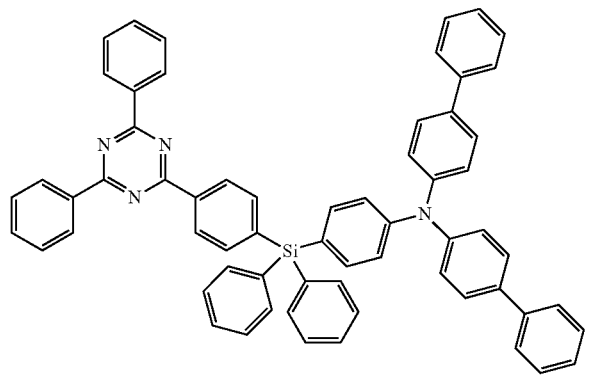
125
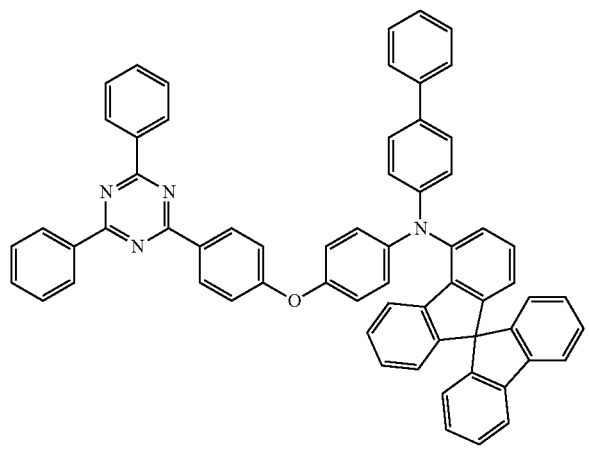
126
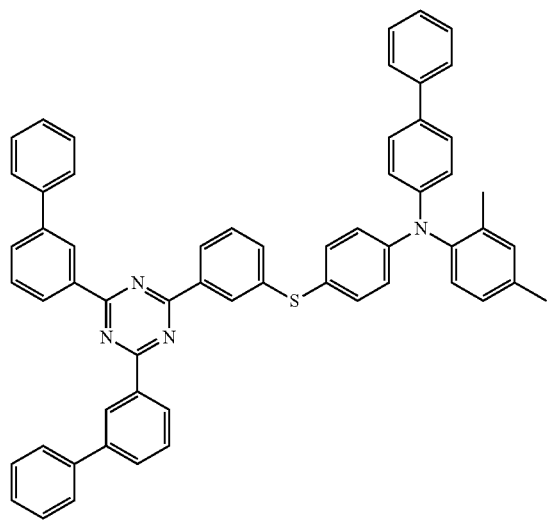

127
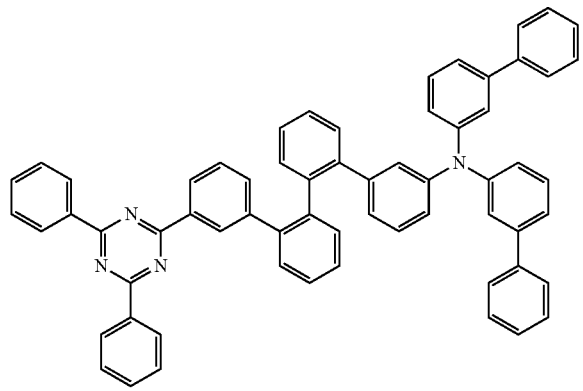
128
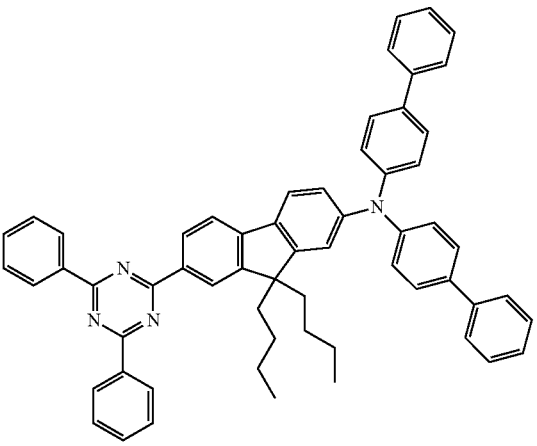
129
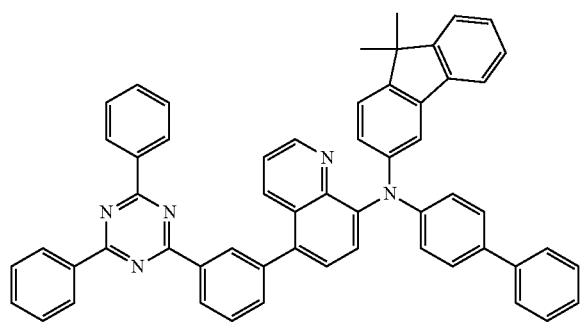
130
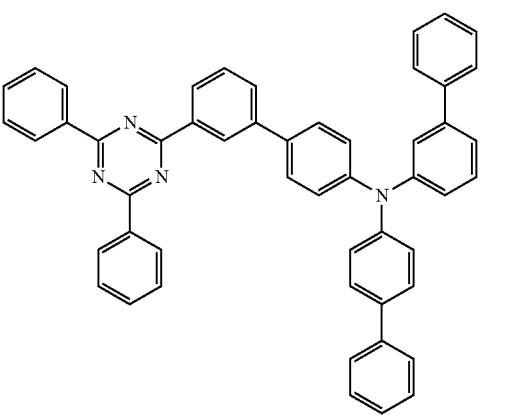
131
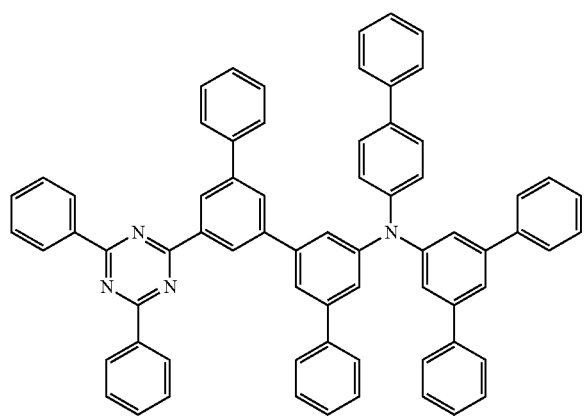
132
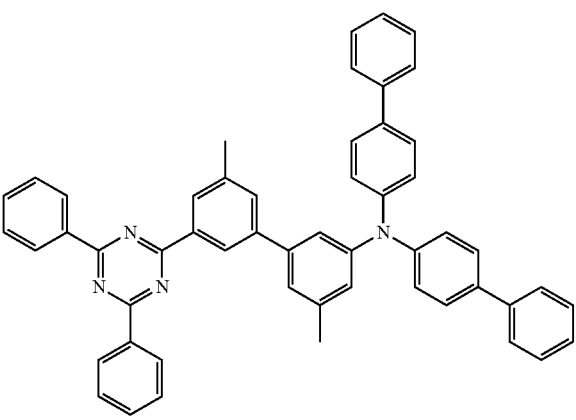

133
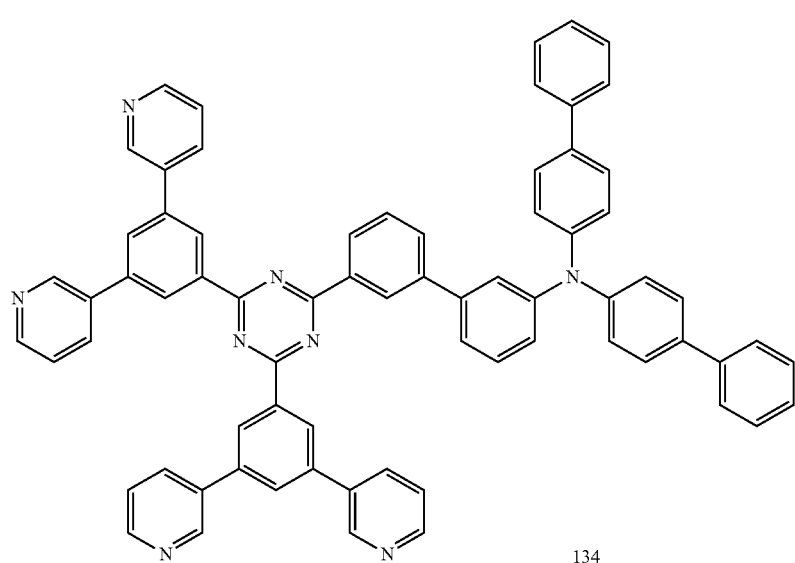
134
135
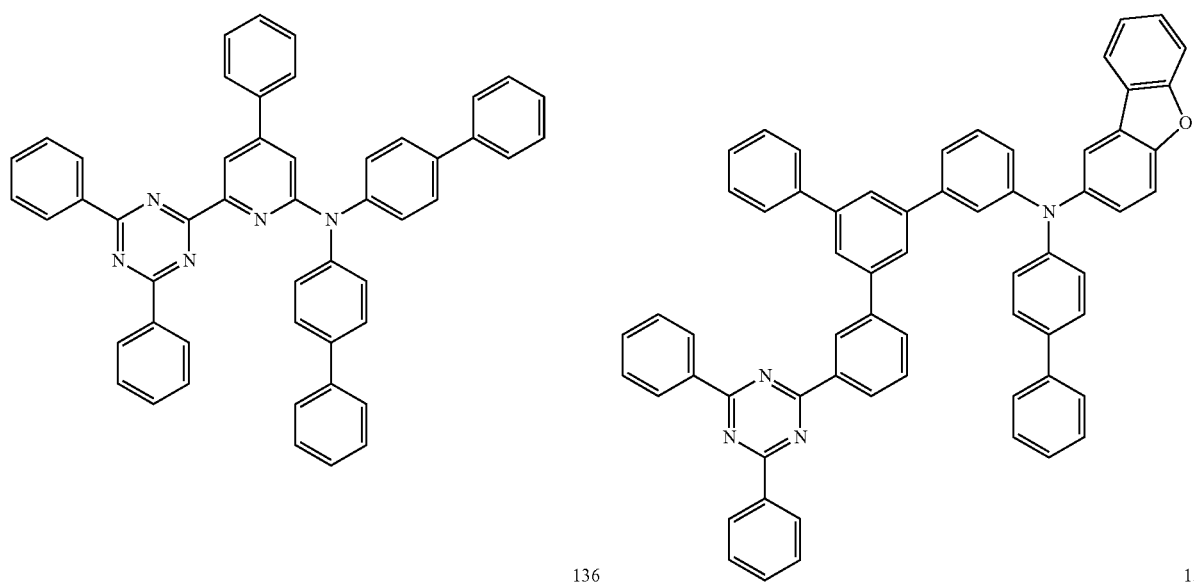
136
137
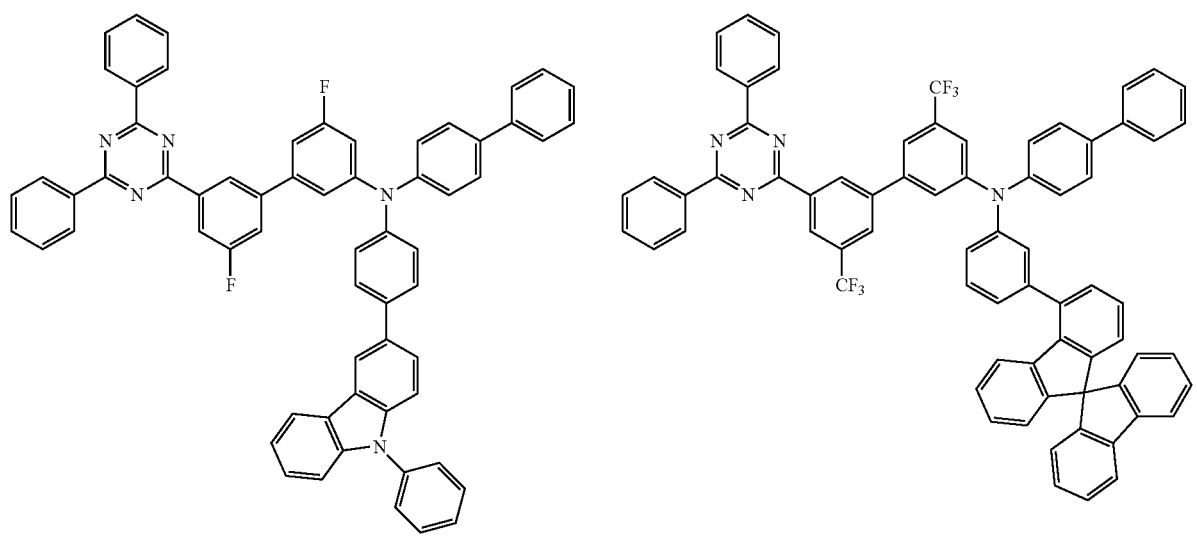

-continued
138
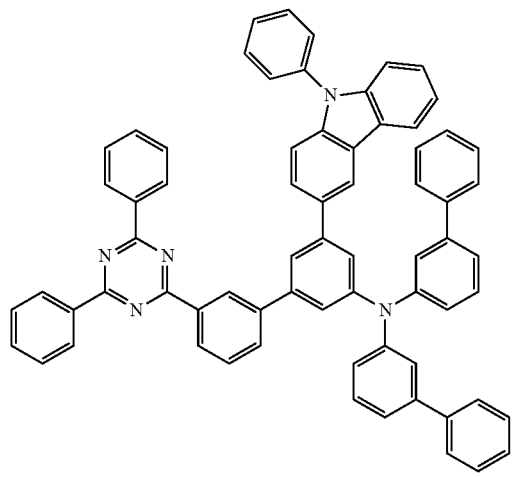
139
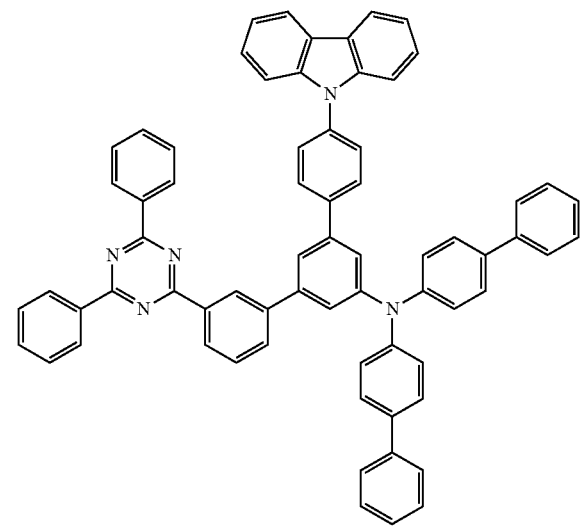
140
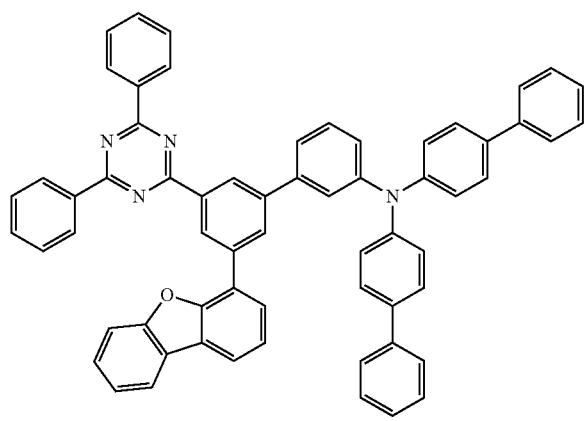
141
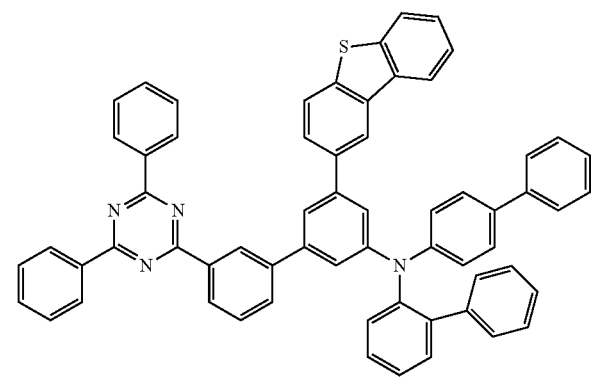
142
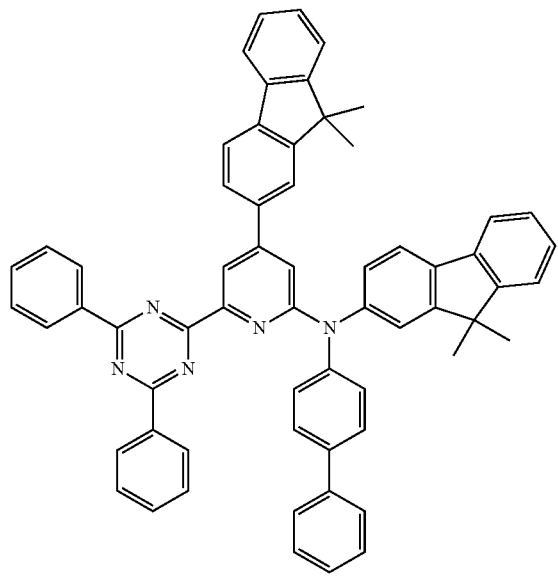
143
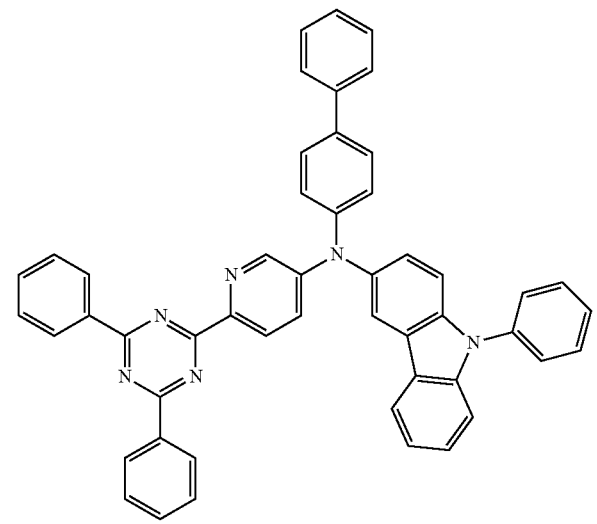

144
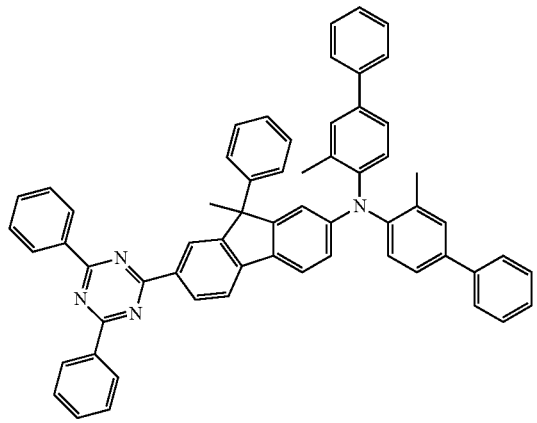

145
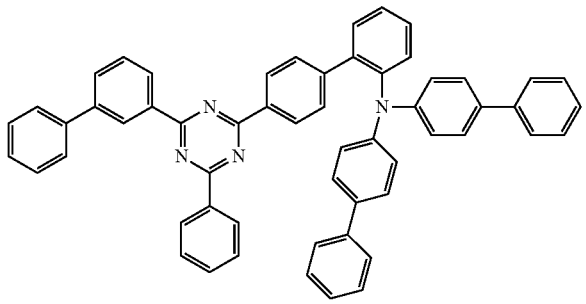

146
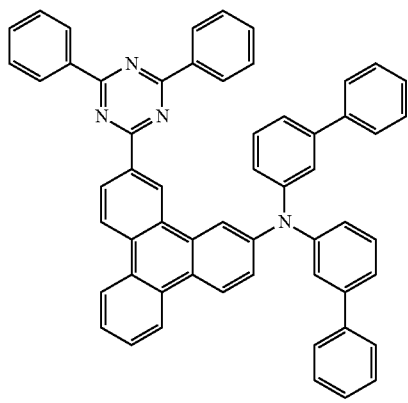

147
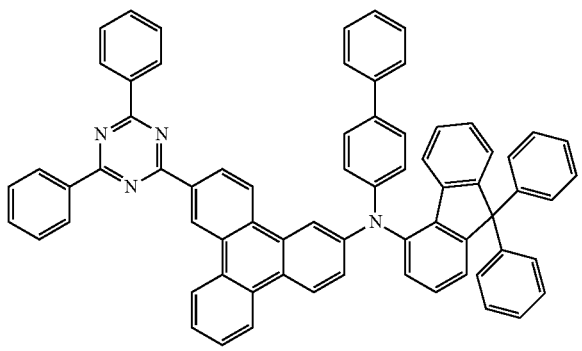

148
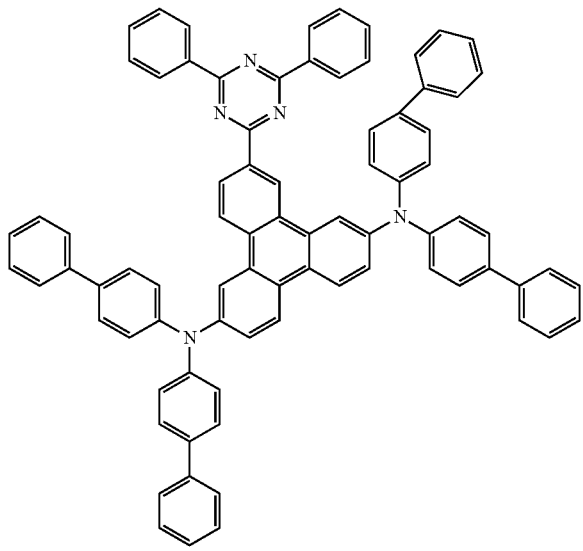

149
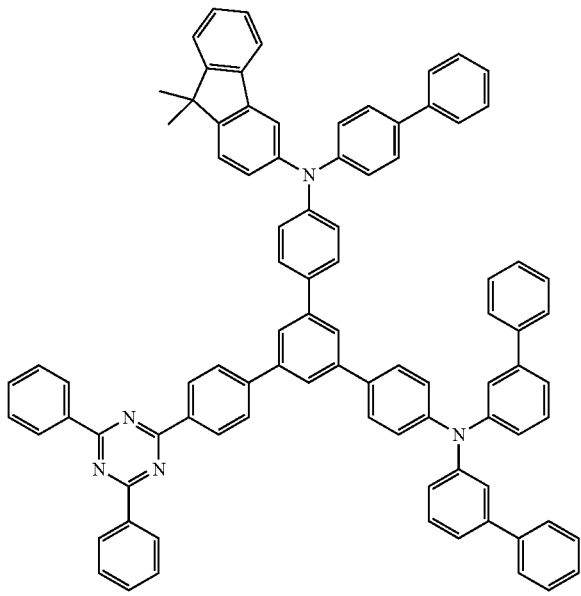

The compounds of the formula (I) can be obtained by means of known organochemical reactions, for example by Suzuki coupling, Buchwald coupling, Ullmann coupling, bromination and boronation.

A preferred process for the preparation of the compounds of the formula (I) is depicted below (Scheme 1). It is only outlined in broad terms. Detailed synthesis procedures for the preparation of compounds of the formula (I) which are based on this process are indicated in the working examples.

Scheme 1

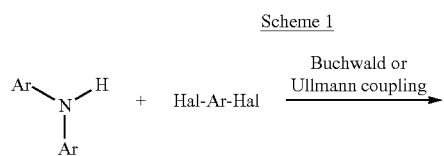

Scheme 2

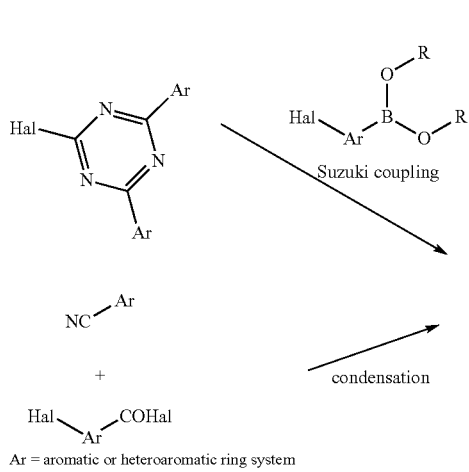

Ar = aromatic or heteroaromatic ring system
R = organic radical
Hal = halogen

-continued

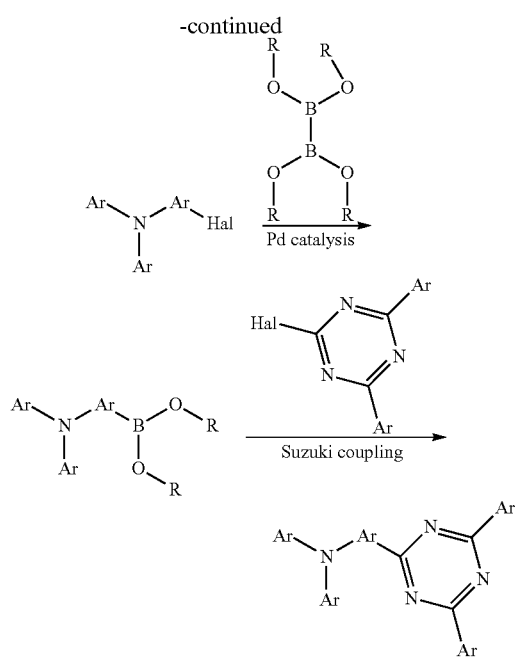

Ar = aromatic or heteroaromatic ring system
R = organic radical
Hal = halogen

To this end, a diarylamino derivative is firstly reacted with an aryl-halogen derivative in an organometallic coupling reaction, for example a Buchwald or Ullmann coupling. A boronation reaction is subsequently carried out. The boric acid derivative obtained is then reacted with a triazine derivative in an organometallic coupling reaction, preferably a Suzuki coupling. The compound obtained here can optionally be reacted further, for example in a functionalisation reaction.

According to an alternative process (Scheme 2), a triazine-arylene derivative is prepared either by a condensation reaction or by Suzuki coupling starting from halogen-substituted triazine and an arylboronic acid. In a further step, the arylamino group is then introduced by Buchwald coupling.

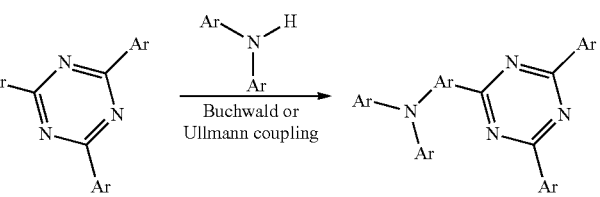

The processes indicated represent illustrative processes, in many cases particularly suitable, for the preparation of compounds of the formula (I). The person skilled in the art will be able to use them in unchanged form or he will be able to adapt them within the scope of his general expert knowledge or replace them by more suitable processes if the circumstances of the specific case require it.

The invention thus relates to a process for the preparation of a compound of the formula (I), characterised in that at least one organometallic coupling reaction is used, preferably at least one Buchwald coupling reaction.

The compounds according to the invention described above, in particular compounds which are substituted by reactive leaving groups, such as bromine, iodine, chlorine, boronic acid or boronic acid ester, can be used as monomers for the production of corresponding oligomers, dendrimers or polymers. Suitable reactive leaving groups are, for example, bromine, iodine, chlorine, boronic acids, boronic acid esters, amines, alkenyl or alkynyl groups having a terminal C—C double bond or C—C triple bond, oxiranes, oxetanes, groups which undergo a cycloaddition, for example a 1,3-dipolar cycloaddition, such as, for example, dienes or azides, carboxylic acid derivatives, alcohols and silanes.

The invention therefore furthermore relates to oligomers, polymers or dendrimers containing one or more compounds of the formula (I), where the bond(s) to the polymer, oligomer or dendrimer may be localised at any desired positions in formula (I) which are substituted by $R^1$ or $R^2$. Depending on the linking of the compound of the formula (I), the compound is a constituent of a side chain of the oligomer or polymer or a constituent of the main chain. An oligomer in the sense of this invention is taken to mean a compound which is built up from at least three monomer units. A polymer in the sense of the invention is taken to mean a compound which is built up from at least ten monomer units. The polymers, oligomers or dendrimers according to the invention may be conjugated, partially conjugated or non conjugated. The oligomers or polymers according to the invention may be linear, branched or dendritic. In the structures linked in a linear manner, the units of the formula (I) may be linked directly to one another or they may be linked to one another via a divalent group, for example via a substituted or unsubstituted alkylene group, via a heteroatom or via a divalent aromatic or heteroaromatic group. In branched and dendritic structures, for example, three or more units of the formula (I) may be linked via a trivalent or polyvalent group, for example via a trivalent or polyvalent aromatic or heteroaromatic group, to form a branched or dendritic oligomer or polymer.

The same preferences as described above for compounds of the formula (I) apply to the recurring units of the formula (I) in oligomers, dendrimers and polymers.

For the preparation of the oligomers or polymers, the monomers according to the invention are homopolymerised or copolymerised with further monomers. Suitable and preferred comonomers are selected from fluorenes (for example in accordance with EP 842208 or WO 00/22026), spirobifluorenes (for example in accordance with EP 707020, EP 894107 or WO 06/061181), para-phenylenes (for example in accordance with WO 1992/18552), carbazoles (for example in accordance with WO 04/070772 or WO 2004/113468), thiophenes (for example in accordance with EP 1028136), dihydrophenanthrenes (for example in accordance with WO 2005/014689 or WO 2007/006383), cis- and trans-indenofluorenes (for example in accordance with WO 2004/041901 or WO 2004/113412), ketones (for example in accordance with WO 2005/040302), phenanthrenes (for example in accordance with WO 2005/104264 or WO 2007/017066) or also a plurality of these units. The polymers, oligomers and dendrimers usually also contain further units, for example emitting (fluorescent or phosphorescent) units, such as, for example, vinyltriarylamines (for example in accordance with WO 2007/068325) or phosphorescent metal complexes (for example in accordance with WO 2006/003000), and/or charge-transport units, in particular those based on triarylamines.

The polymers, oligomers and dendrimers according to the invention have advantageous properties, in particular long lifetimes, high efficiencies and good colour coordinates.

For the processing of the compounds according to the invention from the liquid phase, for example by spin coating or by printing processes, formulations of the compounds according to the invention are necessary. These formulations can be, for example, solutions, dispersions or emulsions. It may be preferred to use mixtures of two or more solvents for this purpose. Suitable and preferred solvents are, for example, toluene, anisole, o-, m- or p-xylene, methyl benzoate, mesitylene, tetralin, veratrol, THF, methyl-THF, THP, chlorobenzene, dioxane, phenoxytoluene, in particular 3-phenoxy-toluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetol, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The invention therefore furthermore relates to a formulation, in particular a solution, dispersion or emulsion, comprising at least one compound of the formula (I) or at least one polymer, oligomer or dendrimer containing at least one unit of the formula (I), and at least one solvent, preferably an organic solvent. The way in which solutions of this type can be prepared is known to the person skilled in the art and is described, for example, in WO 2002/072714, WO 2003/019694 and the literature cited therein.

The compounds according to the invention are suitable for use in electronic devices, in particular in organic electroluminescent devices (OLEDs). The compounds can be employed, inter alia depending on the substitution, in various functions and in various layers. The compounds are preferably employed as matrix materials, preferably as matrix materials for phosphorescent emitters.

The invention furthermore relates to the use of the compounds of the formula (I) in electronic devices. The electronic devices here are preferably selected from the group consisting of organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs), organic laser diodes (O-lasers) and particularly preferably selected from organic electroluminescent devices (OLEDs).

The invention furthermore relates to an electronic device comprising anode, cathode and at least one organic layer, where the organic layer comprises at least one compound of the formula (I). The electronic device here is preferably selected from the above-mentioned devices and particularly preferably an organic electroluminescent device (OLED).

Apart from cathode, anode and emitting layer, the organic electroluminescent device may also comprise further layers. These are selected, for example, from in each case one or more hole-injection layers, hole-transport layers, hole-blocking layers, electron-transport layers, electron-injection layers, electron-blocking layers, exciton-blocking layers, charge-generation layers (IDMC 2003, Taiwan; Session 21 OLED (5), T. Matsumoto, T. Nakada, J. Endo, K. Mori, N. Kawamura, A. Yokoi, J. Kido, *Multi-photon Organic EL Device Having Charge Generation Layer*), coupling-out layers and/or organic or inorganic p/n junctions. The compounds preferably employed in the respective layers and functions are explicitly disclosed in later sections.

The organic electroluminescent device according to the invention may comprise a plurality of emitting layers. These emission layers in this case particularly preferably have in total a plurality of emission maxima between 380 nm and 750 nm, resulting overall in white emission, i.e. various emitting compounds which are able to fluoresce or phosphoresce and which emit blue or yellow or orange or red light are used in the emitting layers. Particular preference is given to three-layer systems, i.e. systems having three emitting layers, where at least one of these layers preferably comprises at least one compound of the formula (I) and where the three layers exhibit blue, green and orange or red emission (for the basic structure see, for example, WO 2005/011013). Alternatively and/or additionally, the compounds according to the invention may also be present in another layer. It should be noted that, for the generation of white light, an emitter compound used individually which emits in a broad wavelength range may also be suitable instead of a plurality of emitter compounds emitting in colour.

In a preferred embodiment of the present invention, the compounds of the formula (I) are employed as matrix material in an emitting layer in combination with one or more emitter compounds, preferably phosphorescent emitter compounds.

The term phosphorescent emitters in accordance with the present application encompasses compounds in which the light emission takes place through a spin-forbidden transition, for example a transition from an excited triplet state or a state having a relatively high spin quantum number, such as a quintet state.

Suitable phosphorescent emitters are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent emitters used are preferably compounds which contain copper, molybdenum, tungsten, rhenium, ruthenium, osmium, rhodium, iridium, palladium, platinum, silver, gold or europium, in particular compounds which contain iridium, platinum or copper.

For the purposes of the present invention, all luminescent iridium, platinum or copper complexes are regarded as phosphorescent compounds.

Examples of phosphorescent emitter compounds are revealed by the applications WO 2000/70655, WO 2001/41512, WO 2002/02714, WO 2002/15645, EP 1191613, EP 1191612, EP 1191614, WO 2005/033244, WO 2005/019373 and US 2005/0258742. In general, all phosphorescent complexes as used in accordance with the prior art for phosphorescent OLEDs and as are known to the person skilled in the art in the area of organic electroluminescent devices are suitable for use in the devices according to the invention. The person skilled in the art will also be able to employ further phosphorescent complexes without inventive step in combination with the compounds according to the invention in OLEDs. Further examples of suitable phosphorescent emitters are revealed by the table following in a later section.

The proportion of the matrix material in the emitting layer in the device according to the invention is preferably between 50.0 and 99.9%, particularly preferably between 80.0 and 99.5% and very particularly preferably between 92.0 and 99.5% for fluorescent emitting layers and between 85.0 and 97.0% for phosphorescent emitting layers. Correspondingly, the proportion of the emitting compound is preferably between 0.1 and 50.0%, particularly preferably between 0.5 and 20.0% and very particularly preferably between 0.5 and 8.0% for fluorescent emitting layers and between 3.0 and 15.0% for phosphorescent emitting layers.

In the present application, the specification of the relative proportions of various compounds in a layer in % is taken to mean % by weight in the case of production of the device from solution, while this is taken to mean % by vol. in the case of production by a gas-phase process.

An emitting layer of an organic electroluminescent device may also comprise systems comprising a plurality of matrix materials (mixed-matrix systems) and/or a plurality of emitting compounds.

In a further preferred embodiment of the invention, the compounds of the formula (I) are used as one component of mixed-matrix systems. The mixed-matrix systems preferably comprise two or three different matrix materials, particularly preferably two different matrix materials. One of the two materials here preferably represents a material having, inter alia, hole-transporting properties and the other material represents a material having, inter alia, electron-transporting properties. The compound of the formula (I) here represents a matrix material having electron-transporting and hole-transporting properties. The two different matrix materials may be present in a ratio of 1:50 to 1:1, preferably 1:20 to 1:1, particularly preferably 1:10 to 1:1 and very particularly preferably 1:4 to 1:1. Preference is given to the use of mixed-matrix systems in phosphorescent organic electroluminescent devices. More precise details on mixed-matrix systems are given, inter alia, in the application WO 2010/108579.

The mixed-matrix systems may comprise one or more emitting compounds. The one or more emitting compounds together have in accordance with the invention a proportion of 0.1 to 50.0% in the mixture as a whole and preferably a proportion of 0.5 to 20.0% in the mixture as a whole. Correspondingly, the matrix components together have a proportion of 50.0 to 99.9% in the mixture as a whole and preferably a proportion of 80.0 to 99.5% in the mixture as a whole.

Particularly suitable matrix materials which can be used in combination with the compounds according to the invention as matrix components of a mixed-matrix system are selected from the preferred matrix materials indicated for phosphorescent emitters or the preferred matrix materials indicated for fluorescent emitters, depending on what type of emitter is employed in the mixed-matrix system.

The further functional materials preferably employed in the electronic device according to the invention are shown below.

The compounds shown in the following table represent particularly suitable phosphorescent emitters.

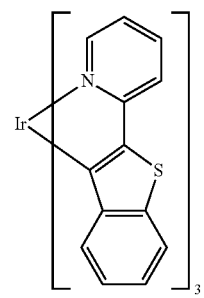

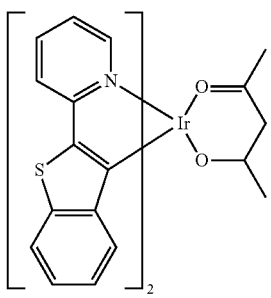

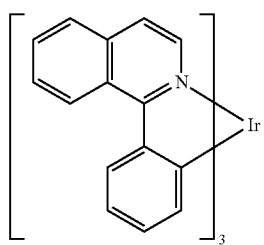
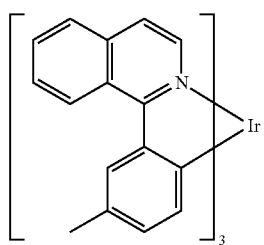
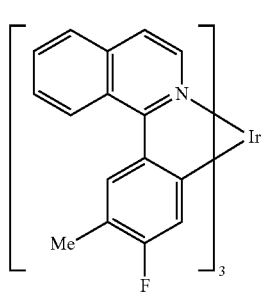
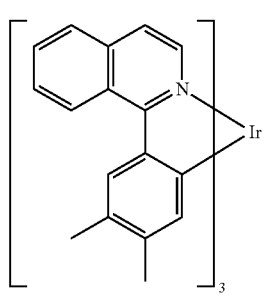
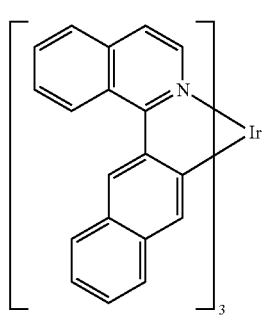
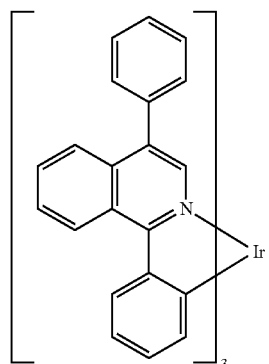
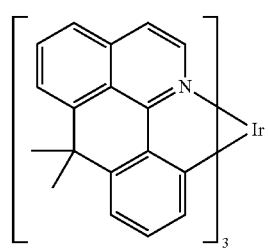
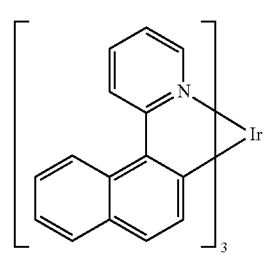
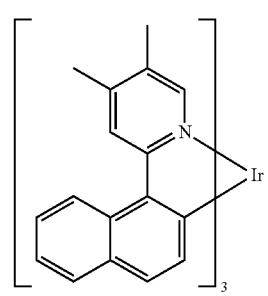
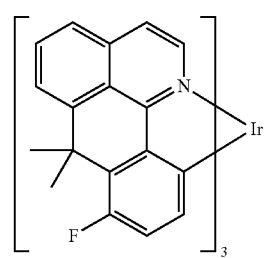

87
-continued
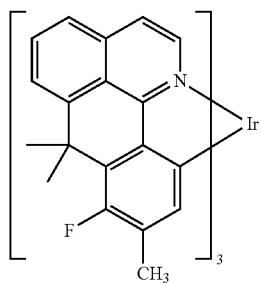
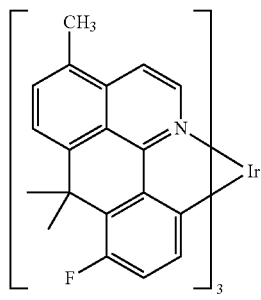
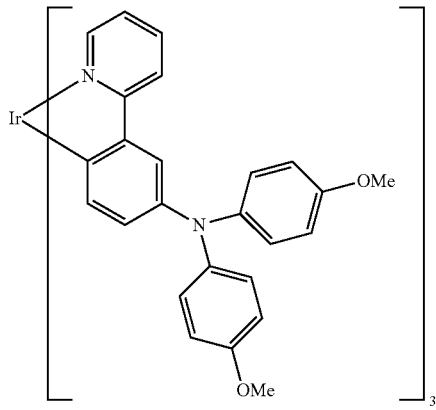
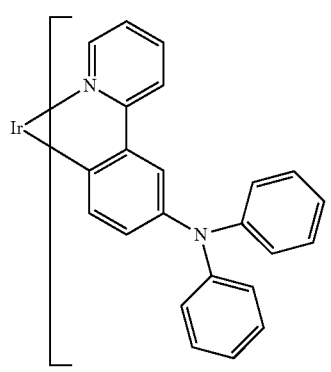
88
-continued
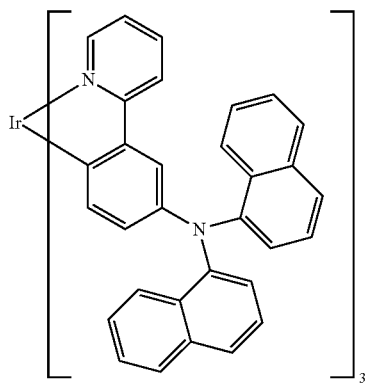
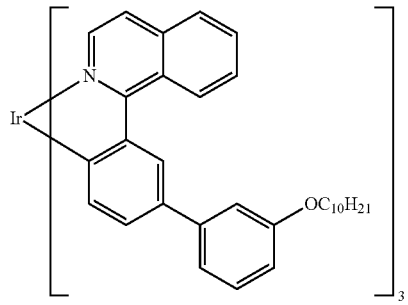
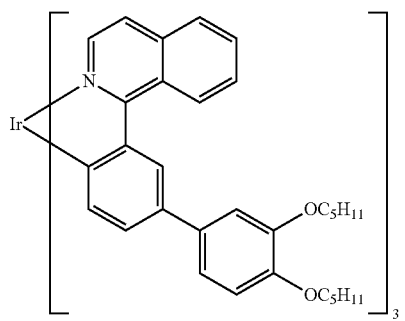
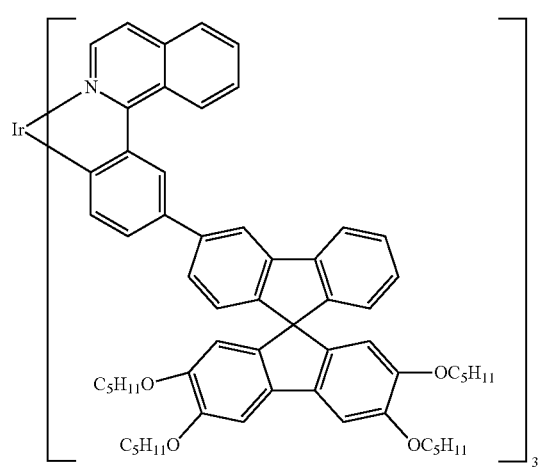

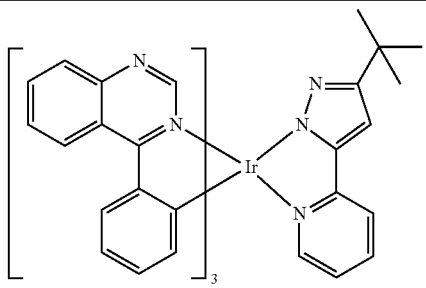
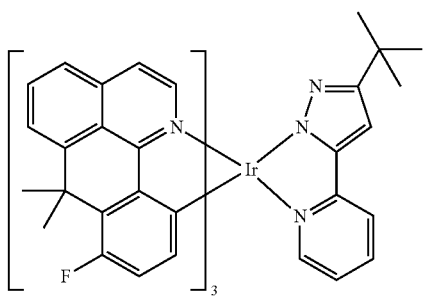
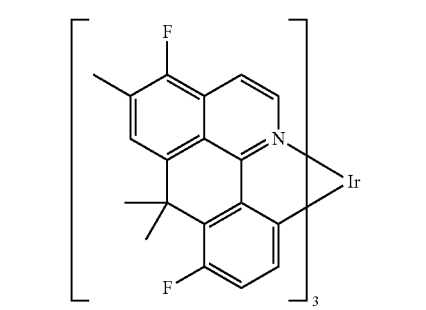
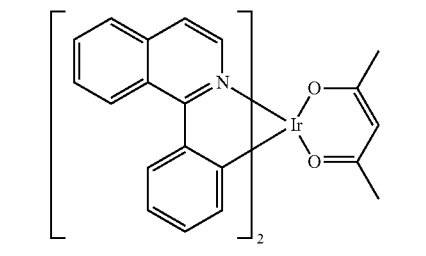
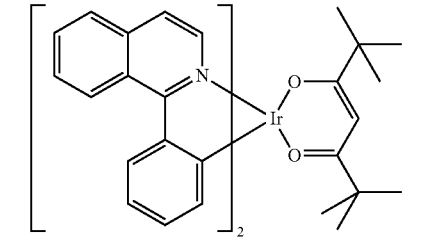
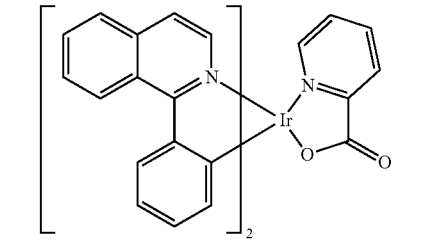
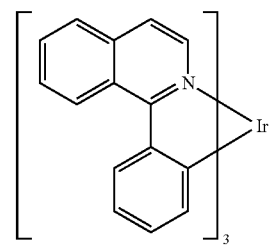
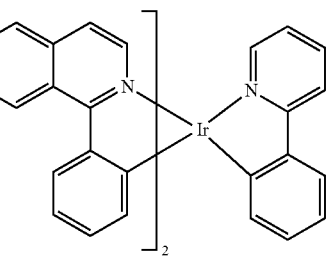
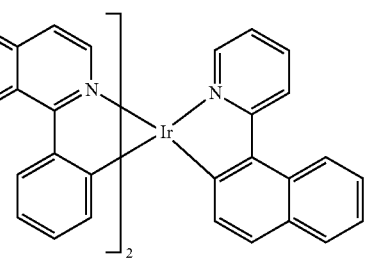
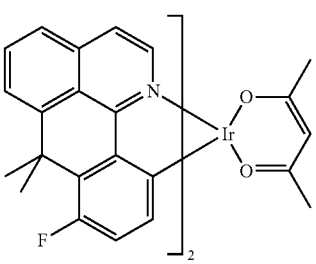
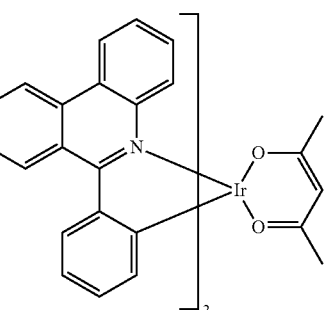
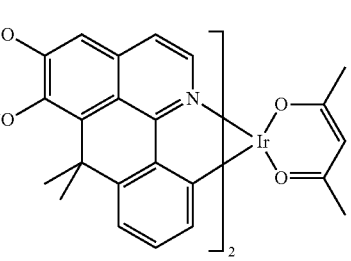

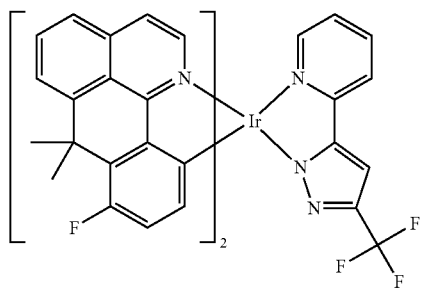
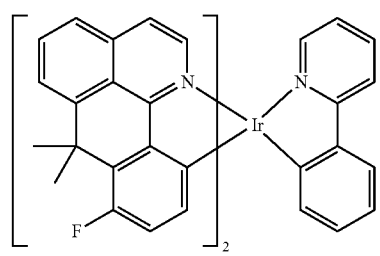
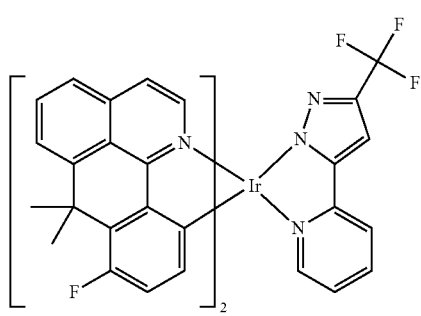
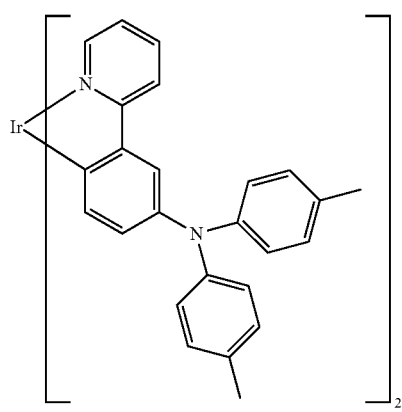
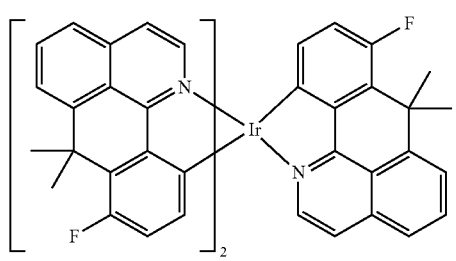
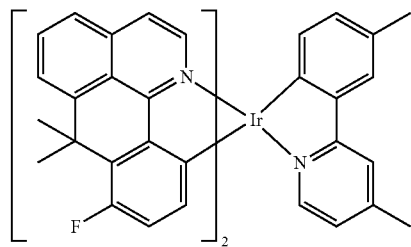
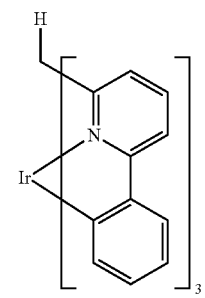
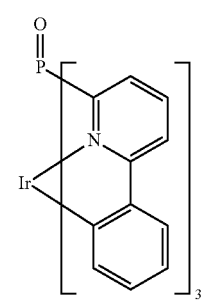
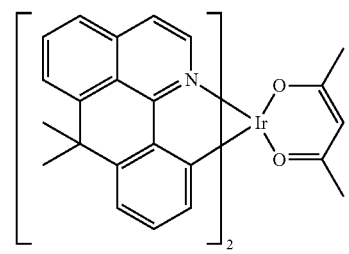
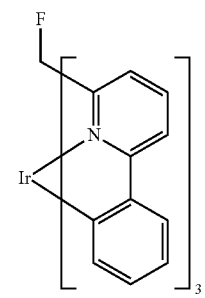

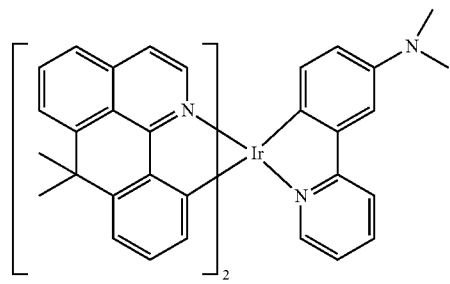
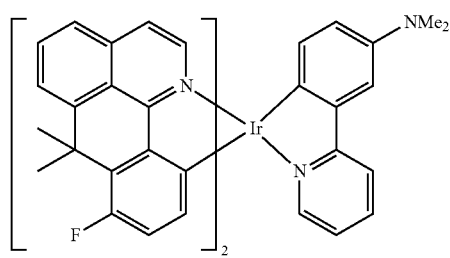
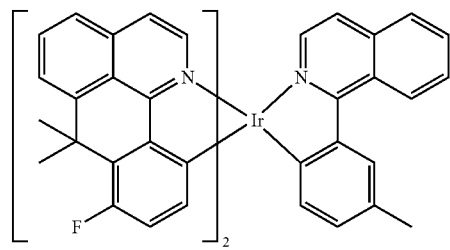
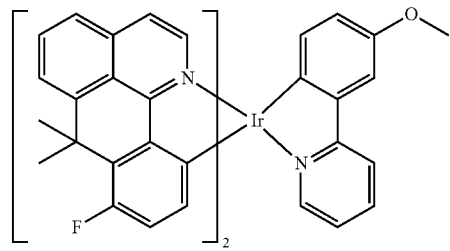
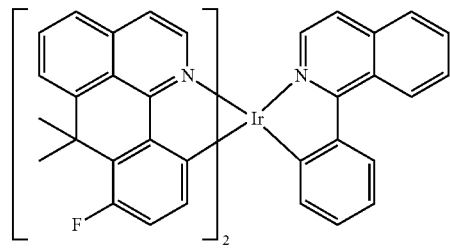
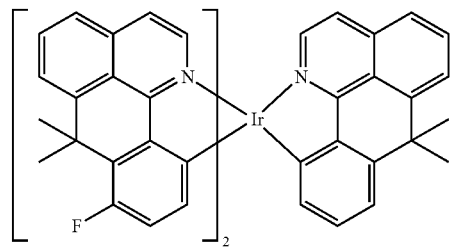
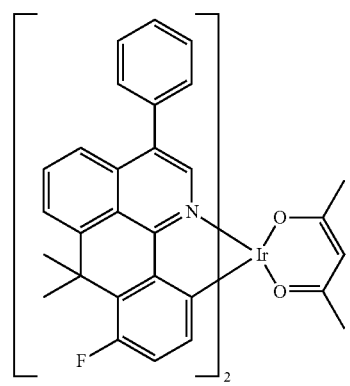
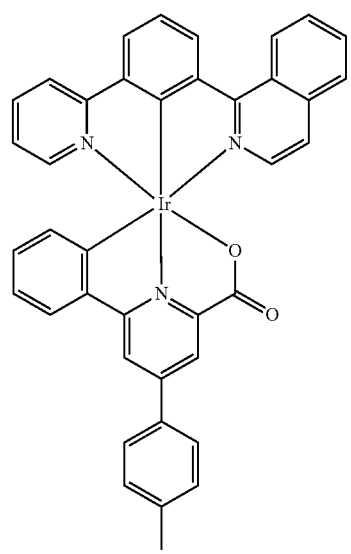
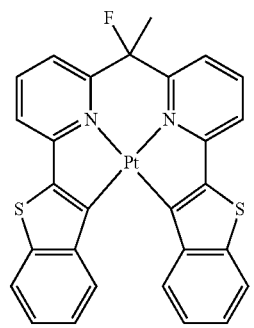

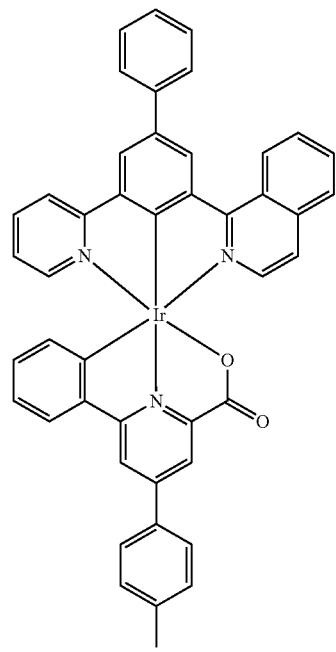
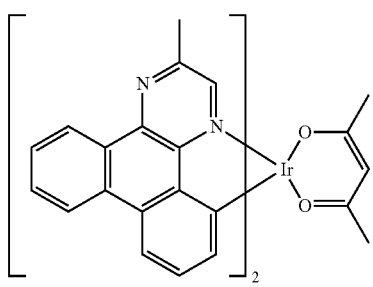
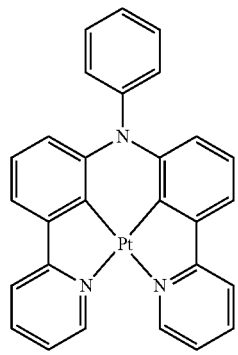
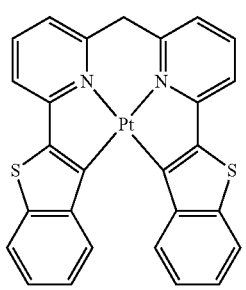
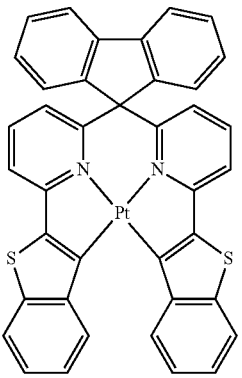
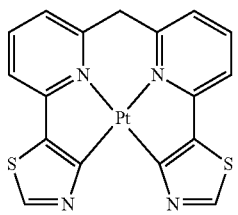
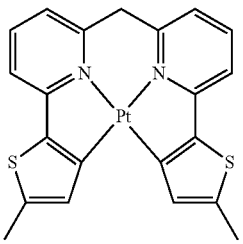
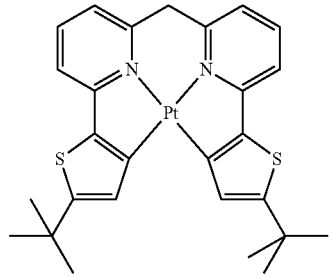
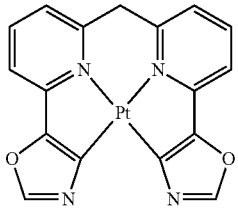
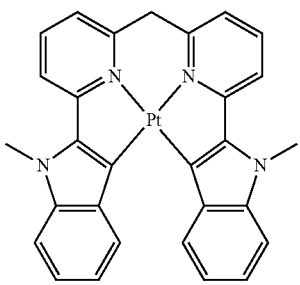

| 97 -continued | 98 -continued |
|---|---|
| 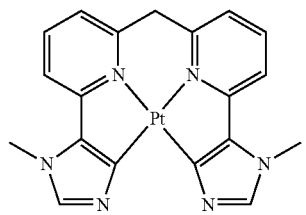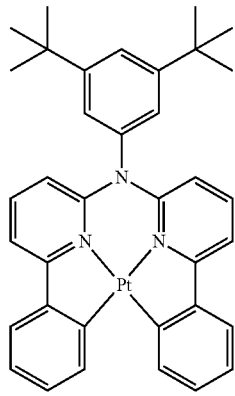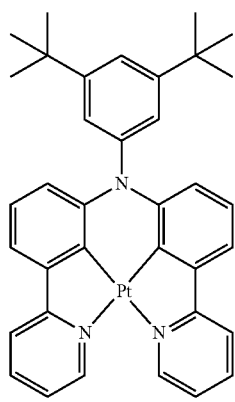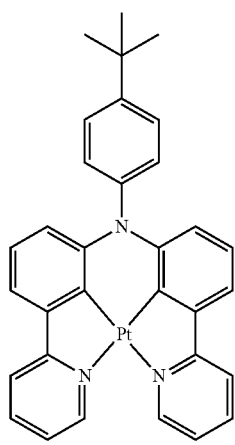 | 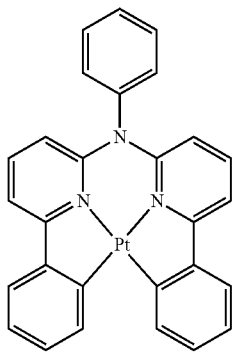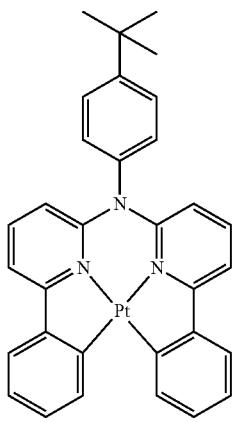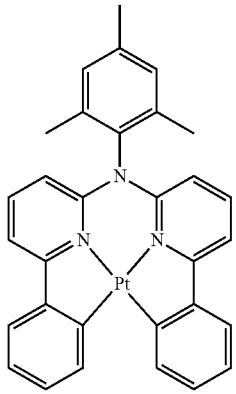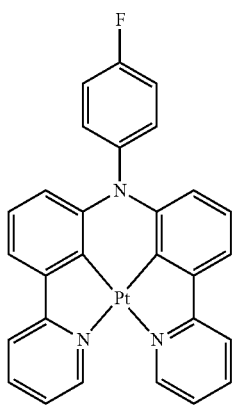 |

| 99 -continued | 100 -continued |
|---|---|
| 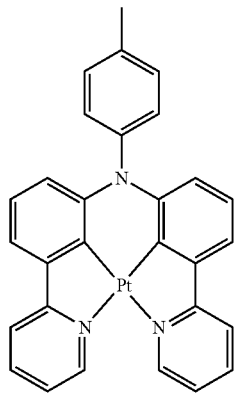 | 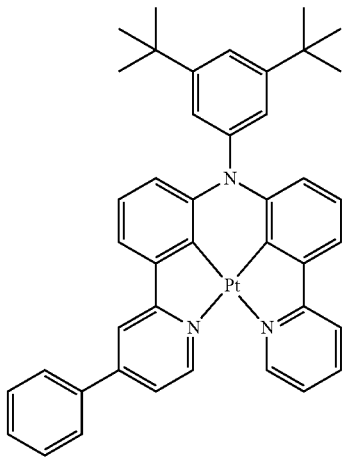 |
| 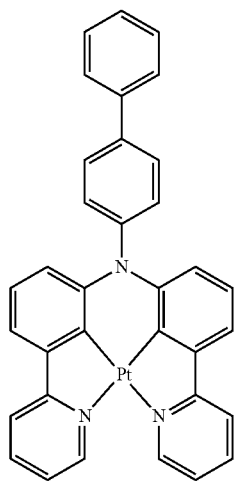 | 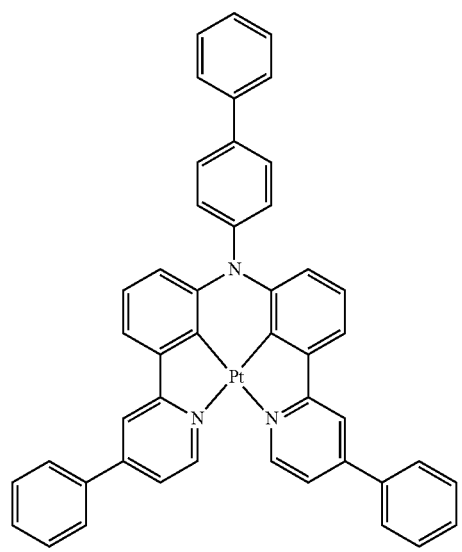 |
| 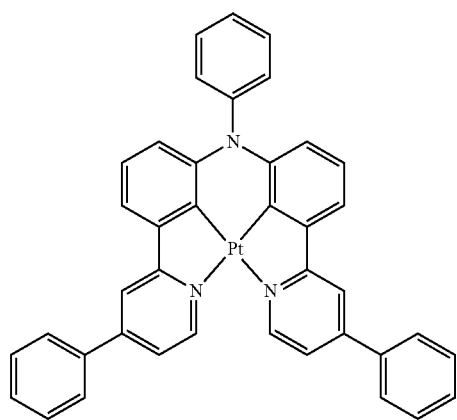 | 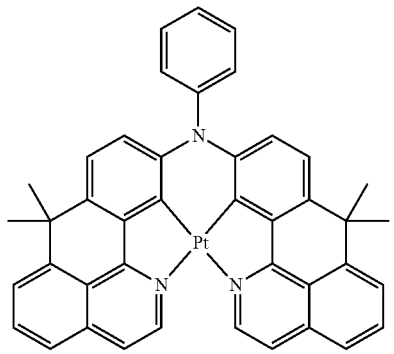 |

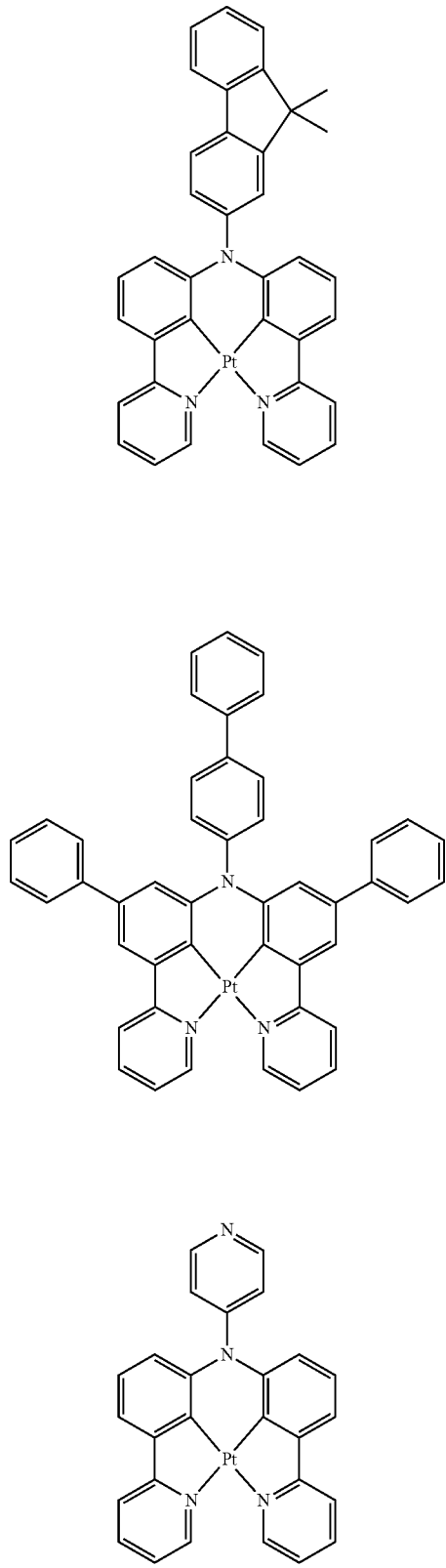

103
-continued
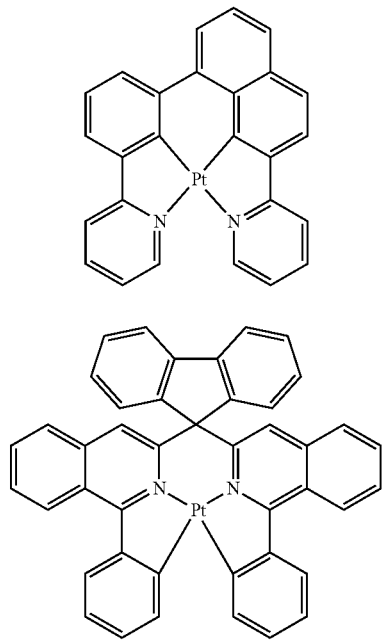
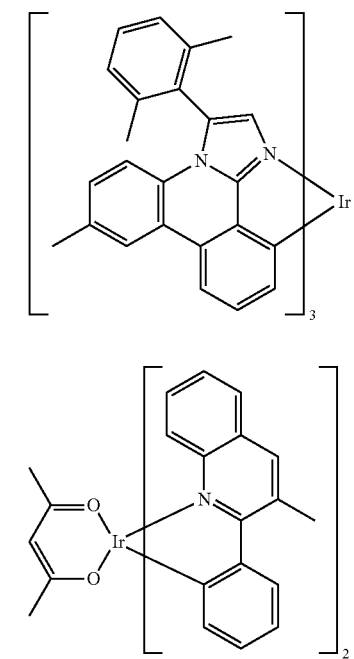
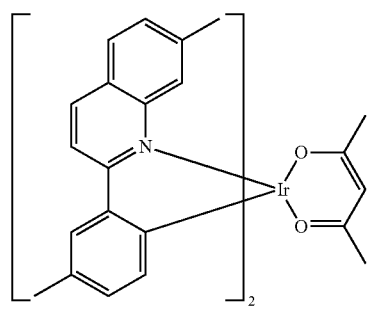
104
-continued
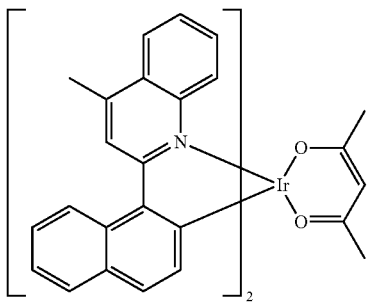
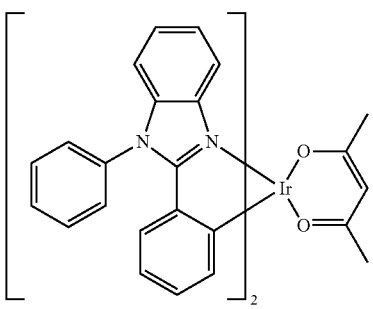
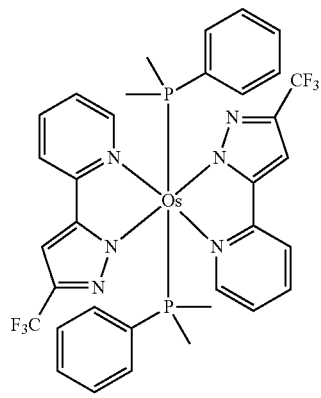
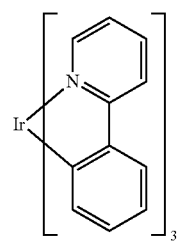
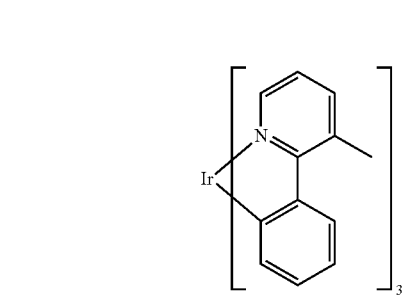

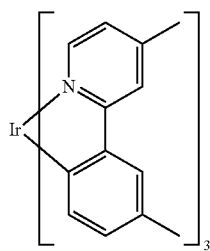
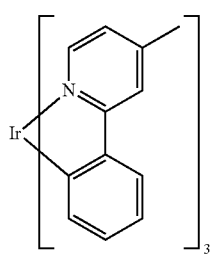
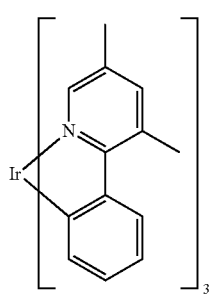
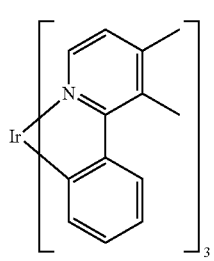
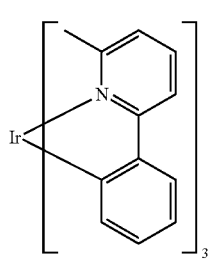
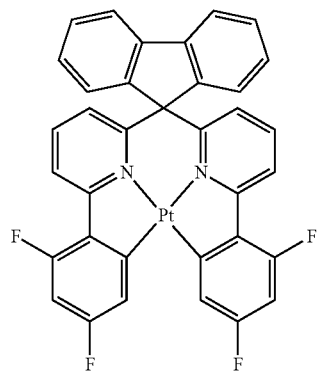
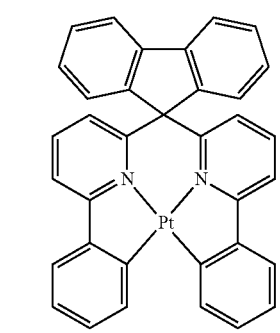
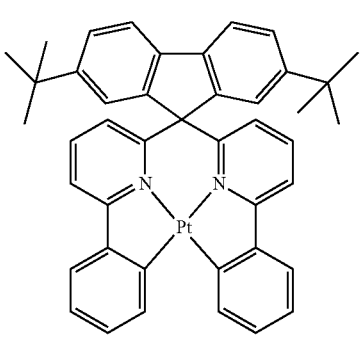
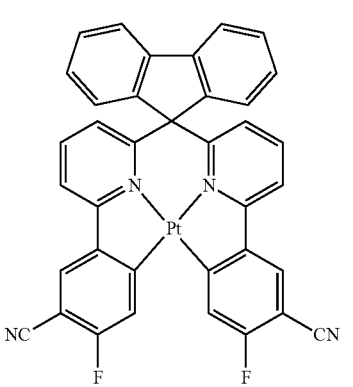

107
-continued
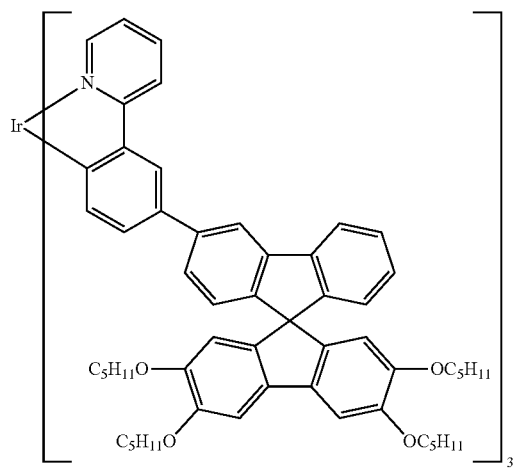
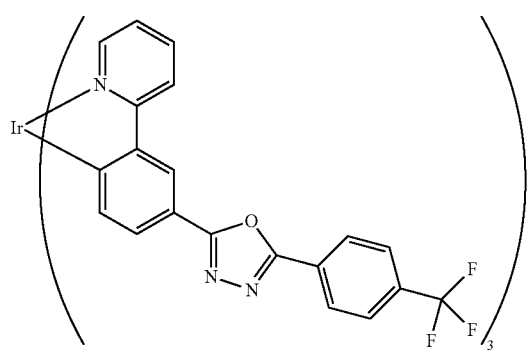
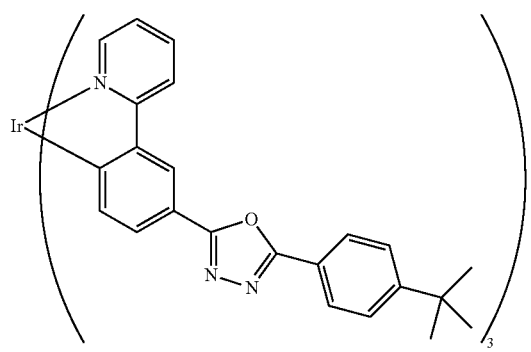
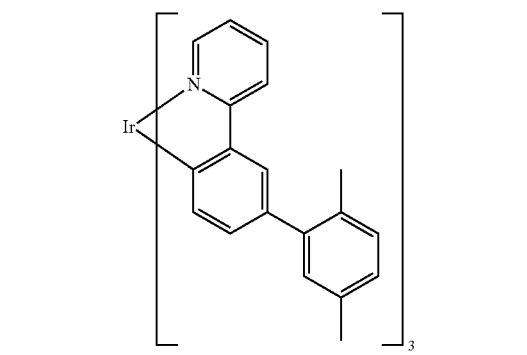
108
-continued
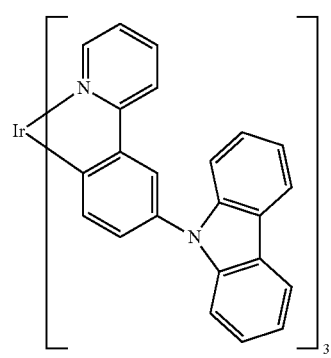
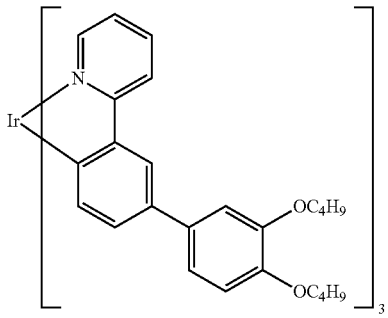
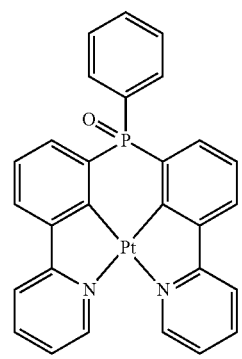
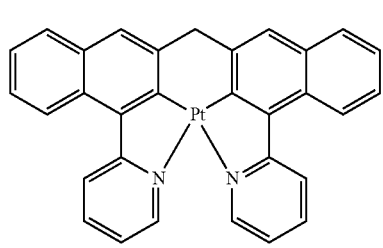

109
-continued
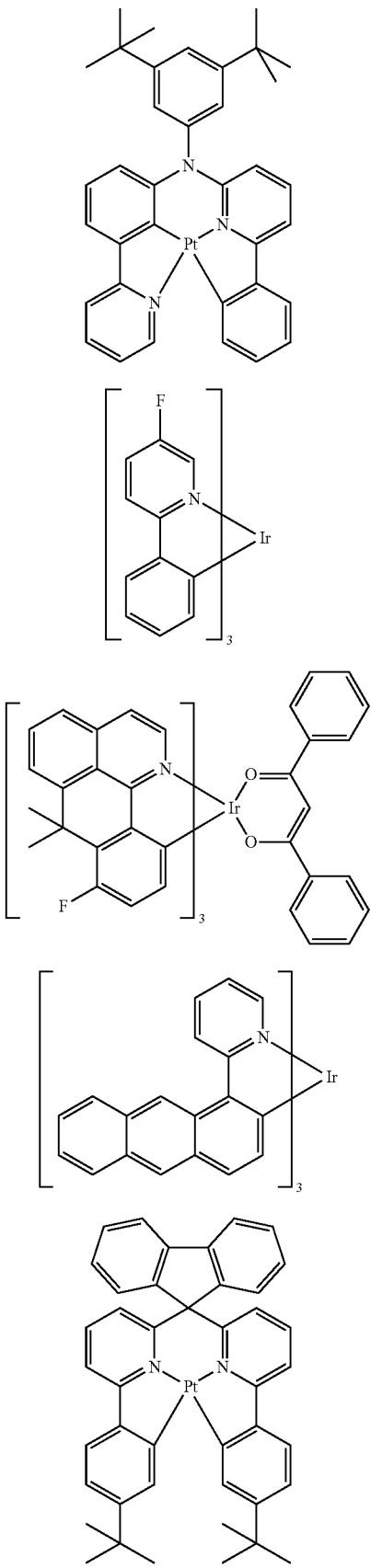
110
-continued
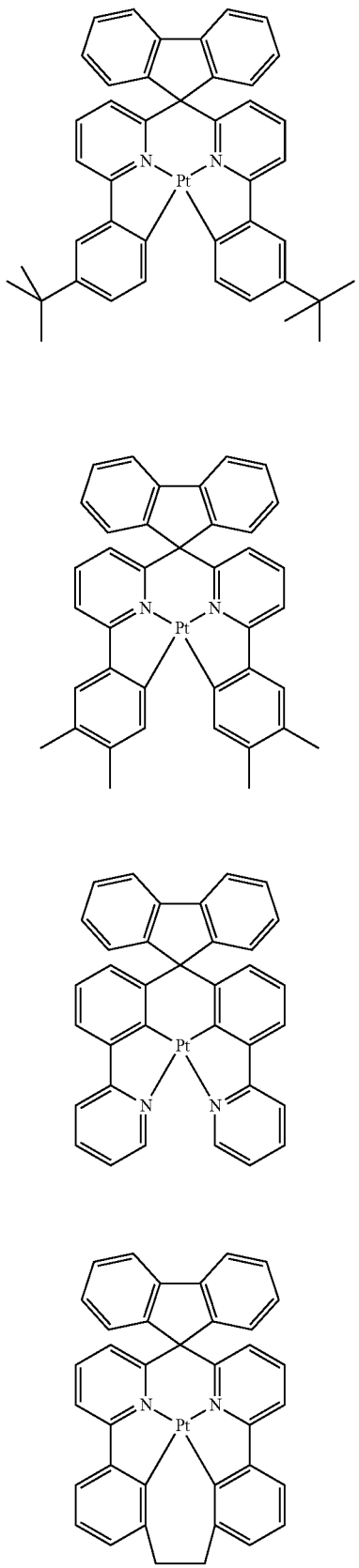

111
-continued
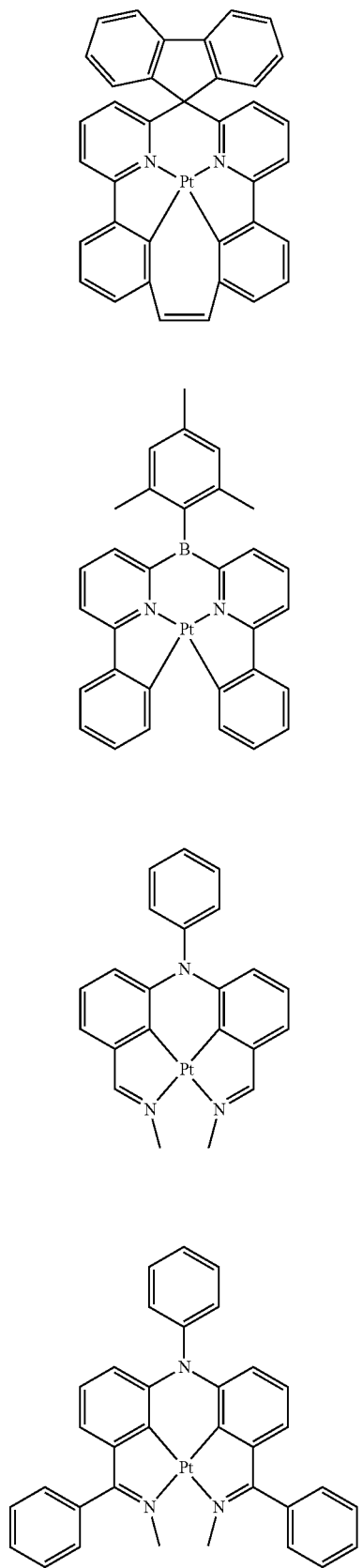
112
-continued
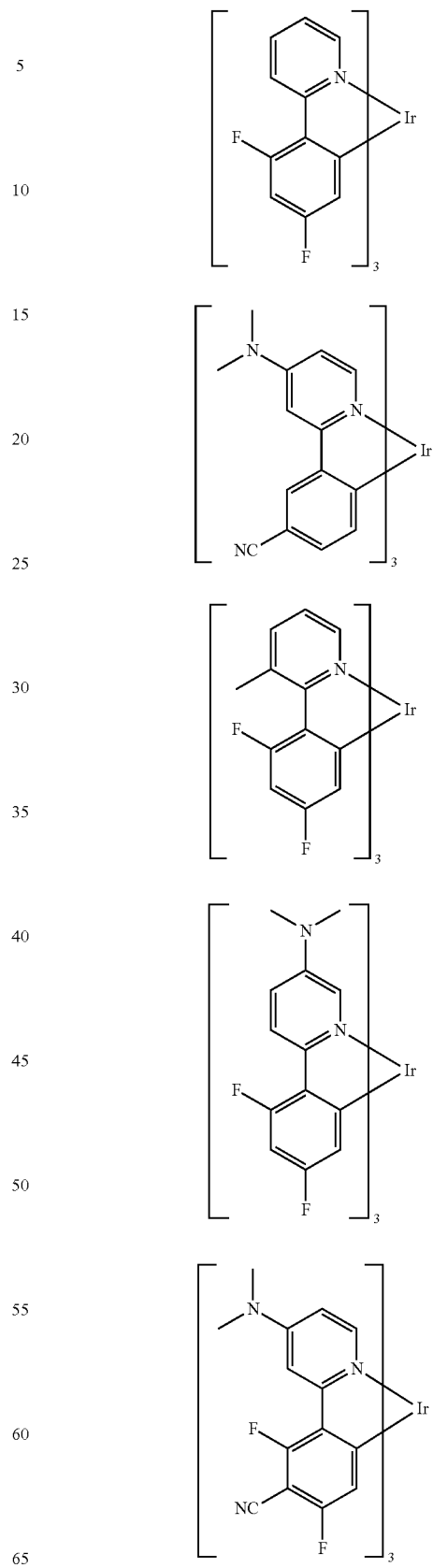

113
-continued
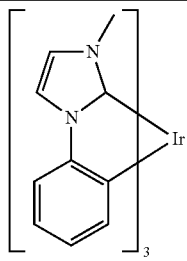
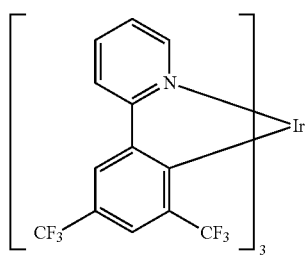
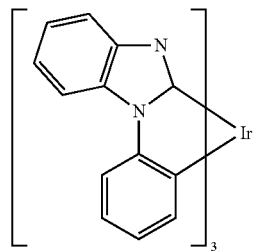
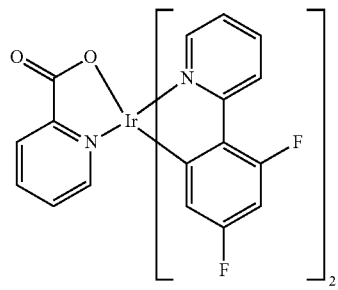
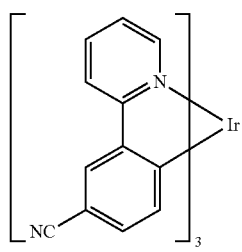
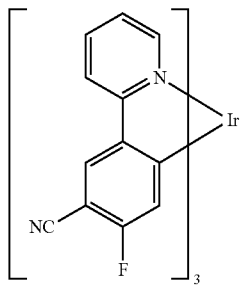
114
-continued
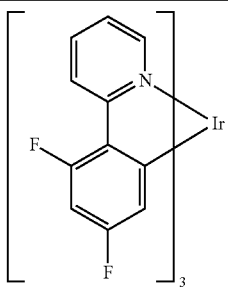
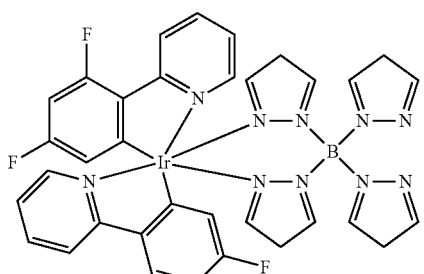
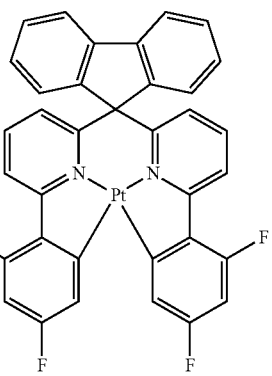
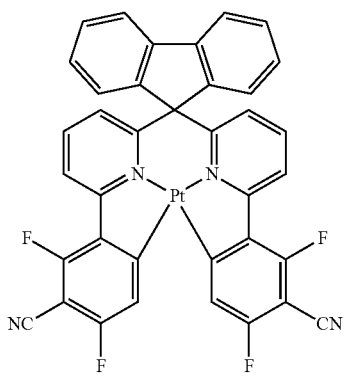
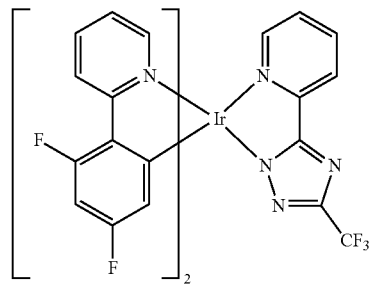

115
-continued
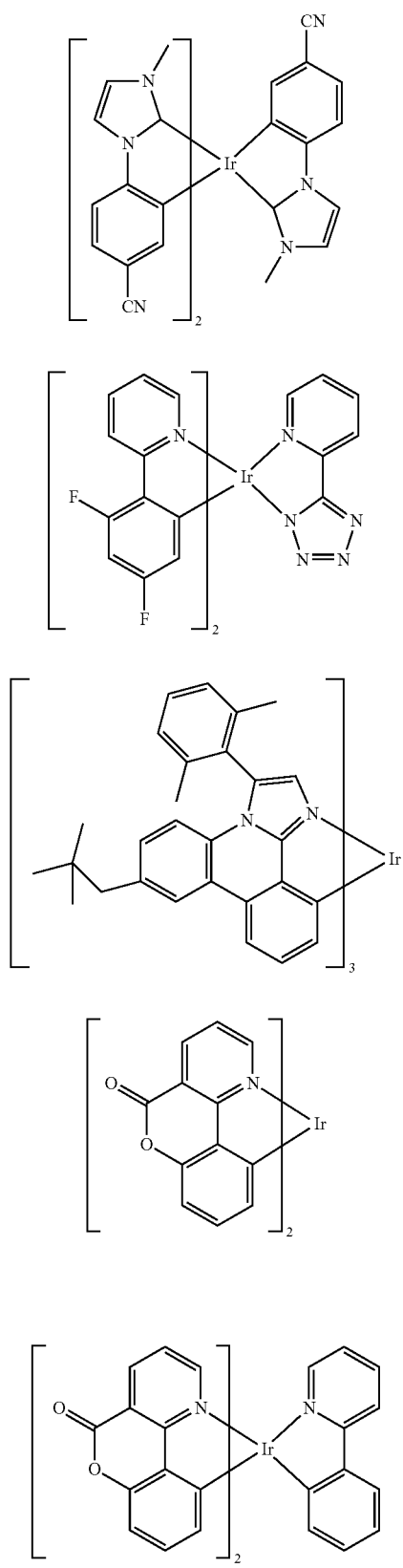
116
-continued
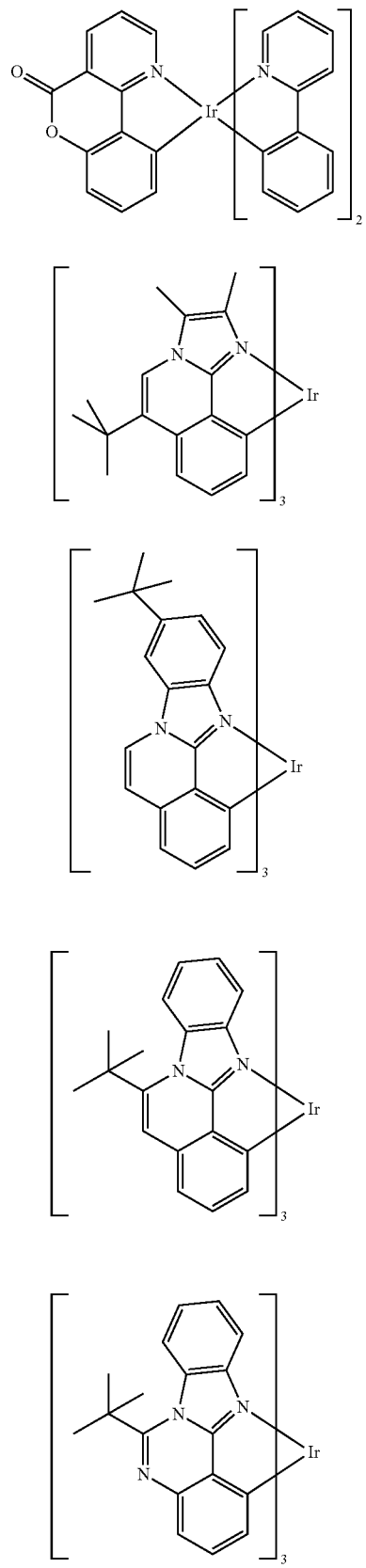

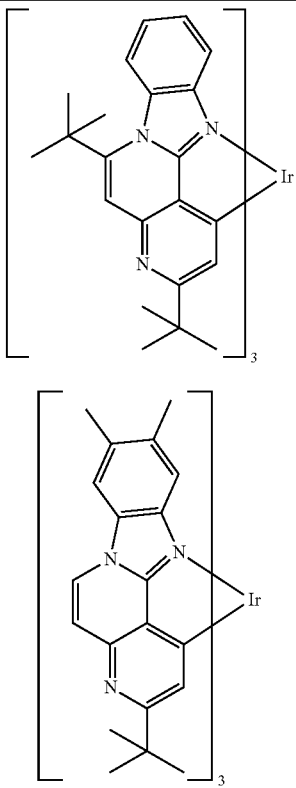

Preferred fluorescent emitters are selected from the class of the arylamines. An arylamine or aromatic amine in the sense of this invention is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms. Preferred examples thereof are aromatic anthracen amines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position. Further preferred emitters are indenofluorenamines or indenofluorenediamines, for example in accordance with WO 2006/108497 or WO 2006/122630, benzoindenofluorenamines or benzoindenofluorenediamines, for example in accordance with WO 2008/006449, and dibenzoindenofluorenamines or dibenzoindenofluorenediamines, for example in accordance with WO 2007/140847, and the indenofluorene derivatives containing condensed aryl groups which are disclosed in WO 2010/012328. Preference is likewise given to the pyrenarylamines disclosed in WO 2012/048780 and the as yet unpublished EP 12004426.8. Preference is likewise given to the benzoindenofluorenamines disclosed in the as yet unpublished EP 12006239.3 and the benzofluorenamines disclosed in the as yet unpublished EP 13000012.8.

Suitable matrix materials, preferably for fluorescent emitters are materials from various classes of substance. Preferred matrix materials are selected from the classes of the oligoarylenes (for example 2,2',7,7'-tetraphenyl-spirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 2004/081017), the hole-conducting compounds (for example in accordance with WO 2004/058911), the electron-conducting corn pounds, in particular ketones, phosphine oxides, sulfoxides, etc. (for example in accordance with WO 2005/084081 and WO 2005/084082), the atropisomers (for example in accordance with WO 2006/048268), the boronic acid derivatives (for example in accordance with WO 2006/117052) or the benzanthracenes (for example in accordance with WO 2008/145239). Particularly preferred matrix materials are selected from the classes of the oligoarylenes, comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes, comprising anthracene, benzanthracene, benzophenanthrene and/or pyrene or atropisomers of these compounds. An oligoarylene in the sense of this invention is intended to be taken to mean a compound in which at least three aryl or arylene groups are bonded to one another. Preference is furthermore given to the anthracene derivatives disclosed in WO 2006/097208, WO 2006/131192, WO 2007/065550, WO 2007/110129, WO 2007/065678, WO 2008/145239, WO 2009/100925, WO 2011/054442 and EP 1553154, and the pyrene compounds disclosed in EP 1749809, EP 1905754 and US 2012/0187826.

Preferred matrix materials for phosphorescent emitters, besides the compounds according to the invention, are aromatic ketones, aromatic phosphine oxides or aromatic sulfoxides or sulfones, for example in accordance with WO 2004/013080, WO 2004/093207, WO 2006/005627 or WO 2010/006680, triarylamines, carbazole derivatives, for example CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example in accordance with WO 2007/063754 or WO 2008/056746, indenocarbazole derivatives, for example in accordance with WO 2010/136109, WO 2011/000455 or WO 2013/041176, azacarbazole derivatives, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, diazasilole or tetraazasilole derivatives, for example in accordance with WO 2010/054729, diazaphosphole derivatives, for example in accordance with WO 2010/054730, bridged carbazole derivatives, for example in accordance with US 2009/0136779, WO 2010/050778, WO 2011/042107, WO 2011/088877 or WO 2012/143080, triphenylene derivatives, for example in accordance with WO 2012/048781, or lactams, for example in accordance with WO 2011/116865 or WO 2011/137951.

Suitable charge-transport materials, as can be used in the hole-injection or hole-transport layer or in the electron-transport layer of the organic electroluminescent device according to the invention, are, for example, the compounds disclosed in Y. Shirota et al., Chem. Rev. 2007, 107(4), 953-1010, or other materials as are employed in these layers in accordance with the prior art.

It is generally preferred for one or more of the hole-transport layers to be p-doped and/or for one or more of the electron-transport layers to be n-doped. p-Dopants and n-dopants which are suitable for this purpose are described, for example, in Chem. Rev. 2007, 107, 1233-1271.

Materials which can be used for the electron-transport layer are all materials as are used in accordance with the prior art as electron-transport materials in the electron-transport layer. Particularly suitable are aluminium complexes, for example $Alq_3$, zirconium complexes, for example $Zrq_4$, benzimidazole derivatives, triazine derivatives, pyrimidine derivatives, pyridine derivatives, pyrazine derivatives, quinoxaline derivatives, quinoline derivatives, oxadiazole derivatives, aromatic ketones, lactams, boranes, diazaphosphole derivatives and phosphine oxide derivatives. Furthermore suitable materials are derivatives of the above-mentioned compounds, as disclosed in JP 2000/053957, WO 2003/060956, WO 2004/028217, WO 2004/080975 and WO 2010/072300.

Preferred hole-transport materials which can be used in a hole-transport, hole-injection or electron-blocking layer in the electroluminescent device according to the invention are indenofluorenamine derivatives (for example in accordance with WO 06/122630 or WO 06/100896), the amine derivatives disclosed in EP 1661888, hexaazatriphenylene derivatives (for example in accordance with WO 01/049806), amine derivatives containing condensed aromatic rings (for example in accordance with U.S. Pat. No. 5,061,569), the amine derivatives disclosed in WO 95/09147, monobenzoindenofluorenamines (for example in accordance with WO 08/006449), dibenzoindenofluorenamines (for example in accordance with WO 07/140847), spirobifluorenamines (for example in accordance with WO 2012/034627 or the as yet unpublished EP 12000929.5), fluorenamines (for example in accordance with the as yet unpublished applications EP 12005369.9, EP 12005370.7 and EP 12005371.5), spirodibenzopyranamines (for example in accordance with WO 2013/083216) and dihydroacridine derivatives (for example in accordance with WO 2012/150001).

The cathode of the organic electroluminescent device preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag or Al, can also be used in addition to the said metals, in which case combinations of the metals, such as, for example, Ca/Ag, Mg/Ag or Ag/Ag, are generally used. It may also be preferred to introduce a thin interlayer of a material having a high dielectric constant between a metallic cathode and the organic semiconductor. Suitable for this purpose are, for example, alkali metal fluorides or alkaline-earth metal fluorides, but also the corresponding oxides or carbonates (for example LiF, $Li_2O$, $BaF_2$, MgO, NaF, CsF, $Cs_2CO_3$, etc.). Furthermore, lithium quinolinate (LiQ) can be used for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example Al/Ni/$NiO_x$, Al/$PtO_x$) may also be preferred. For some applications, at least one of the electrodes must be transparent or partially transparent in order to facilitate either irradiation of the organic material (organic solar cells) or the coupling-out of light (OLEDs, O-lasers). Preferred anode materials here are conductive mixed metal oxides. Particular preference is given to indium tin oxide (ITO) or indium zinc oxide (IZO). Preference is furthermore given to conductive, doped organic materials, in particular conductive, doped polymers. Furthermore, the anode may also consist of a plurality of layers, for example of an inner layer of ITO and an outer layer of a metal oxide, preferably tungsten oxide, molybdenum oxide or vanadium oxide.

The device is appropriately (depending on the application) structured, pro vided with contacts and finally sealed, since the lifetime of the devices according to the invention is shortened in the presence of water and/or air.

In a preferred embodiment, the organic electroluminescent device according to the invention is characterised in that one or more layers are coated by means of a sublimation process, in which the materials are applied by vapour deposition in vacuum sublimation units at an initial pressure of less than $10^{-5}$ mbar, preferably less than $10^{-6}$ mbar. However, it is also possible here for the initial pressure to be even lower, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, nozzle printing or offset printing, but particularly preferably LITI (light induced thermal imaging, thermal transfer printing) or ink-jet printing. Soluble compounds of the formula (I) are necessary for this purpose. High solubility can be achieved through suitable substitution of the compounds.

For the production of an organic electroluminescent device according to the invention, it is furthermore preferred to apply one or more layers from solution and one or more layers by a sublimation process.

In accordance with the invention, the electronic devices comprising one or more compounds of the formula (I) can be employed in displays, as light sources in lighting applications and as light sources in medical and/or cosmetic applications (for example light therapy).

WORKING EXAMPLES

A) Synthesis Examples

Step 1: Synthesis of the Amine Building Block

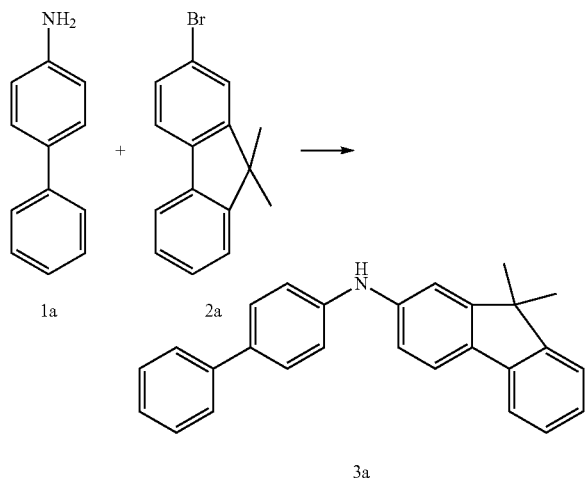

24.0 g (142 mmol, 1.2 eq.) of 4-aminobiphenyl 1a (CAS 92-67-1) are initially introduced in 950 ml of toluene together with 32.0 g (117 mmol, 1.0 eq.) of 2-bromo-9,9'-dimethylfluorene 2a (CAS 28320-31-2) and saturated with argon for 30 minutes. 1.0 g (1.8 mmol, 0.02 eq.) of 1,1*bis(diphenylphosphino)ferrocene (CAS 12150-46-8), 350 mg (1.6 mmol, 0.01 eq.) of palladium(II) acetate (CAS 3375-31-3) and 29 g (300 mmol, 2.6 eq.) of sodium tert-butoxide (CAS 865-48-5) are subsequently added, and the mixture is heated under reflux overnight. When the reaction is complete, the batch is diluted with 300 ml of toluene and extracted with water. The organic phase is dried over sodium sulfate, and the solvent is removed in a rotary evaporator. 50 ml of ethyl acetate are added to the brown oil, and the mixture is added to a mixture of heptane/ethyl acetate 20:1. The solid formed is filtered off with suction and washed with heptane. Drying gives 29 g (80 mmol, 69%) of the desired product 3a having an HPLC purity of 99.1%.

The following compounds can be obtained analogously:

| No. | Starting material 1 | Starting material 2 | Product | Yield |
|---|---|---|---|---|
| 3b | 92-67-1 | 2052-07-5 | | 71% |
| 3c | 92-67-1 | 942615-32-9 | | 61% |

-continued
| No. | Starting material 1 | Starting material 2 | Product | Yield |
|---|---|---|---|---|
| 3d | 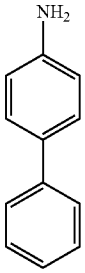 92-67-1 | 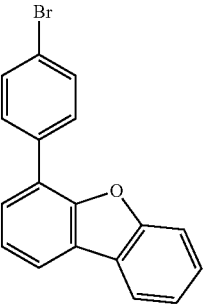 955959-84-9 | 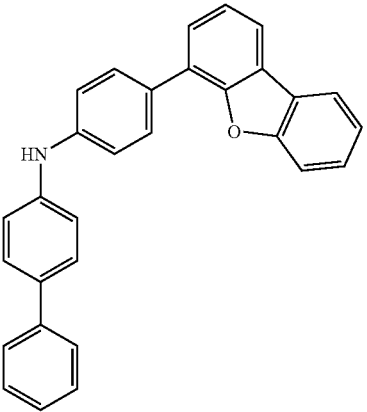 [SMILES: c1ccc(-c2ccc(Nc3ccc(-c4cccc5c4oc4ccccc45)cc3)cc2)cc1] | 78% |
| 3e | 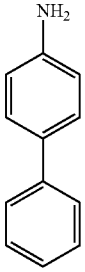 92-67-1 | 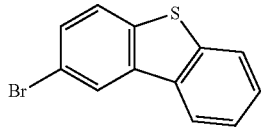 22439-61-8 | 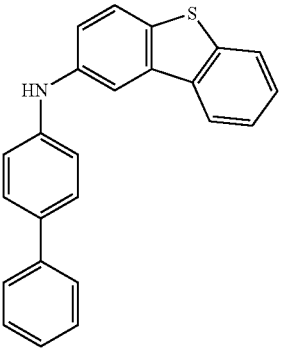 [SMILES: c1ccc(-c2ccc(Nc3ccc4sc5ccccc5c4c3)cc2)cc1] | 82% |
| 3f | 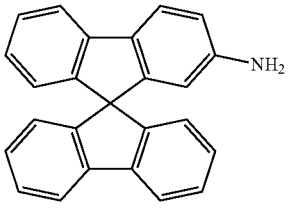 118951-68-1 | 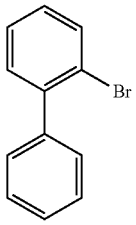 2052-07-5 | 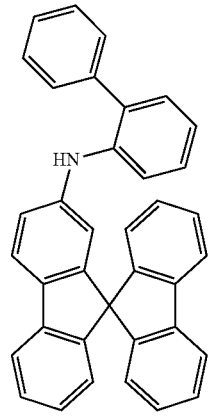 [SMILES: c1ccc(-c2ccccc2Nc2ccc3c(c2)C2(c4ccccc4-c4ccccc42)c2ccccc2-3)cc1] | 62% |

| No. | Starting material 1 | Starting material 2 | Product | Yield |
|---|---|---|---|---|
| 3g | | | | 47% |
| | 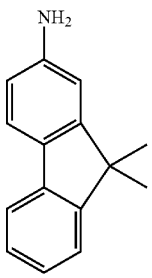<br>108714-73-4 | 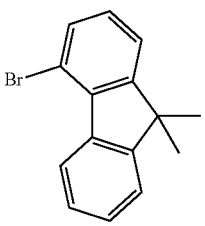<br>942615-32-9 | 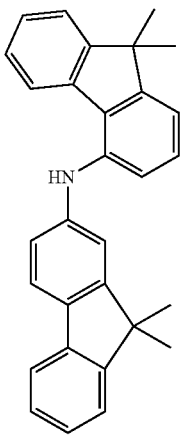 [SMILES: CC1(C)c2ccccc2-c2ccc(Nc3cccc4c3-c3ccccc3C4(C)C)cc21] | |
| 3h | | | | 92% |
| | 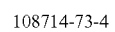<br>63344-48-9 | 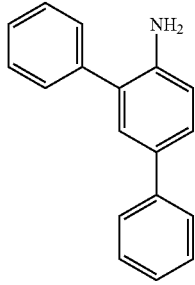<br>90-11-9 | 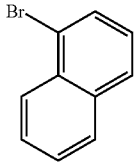 | |
| 3i | | | | 75% |
| | 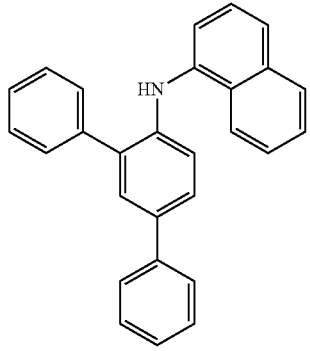 [SMILES: c1ccc(-c2ccc(Nc3cccc4ccccc34)c(-c3ccccc3)c2)cc1]<br>92-67-1 | 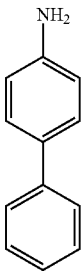<br>171408-76-7 | 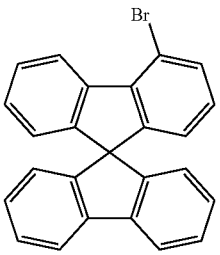 | |

-continued
| No. | Starting material 1 | Starting material 2 | Product | Yield |
|---|---|---|---|---|
| 3j | 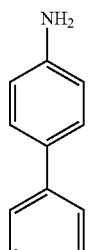 92-67-1 | 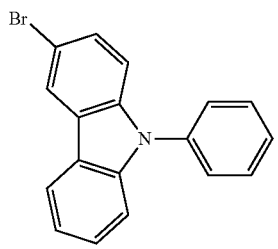 1153-85-1 | 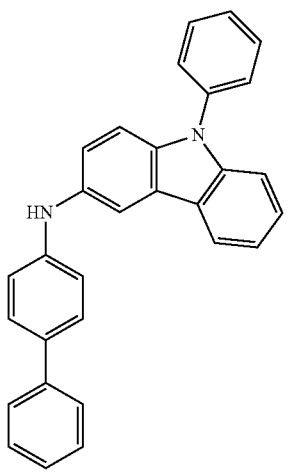 [SMILES: c1ccc(-c2ccc(Nc3ccc4c(c3)c3ccccc3n4-c3ccccc3)cc2)cc1] | 84% |
| 3k | 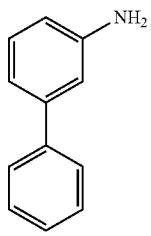 90-41-5 | 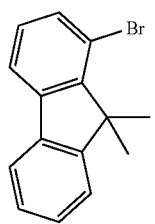 1225053-54-2 | 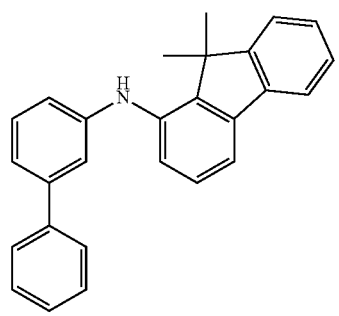 [SMILES: CC1(C)c2ccccc2-c2cccc(Nc3cccc(-c4ccccc4)c3)c21] | 62% |
| 3l | 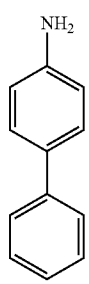 92-67-1 | 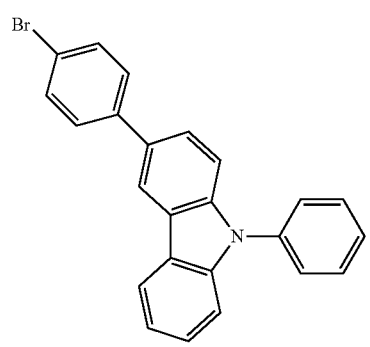 [SMILES: Brc1ccc(-c2ccc3c(c2)c2ccccc2n3-c2ccccc2)cc1] | 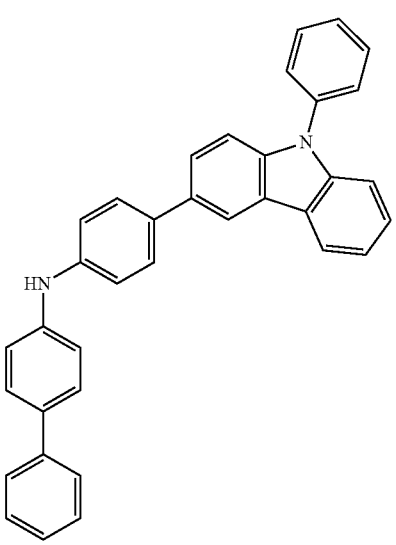 1028647-93-9 | 78% |

-continued
| No. | Starting material 1 | Starting material 2 | Product | Yield |
|---|---|---|---|---|
| 3m | 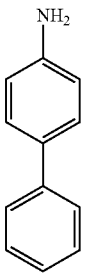 92-67-1 | 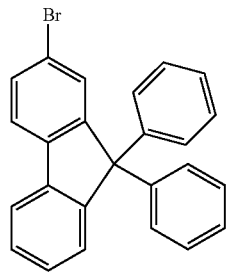 474918-32-6 | 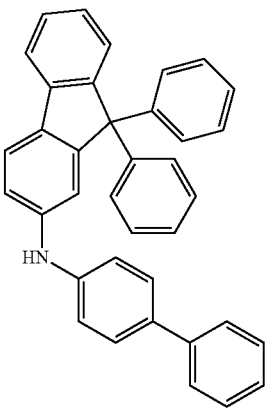 [SMILES: c1ccc(-c2ccc(Nc3ccc4c(c3)C(c3ccccc3)(c3ccccc3)c3ccccc3-4)cc2)cc1] | 74% |
| 3n | 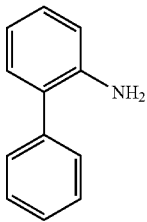 90-41-5 | 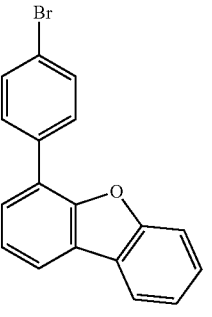 955959-84-9 | 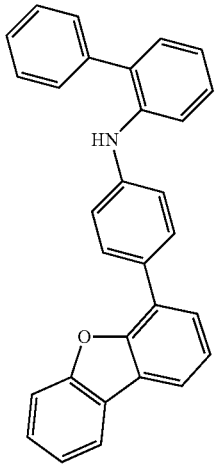 [SMILES: c1ccc(-c2ccccc2Nc2ccc(-c3cccc4c3oc3ccccc34)cc2)cc1] | 62% |
| 3o | 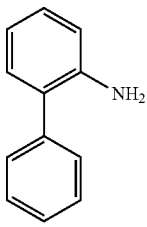 90-41-5 | 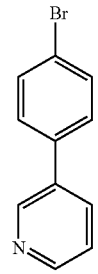 129013-83-8 | 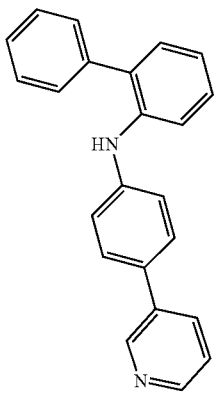 [SMILES: c1ccc(-c2ccccc2Nc2ccc(-c3cccnc3)cc2)cc1] | 67% |

-continued
| No. | Starting material 1 | Starting material 2 | Product | Yield |
|---|---|---|---|---|
| 3p | 90-41-5 | 103068-20-8 | | 93% |
| 3q | 90-41-5 | 715-50-4 | | 88% |
| 3r | 90-41-5 | 28320-31-2 | | 74% |
Step 2: Introduction of the Bridge
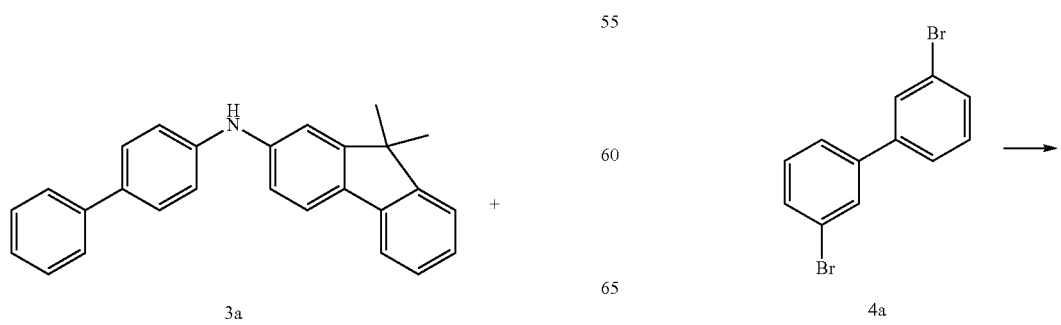
3a +
4a 29 g (80 mmol, 1.0 eq.) of the intermediate 3a are dissolved in 600 ml of toluene together with 25 g (80 mmol, 1.0 eq.) of 3,3'-dibromo-1,1'-biphenyl 4a (CAS 16400-51-4) and degassed for 30 minutes. 45 g (240 mmol, 3.0 eq.) of sodium tert-butoxide, 890 mg (0.40 mmol, 0.050 eq.) of palladium(II) acetate and 8 ml (8.0 mmol, 0.10 eq.) of a 1M tri-tert-butylphosphine solution are subsequently added. The batch is heated under reflux overnight and, when the reaction is complete, filtered twice through aluminium oxide with toluene. After removal of the solvent in a rotary evaporator, the oil is dissolved in a little THF and introduced into heptane. The solid formed is filtered off with suction and purified by means of hot extraction in heptane/toluene 1:1, giving 16.6 g (28 mmol, 35%) of the desired product 5a.

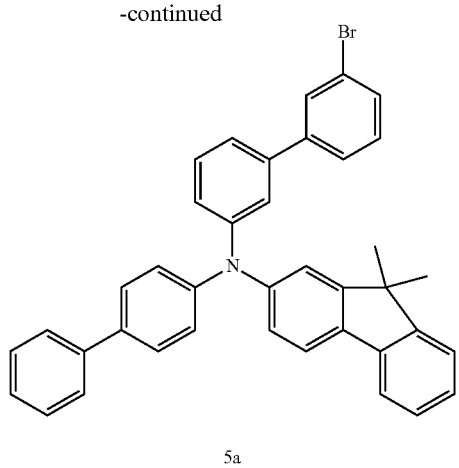

5a

The following compounds can be obtained analogously:

| No. | Starting material 3 | Starting material 4 |
|---|---|---|
| 5b | 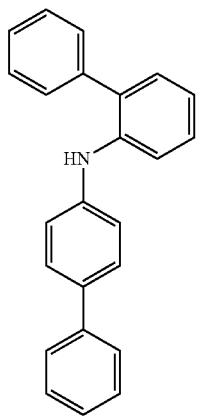 [SMILES: c1ccc(-c2ccc(Nc3ccccc3-c3ccccc3)cc2)cc1] | 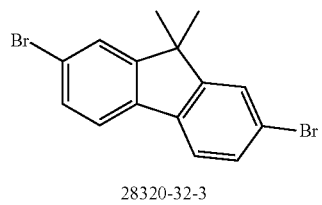 28320-32-3 |
| 5c | 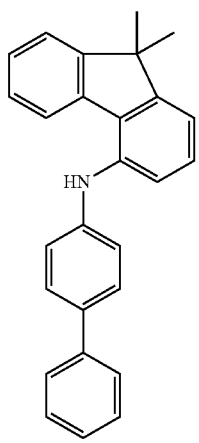 [SMILES: CC1(C)c2ccccc2-c2c(Nc3ccc(-c4ccccc4)cc3)cccc21] | 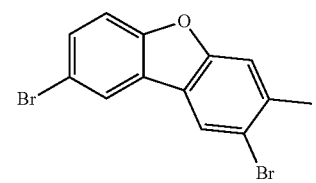 10016-52-1 |

-continued
| | | | |
|---|---|---|---|
| 5d | 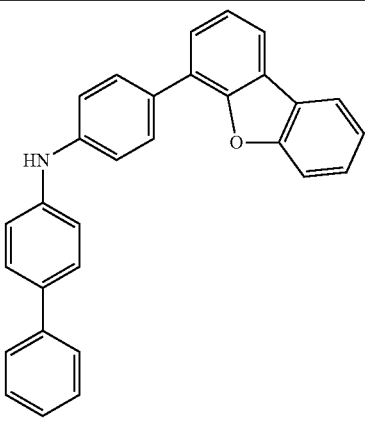 | 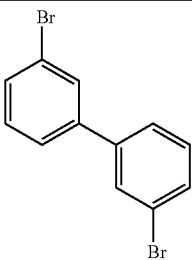16400-51-4 | |
| 5e | 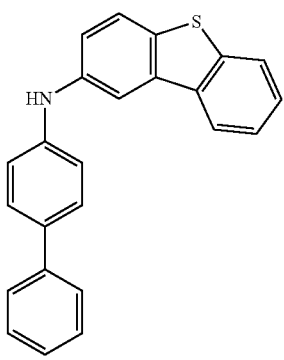 [SMILES: c1ccc(-c2ccc(Nc3ccc4sc5ccccc5c4c3)cc2)cc1] | 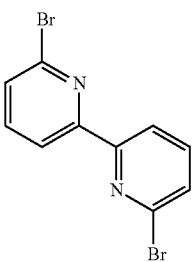49669-22-9 | |
| 5f | 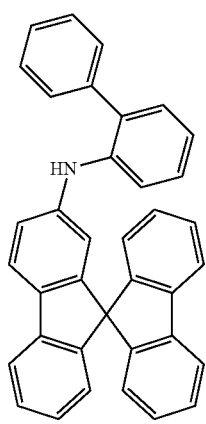 [SMILES: c1ccc(-c2ccccc2Nc2ccc3c(c2)C2(c4ccccc4-c4ccccc42)c2ccccc2-3)cc1] | 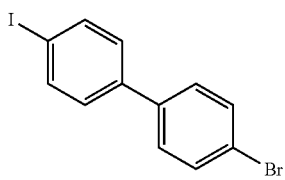105946-82-5 | |
| 5g | 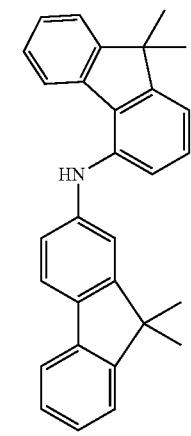 [SMILES: CC1(C)c2ccccc2-c2ccc(Nc3cccc4c3-c3ccccc3C4(C)C)cc21] | 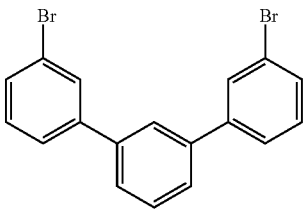95962-62-2 | |

5h
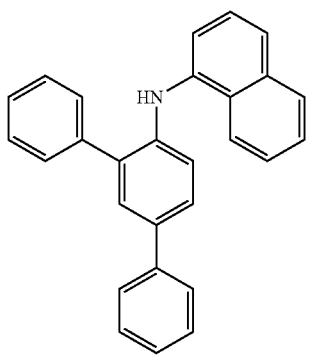 [SMILES: c1ccc(-c2ccc(Nc3cccc4ccccc34)c(-c3ccccc3)c2)cc1]
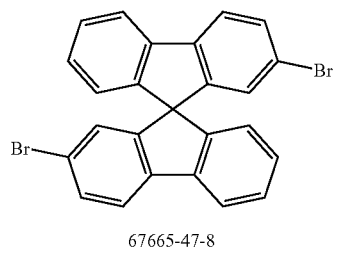 [SMILES: Brc1ccc2c(c1)C1(c3ccccc3-2)c2ccccc2-c2ccc(Br)cc21]
67665-47-8
5i
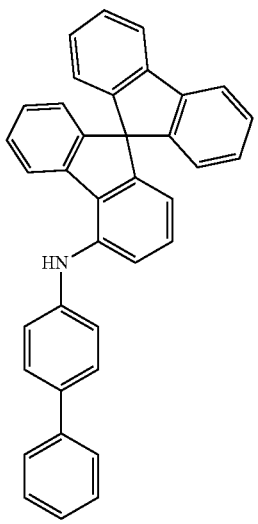 [SMILES: c1ccc(-c2ccc(Nc3cccc4c3-c3ccccc3C43c4ccccc4-c4ccccc43)cc2)cc1]
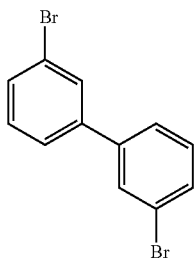
16400-51-4
5j
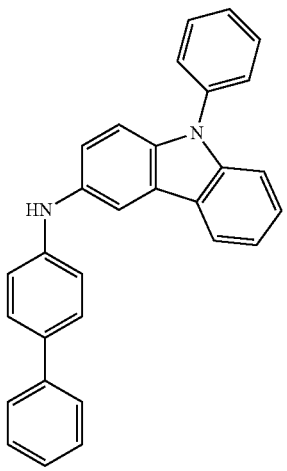 [SMILES: c1ccc(-c2ccc(Nc3ccc4c(c3)c3ccccc3n4-c3ccccc3)cc2)cc1]
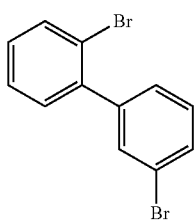
49602-90-6

5k
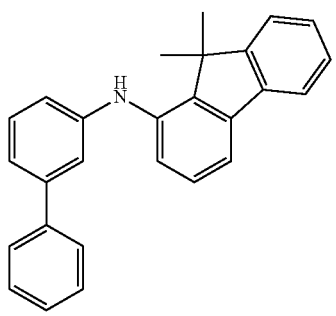 [SMILES: CC1(C)c2ccccc2-c2cccc(Nc3cccc(-c4ccccc4)c3)c21]
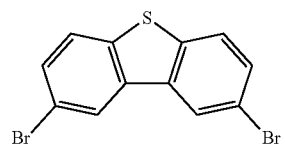
31574-87-5
5l
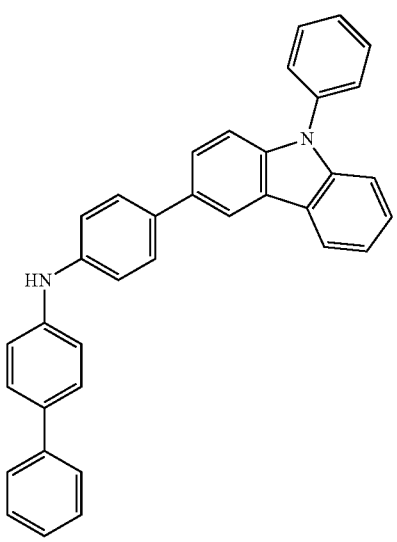 [SMILES: c1ccc(-c2ccc(Nc3ccc(-c4ccc5c(c4)c4ccccc4n5-c4ccccc4)cc3)cc2)cc1]
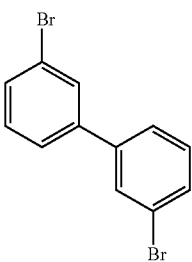
16400-51-4
5m
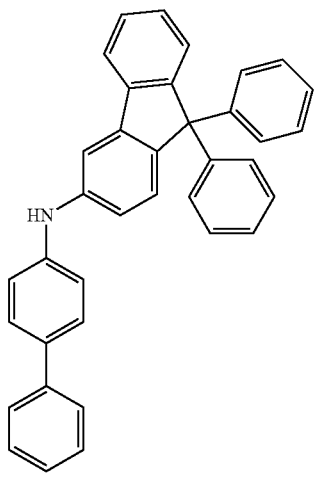 [SMILES: c1ccc(-c2ccc(Nc3ccc4c(c3)-c3ccccc3C4(c3ccccc3)c3ccccc3)cc2)cc1]
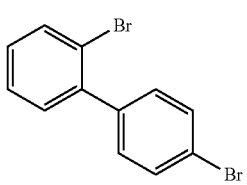
49602-91-7

| | | | |
|---|---|---|---|
| 5n | 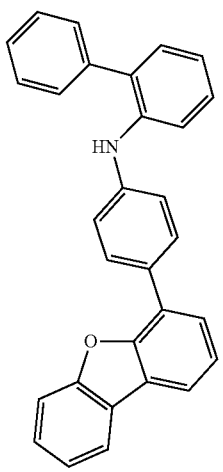 [SMILES: c1ccc(-c2ccccc2Nc2ccc(-c3cccc4c3oc3ccccc34)cc2)cc1] | 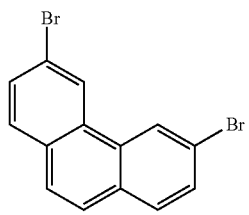 174735-02-5 | |
| 5o | 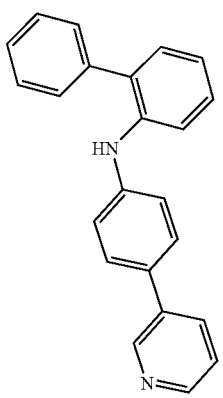 [SMILES: c1ccc(-c2ccccc2Nc2ccc(-c3cccnc3)cc2)cc1] | 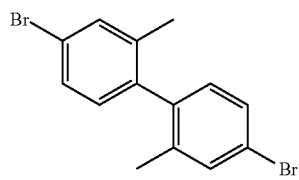 31458-17-0 | |
| 5p | 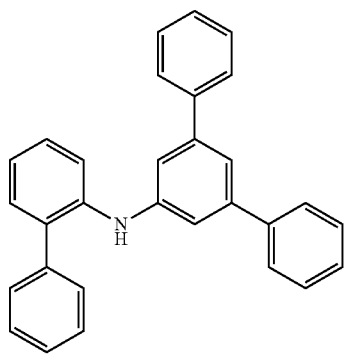 [SMILES: c1ccc(-c2cc(Nc3ccccc3-c3ccccc3)cc(-c3ccccc3)c2)cc1] | 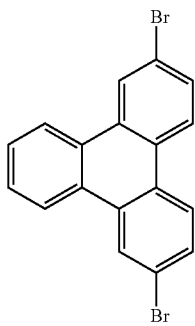 888041-37-0 | |
| 5q | 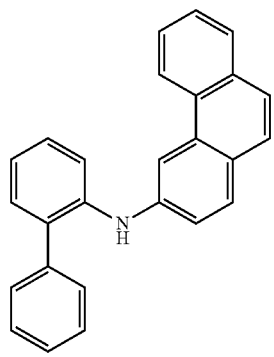 [SMILES: c1ccc(-c2ccccc2Nc2ccc3ccc4ccccc4c3c2)cc1] | 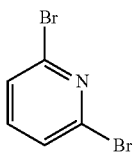 626-05-1 | |

-continued
5r 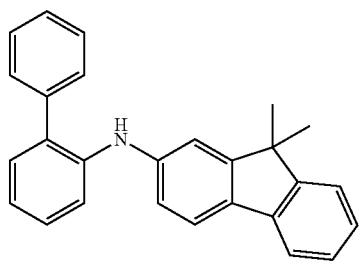 [SMILES: CC1(C)c2ccccc2-c2ccc(Nc3ccccc3-c3ccccc3)cc21] 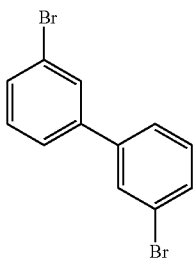
16400-51-4
5s 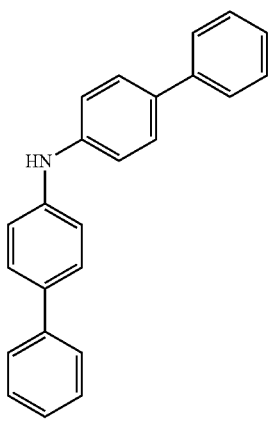 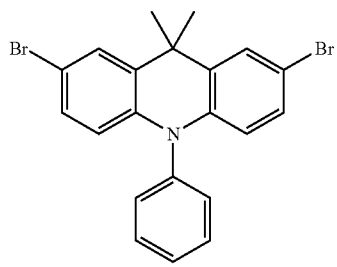
1333316-36-1
5t 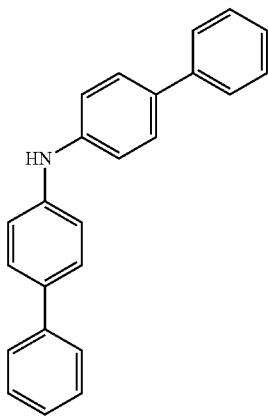 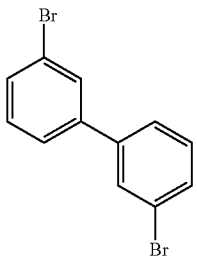
16400-51-4
102113-98-4
5u 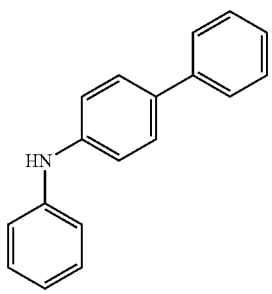 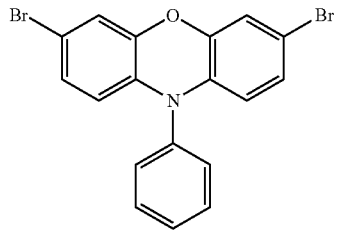
71041-12-8
32228-99-2

5v
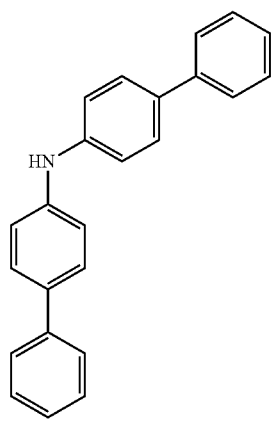 [SMILES: c1ccc(-c2ccc(Nc3ccc(-c4ccccc4)cc3)cc2)cc1]
102113-98-4
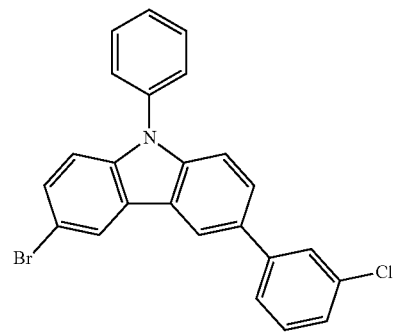 [SMILES: Clc1cccc(-c2ccc3c(c2)c2cc(Br)ccc2n3-c2ccccc2)c1]
| No. | Product | Yield |
|---|---|---|
| 5b | | 49% |
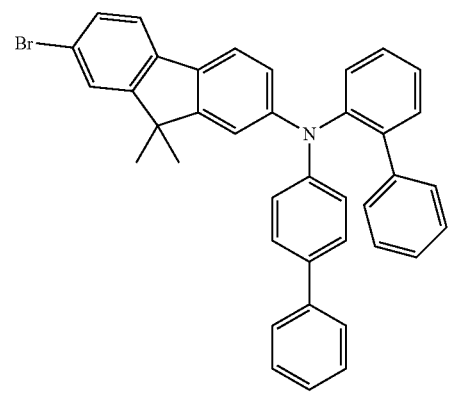 [SMILES: CC1(C)c2cc(Br)ccc2-c2ccc(N(c3ccc(-c4ccccc4)cc3)c3ccccc3-c3ccccc3)cc21]
| 5c | | 37% |
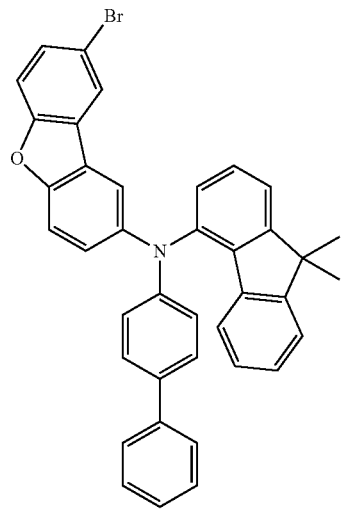 [SMILES: CC1(C)c2ccccc2-c2c(N(c3ccc(-c4ccccc4)cc3)c3ccc4oc5ccc(Br)cc5c4c3)cccc21]

-continued
5d 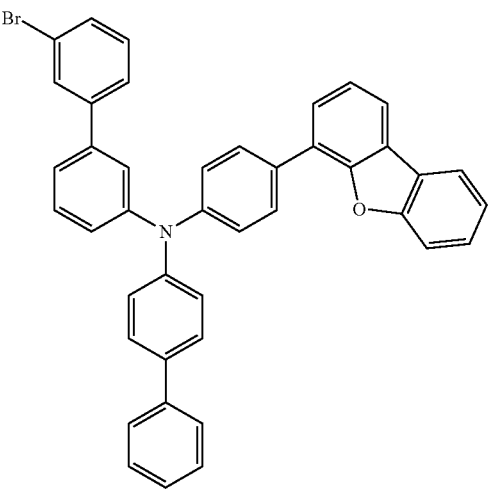 [SMILES: Brc1cccc(-c2cccc(N(c3ccc(-c4ccccc4)cc3)c3ccc(-c4cccc5c4oc4ccccc45)cc3)c2)c1] 72%
5e 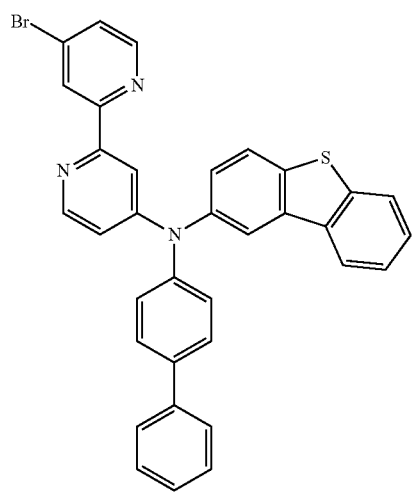 [SMILES: Brc1ccnc(-c2cc(N(c3ccc(-c4ccccc4)cc3)c3ccc4sc5ccccc5c4c3)ccn2)c1] 28%
5f 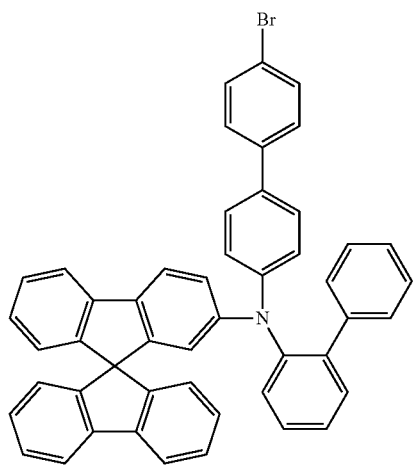 [SMILES: Brc1ccc(-c2ccc(N(c3ccc4c(c3)C3(c5ccccc5-c5ccccc53)c3ccccc3-4)c3ccccc3-c3ccccc3)cc2)cc1] 82%

-continued
| | | |
|---|---|---|
| 5g | 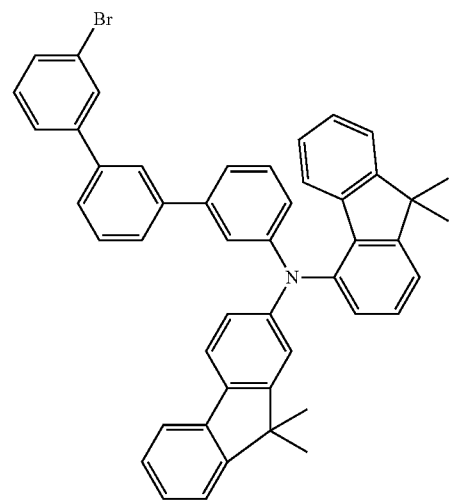 [SMILES: CC1(C)c2ccccc2-c2ccc(N(c3cccc(-c4cccc(-c5cccc(Br)c5)c4)c3)c3cccc4c3-c3ccccc3C4(C)C)cc21] | 32% |
| 5h | 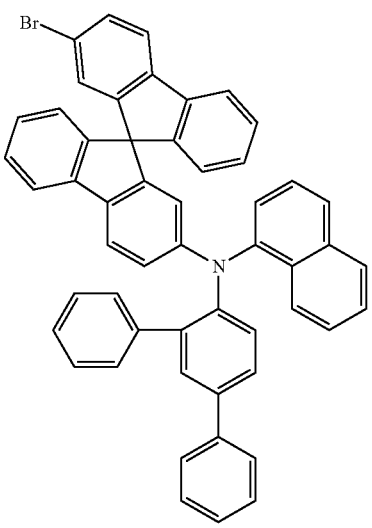 [SMILES: Brc1ccc2c(c1)C1(c3ccccc3-2)c2ccccc2-c2ccc(N(c3ccc(-c4ccccc4)cc3-c3ccccc3)c3cccc4ccccc34)cc21] | 46% |
| 5i | 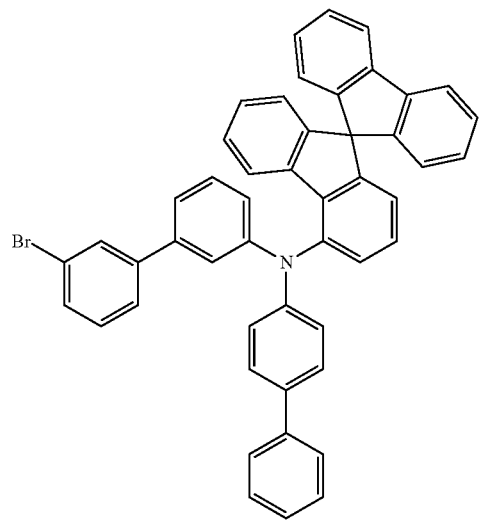 [SMILES: Brc1cccc(-c2cccc(N(c3ccc(-c4ccccc4)cc3)c3cccc4c3-c3ccccc3C43c4ccccc4-c4ccccc43)c2)c1] | 41% |

5j 31%
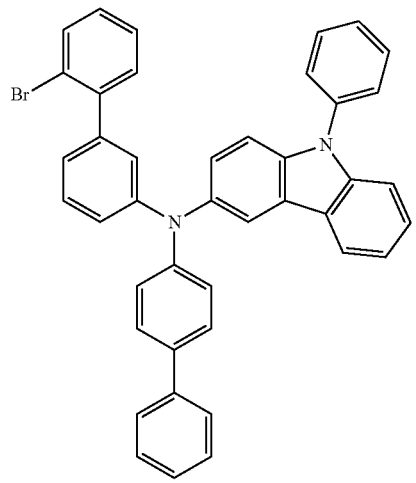 [SMILES: Brc1ccccc1-c1cccc(N(c2ccc(-c3ccccc3)cc2)c2ccc3c(c2)c2ccccc2n3-c2ccccc2)c1]
5k 27%
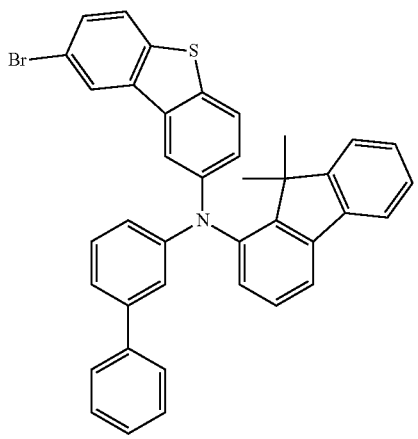 [SMILES: CC1(C)c2ccccc2-c2cccc(N(c3cccc(-c4ccccc4)c3)c3ccc4sc5ccc(Br)cc5c4c3)c21]
5l 38%
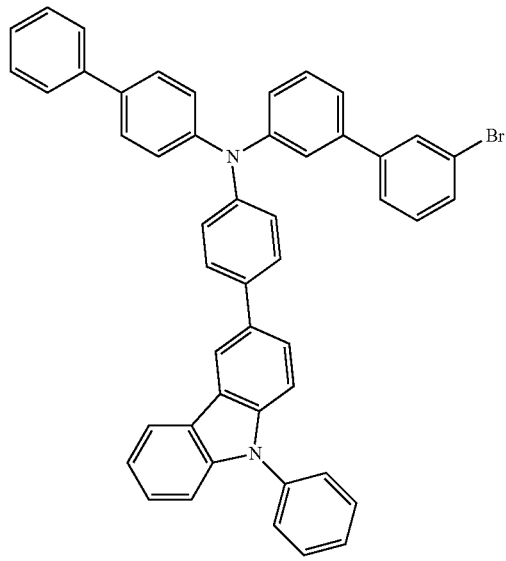 [SMILES: Brc1cccc(-c2cccc(N(c3ccc(-c4ccccc4)cc3)c3ccc(-c4ccc5c(c4)c4ccccc4n5-c4ccccc4)cc3)c2)c1]

-continued
5m 56%
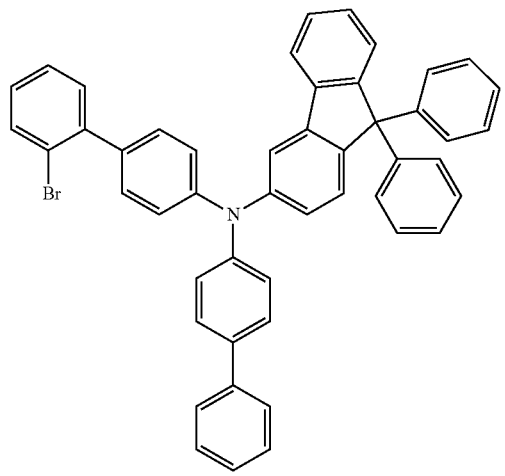 [SMILES: Brc1ccccc1-c1ccc(N(c2ccc(-c3ccccc3)cc2)c2ccc3c(c2)-c2ccccc2C3(c2ccccc2)c2ccccc2)cc1]
5n 33%
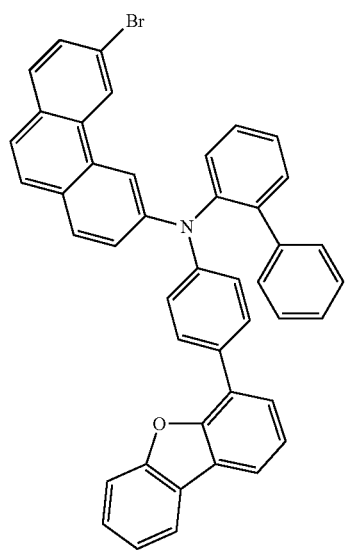 [SMILES: Brc1ccc2ccc3ccc(N(c4ccc(-c5cccc6c5oc5ccccc56)cc4)c4ccccc4-c4ccccc4)cc3c2c1]
5o 47%
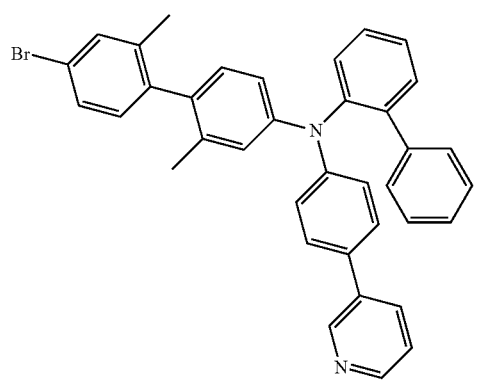 [SMILES: Cc1cc(Br)ccc1-c1ccc(N(c2ccc(-c3cccnc3)cc2)c2ccccc2-c2ccccc2)cc1C]

| | | |
|---|---|---|
| 5p | | 24% |
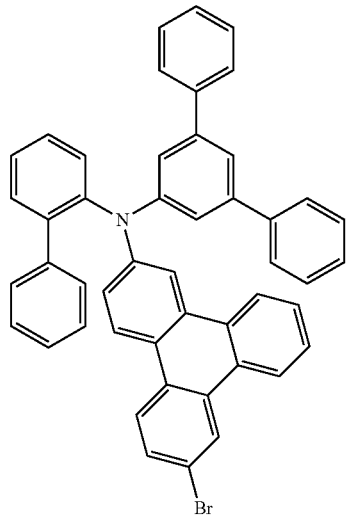 [SMILES: Brc1ccc2c3ccc(N(c4cc(-c5ccccc5)cc(-c5ccccc5)c4)c4ccccc4-c4ccccc4)cc3c3ccccc3c2c1]
| | | |
|---|---|---|
| 5q | | 81% |
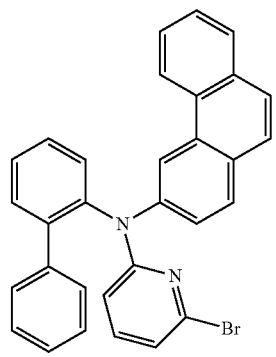 [SMILES: Brc1cccc(N(c2ccc3ccc4ccccc4c3c2)c2ccccc2-c2ccccc2)n1]
| | | |
|---|---|---|
| 5r | | 57% |
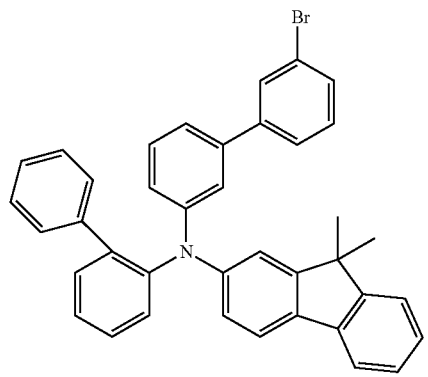 [SMILES: CC1(C)c2ccccc2-c2ccc(N(c3cccc(-c4cccc(Br)c4)c3)c3ccccc3-c3ccccc3)cc21]

5s 29%
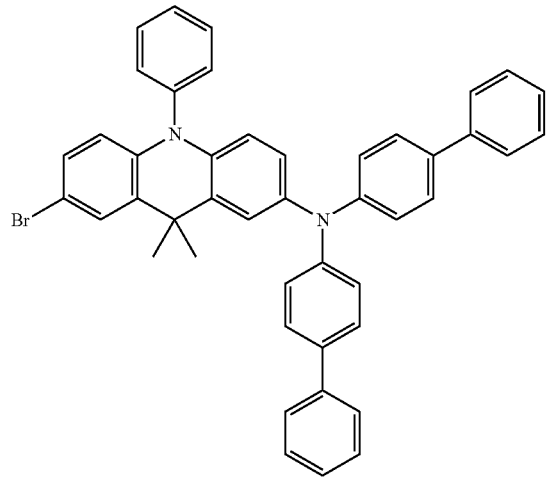 [SMILES: CC1(C)c2cc(Br)ccc2N(c2ccccc2)c2ccc(N(c3ccc(-c4ccccc4)cc3)c3ccc(-c4ccccc4)cc3)cc21]
5t 36%
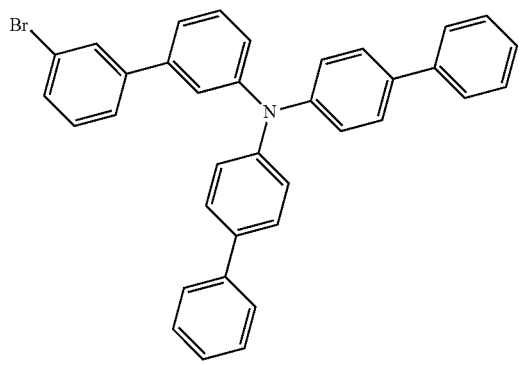 [SMILES: Brc1cccc(-c2cccc(N(c3ccc(-c4ccccc4)cc3)c3ccc(-c4ccccc4)cc3)c2)c1]
5u 44%
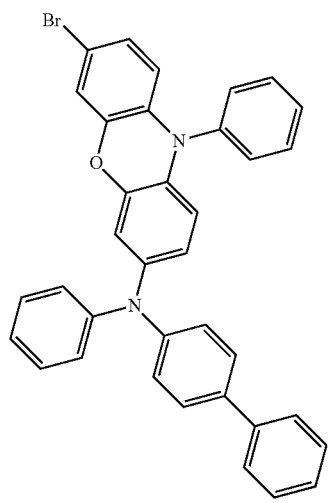 [SMILES: Brc1ccc2c(c1)Oc1cc(N(c3ccccc3)c3ccc(-c4ccccc4)cc3)ccc1N2c1ccccc1]

| 5v | 89% |
|---|---|

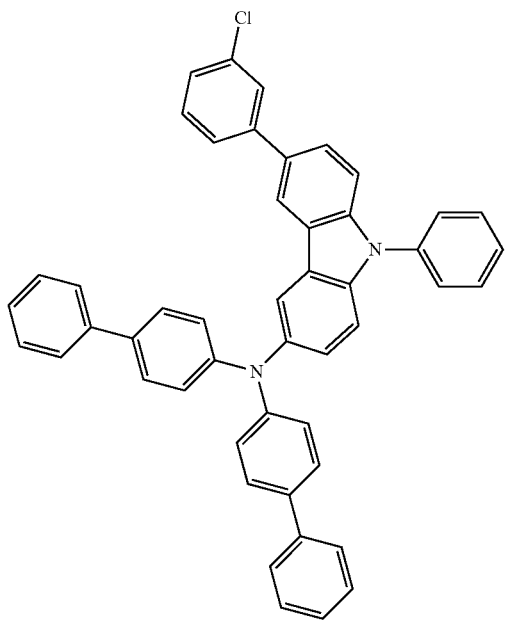 [SMILES: Clc1cccc(-c2ccc3c(c2)c2cc(N(c4ccc(-c5ccccc5)cc4)c4ccc(-c5ccccc5)cc4)ccc2n3-c2ccccc2)c1]

Regarding Example 5v

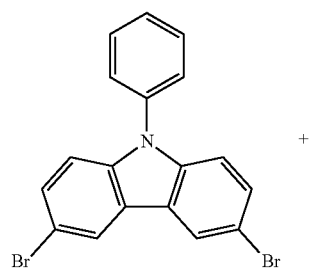

+

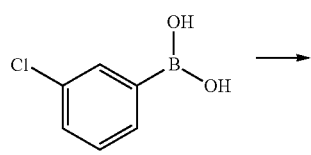

→

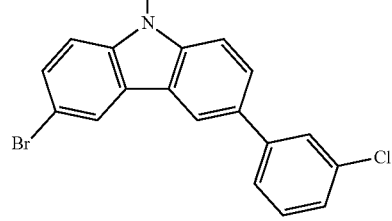

50.0 g (125 mmol, 1.0 eq.) of 3,6-dibromo-9-phenylcarbazole (CAS 57103-20-5) are initially introduced in a mixture of 400 ml of water, 400 ml of dioxane and 400 ml of toluene together with 19.5 g (125 mmol, 1.0 eq.) of 3-chlorobenzeneboronic acid (CAS 6350-60-6) and degassed for 30 minutes. After addition of 280 mg (1.25 mmol, 1 mol-%) of palladium(II) acetate and 1.14 g (3.75 mmol, 3 mol-%) of tri-o-tolylphosphine, the batch is heated under reflux overnight, and, when the reaction is complete, a little water is added. The organic phase is separated off and extracted twice with water, After the organic phase has been dried over sodium sulfate, the residue is recrystallised from heptane/toluene, giving 44.8 g (103 mmol, 83%) of a beige solid.

Step 3: Boronation

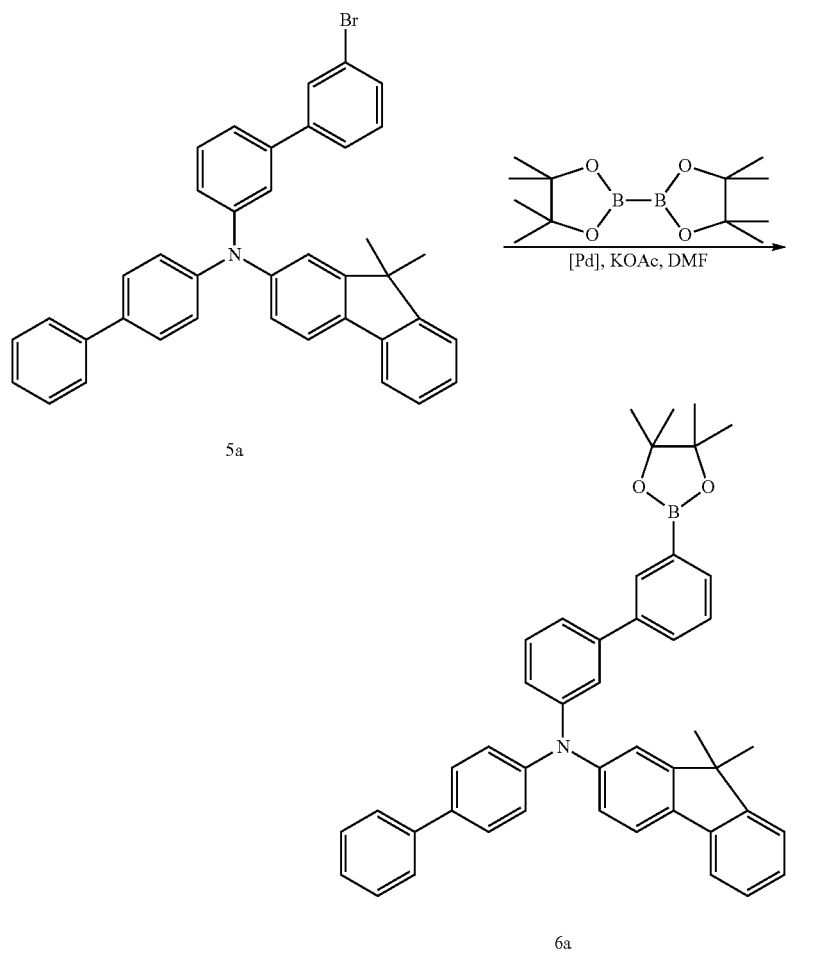

5a

6a 16.6 g (28 mmol, 35%) of the bromide 5a are dissolved in 120 ml of dry DMF together with 8.5 g (34 mmol, 1.2 eq.) of bis(pinacolato)diborane (CAS 73183-34-3) under protective gas in a 500 ml flask and degassed for 30 minutes. 8.2 g (84 mmol, 3.0 eq.) of potassium acetate and 690 mg (0.84 mmol, 3 mol-%) of [1,1'-bis(diphenylphosphino)ferrocene]palladium(II) dichloride complex with dichloromethane (CAS 95464-05-4) are subsequently added, and the batch is heated at 90° C. overnight. When the reaction is complete, the mixture is diluted with 300 ml of toluene and extracted with water. The solvent is removed in a rotary evaporator, and the solid obtained, 14.7 g (23 mmol, 82%), is dried. The boronic ester 6a is reacted without further purification.

The following compounds can be obtained analogously:

| No. | Starting material 5 | Product 6 | Yield |
|---|---|---|---|
| 6b | 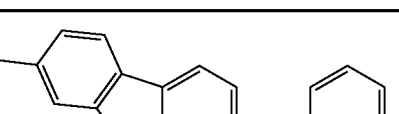 | 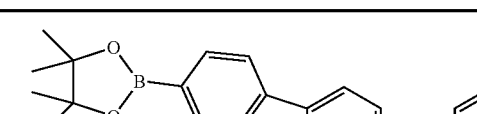 | 88% |

-continued
| No. | Starting material 5 | Product 6 | Yield |
|---|---|---|---|
| 6c | 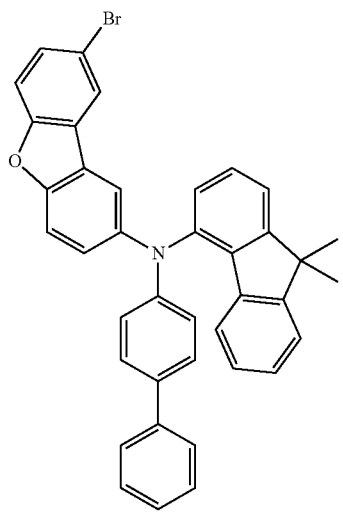 [SMILES: CC1(C)c2ccccc2-c2c(N(c3ccc(-c4ccccc4)cc3)c3ccc4oc5ccc(Br)cc5c4c3)cccc21] | 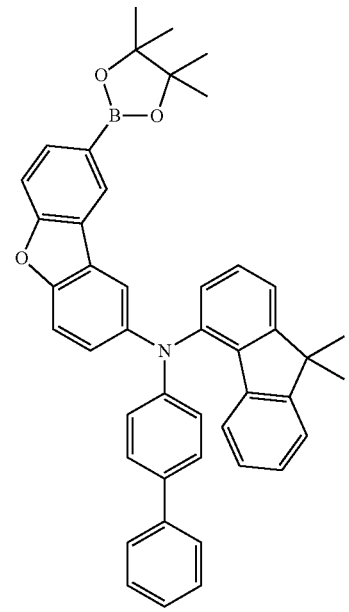 [SMILES: CC1(C)c2ccccc2-c2c(N(c3ccc(-c4ccccc4)cc3)c3ccc4oc5ccc(B6OC(C)(C)C(C)(C)O6)cc5c4c3)cccc21] | 81% |
| 6d | 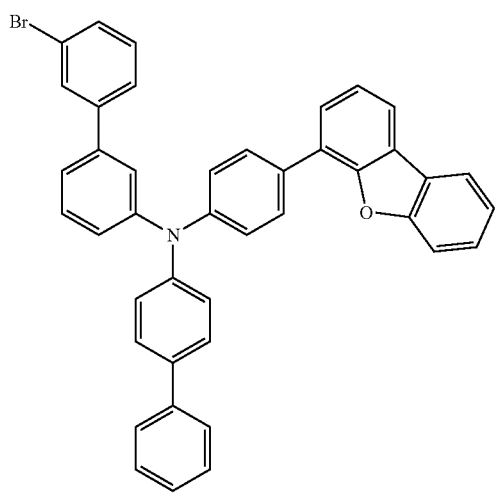 [SMILES: Brc1cccc(-c2cccc(N(c3ccc(-c4ccccc4)cc3)c3ccc(-c4cccc5c4oc4ccccc45)cc3)c2)c1] | 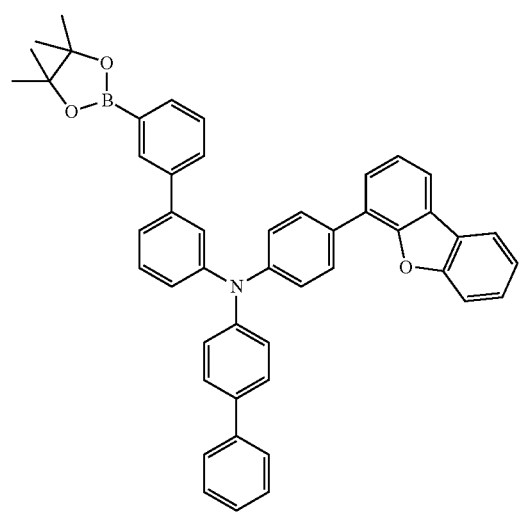 [SMILES: CC1(C)OB(c2cccc(-c3cccc(N(c4ccc(-c5ccccc5)cc4)c4ccc(-c5cccc6c5oc5ccccc56)cc4)c3)c2)OC1(C)C] | 75% |

| No. | Starting material 5 | Product 6 | Yield |
|---|---|---|---|
| 6e | 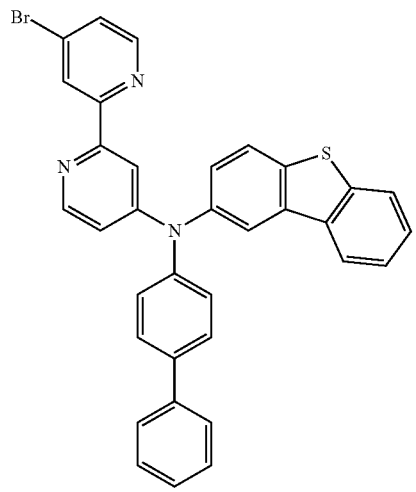 [SMILES: Brc1ccnc(-c2cc(N(c3ccc(-c4ccccc4)cc3)c3ccc4sc5ccccc5c4c3)ccn2)c1] | 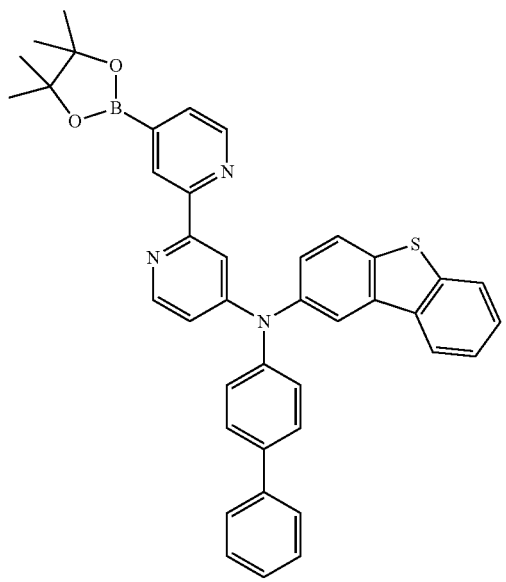 [SMILES: CC1(C)OB(c2ccnc(-c3cc(N(c4ccc(-c5ccccc5)cc4)c4ccc5sc6ccccc6c5c4)ccn3)c2)OC1(C)C] | 67% |
| 6f | 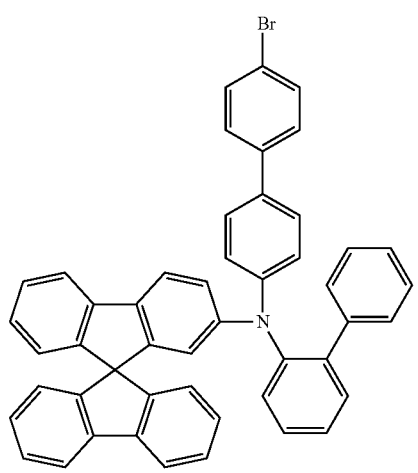 [SMILES: Brc1ccc(-c2ccc(N(c3ccc4c(c3)C3(c5ccccc5-c5ccccc53)c3ccccc3-4)c3ccccc3-c3ccccc3)cc2)cc1] | 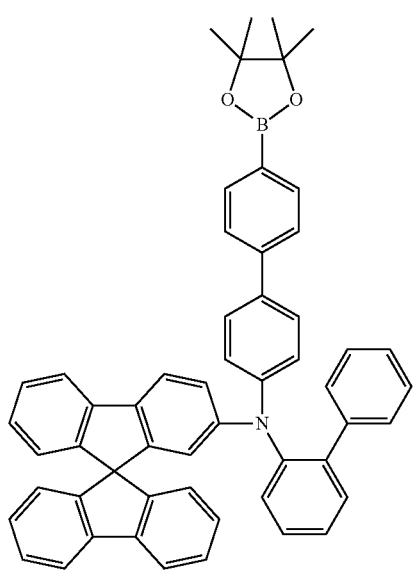 [SMILES: CC1(C)OB(c2ccc(-c3ccc(N(c4ccc5c(c4)C4(c6ccccc6-c6ccccc64)c4ccccc4-5)c4ccccc4-c4ccccc4)cc3)cc2)OC1(C)C] | 79% |

-continued
| No. | Starting material 5 | Product 6 | Yield |
|---|---|---|---|
| 6g | 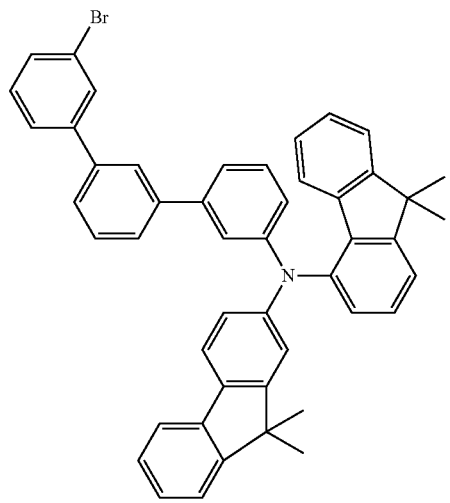 [SMILES: CC1(C)c2ccccc2-c2ccc(N(c3cccc(-c4cccc(-c5cccc(Br)c5)c4)c3)c3cccc4c3-c3ccccc3C4(C)C)cc21] | 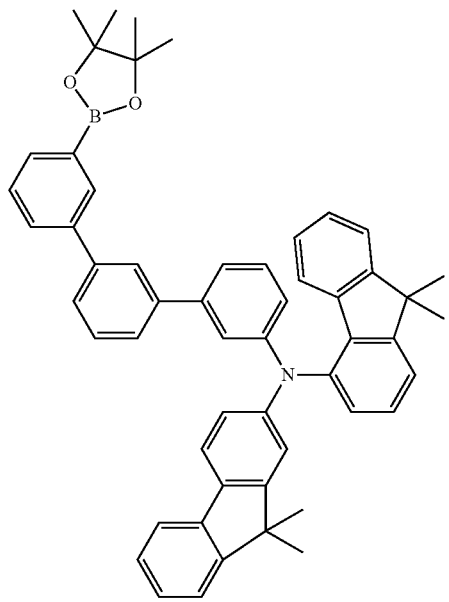 [SMILES: CC1(C)c2ccccc2-c2ccc(N(c3cccc(-c4cccc(-c5cccc(B6OC(C)(C)C(C)(C)O6)c5)c4)c3)c3cccc4c3-c3ccccc3C4(C)C)cc21] | 93% |
| 6h | 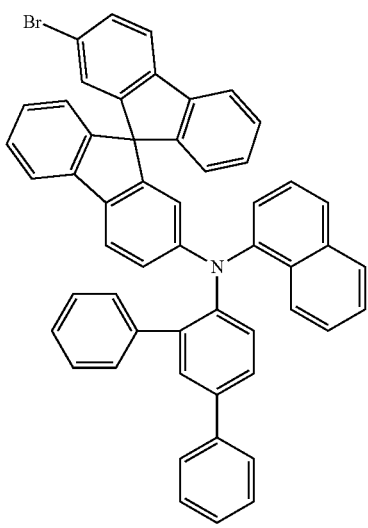 [SMILES: Brc1ccc2c(c1)C1(c3ccccc3-2)c2ccccc2-c2ccc(N(c3ccc(-c4ccccc4)cc3-c3ccccc3)c3cccc4ccccc34)cc21] | 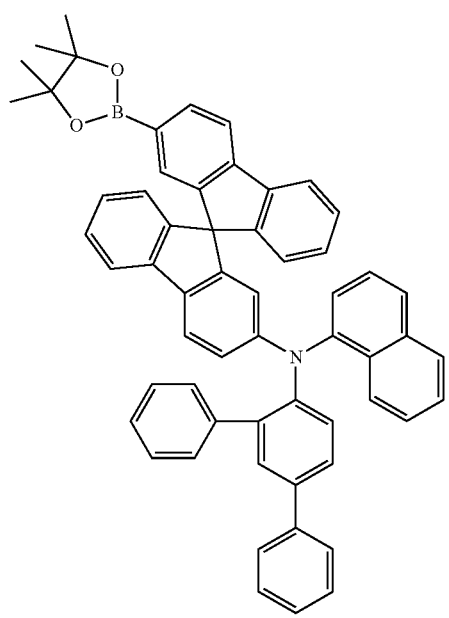 [SMILES: CC1(C)OB(c2ccc3c(c2)C2(c4ccccc4-3)c3ccccc3-c3ccc(N(c4ccc(-c5ccccc5)cc4-c4ccccc4)c4cccc5ccccc45)cc32)OC1(C)C] | 44% |

| No. | Starting material 5 | Product 6 | Yield |
|---|---|---|---|
| 6i | | | 87% |
| 6j | | | 28% |
| 6k | | | 35% |

-continued

| No. | Starting material 5 | Product 6 | Yield |
|---|---|---|---|
| 6l | | | 77% |
| 6m | | | 38% |
| 6n | | | 55% |

-continued

| No. | Starting material 5 | Product 6 | Yield |
|---|---|---|---|
| 6o | | | 41% |
| 6p | | | 67% |
| 6q | | | 82% |

-continued

| No. | Starting material 5 | Product 6 | Yield |
|---|---|---|---|
| 6r | | | 91% |
| 6s | | | 87% |
| 6t | | | 96% |

-continued

| No. | Starting material 5 | Product 6 | Yield |
|---|---|---|---|
| 6u | | | 58% |
| 6v | | | 94% |

Step 4

Synthesis of the Triazine Building Block Step 1

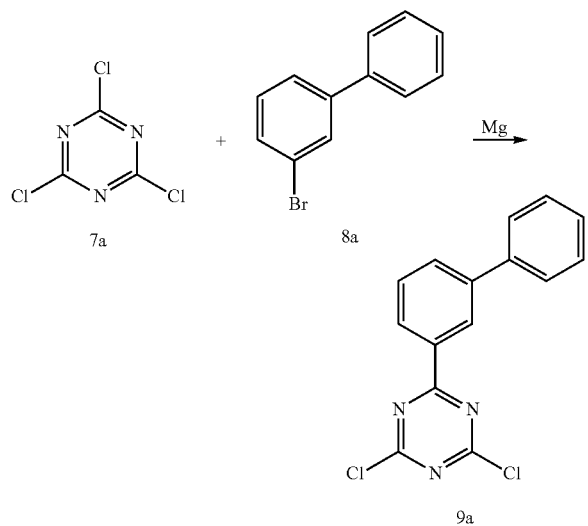

7.9 g (330 mmol, 1.2 eq.) of magnesium turnings are initially introduced in a 1 l four-necked flask, and a THF solution of 63 g (270 mmol, 1.0 eq.) of 3-bromobiphenyl 8a (CAS 2113-57-7) is added sufficiently slowly to maintain the reflux of the reaction mixture. When the addition is complete, the batch is heated under reflux for a further two hours. 50 g (270 mmol, 1 eq.) of 2,4,6-trichloro-1,3,5-triazine 7a (CAS 108-77-0) in 500 ml of THF in a 2 l four-necked flask are cooled to −10° C. The Grignard solution is added dropwise at this temperature sufficiently slowly that the temperature does not exceed 0° C., and finally the batch is stirred at room temperature overnight. For work-up, 270 ml of 1N hydrochloric acid are added dropwise, and the mixture is stirred for one hour. The aqueous phase is subsequently separated off and extracted with diethyl ether. The combined organic phases are dried over sodium sulfate, and the solvent is removed in a rotary evaporator, giving 56 g (69%) of a colourless oil 9a.

The following compounds can be obtained analogously:

| No. | Starting material 7 | Starting material 8 | Product 9 | Yield |
|---|---|---|---|---|
| 9b | | 92-66-0 | | 56% |
| 9c | | 28320-31-2 | | 27% |

| No. | Starting material 7 | Starting material 8 | Product 9 | Yield |
|---|---|---|---|---|
| 9d | Cl-triazine-Cl₂ | 2-bromo-9,9-dimethylfluorene<br>28320-31-2<br>2 eq. employed in each case | bis(9,9-dimethylfluoren-2-yl)-chlorotriazine | 48% |
| 9e | Cl-triazine-Cl₂ | 5-bromo-1,1':3',1''-terphenyl<br>103068-20-8 | dichloro-(terphenyl)-triazine | 71% |

Synthesis of the Triazine Building Block Step 2

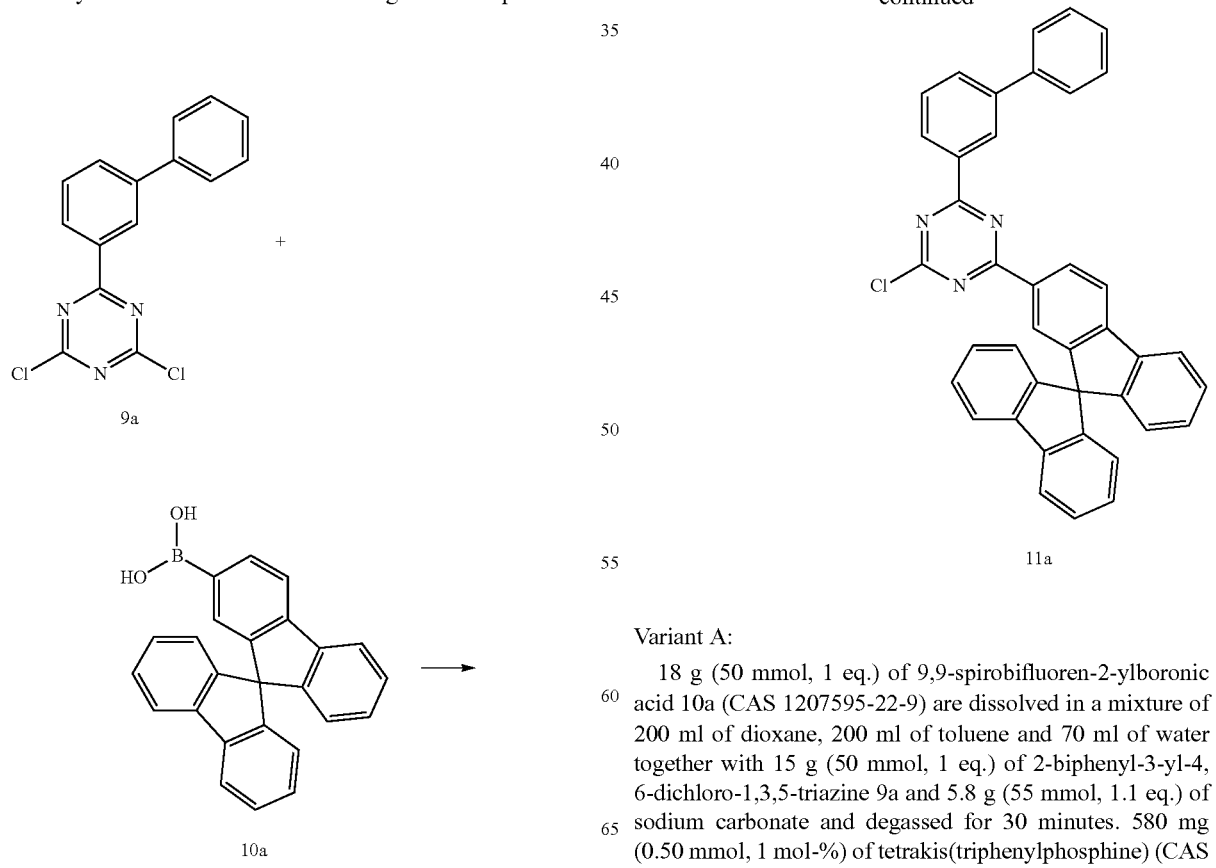

Variant A:

18 g (50 mmol, 1 eq.) of 9,9-spirobifluoren-2-ylboronic acid 10a (CAS 1207595-22-9) are dissolved in a mixture of 200 ml of dioxane, 200 ml of toluene and 70 ml of water together with 15 g (50 mmol, 1 eq.) of 2-biphenyl-3-yl-4,6-dichloro-1,3,5-triazine 9a and 5.8 g (55 mmol, 1.1 eq.) of sodium carbonate and degassed for 30 minutes. 580 mg (0.50 mmol, 1 mol-%) of tetrakis(triphenylphosphine) (CAS 14221-01-3) are subsequently added, and the batch is heated under reflux overnight. The reaction mixture is cooled, and 300 ml of water are added. The aqueous phase is extracted three times with ethyl acetate, the organic phases are combined, and the solvent is removed in a rotary evaporator. Hot extraction in heptane/toluene 4:1 gives 15 g (26 mmol, 51%) of a colourless solid.

Variant B: Analogous to Step 1

The following compounds can be prepared analogously:

| Variant | | Starting material 9 | Starting material 10 |
|---|---|---|---|
| 9b | B | 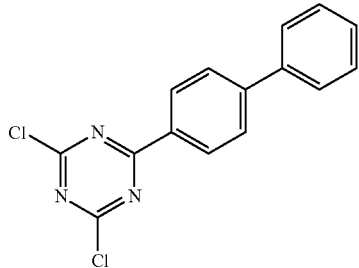 [SMILES: Clc1nc(Cl)nc(-c2ccc(-c3ccccc3)cc2)n1] | 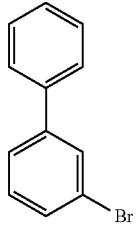 2113-57-7 |
| 9c | A | 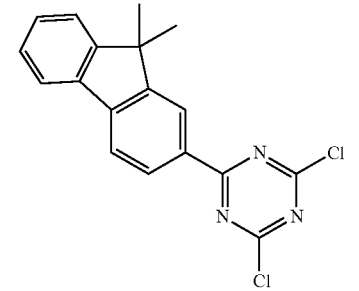 [SMILES: CC1(C)c2ccccc2-c2ccc(-c3nc(Cl)nc(Cl)n3)cc21] | 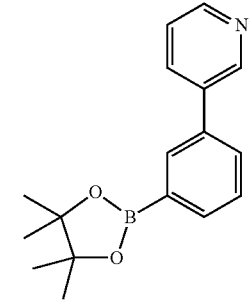 939430-30-5 |
| 9d | A | 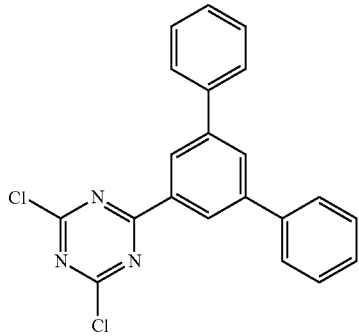 [SMILES: Clc1nc(Cl)nc(-c2cc(-c3ccccc3)cc(-c3ccccc3)c2)n1] | 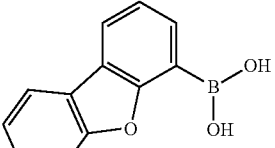 100124-06-9 |
| 9e | A | 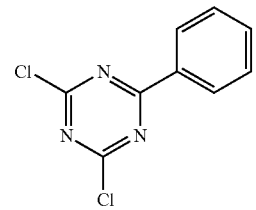 [SMILES: Clc1nc(Cl)nc(-c2ccccc2)n1] | 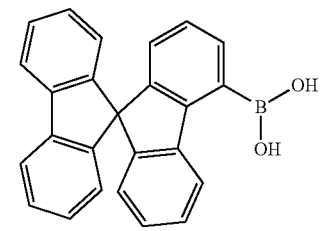 1421789-05-0 |

| | | -continued | |
|---|---|---|---|
| 9f | A | 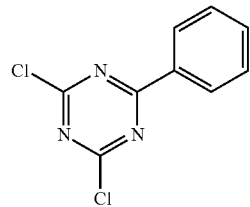 [SMILES: Clc1nc(Cl)nc(-c2ccccc2)n1] | 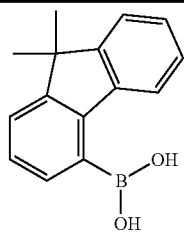<br>1246022-50-3 |
| 9g | A | 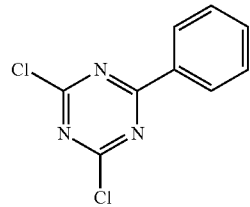 [SMILES: Clc1nc(Cl)nc(-c2ccccc2)n1] | 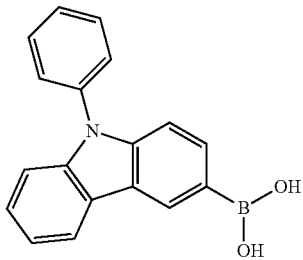<br>854952-58-2 |
| 9h | B | 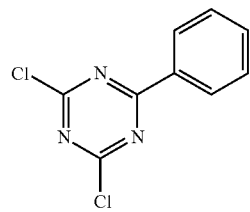 [SMILES: Clc1nc(Cl)nc(-c2ccccc2)n1] | 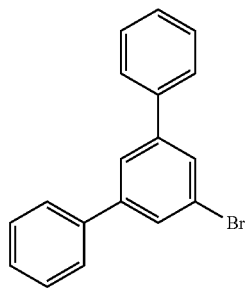<br>103068-20-8 |
| | Product 11 | Yield |
|---|---|---|
| 9b | 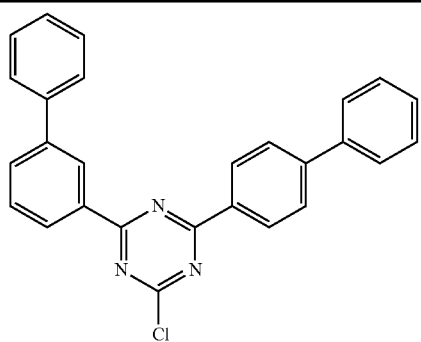 | 68% |
| 9c | 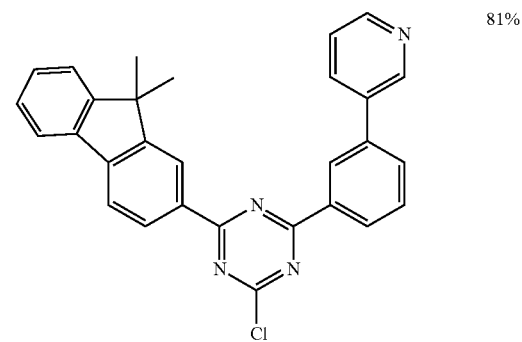 | 81% |

| | |
|---|---|
| 9d | 63% |
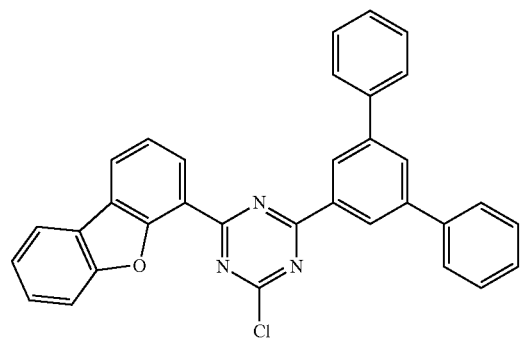 [SMILES: Clc1nc(-c2cc(-c3ccccc3)cc(-c3ccccc3)c2)nc(-c2cccc3c2oc2ccccc23)n1]
| | |
|---|---|
| 9e | 71% |
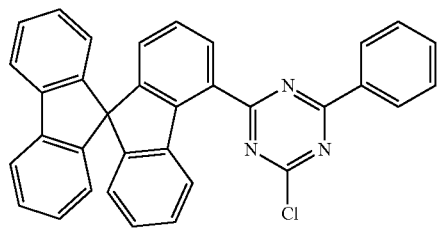 [SMILES: Clc1nc(-c2ccccc2)nc(-c2cccc3c2-c2ccccc2C32c3ccccc3-c3ccccc32)n1]
| | |
|---|---|
| 9f | 53% |
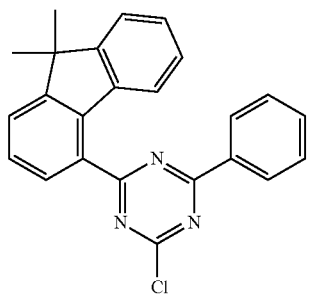 [SMILES: CC1(C)c2ccccc2-c2c(-c3nc(Cl)nc(-c4ccccc4)n3)cccc21]
| | |
|---|---|
| 9g | 68% |
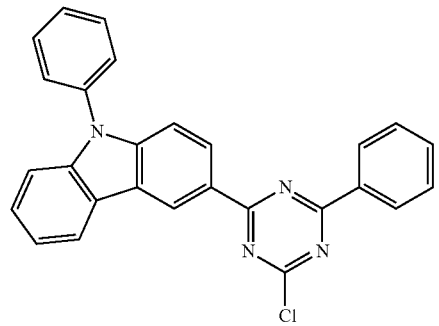 [SMILES: Clc1nc(-c2ccccc2)nc(-c2ccc3c(c2)c2ccccc2n3-c2ccccc2)n1]

| | |
|---|---|
| 9h | 67% |

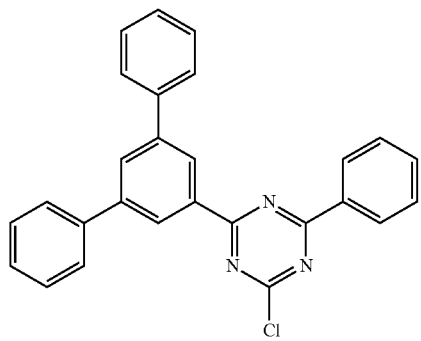 [SMILES: Clc1nc(-c2ccccc2)nc(-c2cc(-c3ccccc3)cc(-c3ccccc3)c2)n1]

Step 5: Preparation of the End Product by Means of Suzuki Coupling

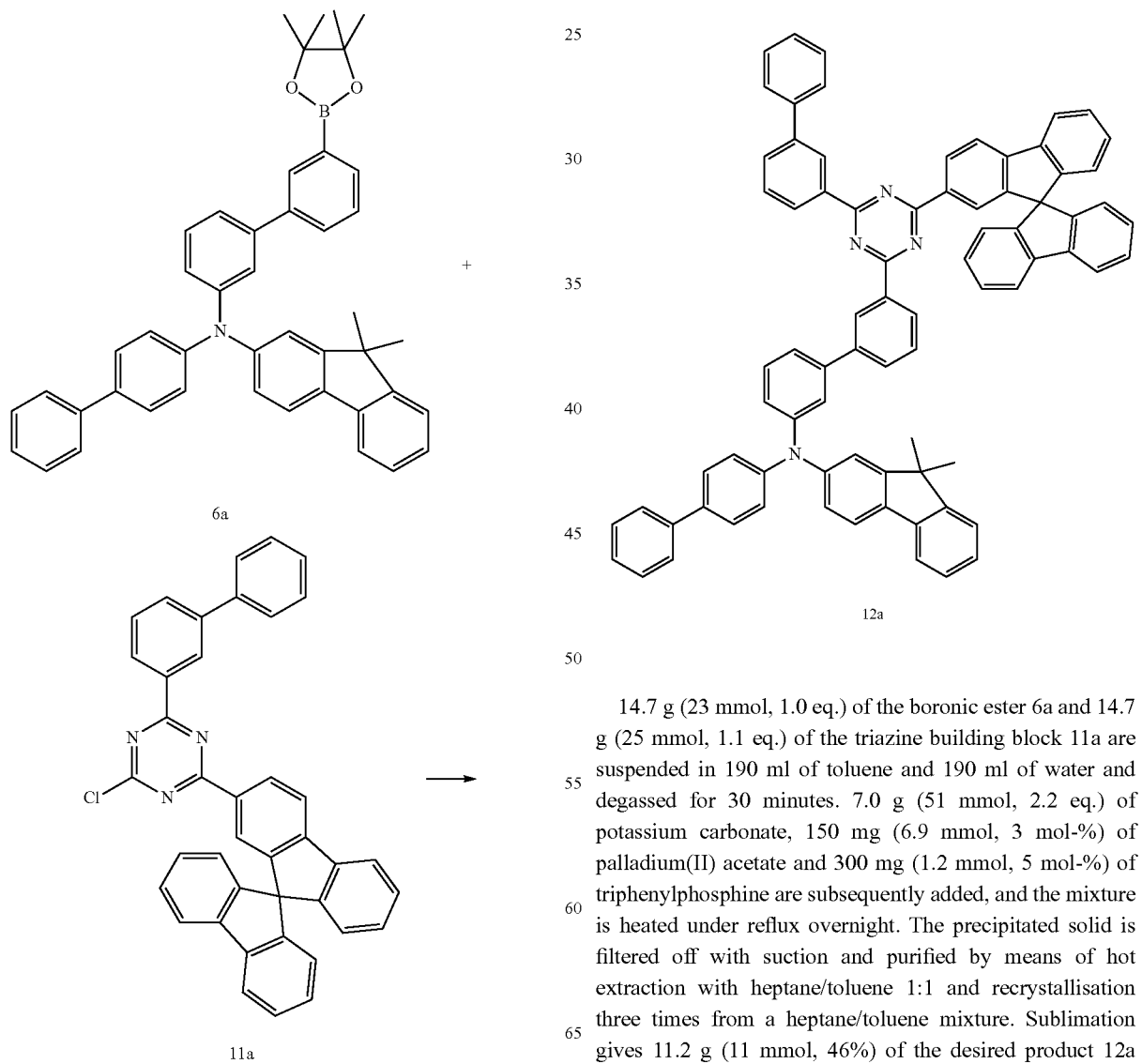

14.7 g (23 mmol, 1.0 eq.) of the boronic ester 6a and 14.7 g (25 mmol, 1.1 eq.) of the triazine building block 11a are suspended in 190 ml of toluene and 190 ml of water and degassed for 30 minutes. 7.0 g (51 mmol, 2.2 eq.) of potassium carbonate, 150 mg (6.9 mmol, 3 mol-%) of palladium(II) acetate and 300 mg (1.2 mmol, 5 mol-%) of triphenylphosphine are subsequently added, and the mixture is heated under reflux overnight. The precipitated solid is filtered off with suction and purified by means of hot extraction with heptane/toluene 1:1 and recrystallisation three times from a heptane/toluene mixture. Sublimation gives 11.2 g (11 mmol, 46%) of the desired product 12a having an HPLC purity of >99.9%.

The following compounds can be obtained analogously:
| No. | Starting material 6 | Starting material 11 |
|---|---|---|
| 12b | 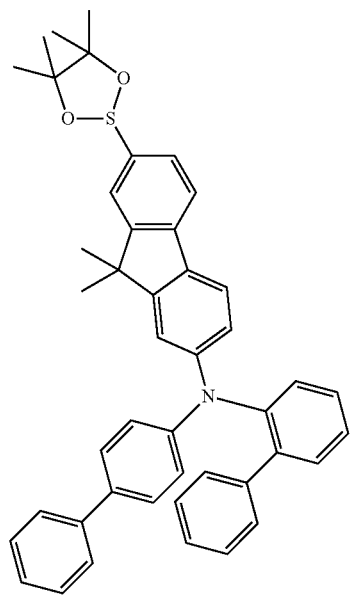 | 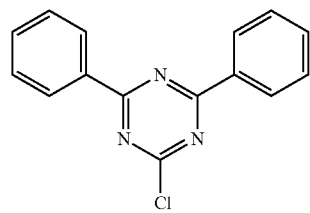
3842-55-5 |
| 12c | 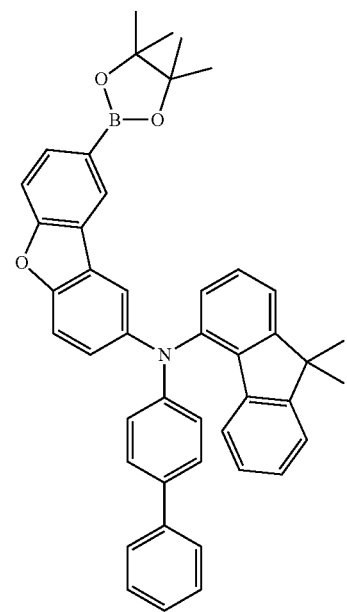 [SMILES: CC1(C)c2ccccc2-c2c(N(c3ccc(-c4ccccc4)cc3)c3ccc4oc5ccc(B6OC(C)(C)C(C)(C)O6)cc5c4c3)cccc21] | 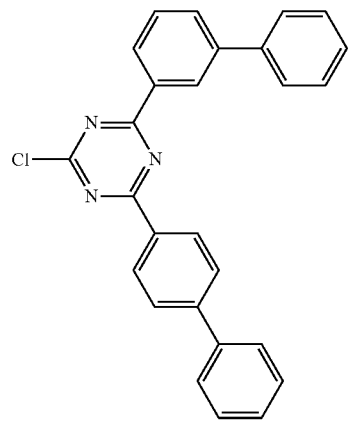 [SMILES: Clc1nc(-c2ccc(-c3ccccc3)cc2)nc(-c2cccc(-c3ccccc3)c2)n1] |

12d
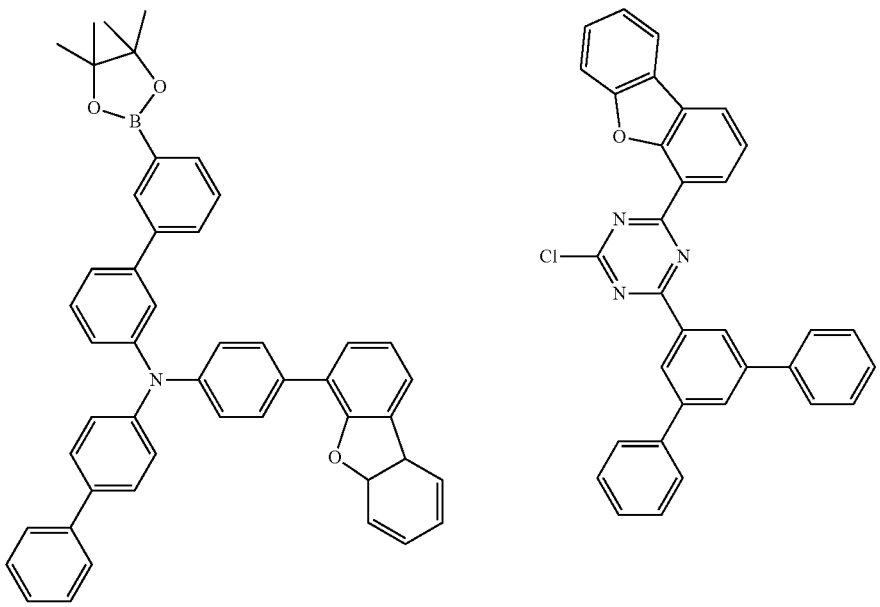
12e
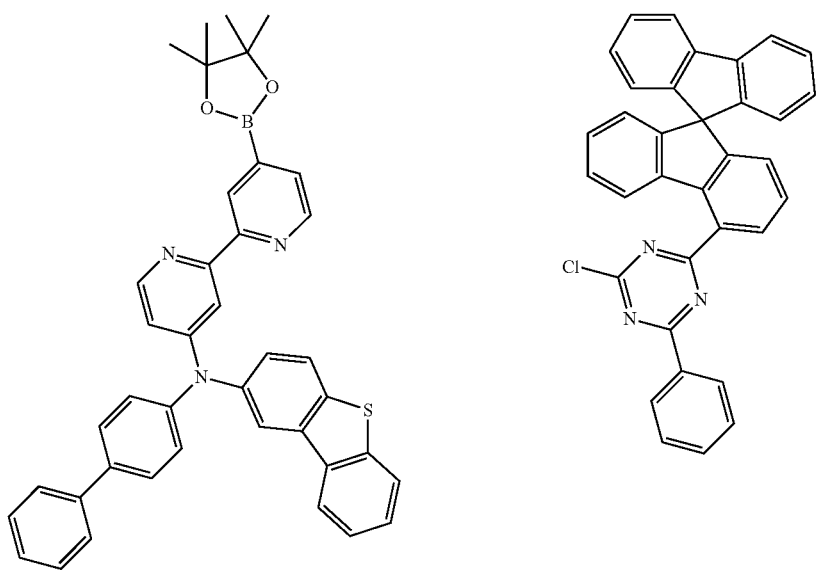

12f
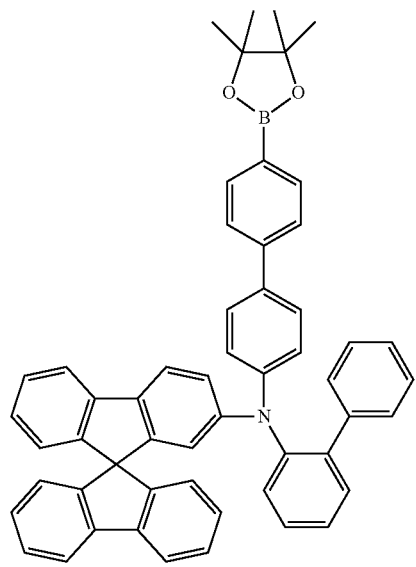 [SMILES: CC1(C)OB(c2ccc(-c3ccc(N(c4ccc5c(c4)C4(c6ccccc6-c6ccccc64)c4ccccc4-5)c4ccccc4-c4ccccc4)cc3)cc2)OC1(C)C]
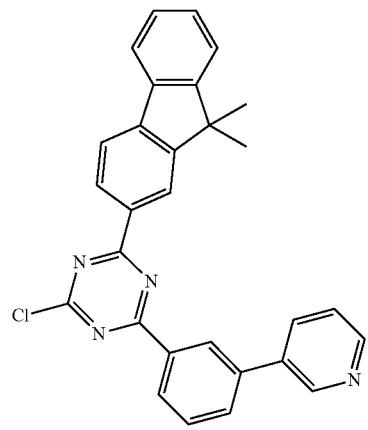 [SMILES: CC1(C)c2ccccc2-c2ccc(-c3nc(Cl)nc(-c4cccc(-c5cccnc5)c4)n3)cc21]
12g
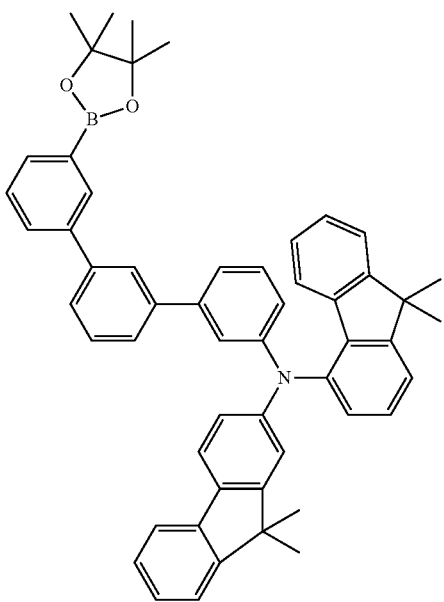 [SMILES: CC1(C)c2ccccc2-c2ccc(N(c3cccc(-c4cccc(-c5cccc(B6OC(C)(C)C(C)(C)O6)c5)c4)c3)c3cccc4c3-c3ccccc3C4(C)C)cc21]
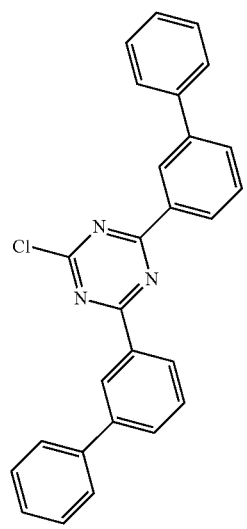
1205748-61-3

-continued
12h
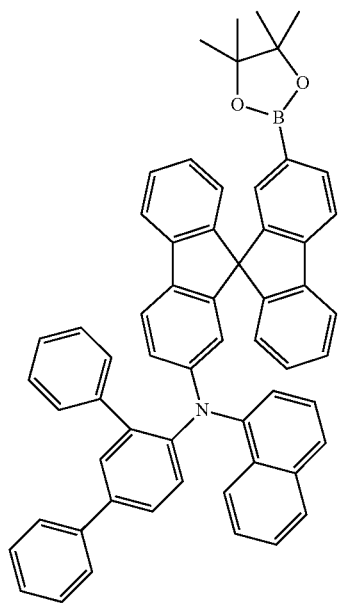 [SMILES: CC1(C)OB(c2ccc3c(c2)C2(c4ccccc4-3)c3ccccc3-c3ccc(N(c4ccc(-c5ccccc5)cc4-c4ccccc4)c4cccc5ccccc45)cc32)OC1(C)C]
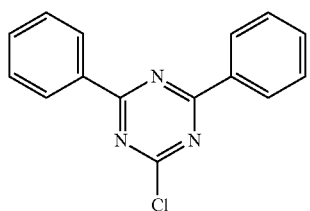
3842-55-5
12i
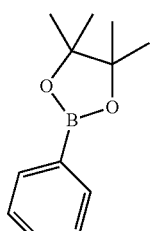
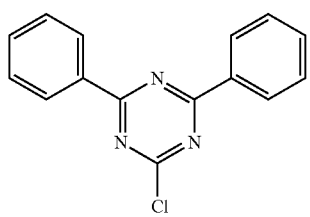
3842-55-5
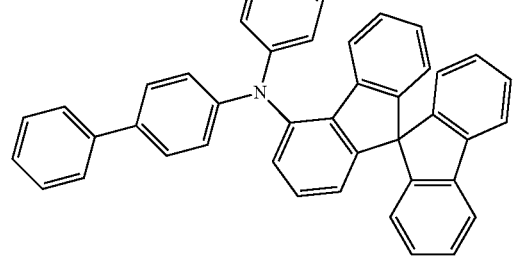
12j
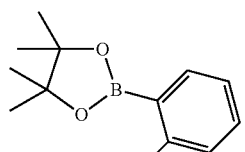
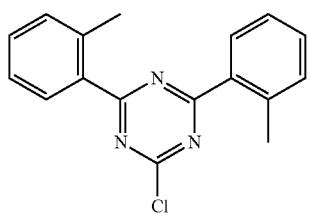
78941-34-1
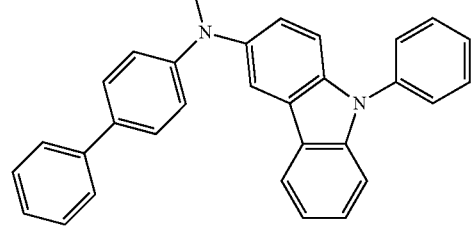

-continued
12k
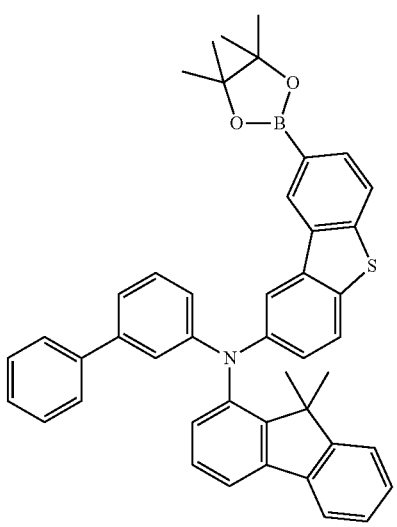 [SMILES: CC1(C)c2ccccc2-c2cccc(N(c3cccc(-c4ccccc4)c3)c3ccc4sc5ccc(B6OC(C)(C)C(C)(C)O6)cc5c4c3)c21]
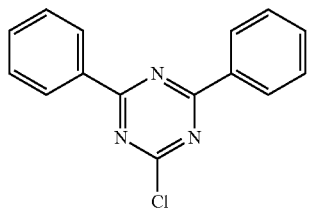
3842-55-5
12l
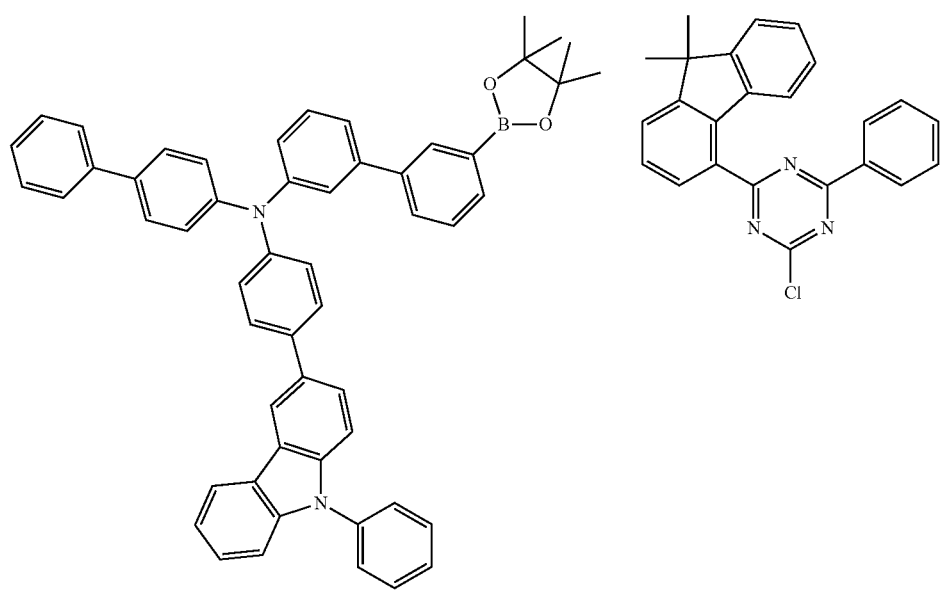
12m
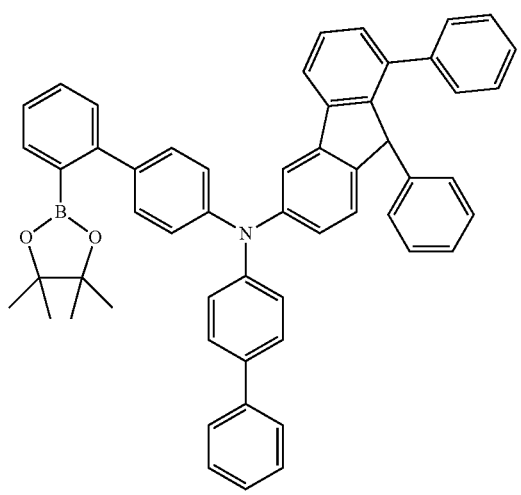 [SMILES: CC1(C)OB(c2ccccc2-c2ccc(N(c3ccc(-c4ccccc4)cc3)c3ccc4c(c3)-c3cccc(-c5ccccc5)c3C4c3ccccc3)cc2)OC1(C)C]
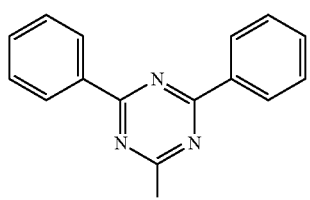
3842-55-5

12n
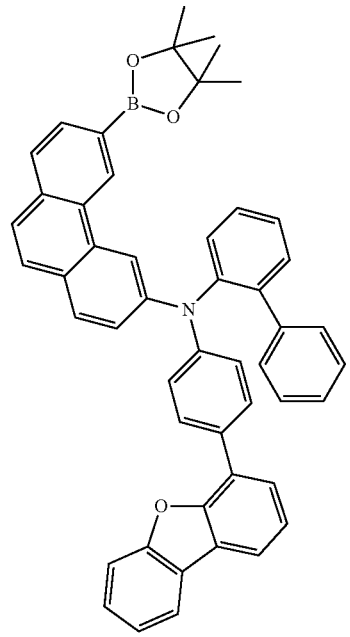 [SMILES: CC1(C)OB(c2ccc3ccc4ccc(N(c5ccc(-c6cccc7c6oc6ccccc67)cc5)c5ccccc5-c5ccccc5)cc4c3c2)OC1(C)C]
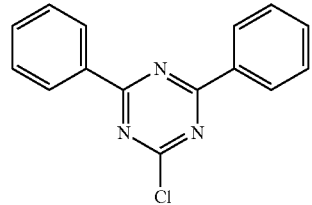
3842-55-5
12o
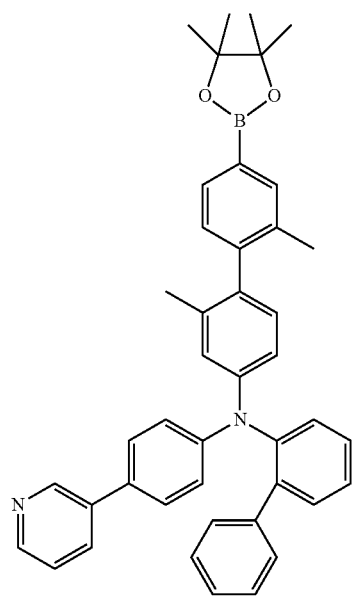 [SMILES: Cc1cc(B2OC(C)(C)C(C)(C)O2)ccc1-c1ccc(N(c2ccc(-c3cccnc3)cc2)c2ccccc2-c2ccccc2)cc1C]
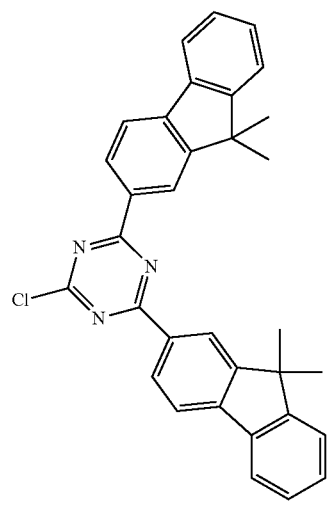 [SMILES: CC1(C)c2ccccc2-c2ccc(-c3nc(Cl)nc(-c4ccc5c(c4)C(C)(C)c4ccccc4-5)n3)cc21]

-continued
12p
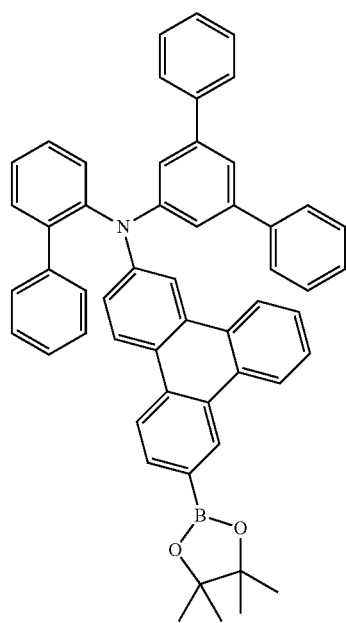 [SMILES: CC1(C)OB(c2ccc3c4ccc(N(c5cc(-c6ccccc6)cc(-c6ccccc6)c5)c5ccccc5-c5ccccc5)cc4c4ccccc4c3c2)OC1(C)C]
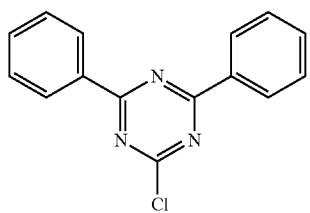
3842-55-5
12q
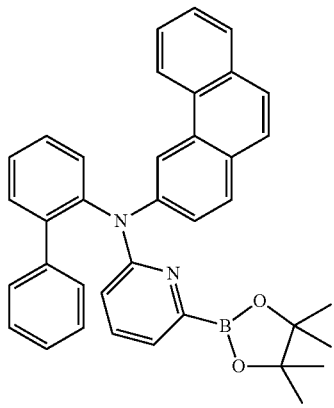 [SMILES: CC1(C)OB(c2cccc(N(c3ccc4ccc5ccccc5c4c3)c3ccccc3-c3ccccc3)n2)OC1(C)C]
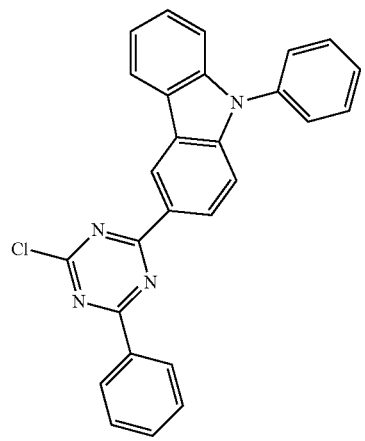 [SMILES: Clc1nc(-c2ccccc2)nc(-c2ccc3c(c2)c2ccccc2n3-c2ccccc2)n1]
12r
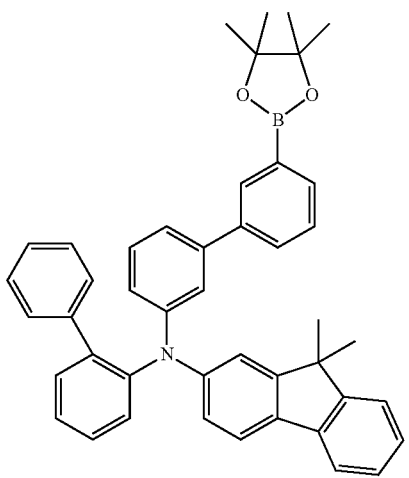 [SMILES: CC1(C)c2ccccc2-c2ccc(N(c3cccc(-c4cccc(B5OC(C)(C)C(C)(C)O5)c4)c3)c3ccccc3-c3ccccc3)cc21]
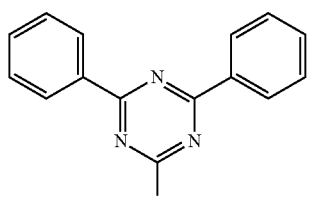
3842-55-5

-continued
12s 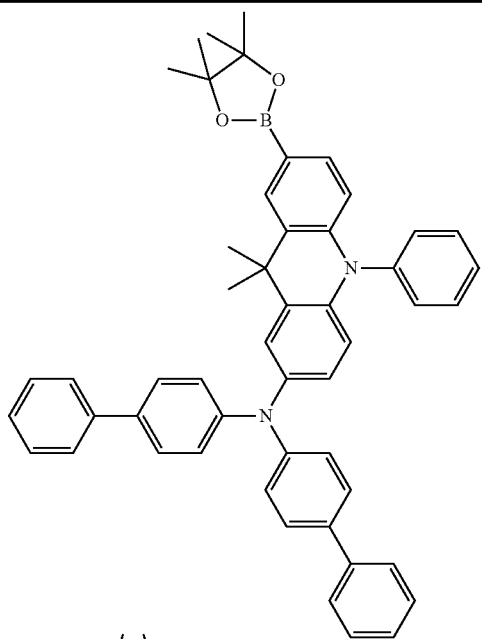
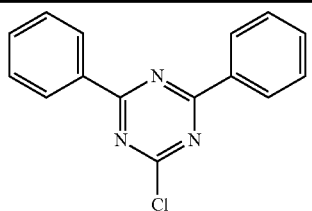
3842-55-5
12t 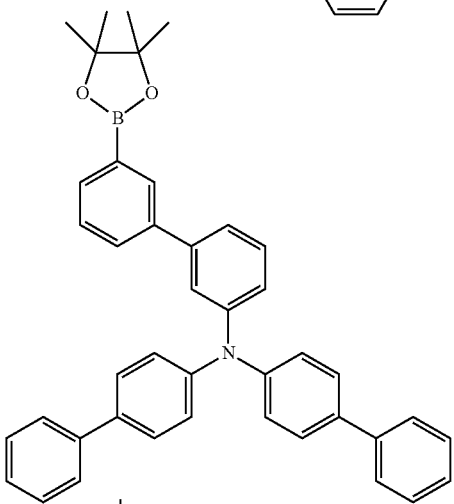
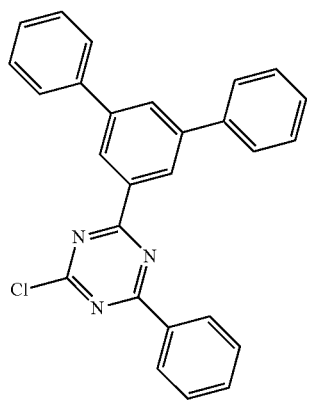 [SMILES: Clc1nc(-c2ccccc2)nc(-c2cc(-c3ccccc3)cc(-c3ccccc3)c2)n1]
12u 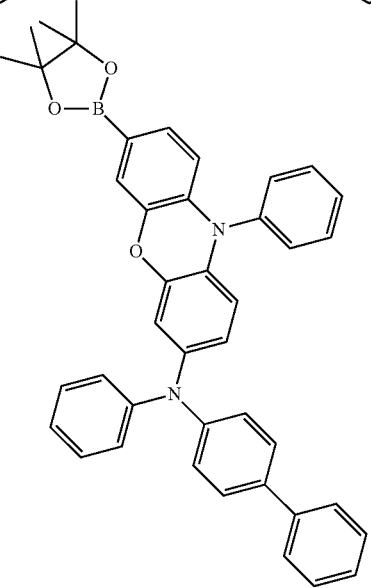 [SMILES: CC1(C)OB(c2ccc3c(c2)Oc2cc(N(c4ccccc4)c4ccc(-c5ccccc5)cc4)ccc2N3c2ccccc2)OC1(C)C]
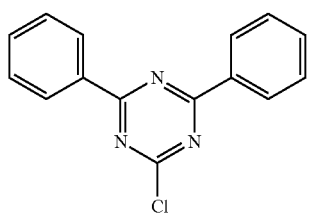
3842-55-5

12v
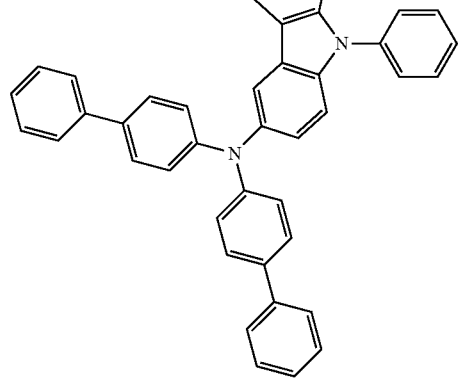
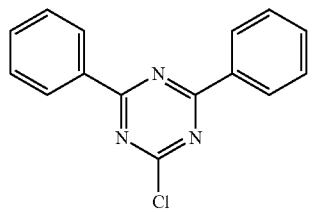
3842-55-5
| No. | Product 12 | Yield |
|---|---|---|
| 12b | | 54% |
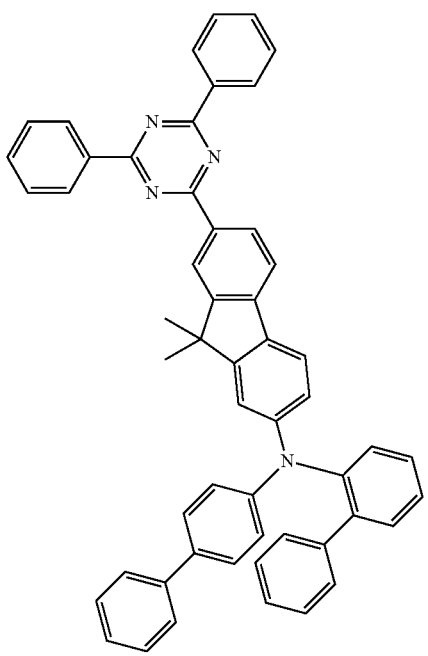 [SMILES: CC1(C)c2cc(-c3nc(-c4ccccc4)nc(-c4ccccc4)n3)ccc2-c2ccc(N(c3ccc(-c4ccccc4)cc3)c3ccccc3-c3ccccc3)cc21]

| 12c | 31% |
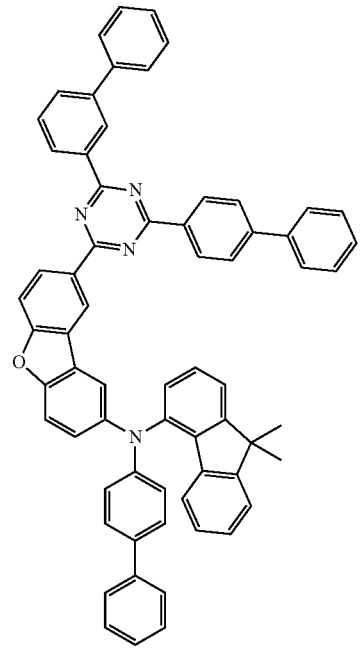 [SMILES: CC1(C)c2ccccc2-c2c(N(c3ccc(-c4ccccc4)cc3)c3ccc4oc5ccc(-c6nc(-c7ccc(-c8ccccc8)cc7)nc(-c7cccc(-c8ccccc8)c7)n6)cc5c4c3)cccc21]
| 12d | 49% |
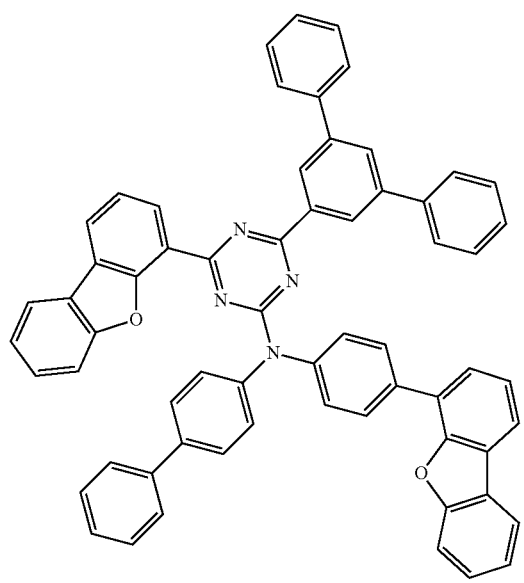 [SMILES: c1ccc(-c2ccc(N(c3ccc(-c4cccc5c4oc4ccccc45)cc3)c3nc(-c4cc(-c5ccccc5)cc(-c5ccccc5)c4)nc(-c4cccc5c4oc4ccccc45)n3)cc2)cc1]

| 12e | 68% |
|---|---|
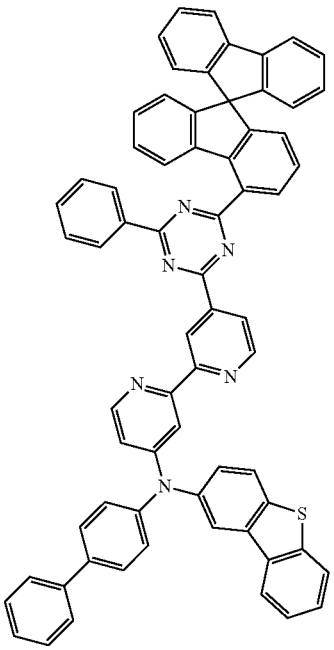 [SMILES: c1ccc(-c2ccc(N(c3ccnc(-c4cc(-c5nc(-c6ccccc6)nc(-c6cccc7c6-c6ccccc6C76c7ccccc7-c7ccccc76)n5)ccn4)c3)c3ccc4sc5ccccc5c4c3)cc2)cc1]
| 12f | 52% |
|---|---|
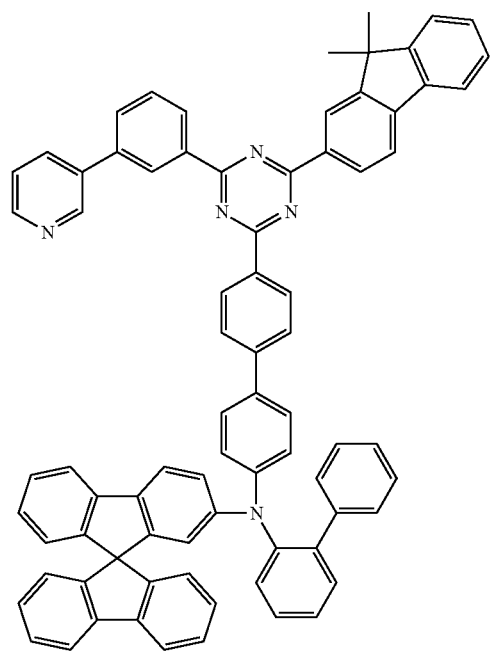 [SMILES: CC1(C)c2ccccc2-c2ccc(-c3nc(-c4ccc(-c5ccc(N(c6ccc7c(c6)C6(c8ccccc8-c8ccccc86)c6ccccc6-7)c6ccccc6-c6ccccc6)cc5)cc4)nc(-c4cccc(-c5cccnc5)c4)n3)cc21]

12g 71%
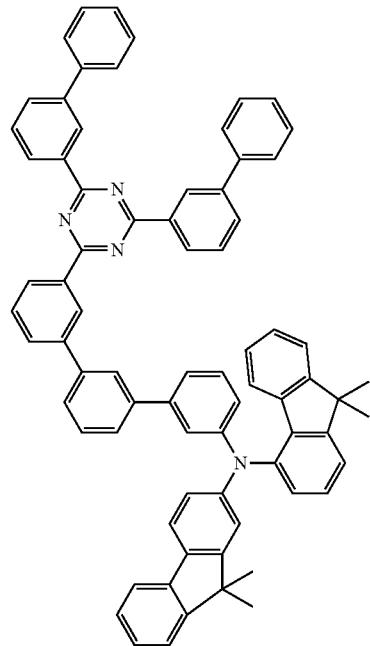 [SMILES: CC1(C)c2ccccc2-c2ccc(N(c3cccc(-c4cccc(-c5cccc(-c6nc(-c7cccc(-c8ccccc8)c7)nc(-c7cccc(-c8ccccc8)c7)n6)c5)c4)c3)c3cccc4c3-c3ccccc3C4(C)C)cc21]
12h 41%
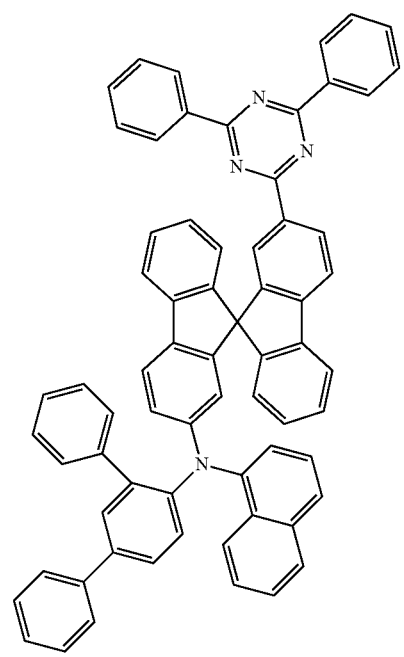 [SMILES: c1ccc(-c2ccc(N(c3ccc4c(c3)C3(c5ccccc5-c5ccc(-c6nc(-c7ccccc7)nc(-c7ccccc7)n6)cc53)c3ccccc3-4)c3cccc4ccccc34)c(-c3ccccc3)c2)cc1]

-continued
| | |
|---|---|
| 12i | 44% |
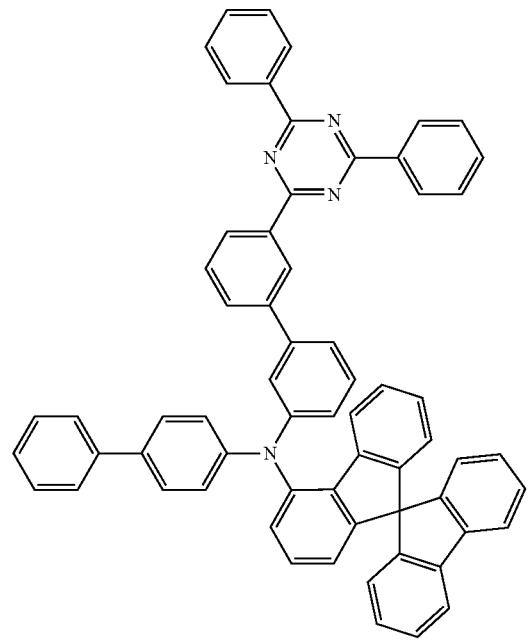 [SMILES: c1ccc(-c2ccc(N(c3cccc(-c4cccc(-c5nc(-c6ccccc6)nc(-c6ccccc6)n5)c4)c3)c3cccc4c3-c3ccccc3C43c4ccccc4-c4ccccc43)cc2)cc1]
| | |
|---|---|
| 12j | 37% |
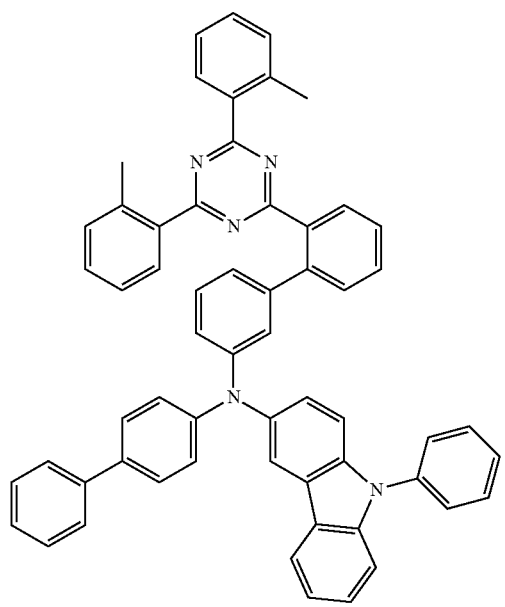 [SMILES: Cc1ccccc1-c1nc(-c2ccccc2C)nc(-c2ccccc2-c2cccc(N(c3ccc(-c4ccccc4)cc3)c3ccc4c(c3)c3ccccc3n4-c3ccccc3)c2)n1]

| 12k | 21% |
|---|---|
| 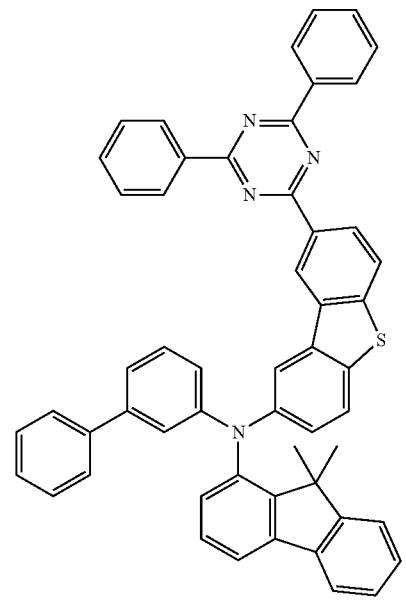 [SMILES: CC1(C)c2ccccc2-c2cccc(N(c3cccc(-c4ccccc4)c3)c3ccc4sc5ccc(-c6nc(-c7ccccc7)nc(-c7ccccc7)n6)cc5c4c3)c21] | |
| 12l | 51% |
|---|---|
| 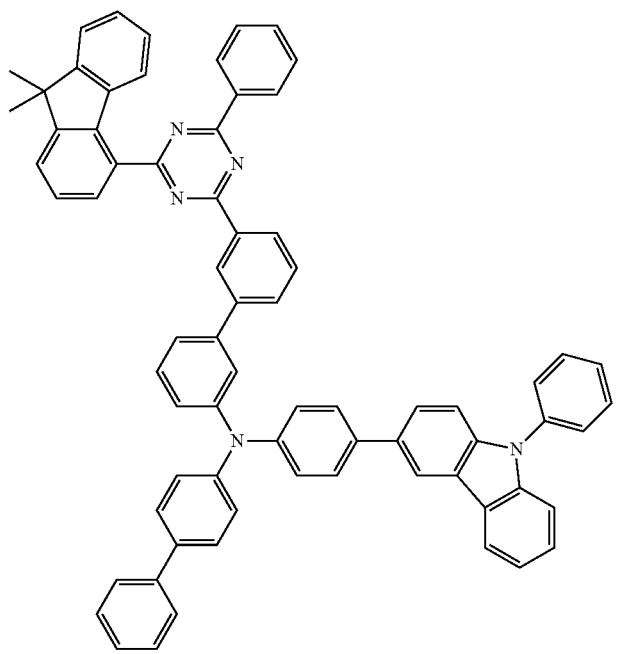 [SMILES: CC1(C)c2ccccc2-c2c(-c3nc(-c4ccccc4)nc(-c4cccc(-c5cccc(N(c6ccc(-c7ccccc7)cc6)c6ccc(-c7ccc8c(c7)c7ccccc7n8-c7ccccc7)cc6)c5)c4)n3)cccc21] | |

| 12m | 17% |
|---|---|
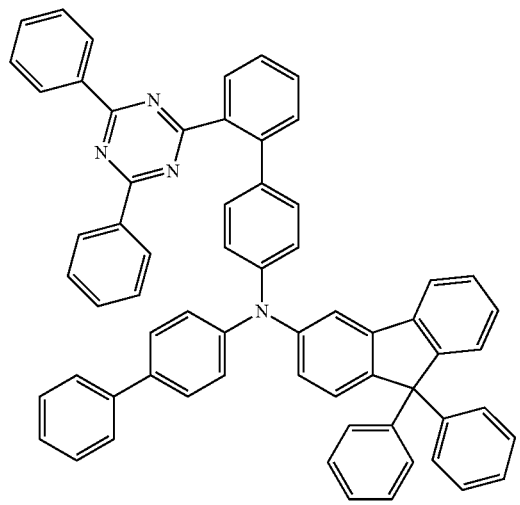 [SMILES: c1ccc(-c2ccc(N(c3ccc(-c4ccccc4-c4nc(-c5ccccc5)nc(-c5ccccc5)n4)cc3)c3ccc4c(c3)-c3ccccc3C4(c3ccccc3)c3ccccc3)cc2)cc1]
| 12n | 58% |
|---|---|
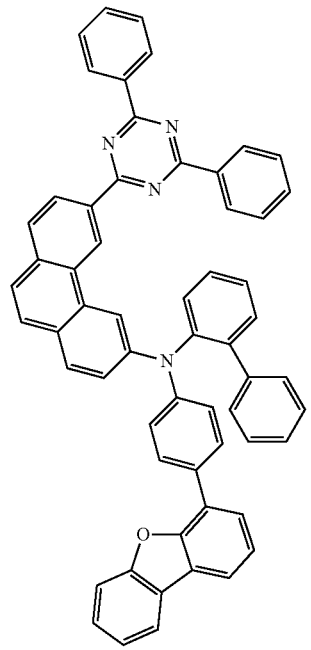 [SMILES: c1ccc(-c2nc(-c3ccccc3)nc(-c3ccc4ccc5ccc(N(c6ccc(-c7cccc8c7oc7ccccc78)cc6)c6ccccc6-c6ccccc6)cc5c4c3)n2)cc1]

| 12o | 74% |
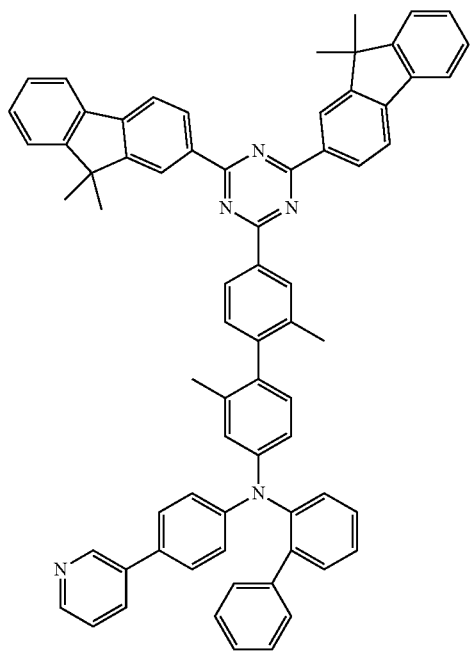 [SMILES: Cc1cc(-c2nc(-c3ccc4c(c3)C(C)(C)c3ccccc3-4)nc(-c3ccc4c(c3)C(C)(C)c3ccccc3-4)n2)ccc1-c1ccc(N(c2ccc(-c3cccnc3)cc2)c2ccccc2-c2ccccc2)cc1C]
| 12p | 29% |
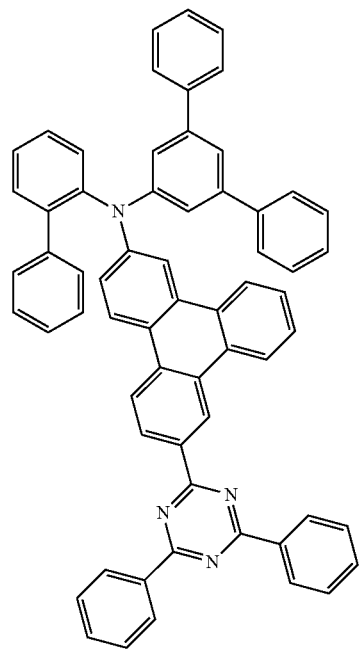 [SMILES: c1ccc(-c2cc(-c3ccccc3)cc(N(c3ccc4c5ccc(-c6nc(-c7ccccc7)nc(-c7ccccc7)n6)cc5c5ccccc5c4c3)c3ccccc3-c3ccccc3)c2)cc1]

| 12q | 14% |
|---|---|
| 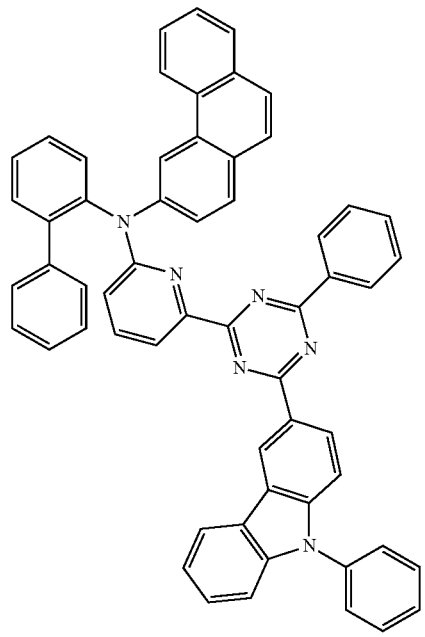 [SMILES: c1ccc(-c2nc(-c3ccc4c(c3)c3ccccc3n4-c3ccccc3)nc(-c3cccc(N(c4ccc5ccc6ccccc6c5c4)c4ccccc4-c4ccccc4)n3)n2)cc1] | |
| 12r | 36% |
| 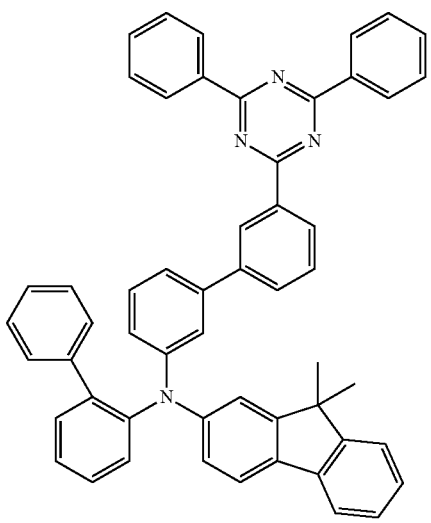 [SMILES: CC1(C)c2ccccc2-c2ccc(N(c3cccc(-c4cccc(-c5nc(-c6ccccc6)nc(-c6ccccc6)n5)c4)c3)c3ccccc3-c3ccccc3)cc21] | |

| | |
|---|---|
| 12s | 82% |
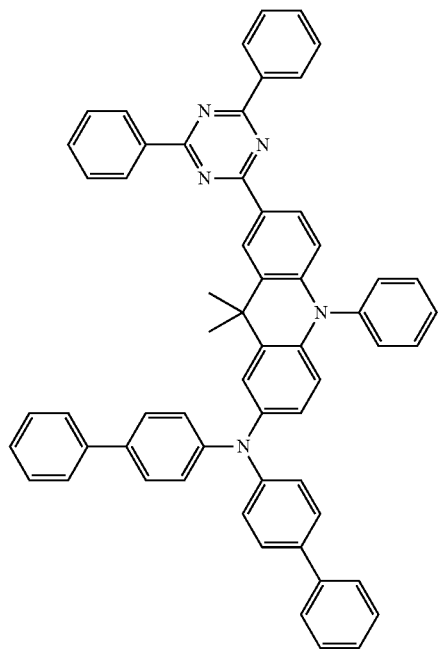 [SMILES: CC1(C)c2cc(-c3nc(-c4ccccc4)nc(-c4ccccc4)n3)ccc2N(c2ccccc2)c2ccc(N(c3ccc(-c4ccccc4)cc3)c3ccc(-c4ccccc4)cc3)cc21]
| | |
|---|---|
| 12t | 75% |
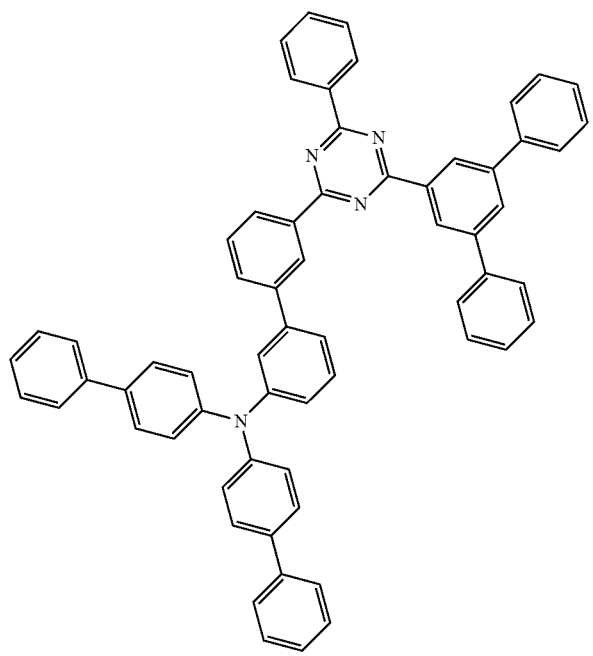 [SMILES: c1ccc(-c2ccc(N(c3ccc(-c4ccccc4)cc3)c3cccc(-c4cccc(-c5nc(-c6ccccc6)nc(-c6cc(-c7ccccc7)cc(-c7ccccc7)c6)n5)c4)c3)cc2)cc1]

-continued

12u 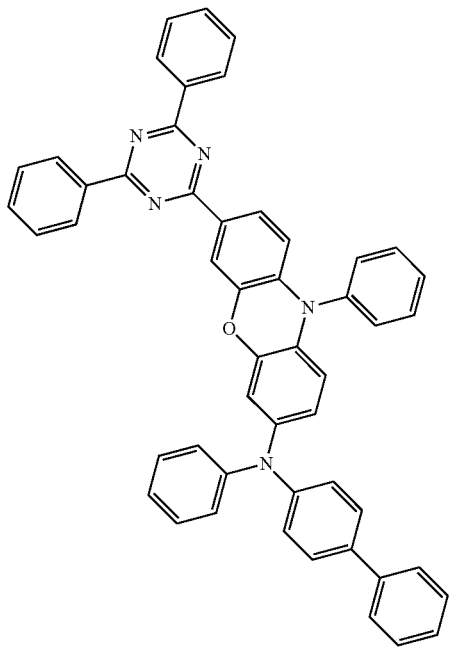 [SMILES: c1ccc(-c2ccc(N(c3ccccc3)c3ccc4c(c3)Oc3cc(-c5nc(-c6ccccc6)nc(-c6ccccc6)n5)ccc3N4c3ccccc3)cc2)cc1] 66%

12v 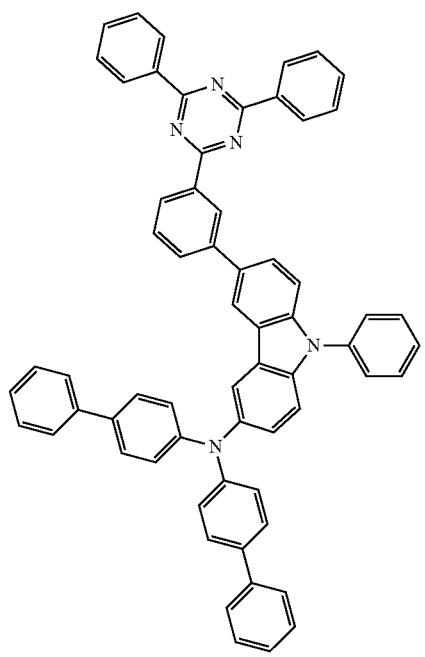 [SMILES: c1ccc(-c2ccc(N(c3ccc(-c4ccccc4)cc3)c3ccc4c(c3)c3cc(-c5cccc(-c6nc(-c7ccccc7)nc(-c7ccccc7)n6)c5)ccc3n4-c3ccccc3)cc2)cc1] 73%

B) Device Examples

B-1) Production of the OLEDs

Cleaned glass plates (cleaning in laboratory dishwasher, detergent Merck Extran) which have been coated with structured ITO (indium tin oxide) in a thickness of 50 nm are coated with 20 nm of PEDOT:PSS (poly(3,4-ethylenedioxythiophene) poly(styrenesulfonate), purchased as CLEVIOS™ P VP AI 4083 from Heraeus Precious Metals GmbH, Germany, applied by spin coating from aqueous solution) for improved processing. These coated glass plates form the substrates to which the OLEDs are applied.

The OLEDs have in principle the following layer structure: substrate/hole-transport layer (HTL)/interlayer (IL)/electron-blocking layer (EBL)/emission layer (EML) hole-blocking layer (HBL)/electron-transport layer (ETL) and finally a cathode. The cathode is formed by an aluminium layer with a thickness of 100 nm. The precise structure of the OLEDs is shown in Table 1. The materials used for the production of the OLEDs are shown in Table 3.

All materials are applied by thermal vapour deposition in a vacuum chamber. The emission layer here always consists of at least one matrix material (host material) and an emitting dopant (emitter), which is admixed with the matrix material or matrix materials in a certain proportion by volume by co-evaporation. An expression such as 12r:IC1:TEG1 (60%:30%:10%) here means that material 12r is present in the layer in a proportion by volume of 60%, IC1 is present in the layer in a proportion of 30% and TEG1 is present in the layer in a proportion of 10%. Analogously, the electron-transport layer consists of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminous density, calculated from current/voltage/luminous density characteristic lines (IUL characteristic lines) assuming Lambert emission characteristics, and the lifetime are determined. The electroluminescence spectra are determined at a luminous density of 1000 cd/m$^2$, and the CIE 1931 x and y colour coordinates are calculated therefrom. The term U1000 in Table 2 denotes the voltage required for a luminous density of 1000 cd/m$^2$. CE1000 and PE1000 denote the current and power efficiency respectively which are achieved at 1000 cd/m$^2$. Finally, EQE1000 denotes the external quantum efficiency at an operating luminous density of 1000 cd/m$^2$.

The lifetime LT is defined as the time after which the luminous density drops from the initial luminous density to a certain proportion L1 on operation at constant current. An expression of L0; j0=4000 cd/m$^2$ and L1=80% in Table 2 means that the lifetime indicated in column LT corresponds to the time after which the initial luminous density drops from 4000 cd/m$^2$ to 3200 cd/m$^2$. Analogously, L0; j0=20 mA/cm$^2$, L1=80%, means that the initial luminous density drops to 80% of its initial value after time LT on operation at 20 mA/cm$^2$.

The data of the various OLEDs are summarised in Table 2. Examples V1-V3 are comparative examples in accordance with the prior art, examples E1-E8 show data of OLEDs comprising materials according to the invention.

Some of the examples are explained in greater detail below in order to illustrate the advantages of the compounds according to the invention. However, it should be pointed out that this only represents a selection of the data shown in Table 2.

In general, very good performance data of the OLEDs, in particular a very good lifetime, power efficiency and operating voltage, are achieved with the compounds according to the invention (see Examples E1 to E8).

Compared with compound C1, compounds 12r and 12i, which are substituted by relatively large aromatic systems on the amino group, exhibit improvements with respect to efficiency and voltage, but in particular with respect to lifetime, on use as matrix material (Examples V1, E1 and E6).

An improvement also arises compared with compound C2, which likewise contains only small aromatic systems on the amino group (Examples V2, E1 and E6).

Compared with compound C3, in which amine and triazine are linked via a phenyl group, significantly better efficiency and a comparable lifetime are achieved with, for example, the similar compound 12t according to the invention (Examples V3, E2).

TABLE 1

Structure of the OLEDs

| Ex. | HTL Thickness | IL Thickness | EBL Thickness | EML Thickness | HBL Thickness | ETL Thickness |
|---|---|---|---|---|---|---|
| V1 | SpA1 70 nm | HATCN 5 nm | SpMA1 90 nm | C1:TEG1 (90%:10%) 30 nm | IC1 10 nm | ST2:LiQ (50%:50%) 30 nm |
| V2 | SpA1 70 nm | HATCN 5 nm | SpMA1 90 nm | C2:TEG1 (90%:10%) 30 nm | IC1 10 nm | ST2:LiQ (50%:50%) 30 nm |
| V3 | SpA1 70 nm | HATCN 5 nm | SpMA1 90 nm | C3:TEG1 (90%:10%) 30 nm | IC1 10 nm | ST2:LiQ (50%:50%) 30 nm |
| E1 | SpA1 70 nm | HATCN 5 nm | SpMA1 90 nm | 12r:TEG1 (90%:10%) 30 nm | IC1 10 nm | ST2:LiQ (50%:50%) 30 nm |
| E2 | SpA1 70 nm | HATCN 5 nm | SpMA1 90 nm | 12t:TEG1 (90%:10%) 30 nm | IC1 10 nm | ST2:LiQ (50%:50%) 30 nm |
| E3 | SpA1 90 nm | HATCN 5 nm | SpMA1 130 nm | 12b:TER3 (92%:8%) 40 nm | IC1 10 nm | ST2:LiQ (50%:50%) 30 nm |
| E4 | SpA1 70 nm | HATCN 5 nm | SpMA1 90 nm | 12c:TEG1 (90%:10%) 30 nm | IC1 10 nm | ST2:LiQ (50%:50%) 30 nm |
| E5 | SpA1 70 nm | HATCN 5 nm | SpMA1 90 nm | 12d:TEG1 (90%:10%) 30 nm | IC1 10 nm | ST2:LiQ (50%:50%) 30 nm |
| E6 | SpA1 70 nm | HATCN 5 nm | SpMA1 90 nm | 12i:TEG1 (90%:10%) 30 nm | IC1 10 nm | ST2:LiQ (50%:50%) 30 nm |
| E7 | SpA1 90 nm | HATCN 5 nm | SpMA1 130 nm | 12p:TER3 (92%:8%) 40 nm | IC1 10 nm | ST2:LiQ (50%:50%) 30 nm |
| E8 | SpA1 90 nm | HATCN 5 nm | SpMA1 130 nm | 12v:TER3 (92%:8%) 40 nm | IC1 10 nm | ST2:LiQ (50%:50%) 30 nm |

TABLE 2

Data of the OLEDs

| Ex. | U1000 (V) | CE1000 (cd/A) | PE1000 (lm/W) | EQE 1000 | CIE x/y at 1000 cd/m$^2$ | L0; j0 | L1 % | LT (h) |
|---|---|---|---|---|---|---|---|---|
| V1 | 3.3 | 60 | 57 | 16.9% | 0.34/0.62 | 20 mA/cm$^2$ | 80 | 70 |
| V2 | 3.6 | 50 | 44 | 14.3% | 0.36/0.61 | 20 mA/cm$^2$ | 80 | 95 |
| V3 | 3.4 | 55 | 50 | 15.4% | 0.34/0.62 | 20 mA/cm$^2$ | 80 | 125 |
| E1 | 3.2 | 63 | 62 | 17.8% | 0.34/0.62 | 20 mA/cm$^2$ | 80 | 110 |

TABLE 2-continued
Data of the OLEDs
| Ex. | U1000 (V) | CE1000 (cd/A) | PE1000 (lm/W) | EQE 1000 | CIE x/y at 1000 cd/m² | L0; j0 | | L1 % | LT (h) |
|---|---|---|---|---|---|---|---|---|---|
| E2 | 3.3 | 61 | 58 | 17.1% | 0.34/0.62 | 20 | mA/cm² | 80 | 135 |
| E3 | 4.3 | 11.0 | 8.0 | 11.9% | 0.67/0.33 | 4000 | cd/m² | 80 | 330 |
| E4 | 3.4 | 58 | 53 | 16.3% | 0.34/0.62 | 20 | mA/cm² | 80 | 90 |
| E5 | 3.3 | 64 | 61 | 18.1% | 0.34/0.62 | 20 | mA/cm² | 80 | 120 |
| E6 | 3.2 | 60 | 59 | 17.0% | 0.35/0.62 | 20 | mA/cm² | 80 | 115 |
| E7 | 4.8 | 10.4 | 6.8 | 11.3% | 0.67/0.33 | 4000 | cd/m² | 80 | 270 |
| E8 | 4.4 | 12.4 | 8.8 | 12.8% | 0.66/0.34 | 4000 | cd/m² | 80 | 305 |
TABLE 3
Structural formulae of the materials for the OLEDs
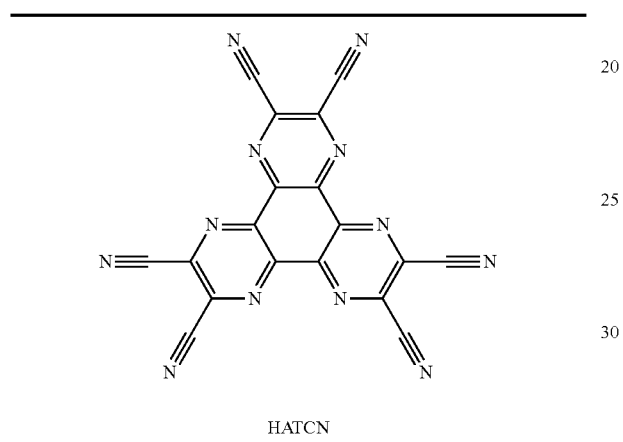
HATCN
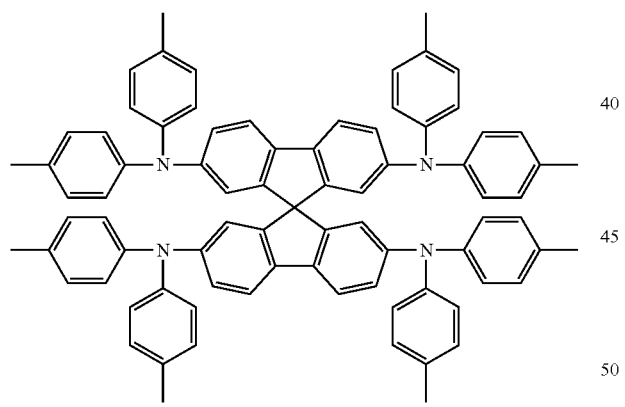
SpA1
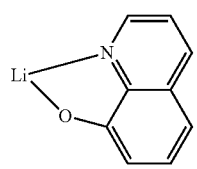
LiQ
TABLE 3-continued
Structural formulae of the materials for the OLEDs
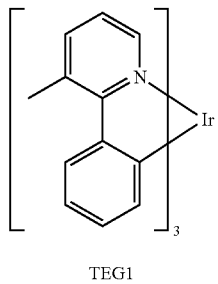
TEG1
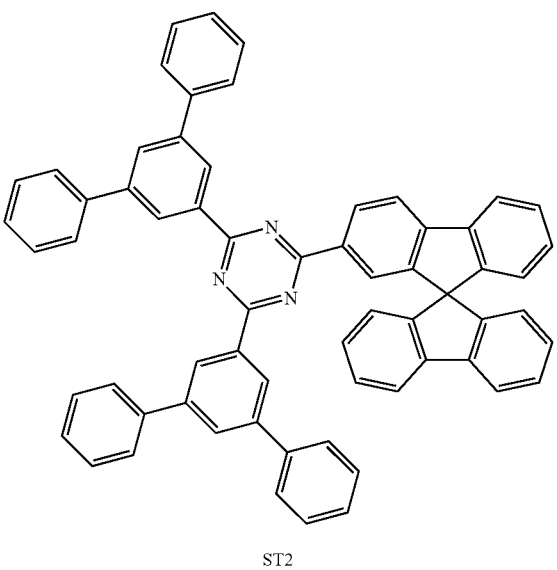
ST2
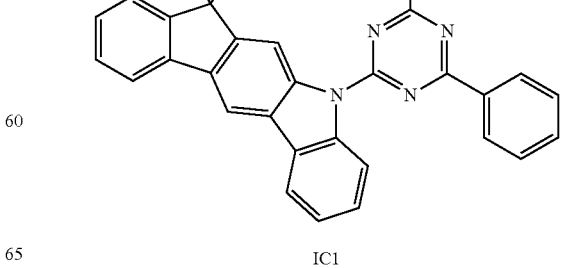
IC1

TABLE 3-continued
Structural formulae of the materials for the OLEDs
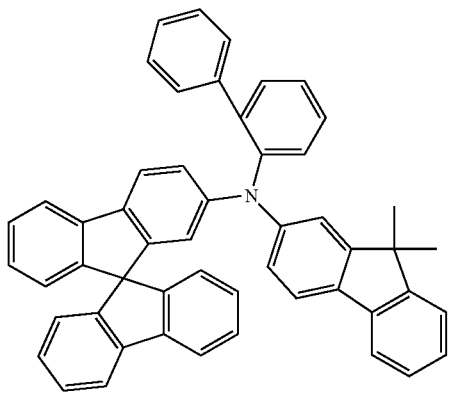 [SMILES: CC1(C)c2ccccc2-c2ccc(N(c3ccc4c(c3)C3(c5ccccc5-c5ccccc53)c3ccccc3-4)c3ccccc3-c3ccccc3)cc21]
SpMA1
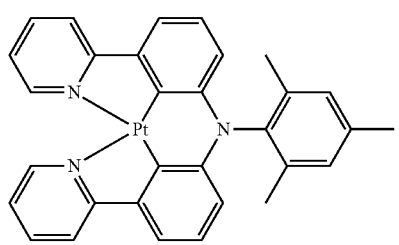
TER3
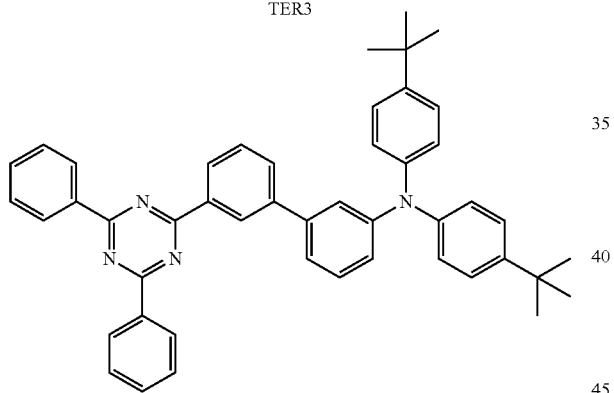
C1
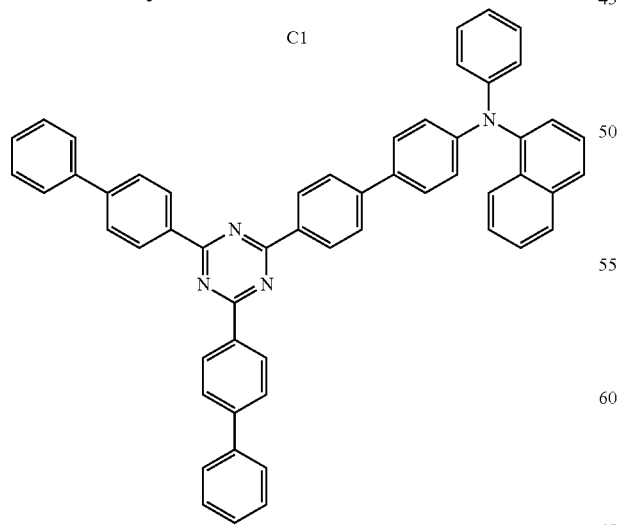
C2
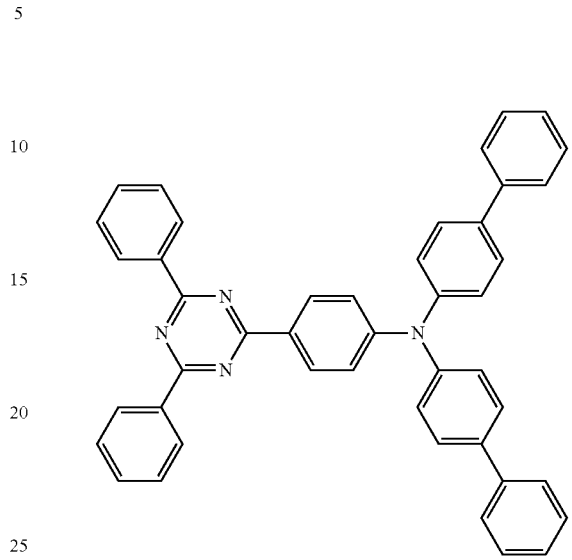
C3
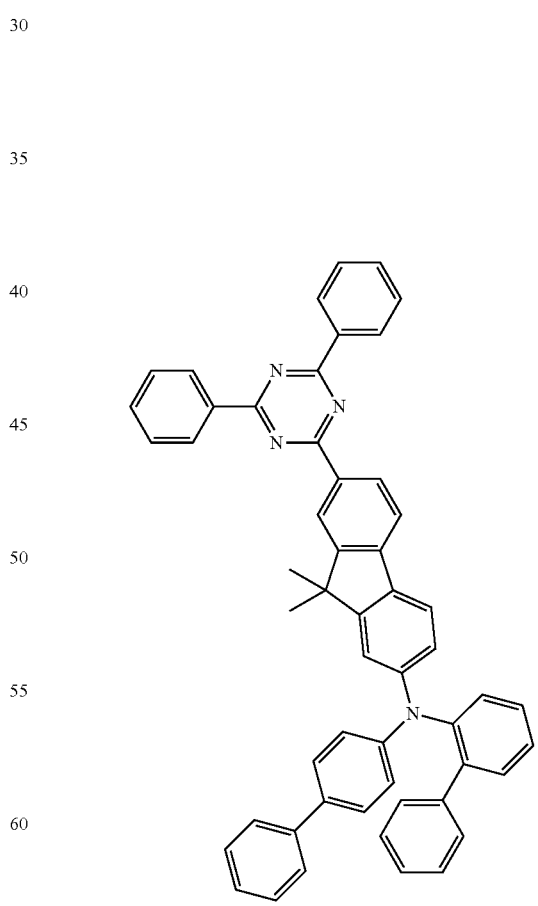
12b TABLE 3-continued
Structural formulae of the materials for the OLEDs
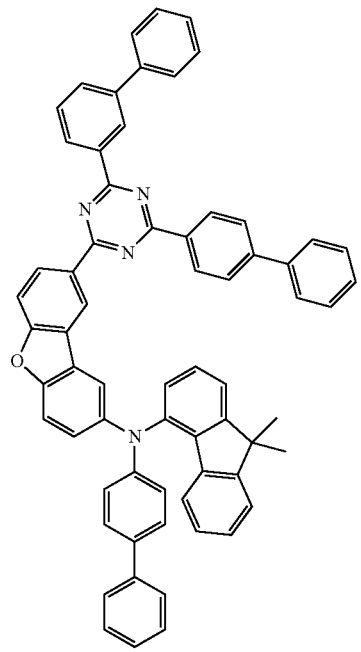 [SMILES: CC1(C)c2ccccc2-c2c(N(c3ccc(-c4ccccc4)cc3)c3ccc4oc5ccc(-c6nc(-c7ccc(-c8ccccc8)cc7)nc(-c7cccc(-c8ccccc8)c7)n6)cc5c4c3)cccc21]
12c
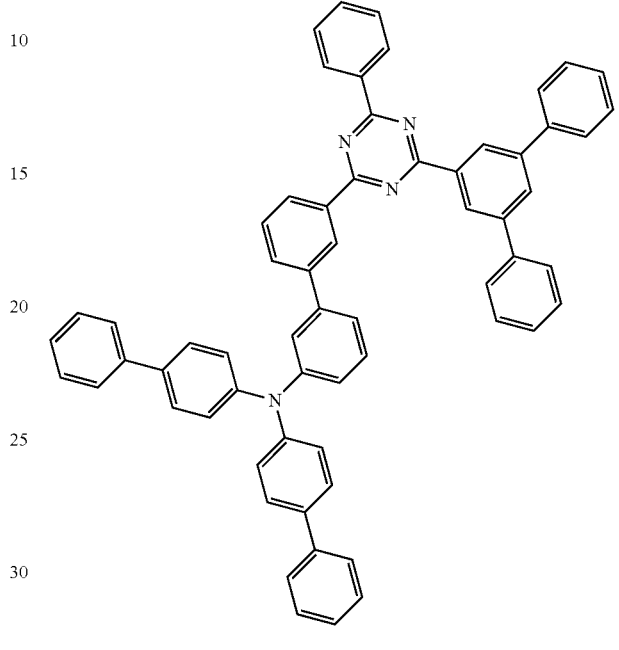
12t
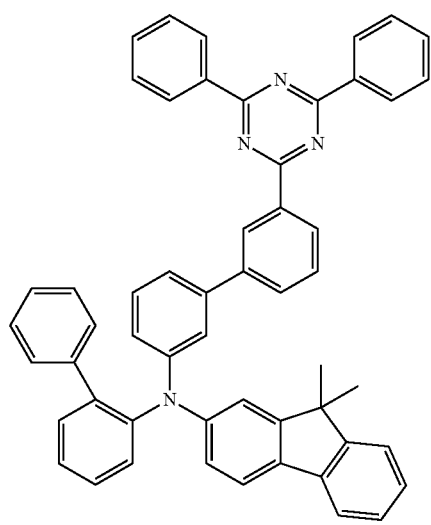 [SMILES: CC1(C)c2ccccc2-c2ccc(N(c3cccc(-c4cccc(-c5nc(-c6ccccc6)nc(-c6ccccc6)n5)c4)c3)c3ccccc3-c3ccccc3)cc21]
12r
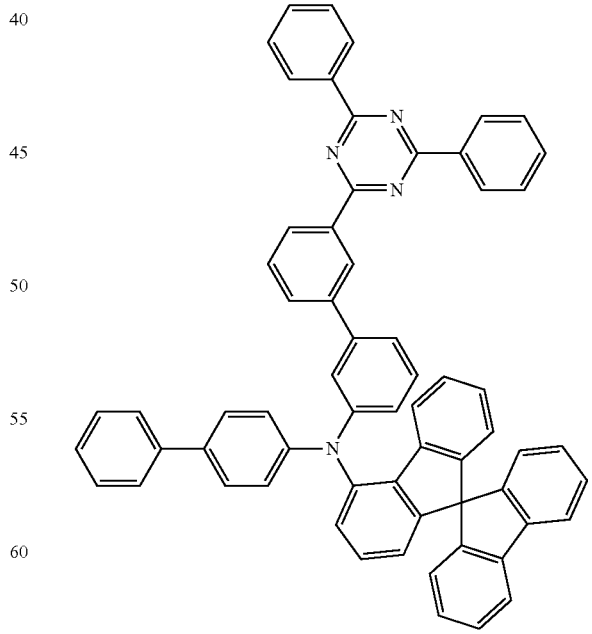
12i TABLE 3-continued Structural formulae of the materials for the OLEDs

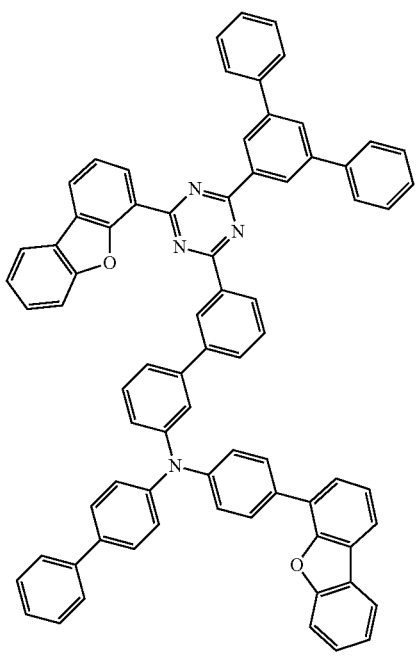 [SMILES: c1ccc(-c2ccc(N(c3ccc(-c4cccc5c4oc4ccccc45)cc3)c3cccc(-c4cccc(-c5nc(-c6cc(-c7ccccc7)cc(-c7ccccc7)c6)nc(-c6cccc7c6oc6ccccc67)n5)c4)c3)cc2)cc1]

12d

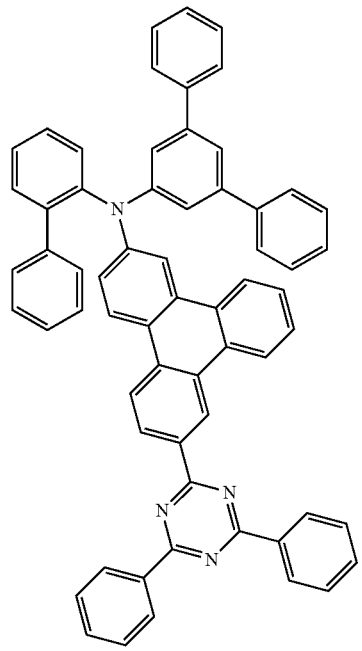 [SMILES: c1ccc(-c2cc(-c3ccccc3)cc(N(c3ccc4c5ccc(-c6nc(-c7ccccc7)nc(-c7ccccc7)n6)cc5c5ccccc5c4c3)c3ccccc3-c3ccccc3)c2)cc1]

12p

TABLE 3-continued

Structural formulae of the materials for the OLEDs

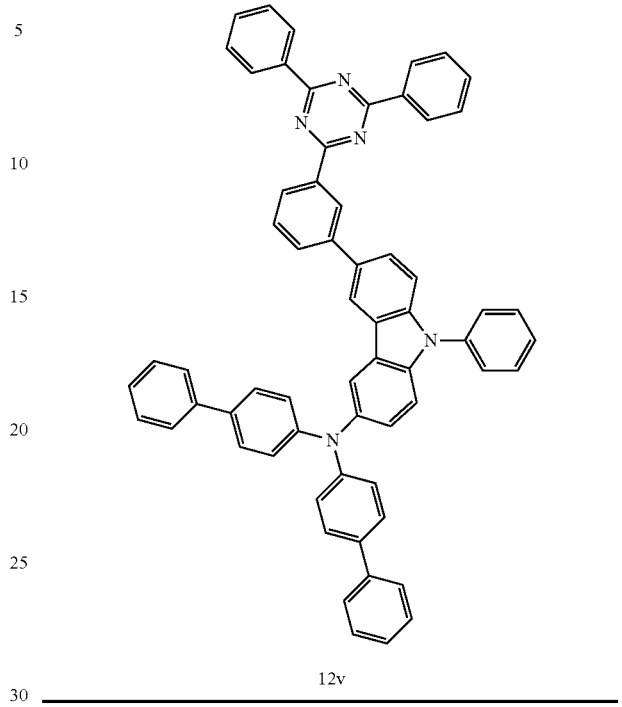

12v

The invention claimed is:
1. A compound of the formula (I)

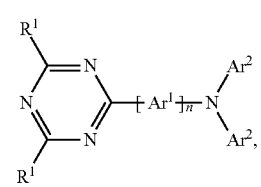

formula (I)

where:
Ar$^1$ is on each occurrence, identically or differently, an aromatic or heteroaromatic ring system selected from the groups of the formula (Ar$^1$-1) to (Ar$^1$ 10) and (Ar$^1$-14) to (Ar$^1$-17),which may be substituted by one or more radicals R$^2$

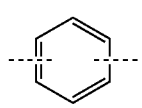

formula (Ar$^1$-1)

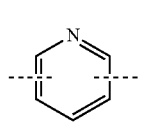

formula (Ar$^1$-2)

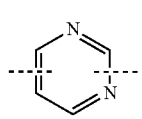

formula (Ar$^1$-3)

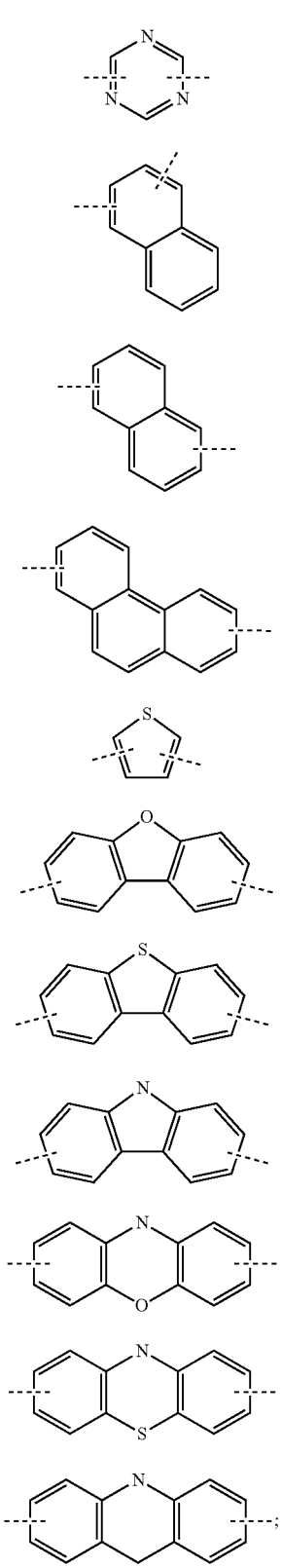

Ar² is on each occurrence, identically or differently, an aromatic or heteroaromatic ring system having 12 to 24 aromatic ring atoms, which may be substituted by one or more radicals R², where the aromatic ring system contains no condensed aryl or heteroaryl group having more than 10 aromatic ring atoms;

$R^1$, $R^2$ are on each occurrence, identically or differently, H, D, F, Cl, Br, I, C(=O)$R^3$, CN, Si($R^3$)$_3$, N($R^3$)$_2$, P(=O)($R^3$)$_2$, O$R^3$, S(=O)$R^3$, S(=O)$_2R^3$, a straight-chain alkyl or alkoxy group having 1 to 20 C atoms or a branched or cyclic alkyl or alkoxy group having 3 to 20 C atoms or an alkenyl or alkynyl group having 2 to 20 C atoms, where the above-mentioned groups may each be substituted by one or more radicals $R^3$ and where one or more CH$_2$ groups in the above-mentioned groups may be replaced by —$R^3$C=C$R^3$—, —C≡C—, Si($R^3$)$_2$, C=O, C=N$R^3$, —C(=O)O—, —C(=O)N$R^3$—, N$R^3$, P(=O)($R^3$), —O—, —S—, SO or SO$_2$, or an aromatic or heteroaromatic ring system having 5 to 30 aromatic ring atoms, which may in each case be substituted by one or more radicals $R^3$, where two or more radicals $R^2$ may be linked to one another and may form a ring;

$R^3$ is on each occurrence, identically or differently, H, D, F, Cl, Br, I, C(=O)$R^4$, CN, Si($R^4$)$_3$, N($R^3$)$_2$, P(=O)($R^4$)$_2$, O$R^4$, S(=O)$R^4$, S(=O)$_2R^4$, a straight-chain alkyl or alkoxy group having 1 to 20 C atoms or a branched or cyclic alkyl or alkoxy group having 3 to 20 C atoms or an alkenyl or alkynyl group having 2 to 20 C atoms, where the above-mentioned groups may each be substituted by one or more radicals $R^4$ and where one or more CH$_2$ groups in the above-mentioned groups may be replaced by —$R^4$C=C$R^4$—, —C≡C—, Si($R^4$)$_2$, C=O, C=N$R^4$, —C(=O)O—, —C(=O)N$R^4$—, N$R^4$, P(=O)OR), —O—, —S—, SO or SO$_2$, or an aromatic or heteroaromatic ring system having 5 to 30 aromatic ring atoms, which may in each case be substituted by one or more radicals $R^4$, where two or more radicals $R^3$ may be linked to one another and may form a ring;

$R^4$ is on each occurrence, identically or differently, H, D, F or an aliphatic, heteroaliphatic, aromatic or heteroaromatic organic radical having 1 to 20 C atoms, in which, in addition, one or more H atoms may be replaced by D or F; two or more substituents $R^4$ here may be linked to one another and may form a ring;

n is equal to 1, 2, 3 or 4;

with the proviso that the following is excluded:
when n=1, the group Ar¹ is a group of the formula (Ar¹-1) or (Ar¹-14), and
when n=2, both groups Ar¹ correspond to a group of the formula (Ar¹-1).

2. The compound according to claim 1, wherein the compound contains precisely one amino group.

3. The compound according to claim 1, wherein the compound contains precisely one triazine group.

4. The compound according to claim 1, wherein the compound contains no condensed aryl group having more than 14 aromatic ring atoms.

5. The compound according to claim 1, wherein $R^1$ is selected on each occurrence, identically or differently, from CN, an alkyl group having 1 to 10 C atoms or an alkenyl group having 2 to 10 C atoms, where the above-mentioned groups may be substituted by one or more radicals $R^3$, or an aromatic or heteroaromatic ring system having 5 to 30 aromatic ring atoms, which may be substituted by one or more radicals $R^3$.

6. An oligomer, polymer or dendrimer containing one or more compounds according to claim 1, where the bond(s) to the polymer, oligomer or dendrimer may be localised at any positions in formula (I) which are substituted by $R^1$ or $R^2$.

7. A formulation comprising at least one compound according to claim 1 and at least one solvent.

8. A formulation comprising at least one polymer, oligomer or dendrimer according to claim 6 and at least one solvent.

9. An electronic device comprising the compound according to claim 1.

10. An electronic device comprising anode, cathode and at least one organic layer, where the organic layer comprises at least one compound according to claim 1.

11. The electronic device according to claim 9, wherein the device is selected from the group consisting of organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs), organic laser diodes (O-lasers) and organic electroluminescent devices (OLEDs).

12. An organic electroluminescent device comprising the compound according to claim 1 is employed as matrix material in an emitting layer in combination with one or more emitter compounds.

13. A compound of the formula (I)

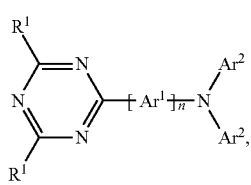

formula (I)

where:

Ar$^1$ is on each occurrence, identically or differently, an aromatic or heteroaromatic ring system selected from the groups of the formula (Ar$^1$-1) to (Ar$^1$ 10) and (Ar$^1$-14) to (Ar$^1$-17), which may be substituted by one or more radicals R$^2$

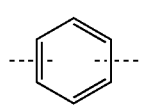

formula (Ar$^1$-1)

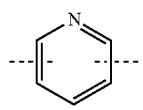

formula (Ar$^1$-2)

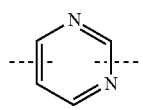

formula (Ar$^1$-3)

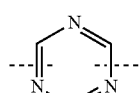

formula (Ar$^1$-4)

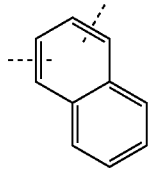

formula (Ar$^1$-5)

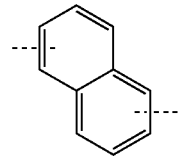

formula (Ar$^1$-6)

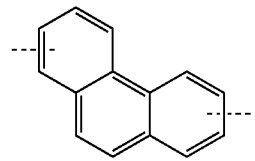

formula (Ar$^1$-7)

formula (Ar$^1$-8)

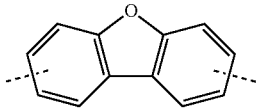

formula (Ar$^1$-9)

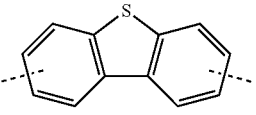

formula (Ar$^1$-10)

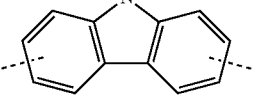

formula (Ar$^1$-14)

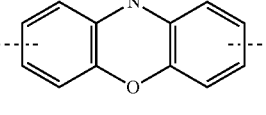

formula (Ar$^1$-15)

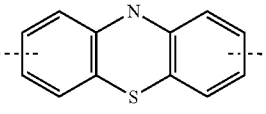

formula (Ar$^1$-16)

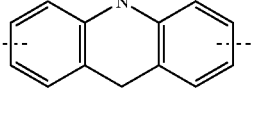

formula (Ar$^1$-17)

Ar$^2$ is on each occurrence, identically or differently, an aromatic or heteroaromatic ring system having 5 to 24 aromatic ring atoms, which may be substituted by one or more radicals R$^2$,
where at least one group Ar$^2$ in the compound of the formula (I) represents a group Ar$^2$*;

Ar$^2$* is on each occurrence, identically or differently, an aromatic or heteroaromatic ring system having 12 to 24 aromatic ring atoms, which may be substituted by one or more radicals R², where the aromatic ring system contains no condensed aryl or heteroaryl group having more than 10 aromatic ring atoms;

R¹, R² are on each occurrence, identically or differently, H, D, F, Cl, Br, I, C(=O)R³, CN, Si(R³)₃, N(R³)₂, P(=O)(R³)₂, OR³, S(=O)R³, S(=O)₂R³, a straight-chain alkyl or alkoxy group having 1 to 20 C atoms or a branched or cyclic alkyl or alkoxy group having 3 to 20 C atoms or an alkenyl or alkynyl group having 2 to 20 C atoms, where the above-mentioned groups may each be substituted by one or more radicals R³ and where one or more CH₂ groups in the above-mentioned groups may be replaced by —R³C=CR³—, —C≡C—, Si(R')₂, C=O, C=NR³, —C(=O)O—, —C(=O)NR³—, NR³, P(=O)(R³), —O—, —S—, SO or SO₂, or an aromatic or heteroaromatic ring system having 5 to 30 aromatic ring atoms, which may in each case be substituted by one or more radicals R³, where two or more radicals R² may be linked to one another and may form a ring;

R³ is on each occurrence, identically or differently, H, D, F, Cl, Br, I, C(=O)R⁴, CN, Si(R⁴)₃, N(R³)₂, P(=O)(R⁴)₂, OR⁴, S(=O)R⁴, S(=O)₂R⁴, a straight-chain alkyl or alkoxy group having 1 to 20 C atoms or a branched or cyclic alkyl or alkoxy group having 3 to 20 C atoms or an alkenyl or alkynyl group having 2 to 20 C atoms, where the above-mentioned groups may each be substituted by one or more radicals R⁴ and where one or more CH₂ groups in the above-mentioned groups may be replaced by —R⁴C=CR⁴—, —C≡C—, Si(R⁴)₂, C=O, C=NR⁴, —C(=O)O—, —C(=O)NR⁴—, NR⁴, P(=O)(R⁴), —O—, —S—, SO or SO₂, or an aromatic or heteroaromatic ring system having 5 to 30 aromatic ring atoms, which may in each case be substituted by one or more radicals R⁴, where two or more radicals R³ may be linked to one another and may form a ring;

R⁴ is on each occurrence, identically or differently, H, D, F or an aliphatic, heteroaliphatic, aromatic or heteroaromatic organic radical having 1 to 20 C atoms, in which, in addition, one or more H atoms may be replaced by D or F; two or more substituents R⁴ here may be linked to one another and may form a ring;

n is equal to 1, 2, 3 or 4;

with the proviso that the following is excluded: when n=1 or 2, the group Ar¹ is a group of the formula (Ar¹-1) or (Ar¹-14).

14. The compound according to claim 13, wherein the compound contains precisely one amino group.

15. The compound according to claim 13, wherein the compound contains precisely one triazine group.

16. The compound according to claim 13, wherein the compound contains no condensed aryl group having more than 14 aromatic ring atoms.

17. The compound according to claim 13, wherein both groups Ar² are selected from identical or different groups Ar²*.

18. The compound according to claim 13, wherein Ar² is selected on each occurrence, identically or differently, from an aromatic or heteroaromatic ring system having 5 to 20 aromatic ring atoms, which may be substituted by one or more radicals R².

19. The compound according to claim 13, wherein Ar² is selected on each occurrence, identically or differently, from phenyl, biphenyl, terphenyl, quaterphenyl, fluorenyl, spirobifluorenyl, indenofluorenyl, naphthyl, anthracenyl, phenanthrenyl, chrysenyl, benzanthracenyl, pyrenyl, triphenylenyl, fluoranthenyl, furanyl, benzofuranyl, dibenzofuranyl, thiophenyl, benzothiophenyl, dibenzothiophenyl, indolyl, carbazolyl, indolocarbazolyl, indenocarbazolyl, pyridyl, quinolinyl, acridyl, dihydroacridyl, pyrazolyl, imidazolyl, benzimidazolyl, pyridazyl, pyrimidyl, pyrazinyl and phenanthrolyl, each of which is optionally substituted by one or more radicals R².

20. The compound according to claim 13, wherein R¹ is selected on each occurrence, identically or differently, from CN, an alkyl group having 1 to 10 C atoms or an alkenyl group having 2 to 10 C atoms, where the above-mentioned groups may be substituted by one or more radicals R³, or an aromatic or heteroaromatic ring system having 5 to 30 aromatic ring atoms, which may be substituted by one or more radicals R³.

21. An oligomer, polymer or dendrimer containing one or more compounds according to claim 13, where the bond(s) to the polymer, oligomer or dendrimer may be localised at any positions in formula (I) which are substituted by R¹ or R².

22. A formulation comprising at least one compound according to claim 13 and at least one solvent.

23. A formulation comprising at least one polymer, oligomer or dendrimer according to claim 21 and at least one solvent.

24. An electronic device comprising the compound according to claim 13.

25. An electronic device comprising anode, cathode and at least one organic layer, where the organic layer comprises at least one compound according to claim 13.

26. The electronic device according to claim 24, wherein the device is selected from the group consisting of organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs), organic laser diodes (O-lasers) and organic electroluminescent devices (OLEDs).

27. An organic electroluminescent device comprising the compound according to claim 13 is employed as matrix material in an emitting layer in combination with one or more emitter compounds.

\* \* \* \* \*